United States Patent
Baum et al.

(10) Patent No.: US 12,319,716 B2
(45) Date of Patent: Jun. 3, 2025

(54) PROTEINS TOXIC TO HEMIPTERAN INSECT SPECIES

(71) Applicant: Monsanto Technology LLC, St. Louis, MO (US)

(72) Inventors: James A. Baum, Webster Groves, MO (US); Artem G. Evdokimov, Orchard Park, NY (US); Stanislaw Flasinski, Ballwin, MO (US); Farhad Moshiri, Chesterfield, MO (US); Timothy J. Rydel, St. Charles, MO (US); Eric J. Sturman, Wildwood, MO (US); Moritz von Rechenberg, Waltham, MA (US); Halong Vu, Arlington, MA (US); Andrew M. Wollacott, Boston, MA (US); Meiying Zheng, Wildwood, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 18/595,330

(22) Filed: Mar. 4, 2024

(65) Prior Publication Data
US 2024/0262872 A1 Aug. 8, 2024

Related U.S. Application Data

(60) Division of application No. 17/742,215, filed on May 11, 2022, now Pat. No. 11,981,709, which is a continuation of application No. 17/127,310, filed on Dec. 18, 2020, now Pat. No. 11,459,359, which is a continuation of application No. 16/594,713, filed on Oct. 7, 2019, now Pat. No. 10,897,910, which is a continuation of application No. 16/209,501, filed on Dec. 4, 2018, now Pat. No. 10,485,238, which is a continuation of application No. 15/651,727, filed on Jul. 17, 2017, now Pat. No. 10,188,115, which is a division of application No. 15/015,957, filed on Feb. 4, 2016, now Pat. No. 9,713,334, which is a continuation of application No. 13/857,196, filed on Apr. 5, 2013, now Pat. No. 9,322,033.

(60) Provisional application No. 61/621,436, filed on Apr. 6, 2012.

(51) Int. Cl.
| | |
|---|---|
| C07K 14/325 | (2006.01) |
| A01N 37/46 | (2006.01) |
| C07K 14/00 | (2006.01) |
| C07K 14/32 | (2006.01) |
| C07K 14/435 | (2006.01) |
| C12N 15/82 | (2006.01) |

(52) U.S. Cl.
CPC ............ *C07K 14/325* (2013.01); *A01N 37/46* (2013.01); *C07K 14/001* (2013.01); *C07K 14/32* (2013.01); *C07K 14/43577* (2013.01); *C12N 15/8286* (2013.01); *Y02A 40/146* (2018.01)

(58) Field of Classification Search
CPC ................................. C12N 9/90; C07K 14/325
See application file for complete search history.

(56) References Cited

U.S. PATENT DOCUMENTS

| | | | |
|---|---|---|---|
| 5,723,440 | A | 3/1998 | Stockhoff et al. |
| 5,885,963 | A | 3/1999 | Stockhoff et al. |
| 5,942,658 | A | 8/1999 | Donovan et al. |
| 7,473,821 | B2 | 1/2009 | Abad et al. |
| 7,524,810 | B1 | 4/2009 | Schnepf |
| 7,615,686 | B2 | 11/2009 | Miles et al. |
| 9,713,334 | B2 | 7/2017 | Baum et al. |
| 11,981,709 | B2 | 5/2024 | Baum |
| 12,054,522 | B2 | 8/2024 | Baum et al. |
| 2006/0021087 | A1 | 1/2006 | Baum et al. |
| 2006/0242732 | A1 | 10/2006 | Carozzi et al. |
| 2008/0295207 | A1 | 11/2008 | Baum et al. |
| 2010/0064394 | A1 | 3/2010 | Baum et al. |
| 2010/0298207 | A1 | 11/2010 | Sampson et al. |
| 2013/0269060 | A1 | 10/2013 | Baum et al. |
| 2022/0356215 | A1 | 11/2022 | Baum et al. |

FOREIGN PATENT DOCUMENTS

| | | |
|---|---|---|
| EP | 2834266 B1 | 6/2019 |
| WO | 19930014205 A1 | 7/1993 |
| WO | 19960039843 A1 | 12/1996 |
| WO | 20010071042 A2 | 9/2001 |
| WO | 20020078437 A2 | 10/2002 |
| WO | 20050110068 A2 | 11/2005 |
| WO | 20060107761 A2 | 10/2006 |
| WO | 20070027776 A2 | 3/2007 |
| WO | 20080134072 A2 | 11/2008 |
| WO | 20100025320 A1 | 3/2010 |
| WO | 20100099365 A2 | 9/2010 |

OTHER PUBLICATIONS

Baum et al., "Binary Toxins from Bacillus thuringiensis Active against the Western Corn Rootworm," Diabrotica virgifera virgifera LeConte, Applied and Environmental Microbiology, 70(8):4889-4898 (2004).

(Continued)

*Primary Examiner* — Tekchand Saidha
(74) *Attorney, Agent, or Firm* — Dentons US LLP; David Lanzotti

(57) ABSTRACT

The present invention discloses Hemipteran insect inhibitory proteins, methods of using such proteins, nucleotide sequences encoding such proteins, methods of detecting and isolating such proteins, and their use in agricultural systems.

22 Claims, 3 Drawing Sheets
Specification includes a Sequence Listing.

(56) References Cited

OTHER PUBLICATIONS

Chan et al., "Unusual Amino Acid Determinants of Host Range in the Mtx2 Family of Mosquitocidal Toxins," The Journal of Biological Chemistry, 271(24):14183-14187 (1996).
Chougule et al., "Toxins for Transgenic Resistance to Hemipteran Pests," Toxins 4:405-429 (2012).
Correspondence from NCBI dated Sep. 24, 2010 re Date of First Public Release for DQ836184, 2 pages.
Crickmore et al., "Revision of the Nomenclature for the Bacillus thuringiensis Pesticidal Crystal Proteins," Microbiology and Molecular Biology Review, 62(3):807-813 (1998).
Donovan et al., "Characterization of Two Genes Encoding Bacillus thuringiensis Insecticidal Crystal Proteins Toxic to *Coleoptera* Species," Applied and Environmental Microbiology, 58(12):3921-3927 (1992).
EBI Accession No. GSP: ABB68459, "*Drosophila melanogaster* Polypeptide SEQ ID No. 32169. Dyderpskrp Rgkptagtag Rkisprkpgr Veerrsnfned Rplgrrrsek Erttpssald", XP 002600478, Mar. 2002, Database Geneseq.
EMBL Accession No. DQ836184, Bacillus thuringiensis strain F14-1 Cry51 Aal (cry51Aa1) gene, complete CDs, http://srs.ebi.ac.us/srsbin/cgi-bin/wget?-e+[EMBL:DQ836184]+-newld, created Aug. 1, 2007, 2 pages.
Extended European Search Report dated Oct. 6, 2010, in European Patent Application No. 08754143.9, 6 pages.
Extended European Search Report dated Sep. 14, 2015, in European Patent Application No. 13772577.6, 7 pages.
GenBank Accession No. DQ836184, Bacillus thuringiensis strain F14-1 Cry51Aa1 (cry51Aa1) gene, complete cds, 1 page. Aug. 1, 2007, Web, Apr. 11, 2009 http://www.ncbi.nlm.nih.gov/nuccore/112253718.
Hofte et al. "Insecticidal Crystal Proteins of Bacillus thuringiensis," Microbiological Reviews, American Society for Microbiology, 53(2):242-255 (1989).
Huang et al., "Microbial Control and Biotechnology Research on Bacillus thuringiensis in China," Journal of Invertebrate Pathology, 95(3): 175-180 (2007).
International Search Report and Written Opinion dated Nov. 24, 2008, in International Application No. PCT/US2008/005542.
Lambert et al., "Novel Bacillus thuringiensis Insecticidal Crystal Protein with a Silent Activity against Coleopteran Larvae," Applied and Environmental Microbiology, 58(8)2536-2542 (1992).
Liu et al., "New Gene from Nine Bacillus sphaericus Strains Encoding Highly Conserved 35.8-Kilodalton Mosquitocidal Toxins," Applied and Environmental Microbiology, 62(6):2174-2176 (1996).
NCBI Accession No. D0836184, Bacillus thuringiensis strain F14-1 Cry51Aa1 (cry51Aa1) gene, obtained Oct. 1, 2010 from http://ncbi.nil.nih.gov/nuccore/112253718, 1 page.
NCBI Sample GenBank Record obtained Oct. 1, 2010 from http://www.ncbi.nilm.gov/Sitemap/samplerecord.html, 17 pages.
New England Biolabs, Random Primer 12, Jun. 2004, http://web.archive.org/web/20040619083054/http://www.neb.com/nebecomm/productS1256.asp, 1 page.
New England Biolabs, Random Primer 24, Jun. 2004, http://web.archive.org/web/20040619083054/http://www.neb.com/nebecomm/productS1256.asp, 1 page.
Revision history for NCBI Accession DQ836184, Bacillus thuringiensis strain F14-1 Cry51Aa1(crry51Aa1) gene, obtained on Oct. 1, 2010 from http://www.ncbi.nlm.nih.gov/sviewer/girevhist.cgi?val=DQ836184.1&log$=seq-view, 1 page.
Soberon et al., "Engineering Modified Bt toxins to Counter Insect Resistance," Science, 31895856):1640-1642 (2007).
Thanabalu et al., "A Bacillus sphaericus Gene Encoding a Novel Type of Mosquitocidal Toxin of 31.8 kDa, Gene," 170(1):85-89 (1996).
UniProt Accession No. A7IE5_BACTU, 1 page, accessed on Oct. 13, 2015 http://www.genome.jp/dbget-bin/www_bget?uniprot:A7IZR5_BACTU.
Vita et al., "Scorpion Toxins as Natural Scaffolds for Protein Engineering," Proc. Natl. Acad. Sci. USA, 92:6404-6408 (1995).
Von Tersch et al., "Membrane-Permeabilizing Activities of Bacilllus thuringiensis Coleopteran-Active Toxin CryIIIB2 and CryIIIB2 Domain I Peptide," Applied and Environmental Microbiology, 60(10):3711-3717 (1994).
Wellman-Desbiens, et al., "Development of a Bacillus thuringiensis-Based Assay on Lygus hesperus," J. Economic Entomology, 98(5):1469-1479 (2005).

FIGURE 3

Measured LC50 Values of Lygus Toxic Proteins

PROTEINS TOXIC TO HEMIPTERAN INSECT SPECIES

CROSS REFERENCE TO RELATED APPLICATIONS

This application is a divisional of U.S. patent application Ser. No. 17/742,215, filed May 11, 2022, which is a continuation of U.S. patent application Ser. No. 17/127,310, filed Dec. 18, 2020, now U.S. Pat. No. 11,459,359, which is a continuation of U.S. patent application Ser. No. 16/594,713, filed Oct. 7, 2019, now U.S. Pat. No. 10,897,910, which is a continuation of U.S. patent application Ser. No. 16/209,501, filed Dec. 4, 2018, now U.S. Pat. No. 10,485,238, which is a continuation of U.S. patent application Ser. No. 15/651,727, filed Jul. 17, 2017, now U.S. Pat. No. 10,188,115, which is a divisional of U.S. patent application Ser. No. 15/015,957, filed Feb. 4, 2016, now U.S. Pat. No. 9,713,334, which is a continuation of U.S. patent application Ser. No. 13/857,196, filed Apr. 5, 2013, now U.S. Pat. No. 9,322,033, which claims the benefit of priority to U.S. Provisional Application Ser. No. 61/621,436 filed Apr. 6, 2012, each of the disclosures of which are incorporated herein by reference in their entirety.

INCORPORATION OF SEQUENCE LISTING

The Sequence Listing contained in the file named "MONS514USD2_ST26.xml", which is 395,049 bytes in size (measured in operating system MS-Windows) and was created on Feb. 28, 2024, is contemporaneously filed by electronic submission (using the United States Patent Office Patent Center filing system) and is incorporated herein by reference in its entirety.

FIELD OF THE INVENTION

The present invention generally relates to the field of insect inhibitory proteins. In particular, the present invention relates to proteins exhibiting insect inhibitory activity against agriculturally relevant pests of crop plants and seeds, particularly Hemipteran species of insect pests.

BACKGROUND OF THE INVENTION

Insect inhibitory proteins derived from *Bacillus thuringiensis* (Bt) are non-toxic to humans, vertebrates, and plants. These proteins are also biodegradable, safe, and effective in controlling pest insects. Some of these proteins have been and are being used to control agriculturally relevant pests of crop plants by spraying plants with formulations containing these proteins or with microorganisms that express them, treating seeds with treatments containing these proteins, or expressing these proteins in crop plants and seeds of crop plants as plant-incorporated protectants.

Certain Hemiptera species, particularly *Amrasca, Empoasca* and *Lygus* bugs, are pests of cotton and alfalfa, and typically are only controlled using broad spectrum chemistries, e.g., endosulfan, acephate, and oxamyl, which can persist in and are harmful to the environment. A few Bt proteins have been developed in formulations or as transgenic traits in crop plants for commercial use by farmers to control Coleopteran and Lepidopteran pest species, but no Bt proteins have been developed for use in commercial control of Hemipteran pest species.

Hemipteran specific toxic proteins have been reported in the art. TIC807 is a *Bacillus thuringiensis* protein disclosed in U.S. Patent Application Publication No. US 2008-0295207 A1 as being toxic to Hemipteran pest species. A Cry51Aa1 protein reported as toxic to Lepidopteran species that closely resembles the amino acid sequence of TIC807 has also been disclosed (Huang et al., (2007) J. Invertebr. Pathol. 95(3), 175-180), but no Hemipteran specific activity was reported. Baum et al. disclosed TIC853, a protein reported to be toxic to *Lygus* pest species (U.S. Patent Application Publication No. US 2010-0064394 A1). A protein referred to as AXMI-171 was reported to exhibit some limited inhibition of Hemipteran insects (U.S. Patent Application Publication No. US2010-0298207 A1, example 18), particularly *Lygus hesperus*.

All of these proteins exhibit a narrow range of toxicity only against *Lygus hesperus* and exhibit toxic effects against other *Lygus* pest species only in high doses which are not considered to be achievable by expression in plants. Compared to the Hemipteran toxic proteins in the prior art, there is a need for toxin proteins that can be used on and in plants that exhibit a broad host range against Hemipteran pest species and at low concentration effective doses.

BRIEF SUMMARY OF THE INVENTION

Recombinantly engineered Hemipteran toxic proteins described herein (referred to herein as "engineered toxin proteins", "engineered toxic proteins", "engineered Hemipteran toxic proteins", or "engineered Hemipteran toxin proteins", are also referred to herein in truncated form as "eHTP's" when referred to in groups of two or more such proteins, and "eHTP" when referred to singularly) are derivatives of naturally occurring *Bacillus thuringiensis* insecticidal toxins, TIC807 (SEQ ID NO:2), TIC807 M2 (SEQ ID NO:8), Cry51Aa1 (SEQ ID NO:182), TIC853 (SEQ ID NO:184), and AXMI-171 (SEQ ID NO:206) have been described previously to exhibit bio-control activity directed to Hemipteran pest species, particularly *Lygus hesperus* insect species (references cited elsewhere herein). The recombinant Hemipteran insect toxic proteins of the present invention are particularly toxic to insects of the *Amrasca, Empoasca* and *Lygus* species of insect pests and to other insect pest species that are phylogenetically related to each of these species of insect pests, and additionally to insect pests that feed on plants using a piercing and sucking mechanism used by the pest species *Amrasca, Empoasca* and *Lygus* species of the order Hemiptera. Unlike the precursor insecticidal toxins TIC807 (SEQ ID NO:2), TIC807 M2 (SEQ ID NO:8), Cry51Aa1 (SEQ ID NO:182), TIC853 (SEQ ID NO:184), and AXMI-171 (SEQ ID NO:206) from which they are derived, which each require moderately high to high doses of protein to achieve toxic effects upon one *Lygus* species and exhibit very low or virtually undetectable toxic effects upon a second closely related species of *Lygus*, the eHTP proteins of the present invention exhibit surprising and unexpected low dose toxic effects against insect pests of the order Hemiptera, including host range toxic effects that span the spectrum of pests within the order.

The eHTP's of the present invention each contain at least one amino acid substitution, one amino acid addition, or one amino acid deletion compared to the primary amino acid sequence of one or more of the toxin proteins set forth in any of SEQ ID NO:2, SEQ ID NO:8, SEQ ID NO: 182, or SEQ ID NO: 184. In certain embodiments, an eHTP is provided that contains at least from about 2 to about 260 fold greater inhibitory activity against a *Lygus* pest species than any one or more of the toxins set forth in any of SEQ ID NO:2

(TIC807), SEQ ID NO:8 (TIC807 M2), SEQ ID NO:182 (Cry51Aa1), SEQ ID NO:184 (TIC853), and/or SEQ ID NO:206 (AXMI-171). Optionally the eHTP exhibits at least about 95% amino acid sequence identity to the toxin protein selected from the group consisting of SEQ ID NO:2 (TIC807) and SEQ ID NO:182 (Cry51Aa1). In certain embodiments, an eHTP is provided that contains at least one amino acid substitution, at least one amino acid addition, or at least one amino acid deletion when compared to the amino acid sequence of any of SEQ ID NO:2, SEQ ID NO:8, SEQ ID NO: 182, or SEQ ID NO: 184. The eHTP exhibits an increased or greater *Lygus* inhibitory activity and target pest species spectrum compared to the activity and target pest species spectrum of the *Bacillus thuringiensis* proteins of set forth in SEQ ID NO:2, SEQ ID NO:8, SEQ ID NO: 182, and SEQ ID NO: 184. Each of the aforementioned eHTP's contain at least, collectively or in the alternative: (i) the amino acid substitution, addition, or deletion in a solvent accessible amino acid residue of SEQ ID NO:2; (ii) the amino acid substitution, addition, or deletion within 3 consecutive residues of a solvent accessible amino acid residue of SEQ ID NO:2; or, (iii) an amino acid sequence as set forth in SEQ ID NO: 180. The aforementioned eHTP's will each contain at least, with reference to the amino acid sequence positions as numbered according to the amino acid positions of TIC807, one substitution or deletion selected from the group consisting of asparagine at position 12 replaced by aspartic acid, phenylalanine at position 46 replaced by serine, isoleucine at position 52 replaced by methionine, tyrosine at position 54 replaced by histidine, threonine at position 68 replaced by alanine, glutamine at position 70 replaced by alanine, alanine at position 87 replaced by serine, threonine at position 93 replaced by alanine, serine at position 95 replaced by alanine, glycines at position 105 replaced by alanine, serine at position 117 replaced by alanine, serine at position 119 replaced by alanine, glutamate at position 125 replaced by cysteine, histidine, arginine, phenylalanine, serine, glutamine, lysine, threonine, asparagine, alanine, leucine, valine, methionine, aspartic acid, or tyrosine, glycines at position 128 replaced by alanine, threonine at position 133 replaced by glutamic acid, tyrosine, or tryptophan, isoleucine at position 134 replaced by alanine, valine, leucine, phenylalanine, lysine, cysteine, or methionine, glutamate at position 135 replaced by serine, alanine, valine, tryptophan, or threonine, asparagine at position 137 replaced by histidine, tyrosine, threonine, glutamic acid, serine, alanine, glutamine, glycine, isoleucine, tryptophan, lysine, cysteine, methionine, aspartic acid, phenylalanine, or arginine, phenylalanine at position 138 replaced by valine, Ala139 replaced by serine, Thr145 replaced by alanine, Phe147 replaced by serine, valine, threonine, cysteine, leucine, aspartic acid, alanine, glycine, glutamic acid, isoleucine, tyrosine, methionine, asparagine, glutamine, hystidine, alanine, arginine, tryptophan, or proline, glutamine at position 148 replaced by alanine, glutamine at position 149 replaced by aspartic acid, glutamic acid, cysteine, alanine, or phenylalanine, alanine at position 150 replaced by serine, leucine, valine, glycine, aspartic acid, tryptophan, glutamic acid, asparagine, tyrosine, phenylalanine, proline, lysine, threonine, glutamine, or arginine, seroine at position 151 replaced by alanine, aspartate at position 153 replaced by alanine, glutamate at position 155 replaced by cysteine, isoleucine, lysine, aspartic acid, histidine, tyrosine, glutamine, lysine, asparagine, threonine, alanine, phenylalanine, arginine, methionine, proline, tryptophan, serine, or valine, asparagine at position 157 replaced by cysteine, aspartic acid, tryptophan, tyrosine, methionine, alanine, phenylalanine, valine, leucine, proline, glutamic acid, threonine, glycine, isoleucine, or arginine, isoleucine at position 158 replaced by alanine, serine at position 159 replaced by alanine or threonine, serine at position 167 replaced by arginine or alanine, valine at position 175 replaced by alanine, methionine at position 177 replaced by alanine, asparagine at position 180 replaced by aspartic acid, threonine at position 182 replaced by alanine, leucine at position 187 replaced by alanine, histidine at position 196 deleted, tyrosine at position 197 deleted, serine at position 198 deleted, histidine at position 199 deleted, tyrosine at position 200 replaced by alanine, tyrosine at position 200 deleted, Ser201 replaced by alanine, serine at position 201 deletion, tryptophan at position 208 replaced by alanine, serine at position 217 replaced by asparagine, proline at position 219 replaced by arginine, tryptophan at position 223 replaced by tyrosine, phenylalanine at position 235 replaced by alanine, asparagine at position 239 replaced by alanine, aspartate at position 241 replaced by alanine, threonine at position 243 replaced by alanine, valine at position 244 replaced by isoleucine, threonine at position 245 replaced by alanine, tyrosine at position 246 replaced by phenylalanine, threonine at position 247 replaced by alanine or lysine, serine at position 249 replaced by alanine or arginine, valine at position 250 replaced by alanine, valine at position 251 replaced by alanine, serine at position 252 replaced by alanine, arginine at position 273 replaced by tryptophan, threonine at position 274 replaced by alanine, isoleucine at position 275 replaced by alanine, arginine at position 282 replaced by alanine, histidine at position 287 replaced by alanine or phenylalanine, serine at position 293 replaced by alanine, asparagine at position 295 replaced by alanine, glutamate at position 299 replaced by alanine, methionine at position 300 replaced by alanine, threonine at position 303 replaced by alanine, proline at position 305 replaced by alanine, isoleucine at position 306 replaced by alanine, and threonine at position 308 replaced by alanine, or wherein the protein comprises any combination of the referenced substitutions and/or deletions. eHTP's contain at least one amino acid substitution, one amino acid addition, or one amino acid deletion at an amino acid residue of SEQ ID NO:2, or the corresponding amino acid position of SEQ ID NO:8, SEQ ID NO: 182, or SEQ ID NO: 184, selected from the group consisting of (i) an amino acid residue having a relative solvent-accessibility of from at least about 15% to at least about 36%; and (ii) an amino acid residue located within a distance of about 3 consecutive residues from an amino acid having from at least about 15% to at least about 36% relative solvent-accessibility. An eHTP of the present invention contains at least one amino acid substitution, addition, or deletion at an amino acid residue selected from the group consisting of Thr93, Ser95. Ser97, Phe147, Gln149, Ser151, Asn180, Thr182, Val251, Gln253, and Ser255 of SEQ ID NO:2. Any of the aforementioned eHTP's can contain at least one additional amino acid substitution, addition, or deletion at an amino acid residue selected from the group consisting of Vail°, 11e14, Asn22, Asn23, Gly24, 11e25, Gln26, Gly27, Phe30, Gln38, 11e39, Asp40, Thr41, 11e43, Ser193, Thr194, Glu195, His196, Tyr197, Ser198, His199, Tyr200, Ser201, Gly202, Tyr203, Pro204, 11e205, Leu206, Thr207, Trp208, 11e209, Ser210, Tyr216, Ser217, Gly218, Pro219, Pro220, Met221, Ser222, Trp223, Tyr224, Phe225, Asn239, and Val244 of SEQ ID NO: 2 or the corresponding amino acid residue position of SEQ ID NO:8, SEQ ID NO:182, or SEQ ID NO:184. Any of the aforementioned eHTP's may contain one or more modifications selected from the group consisting of S95A, F147A, Q149E, V251A, P219R, and a deletion of any three consecutive amino acids from amino acid residues 196-201 as set forth in SEQ ID NO:2. Any of the eHTP's of the present invention can be further modified to exhibit increased solubility compared to the underlying naturally occurring *Bacillus thuringiensis* protein as set forth in any of SEQ ID NO:2, SEQ ID NO:8, SEQ ID NO:182, or SEQ ID NO:184 in which the eHTP contains at least one or more amino acid sequence modifications relative to the amino acid sequence as set forth in SEQ ID NO:2. The modification(s) contain at least a lysine substitution at one or more of the amino acid positions defined as 58, 59, 198, 199, 201, or 202 in SEQ ID NO:2; a glutamic acid residue substitution at one or more of the amino acid positions defined as 198, 248, or 301 in SEQ ID NO:2; or an arginine residue substitution at one or more of the amino acid positions defined as 246, 250, or 253 in SEQ ID NO:2. An eHTP having an amino acid sequence selected from the group consisting of SEQ ID NO:6, SEQ ID NO:8, SEQ ID NO:10, SEQ ID NO: 12, SEQ ID NO:14, SEQ ID NO: 16, SEQ ID NO:18, SEQ ID NO:20, SEQ ID NO:28, SEQ ID NO:30, SEQ ID NO:32, SEQ ID NO:34, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO:116, SEQ ID NO:117, SEQ ID NO:118, SEQ ID NO:119, SEQ ID NO:120, SEQ ID NO:121, SEQ ID NO:122, SEQ ID NO:13, SEQ ID NO:124, SEQ ID NO:125, SEQ ID NO:126, SEQ ID NO:127, SEQ ID NO:128, SEQ ID NO: 129, SEQ ID NO: 130, SEQ ID NO:131, SEQ ID NO:132, SEQ ID NO:133, SEQ ID NO:134, SEQ ID NO: 135, SEQ ID NO: 136, SEQ ID NO: 137, SEQ ID NO: 138, SEQ ID NO: 139, SEQ ID NO: 140, SEQ ID NO:141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO:152, SEQ ID NO: 153, SEQ ID NO: 154, SEQ ID NO: 155, SEQ ID NO:156, SEQ ID NO: 157, SEQ ID NO:158, SEQ ID NO: 159, SEQ ID NO:160, SEQ ID NO: 161, SEQ ID NO: 162, SEQ ID NO:163, SEQ ID NO: 164, SEQ ID NO: 165, SEQ ID NO: 166, SEQ ID NO:167, SEQ ID NO: 168, SEQ ID NO: 169, SEQ ID NO:170, SEQ ID NO:171, SEQ ID NO: 172, SEQ ID NO:173, SEQ ID NO: 174, SEQ ID NO: 175, SEQ ID NO: 176, SEQ ID NO:177, SEQ ID NO: 178, SEQ ID NO:179, SEQ ID NO:202, and SEQ ID NO:204, or an insect inhibitory fragment thereof, is a preferred embodiment of the present invention. The target Hemipteran pest species inhibited by the eHTP's of the present invention include at least *Lygus hesperus, Lygus lineolaris, Empoasca fabae* and *Amrasca devastans*, as well as other pests within the order Hemiptera that are phylogenetically related to each other or which use a piercing and sucking approach for feeding on plants.

Methods of controlling a Hemipteran pest by contacting the pest with a Hemipteran inhibitory amount of a eHTP of the present invention, as well as an insect inhibitory composition that contains at least a Hemipteran controlling amount (or Hemipteran inhibitory amount) of one or more of the eHTP's of the present invention, are also provided. In certain embodiments, an insect inhibitory composition comprising any of the eHTP's disclosed herein is provided. In certain embodiments of these methods, the Hemipteran pest is in a cotton field, a soybean field or an alfalfa field. Hemipteran toxic or Hemipteran controlling compositions can contain at least one or more eHTP along with a supplemental agent that is selected from the group consisting of an insect inhibitory protein, an insect inhibitory dsRNA molecule, and an insect inhibitory chemistry. Each of these agents can exhibit Hemipteran controlling properties, can exhibit properties for controlling pests unrelated to Hemipteran species such as Lepidopteran species or Coleopteran species, or may exhibit dual mode of action properties in which one or more Hemipteran species and one or more Lepidopteran or Coleopteran species are simultaneously controlled.

Recombinant polynucleotides that encode eHTP's of the present invention are provided. Microbes are also provided that contain the polynucleotides of the present invention, and such polynucleotides within such microbes are functionally positioned within expression cassettes designed to express the eHTP's of the present invention from operably linked functional genetic regulatory elements. Microbes are intended to include bacterial cells, as well as transgenic plant cells. Such transgenic plant cells can be regenerated into whole plants, or plant parts that also contain the recombinant polynucleotide. Methods of controlling a Hemipteran pest by exposing the pest to the microbe, whether bacterial cell or transgenic plant cell, plant or plant part, each of which expresses a Hemipteran inhibitory amount of an eHTP are also provided. The recombinant polynucleotide may contain a nucleotide sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO: 19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO: 186, SEQ ID NO:187, SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO:199, SEQ ID NO:200, SEQ ID NO:201, and SEQ ID NO:203, or other sequences that can be assembled to encode one or more of the proteins of the present invention. In certain embodiments, the recombinant polynucleotide can further comprise a nucleotide sequence encoding one or more insect inhibitory agents that are different from the eHTP encoded by the recombinant polynucleotide. The transgenic plant part is a seed, a boll, a leaf, a flower, pollen, a stem, a root, or any portion thereof. The transgenic plant part may be a non-regenerable portion of the seed, boll, leaf, flower, stem, or root. Also provided are methods of controlling a Hemipteran pest, comprising exposing the transgenic microbe, bacteria, plant cell, plant or plant part to the target pest, wherein the microbe, bacteria, plant cell, plant or plant part expresses a Hemipteran inhibitory amount of a eHTP encoded by the recombinant polynucleotide.

Processed plant products that contain a detectable amount of a recombinant polynucleotide encoding an eHTP or any distinguishing Hemipteran controlling portion thereof are also provided. Such processed products include, but are not limited to, plant biomass, oil, meal, animal feed, flour, flakes, bran, lint, hulls, and processed seed. The processed product may be non-regenerable.

Methods of making a transgenic plant by introducing the recombinant polynucleotide into a plant cell and selecting a transgenic plant that expresses an insect inhibitory amount of an eHTP encoded by a recombinant polynucleotide are also provided. The methods include introducing the recombinant polynucleotide encoding any of the eHTP's provided herein into a plant cell and selecting a transgenic plant that expresses an insect inhibitory amount of the eHTP encoded by the recombinant polynucleotide.

Other embodiments, features, and advantages of the invention will be apparent from the following detailed description, the examples, and the claims.

BRIEF DESCRIPTION OF THE DRAWINGS

Figure 3:
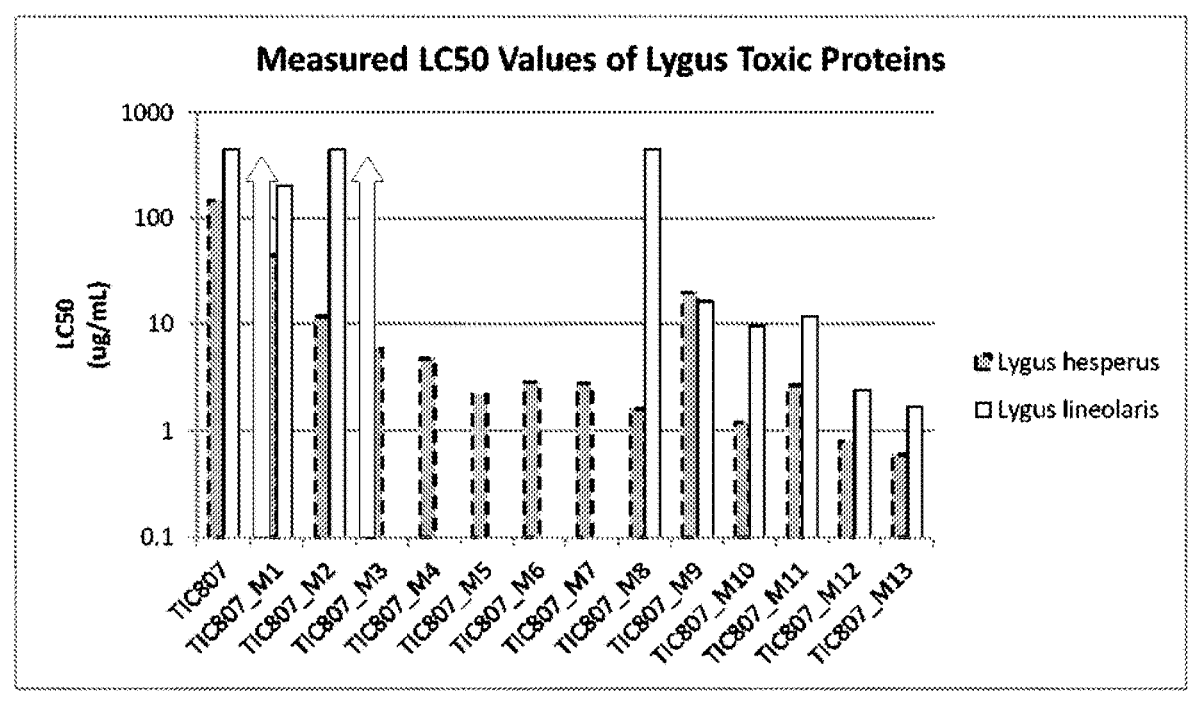

FIG. 3 is a chart view illustrating the population mortality of *Lygus* species for thirteen different eHTP's compared to each other and to the naturally occurring TIC807 protein.

DETAILED DESCRIPTION

Figure 1A:
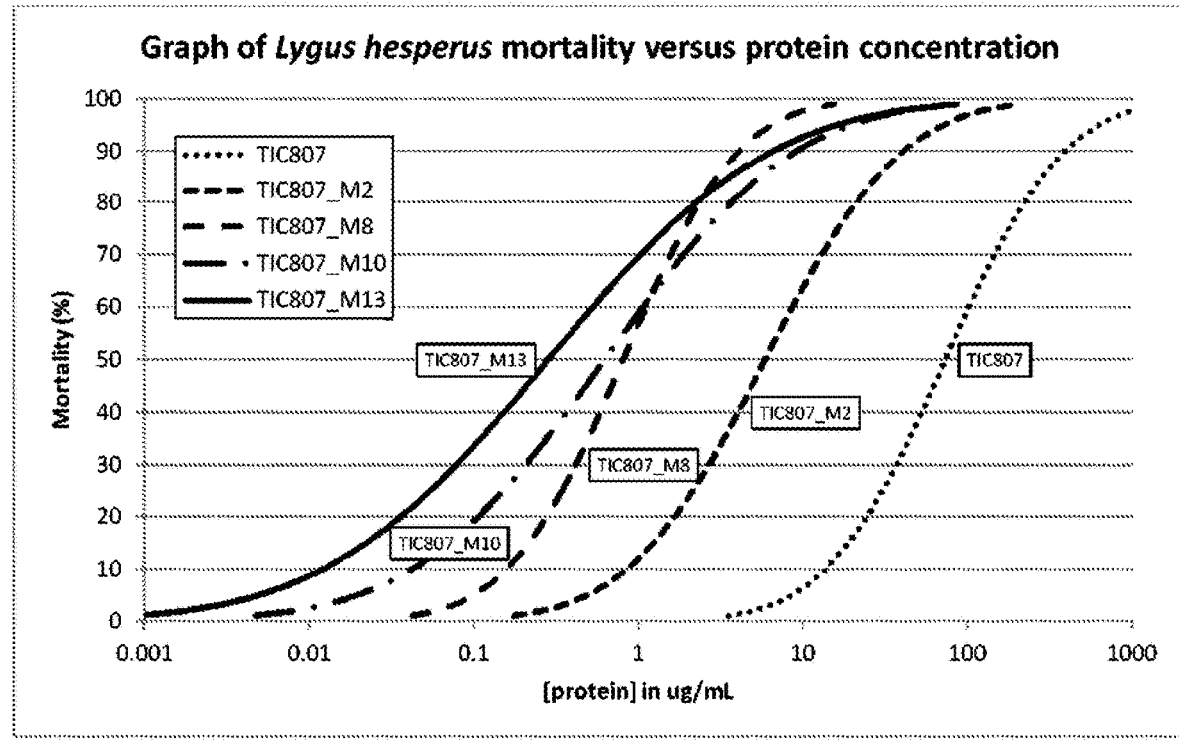
FIG. 1A illustrates the mortality of *Lygus hesperus* populations in response to various concentrations of four different eHTP's compared to a control sample containing the naturally occurring TIC807 protein.

This application describes eHTP's (engineered Hemipteran species toxic proteins). The eHTP's of the present invention are to be distinguished from proteins such as TIC807, TIC853, Cry51Aa1 and AXMI-171, which are known in the art and are not to be considered to be within the scope or definition of the term eHTP, as the prior art proteins are not engineered to exhibit improved toxic properties directed to one or more Hemipteran pest species and do not exhibit broad host range levels of inhibitory activity. eHTP's surprisingly and unexpectedly exhibit high levels of toxic activity against Hemipteran and related pest species. An additional feature of these eHTP's that is even more unexpected and surprising is the finding that these proteins exhibit broader host range toxic properties compared to progenitor proteins which provide the foundational basis for the eHTP's of the present invention. The foundational or baseline scaffold toxin proteins, such as TIC807 (SEQ ID NO:2), Cry51Aa1 (SEQ ID NO:8), TIC853 (SEQ ID NO:184), and AXMI-171 (SEQ ID NO:206) do not exhibit the breadth and scope of biological anti-Hemipteran activity or host range of the eHTP proteins of the present invention.

More than 2000 different amino acid sequence variants of Hemipteran toxic proteins derived from *Bacillus thuringiensis* species were tested to identify the specific amino acid insertions, substitutions, or deletions described herein which confer expanded Hemipteran species host range inhibitory spectrum and also provide dramatically increased Hemipteran species inhibitory activity when compared to the spectrum and activity of the baseline scaffold protein. TIC807, TIC853, and Cry51Aa1. Amino acid residues are identified in the baseline scaffold proteins that (a) can be modified to yield enhanced Hemipteran inhibitory spectrum and/or improved *Lygus* inhibitory activity relative to one or more of the scaffold proteins, (b) accumulate in surface patches of a folded insect inhibitory protein exhibiting the fold structure of one or more of the scaffold proteins, and/or (c) occur in specific positions of one or more fo the scaffold protein amino acid sequence that are result effective in decreasing the resulting eHTP proteins' mean effective dose for controlling a Hemipteran species and broadening the range of Hemipteran species that are affected by the eHTP protein.

Figure 1B:
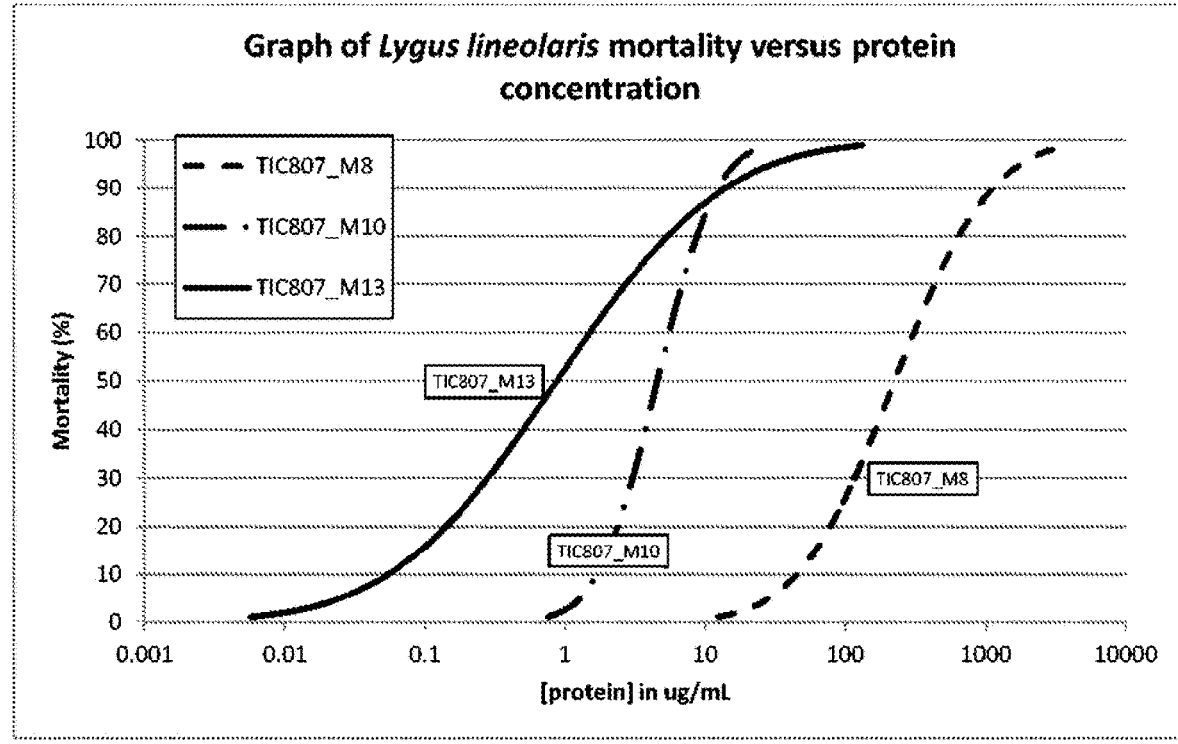
FIG. 1B illustrates the mortality of *Lygus lineolaris* populations in response to various protein concentrations of three different eHTP's compared to a control sample containing the naturally occurring TIC807 protein.
Figure 2:
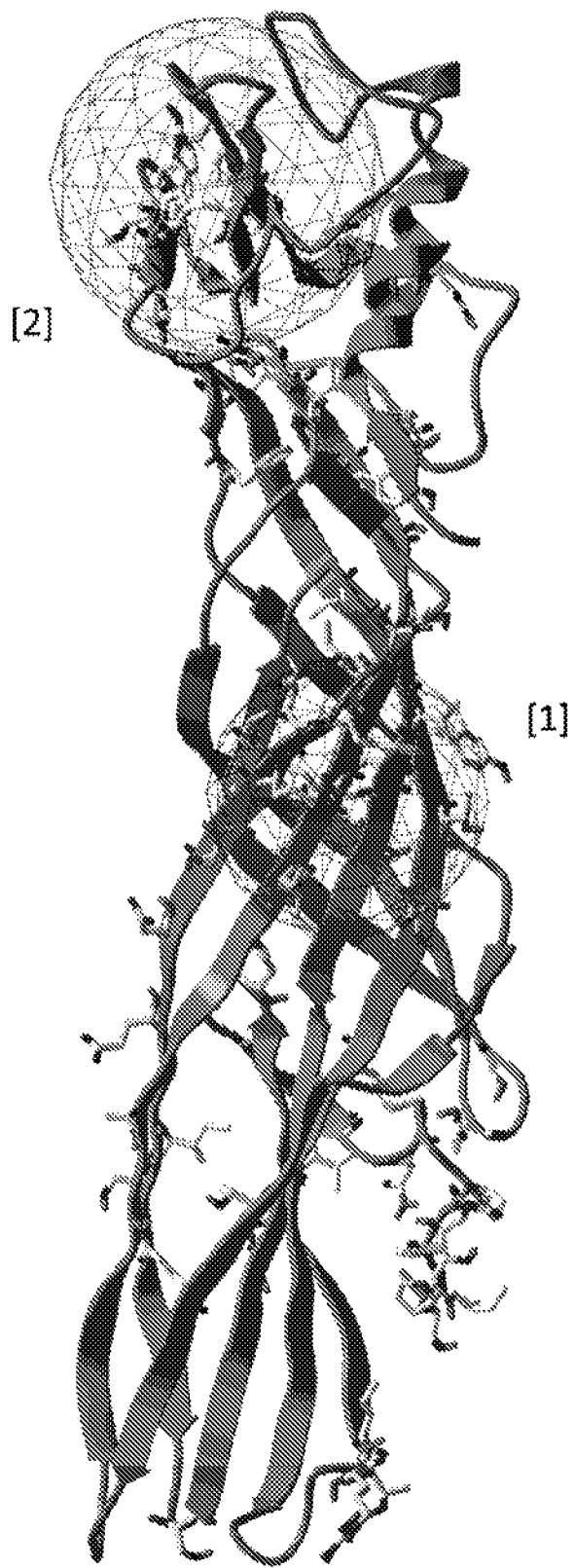
FIG. 2 illustrates a ribbon diagram of the atomic structure of a Hemipteran toxic protein of the present invention showing the relative positions of the result effective changes increasing toxic effects and/or broadening host range specificity compared to the relative position of the same amino acid position within a TIC807 or related protein. Two surface patches are illustrated by spheres encircling particular residue positions within the atomic structure in the ribbon diagram: [1] one sphere has an atomic radius of from about 9.2 to about 12.2 Angstroms from the beta carbon atom of S95 (relative to the S95 position as set forth in SEQ ID NO:2); [2] another sphere has an atomic radius of from about 9.2 to about 12.2 Angstroms from the beta carbon atom of P219 (relative to the P219 position as set forth in SEQ ID NO:2). Changes to the amino acids within the ribbon structure that fall within these spheres are result effective in causing increased toxic properties and broader host range toxic effects compared to a protein having a naturally occurring amino acid at that particular position.

The Hemipteran pest species are intended to mean insects that feed upon plants and plant tissues by slashing or piercing the outer surface of the target plant, and then consume macerated plant exudates pooling in the slash or pierce location by sucking or wicking the pooled exudates. Such insects include adults and nymphs, including but not limited to the following listing of plant bugs: the Family Miridae, cicadas from the Family Cicadidae, leafhoppers (e.g., *Empoasca* spp., *Amrasca* spp.) from the Family Cicadellidae, planthoppers from the families Fulgoroidea and Delphacidae, trechoppers from the Family Membracidae, psyllids from the Family Psyllidae, whiteflies from the Family Aleyrodidae, aphids from the Family Aphididae, *phylloxera* from the Family Phylloxeridae, mealybugs from the Family Pseudococcidae, scales from the families Coccidae, Diaspididae and Margarodidae, lace bugs from the Family Tingidae, stink bugs from the Family Pentatomidae, cinch bugs (e. g., *Blissus* spp.) and other seed bugs from the Family Lygaeidae, spittlebugs from the Family Cercopidae squash bugs from the Family Corcidae, and red bugs and cotton stainers from the Family Pyrrhocoridae. Other pests from the order Hemiptera include *Acrosternum hilare* (green stink bug), *Anasa tristis* (squash bug), *Blissus leucopterus leucopterus* (chinch bug), *Corythuca gossypii* (cotton lace bug), *Cyrtopeltis modesta* (tomato bug), *Dysdercus suturellus* (cotton stainer), *Euschistus servus* (brown stink bug), *Euschistus variolarius* (one-spotted stink bug), *Graptostethus* spp. (complex of seed bugs), *Leptoglossus corculus* (leaf-footed pine seed bug), *Lygus lineolaris* (tarnished plant bug), *Lygus hesperus* (Western tarnish plant bug), *Nezara viridula* (southern green stink bug), *Oebalus pugnax* (rice stink bug), *Oncopeltus fasciatus* (large milkweed bug), and *Pseudatomoscelis seriatus* (cotton fleahopper). More specifically, the Family Cicadellidae includes, but is not limited to the tribe Empoascini, e.g. *Amrasca biguttula, Amrasca devastans, Austroasca viridigrisea, Asymmetrasca decedens, Empoasca decipiens, Empoasca distinguenda, Empoasca dolichi, Empoasca fabae, Empoasca kerri, Empoasca kraemeri, Empoasca onukii, Empoasca sakaii, Empoasca smithi, Empoasca vitis, Jaciobiasca lybica, Sonasasca Solana*, tribe Erythroncurini, e.g. *Empoascanara nagpurensis, Thaiaassamensis, Zygnidia quyumi*, tribe Nirvaniae, e.g. *Sophonia rufofascia*, Family Delphacidae, e.g. *Nilapoanvata lugens, Sogatella furcifera, Unkanodes sapporonus*, and Family Lophopidae. e.g. *Zophiuma lobulata*.

eHTP's of the present invention contain one or more amino acid sequence modifications compared to one or more of the scaffold proteins, including substitutions and deletions, of amino acid residues at seventy-two (72) different amino acid positions. Such modifications provide eHTP's with increased toxicity and/or an enhanced inhibitory spectrum against Hemipteran insects when compared to one or more of the scaffold proteins which include but are not limited to TIC807 (SEQ ID NO:2), or related protein such as TIC807 M2 (SEQ ID NO:8). Cry51Aa1 (SEQ ID NO:182), and TIC853 (SEQ ID NO: 184). eHTP's include, but are not limited to, modifications of at least one amino acid substitution or one amino acid deletion at any of these seventy-two positions, described as "X" in the amino acid sequence set forth as SEQ ID NO:180 but do not include the amino acid sequences of SEQ ID NO:2, SEQ ID NO:8, SEQ ID NO:182, or SEQ ID NO:184. eHTP's of the present invention also exhibit enhanced Hemipteran inhibitory spectrum and/or improved Hemipteran inhibitory activity when compared to the spectrum and activity of the baseline or scaffold proteins.

eHTP's include at least one amino acid modification of the relative positions of TIC807 (SEQ ID NO:2) as set forth above in paragraph [0009]. eHTP's can also include at least two, three, four, or more of these aforementioned amino acid substitutions and/or deletions and can also include at least two, three, four, or more of these amino acid substitutions and/or deletions as well as a deletion of any three contiguous amino acids within residues 196-201 of SEQ ID NO:2. Accordingly, eHTP's include proteins set forth as SEQ ID NO:6, SEQ ID NO:8, SEQ ID NO: 10, SEQ ID NO: 12, SEQ ID NO: 14, SEQ ID NO:16, SEQ ID NO:18, SEQ ID NO:20, SEQ ID NO:28, SEQ ID NO:30, SEQ ID NO:32, SEQ ID NO:34, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO: 69, SEQ ID NO: 70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO: 88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO: 100, SEQ ID NO:101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO:112, SEQ ID NO: 113, SEQ ID NO:114, SEQ ID NO:115, SEQ ID NO:116, SEQ ID NO: 117, SEQ ID NO:118, SEQ ID NO: 119, SEQ ID NO: 120, SEQ ID NO: 121, SEQ ID NO:122, SEQ ID NO:123, SEQ ID NO: 124, SEQ ID NO:125, SEQ ID NO:126, SEQ ID NO:127, SEQ ID NO:128, SEQ ID NO:129, SEQ ID NO: 130, SEQ ID NO:131, SEQ ID NO: 132, SEQ ID NO: 133, SEQ ID NO: 134, SEQ ID NO: 135, SEQ ID NO:136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO:148, SEQ ID NO: 149, SEQ ID NO: 150, SEQ ID NO: 151, SEQ ID NO: 152, SEQ ID NO: 153, SEQ ID NO: 154, SEQ ID NO: 155, SEQ ID NO: 156, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO:166, SEQ ID NO: 167, SEQ ID NO: 168, SEQ ID NO: 169, SEQ ID NO: 170, SEQ ID NO:171, SEQ ID NO: 172, SEQ ID NO: 173, SEQ ID NO: 174, SEQ ID NO: 175, SEQ ID NO: 176, SEQ ID NO: 177, SEQ ID NO:178, SEQ ID NO: 179, SEQ ID NO:202, and SEQ ID NO:204, and insect inhibitory fragments thereof.

eHTP's of the present invention exhibit any amino acid sequence different from any one or more of the scaffold proteins, including SEQ ID NO:2 (TIC807), in at least one amino acid position where the different amino acid residue either (i) has a relative amino acid solvent-accessibility of at least from about 15% to at least about 36% compared to the same residue positions in any one or more of the scaffold proteins; and/or (ii) is located within a distance of about 3 consecutive amino acid residues from an amino acid having at least from about 15% to at least about 36% relative solvent-accessibility compared to the corresponding amino acid residue positions in the primary amino acid sequence of one or more of the scaffold proteins, and exhibits broadened Hemipteran inhibitory spectrum and/or increased Hemipteran inhibitory activity when compared to the activity correlated with one or more of the scaffold proteins. The words "increased spectrum" are intended to mean, with reference to two different proteins exhibiting toxic effects to a particular single pest, the protein exhibiting increased spectrum exhibits toxic effects to that particular single pest as well as to one or more other pests within the same phylogenetic order or to one or more other pests in one or more different phylogenetic orders other than the order to which the particular single pest belongs. The words "increased Hemipteran inhibitory activity" are intended to mean that a particular protein exhibiting such increased activity requires, under standardized conditions, a lower amount of that protein to achieve a particular affect, such as mortality, stunting, morbidity, cessation of feeding, or another measureable phenotypic effect upon a particular single pest, than a control protein.

eHTP's exhibit an amino acid sequence that differs from one or more of the scaffold proteins, including particularly TIC807, in at least one amino acid residue located within at least one of the two different surface patches of a folded insect inhibitory protein (see FIG. 2 and Table 3 data). One surface patch is defined as including the amino acid residues encompassed within a sphere having an atomic radius of from about 9.2 to about 12.2 Angstroms (FIG. 2, sphere [1]) relative to the beta-carbon (Cb) atom of Ser95 as set forth in SEQ ID NO:2 when that protein is folded into a three dimensional structure under physiological conditions; which includes residues Thr93, Ser95, Ser97, Phe147, Gln149, Ser151, Asn180, Thr182, Val251, Gln253, and Ser255. As used herein, the phrase "Cb atom" refers to the beta-carbon atom in the amino acid residue side chain. The Cb atom is thus the first carbon in the protein side chain that is present in all amino acid residues with the exception of Glycyl residues. With reference to FIG. 1, eHTP's can include, but are not limited to, one or more conservative or non-conservative substitutions of surface patch [1] amino acid residues T93, S95, S97, F147, Q149, S151, N180, T182, V251, Q253, and 5255 or the equivalent amino acids within one or more of the scaffold proteins, particularly SEQ ID NO:2 (TIC807). eHTP's can include, but are not limited to, one or more substitutions of surface patch [1] amino acid residues such as: T93A; S95A, S95V, S95L, or S95I; F147T, F147C, F147D, F147G, F147E, F147Y, F147M, F147N, F147Q, F147H, F147R, F147W, F147P, F147A, F147V, F147L, or F147I; Q149A, Q149C, Q149F, Q149E or Q149D; S151A; N180D; T182A; V251E or V251A, and/or Q253R. The other or second surface patch that has been identified as amino acid residues that are receptive to modifications which are result effective in conferring improved Hemipteran inhibitory bioactivity in the form of eHTP's of the present invention is defined as including the amino acid residues encompassed within a sphere having an atomic radius of from about 9.2 to about 12.2 Angstroms (FIG. 2, sphere [2]) relative to the beta-carbon atom of Pro219 or the equivalent amino acid position in one or more of the scaffold proteins, particularly as set forth in SEQ ID NO:2, when any one of the applicable scaffold proteins is folded into a three dimensional structure under physiological conditions, which includes residues Vail°, Ile14, Asn22, Asn23, Gly24, 11e25, Gln26, Gly27, Phe30, Gln38, 11e39, Asp40, Thr41, 11e43, Ser193, Thr194, Glu195, His196, Tyr197, Ser198, His199, Tyr200, Ser201, Gly202, Tyr203, Pro204, 11e205, Leu206, Thr207, Trp208, 11e209, Ser210, Tyr216, Ser217, Gly218, Pro219, Pro220, Met221, Ser222, Trp223, Tyr224, Phe225, Asn239, and Va1244. Such eHTP's can include, but are not limited to, one or more conservative or non-conservative amino acid residues substitutions and/or one or more amino acid deletions within surface patch [2] including Vail°, Ile14, Asn22, Asn23, Gly24, Ile25, Gln26, Gly27, Phe30, Gln38, Ile39, Asp40, Thr41. Ile43, Ser193, Thr194, Glu195, His196, Tyr197, Ser198, His199, Tyr200, Ser201, Gly202. Tyr203, Pro204. Ile205, Leu206, Thr207, Trp208, Ile209, Ser210, Tyr216, Ser217, Gly218, Pro219, Pro220, Met221, Ser222. Trp223, Tyr224, Phe225, Asn239, and Va1244 of SEQ ID NO:2 (TIC807), eHTP's can include, but are not limited to, one or more substitutions and/or deletions within the amino acid residues located within surface patch [2] such as: a deletion of any three contiguous amino acid residues in the sequence His196, Tyr197, Ser198, His199, Tyr200, Ser201; Ser217Asn, Ser217Gln, Ser217Arg; and/or Pro219Arg, Pro219Asn, Pro219Gln, eHTP's can include, but are not limited to, one or more amino acid residue substitutions and/or deletions within surface patch [2] such as: a deletion of any three contiguous HisTyrSer residues in the sequence His196, Tyr197, Ser198, His199, Tyr200, Ser201; Ser217Asn, Ser217Gln, Ser217Arg; and/or Pro219Arg, Pro219Asn, Pro219Gln. An eHTP can have at least one amino acid modification in each of the two aforementioned surface patches of the folded insect inhibitory protein. eHTP can have one, or a combination of more than one modification at residues T93, S95, F147, Q149, 5151, N180, T182. H196, Y197, 5198, H199, Y200, 5201, W208, 5217, P219, W223, N239, V244, or V251 relative to SEQ ID NO:2 (TIC807). Conservative amino acid changes can be made by substituting an acidic, basic, neutral polar, or neutral non-polar-type amino acid with another amino acid of the same type. Non-conservative amino acid changes can be made by substituting an acidic, basic, neutral polar, or neutral non-polar amino acid-type with an amino acid of a different type. Furthermore, of the eHTP proteins listed in Table 4B, all 267 are amino acid sequence variants that exhibit increased toxicity to *Lygus* spp. when compared to one or more of the scaffold proteins, including scaffold protein TIC807. Only ten of these amino acid sequence variants exhibit modified amino acid residues compared to one or more of the scaffold proteins that are positioned outside of the two referenced surface patches.

The prior art teaches solubility problems associated with the scaffold proteins. eHTP's exhibit improved solubility compared to the scaffold proteins, and generally exhibit increased solubility at a pH of less than 9.0, in contrast to the observed solubility profile of one or more of the scaffold proteins. This increased solubility at more physiological pH is evident when the eHTP is expressed in *E. coli*, in a plant cell, in a plant cell cytoplasm, a plant cell apoplast, or in or targeted for import into a plastid of a plant cell. Amino acid modifications that improve solubility relative to one or more of the scaffold proteins, including SEQ ID NO:2 (TIC807) include but are not limited to, substitution of a lysine amino acid residue at one or more of the following amino acid positions in TIC807 or the applicable residue in any of the other scaffold proteins: 58, 59, 198, 199, 201, or 202; or, substitution of a glutamic acid amino acid residue at one or more of amino acid positions 198, 248 or 301; or, substitution of a arginine amino acid residue at one or more of amino acid positions 246, 250 or 253.

Insect inhibitory compositions comprising the above described eHTP's are also provided. Such compositions may further comprise at least one additional insect inhibitory agent different from the eHTP included in the composition. The insect inhibitory agent is selected from any number of insect inhibitory agents including an insect inhibitory protein, an insect inhibitory dsRNA molecule, and one or more chemical agents useful in controlling insect pests. Examples of additional inhibitory agents includes, but are not limited to, a TIC1415 protein, a dsRNA directed towards Hemipteran orthologs of *Nilaparvata lugens* V-ATPase-E, 21E01, a dsRNA directed towards Hemipteran orthologs of actin ortholog, ADP/ATP translocase, a-tubulin, ribosomal protein L9 (R PL9) or V-ATPase A subunit, AXMI-171 (US20100298207A1), Cry3A, Cry4Aa, Cry11Aa, and Cyt-lAa, DIG11, DIGS, Cry7, cCry3.1Ab, mCry3A, Cry8, Cry34/Cry35, Cry3, DIG2, Cry1, Cry1A, 105, Cry2, Cry1F, VIP3, 5307, and Cry9. Chemical agents useful in controlling Hemipteran species include but are not limited to pyrethrins and synthetic pyrethroids; oxadizine derivatives; chloronicotinyls; nitroguanidine derivatives; triazoles; organophosphates; pyrrols; pyrazoles; phenyl pyrazoles; diacylhydrazines; biological/fermentation products; and carbamates. Known pesticides within these categories are listed in The Pesticide Manual, 11th Ed., C. D. S. Tomlin, Ed., British Crop Protection Council, Farnham, Surry, UK (1997).

Pyrethroids that are useful in the present composition include pyrethrins and synthetic pyrethroids. The pyrethrins that are preferred for use in the present method include, without limitation, 2-allyl-4-hydroxy-3-methyl-2-cyclopenten-1-one ester of 2,2-dimethyl-3-(2methyl propenyl)-cyclopropane carboxylic acid, and/or (2-methyl-1-propeny 1)-2-methoxy-4-oxo-3-(2 propeny 1)-2-cyclopenten-1-yl ester and mixtures of cis and trans isomers thereof (Chemical Abstracts Service Registry Number ("CAS RN") 8003-34-7).

Synthetic pyrethroids that are preferred for use in the present invention include (s)-cyano(3-phenoxyphenyl)

methyl 4-chloro alpha (1-methylethyl)benzeneacetate (fenvalerate, CAS RN 51630-58-1), (S)-cyano (3-phenoxyphenyl) methyl (S)-4-chloro-alpha-(1-methylethyl) benzeneacetate (esfenvalerate, CAS RN 66230-04-4), (3-phenoxypheny 1)-methyl(+)cis-trans-3-(2,2-dichoroetheny 1)-2,2-dimethylcyclopropanecarboxylate (permethrin, CAS RN 52645-53-1), (±) alpha-cyano-(3-phenoxyphenyl) methyl(+)-cis.trans-3-(2,2-dichloroctheny 1)-2,2-dimethyl-cyclopropane carboxylate (cypermethrin, CAS RN 52315-07-8), (beta-cypermethrin, CAS RN 65731-84-2), (theta cypermethrin, CAS RN 71697-59-1), S-cyano (3-phenoxyphenyl) methyl (±) cis/trans 3-(2,2-dichloroethenyl) 2,2 dimethylcyclopropane carboxylate (zeta-cypermethrin, CAS RN 52315-07-8), (s)-alpha-cyano-3-phenoxybenzyl (IR,3R)-3-(2,2-dibromovinyl)-2,2-dimethyl cyclopropanecarboxylate (deltamethrin, CAS RN 52918-63-5), alpha-cyano-3-phenoxybenzyl 2,2,3,3,-tetramethyl cyclopropoanecarboxylate (fenpropathrin, CAS RN 64257-84-7), (RS)-alpha-cyano-3-phenoxybenzyl(R)-2-[2-chloro-4-(trifluoromethyl)anilino]-3-methylbutanoate (tau-fluvalinate, CAS RN 102851-06-9), (2,3,5,6-tetrafluoro-4-methylphenyl)-methyl-(1 alpha, 3 alpha)-(Z)-(±)-3-(2-chloro-3,3,3-trifluoro-1-propenyl)-2,2-dimethylcyclopropane carboxylate (tefluthrin, CAS RN 79538-32-2), (±)-cyano (3-phenoxyphenyl) methyl (±)-4-(difluoromethoxy)-alpha-(1-methyl ethyl) benzeneacetate (flucythrinate, CAS RN 70124-77-5), cyano(4-fluoro-3-phenoxyphenyl)methyl3-[2-chloro-2-(4-chlorophenyl)ethenyl]-2,2-dimethylcyclopropanecarboxylate (flumethrin, CAS RN 69770-45-2), cyano(4-fluoro-3-phenoxyphenyl)methyl 3-(2, 2-dichloroethenyl)-2,2-dimethyl-cyclopropanedarboxylate (cyfluthrin, CAS RN 68359-37-5), (beta cyfluthrin, CAS RN 68359-37-5), (transfluthrin, CAS RN 118712-89-3), (S)-alpha-cyano-3-phenoxybenzyl(Z)—(IR-cis)-2,2-dimethyl-3-[242,2,2-trifluoro-trifluoromethyl-ethoxycarbonyl)vinyl] cyclopropane carboxylate (acrinathrin, CAS RN 101007-06-1), (IR cis) S and (IS cis) R enantiomer isomer pair of alpha-cyano-3-phenoxybenzy 1-3-(2,2dichlorovinyl)-2,2-dimethylcyclopropane carboxylate (alpha-cypermethrin, CAS RN 67375-30-8), [IR,3 S)3 (1'RS)(1',2',2',2'-tetra-bromo ethyl)]-2,2-dimethyl cyclopropanecarboxylic acid (s)-alpha-cyano-3-phenoxybenzyl ester (tralomethrin, CAS RN 66841-25-6), cyano-(3-phenoxyphenyl) methyl 2,2-dichloro-1-(4-ethoxyphenyl)cyclopropane carboxylate (cycloprothrin, CAS RN 63935-38-6), [1a, 3a(Z)]-(±)-cyano-(3-phenoxyphenyl)methyl 3-(2-chloro-3,3,3-trifluoro-1-propeny 1)-2,2-cimethylcyclopropanecarboxylate (cyhalothrin, CAS RN 68085-85-8), [1 alpha (s), 3 alpha (z)]-cyano(3-phenoxyphenyl) methyl-3-(2-chloro-3,3,3-trifluoro-1-propenyl)-2,2-dimethylcyclopropane carboxylate (lambda cyhalothrin, CAS RN 91465-08-6), (2-methyl [1,1'-biphenyl]-3-yl) methyl 3-(2-chloro-3,3,3-trifluoro-1-propenyl)-2,2-dimethyl-cyclopropanecarboxylate (bifenthrin, CAS RN 82657-04-3), 5-1-benzyl-3-furylmethyl-d-cis(1R, 3S,E)2,2-dimethyl-3-(2-oxo,-2,2,4,5tetrahydro thiophenylidenemethyl)cyclopropane carboxylate (kadethrin, RU15525, CAS RN 58769-20-3), [5-(phenyl methyl)-3-furanyl]-3-furanyl 2,2-dimethy 1-3-(2-methyl-1-propenyl) cyclopropane carboxylate (resmethrin, CAS RN 10453-86-8), (1R-trans)-[5-(phenylmethyl)-3-furanyl]methyl 2,2-dimethyl-3-(2-methyl-1-propenyl)cyclopropanecarboxylate (bioresmethrin, CAS RN 28434-01-7), 3,4,5,6-tetra hydrophthalimidomethyl-(IRS)-cis-trans-chrysanthemate (tetramethrin, CAS RN 7696-12-0), 3-phenoxybenzyl-d,l-cis,trans 2,2-dimethyl-3-(2-methylpropenyl) cyclopropane carboxylate (phenothrin, CAS RN 26002-80-2); (empenthrin, CAS RN 54406-48-3); (cyphenothrin; CAS RN 39515-40-7), (prallethrin, CAS RN 23031-36-9), (imiprothrin, CAS RN 72963-72-5), (RS)-3-ally 1-2-methy 1-4-oxcyclopent-2-enyl-(1A,3R; 1R,3S)-2,2-dimethyl-3-(2-methylprop-1-enyl) cyclopropane carboxylate (allethrin, CAS RN 584-79-2), (bioallethrin, CAS RN 584-79-2), and (ZXI8901, CAS RN 160791-64-0). It is believed that mixtures of one or more of the aforementioned synthetic pyrethroids can also be used in the present invention. Particularly preferred synthetic pyrethroids are tefluthrin, lambda cyhalothrin, bifenthrin, permethrin and cyfluthrin. Even more preferred synthetic pyrethroids are tefluthrin and lambda cyhalothrin, and yet more preferred is tefluthrin.

Insecticides that are oxadiazine derivatives are useful in the subject invention. The oxadizine derivatives that are preferred for use in the present invention are those that are identified in U.S. Pat. No. 5,852,012. More preferred oxadiazine derivatives are 542-chloropyrid-5-ylmethyl)-3-methyl-4-nitro iminop erhydro-1,3,5-o xadiazine, 5-(2-chlorothiazol-5-ylmethyl)-3-methyl-4-nitro iminop erhydro-1,3, 5-oxadiazine, 3-methyl-4-nitro imino-5-(1-o xido-3-pyridino methyl) p erhydro-1,3,5-o xadiazine, 5-(2-chloro-1-o xido-5-pyridinio methyl)-3-methyl-4-nitro iminop erhydro-1,3,5-o xidiazine; and 3-methyl-5-(2-methylpyrid-5-ylmethyl)-4-nitroiminoperhydro-1,3,5-oxadiazine. Even more preferred is thiamethoxam (CAS RN 15371923-4)

Chloronicotinyl insecticides are also useful in the subject invention. Chloronicotinyls that are preferred for use in the subject composition are described in U.S. Pat. No. 5,952, 358, and include acetamiprid ((E)-N-[(6-chloro-3-pyridinyl) methyl]-N'-cyano-N-methyleneimidamide, CAS RN 135410-20-7), imidacloprid (1-[(6-chloro-3-pyridinyl) methol]-N-nitro-2-imidazolidinimime, CAS RN 138261-41-3), and nitenpyram (N-[(6-chloro-3-pyridinyl)methy 1]-N-ethyl-N'-methyl-2-nitro-1,1-ethenediamine, CAS RN 120738-89-8).

Nitroguanidine insecticides are useful in the present invention. Such nitroguanidines can include those described in U.S. Pat. Nos. 5,633,375, 5,034,404 and 5,245,040.

Pyrrols, pyrazoles and phenyl pyrazoles that are useful in the present invention include those that are described in U.S. Pat. No. 5,952,358. Preferred pyrazoles include chlorfenapyr (4-bro mo-2-(4-chlorophenyl 1)-1-etho xymethyl-5-trifluoromethylpyrro le-3-carbonitrile, CAS RN 122453-73-0), fenpyroximate ((E)-1,1-dimethylethyl-4[[[[(1,3-dimethyl-5-phenoxy-1H-pyrazole-4-yl)methylene]amino] oxy]methyl]benzoate, CAS RN 111812-58-9), and tebufenpyrad (4-chloro-N[[4-1,1-dimethylethyl)p henyl] methyl]-3-ethyl-1-methyl-1H-pyrazole-5-carboxamide, CAS RN 119168-77-3). A preferred phenyl pyrazole is fipronil (5-amino-[2,6-dichloro-4-(trifluoromethyl)p henyl]-4-[(1R, S)-(trifluoromethyl)sulfInyl]-1H-pyrazo le-3-carbonitrile, CAS RN 120068-37-3).

Diacylhydrazines that are useful in the present invention include halofenozide (4-chlorobenzoate-2-benzoyl-2-(1,1-dimethylethyl)-hydrazide, CAS RN 112226-61-6), methoxyfenozide (RH-2485; N-tert-butyl-N'-(3-methoxy-o-toluoyl)-3,5-xylohydrazide, CAS RN 161050-58-4), and tebufenozide (3,5-dimethylbenzoic acid 1-(1,1-dimethylethyl)-2, (4-ethylbenzoyl)hydrazide, CAS RN 112410-23-8).

Triazoles, such as amitrole (CAS RN 61-82-5) and triazamate are useful in the method of the present invention. A preferred triazole is triazamate (ethyl [[1-[(dimethylamino) carbonyl]-3-(1,1-dimethylethyl)-1H-1,2,4-triazol-5-yl]thio] acetate, CAS RN 112143-82-5).

Biological/fermentation products, such as avermectin (abamectin, CAS RN 71751-41-2) and spinosad (XDE-105, CAS RN 131929-60-7) are useful in the present invention.

Organophosphate insecticides are also useful as one of the components of the present invention. Preferred organophophate insecticides include acephate (CAS RN 30560-19-1), chlorpyrifos (CAS RN 2921-88-2), chlorpyrifos-methyl (CAS RN 5598-13-0), diazinon (CAS RN 333-41-5), fenamiphos (CAS RN 22224-92-6), and malathion (CAS RN 121-75-5).

In addition, carbamate insecticides are useful in the subject invention. Preferred carbamate insecticides are aldicarb (CAS RN 116-06-3), carbaryl (CAS RN 63-25-2), carbofuran (CAS RN 1563-66-2), oxamyl (CAS RN 23135-22-0) and thiodicarb (CAS RN 59669-26-0).

When a chemical insecticide is described herein, it is to be understood that the description is intended to include salt forms of the insecticide as well as any isomeric and/or tautomeric form of the insecticide that exhibits the same insecticidal activity as the form of the insecticide that is described.

The chemical insecticides that are useful in the present invention can be of any grade or purity that pass in the trade as such insecticide. Other materials that accompany the insecticides in commercial preparations as impurities can be tolerated in the subject invention and compositions, as long as such other materials do not destabilize the composition or significantly reduce or destroy the activity of any of the insecticide components or the transgenic event against the target pest(s). One of ordinary skill in the art of the production of insecticides can readily identify those impurities that can be tolerated and those that cannot.

eHTP's are related by amino acid modifications such that the modified proteins exhibit enhanced Hemipteran inhibitory spectrum and/or improved Hemipteran inhibitory activity against *Lygus* spp., *Empoasca* spp. and/or *Amrasca* spp. compared to the parent protein, TIC807. The phrases "more active", "improved activity", "enhanced specificity", "increased toxic potency", "increased toxicity", "improved Hemipteran inhibitory activity, "enhanced Hemipteran inhibitory activity", "improved *Lygus, Empoasca* and/or *Amrasca* inhibitory activity", "greater *Lygus, Empoasca* and/or *Amrasca* inhibitory activity", "greater Hemipteran inhibitory activity" and "enhanced *Lygus, Empoasca* and/or *Amrasca* inhibitory spectrum" and "enhanced Hemipteran inhibitory spectrum" refer to a comparison of the activity of an eHTP and of the activity of a TIC807 (SEQ ID NO:2), TIC807 M2 (SEQ ID NO:8), Cry51Aa1 (SEQ ID NO:182), TIC853 (SEQ ID NO:184), and/or a AXMI-171 (SEQ ID NO:206) protein against a Hemipteran insect, wherein activity attributed by the eHTP of the present invention is greater than the activity attributed to the TIC807 protein (SEQ ID NO:2), TIC807 M2 (SEQ ID NO:8), Cry51Aa1 (SEQ ID NO:182), TIC853 (SEQ ID NO:184, and/or a AXMI-171 (SEQ ID NO:206) protein. eHTP's provided herein exhibit enhanced Hemipteran inhibitory spectrum and/or improved or greater Hemipteran inhibitory activity when compared to the *Bacillus thuringiensis* proteins of SEQ ID NO:2, SEQ ID NO:8, SEQ ID NO: 182, and SEQ ID NO:184, where the Hemipteran pest species include *Lygus hesperus*, *Lygus lineolaris*, *Empoasca fabae*, and *Amrasca devastans*. *Amrasca devastans* is also called *Amrasca biguttula biguttula*. eHTP's exhibiting enhanced insect inhibitory spectrum and/or improved insect inhibitory activity compared to TIC807 can be identified by many different methods. In general, exemplary and non-limiting methods for identifying eHTP proteins can comprise:

(1) administering identical amounts of a test eHTP and of control TIC807 (SEQ ID NO:2), TIC807 M2 (SEQ ID NO:8), Cry51Aa1 (SEQ ID NO:182), TIC853 (SEQ ID NO:184), and/or an AXMI-171 (SEQ ID NO:206) protein to a test insect under controlled assay conditions; and, measuring and comparing the potency of the test and control proteins; and/or, (2) determining the protein doses (e.g., protein concentration in diet) of a test eHTP and of control TIC807 (SEQ-ID NO:2), TIC807 M2 (SEQ ID NO:8), Cry51Aa1 (SEQ ID NO:182), TIC853 (SEQ ID NO:184), and/or an AXMI-171 (SEQ ID NO:206) protein which elicit equivalent insect population responses under controlled assay conditions (i.e. obtaining a dose response curve).

In the second approach, a statistically robust dose response value used for comparison would be the median lethal concentration (LC50) required to kill 50% of a test population. However, in certain embodiments, other values including but not limited to, a median inhibitory concentration ("IC50") required to result in 50% growth inhibition of a test population can be used. In this context, "growth inhibition" can comprise stunting and/or inhibition of Hemipteran development.

As used herein, the phrase "an insect inhibitory amount", refers to an amount of a composition containing an agent that is effective in achieving any measurable inhibition of insect viability, growth, insect development, insect reproduction, insect feeding behavior, insect mating behavior and/or any measurable decrease in the adverse effects caused by insect feeding on a composition containing the agent. Similarly, a "Hemipteran inhibitory amount" refers to an amount of a protein of the present invention alone or with other agents targeting the applicable Hemipteran species for control, that results in any measurable inhibition of target insects belonging to the order Hemiptera related to viability, growth, development, reproduction, feeding behavior, mating behavior, and or any measurable decrease in the adverse effects caused by Hemipteran insects feeding on a plant. Likewise, "*Lygus, Empoasca* and/or *Amrasca* inhibitory amount" refers to an amount of a composition containing one or more proteins of the present invention, i.e., eHTP's, or other agent that results in any measurable inhibition, viability, growth, development, reproduction, feeding behavior, mating behavior and/or any measurable decrease in the adverse effects caused by *Lygus, Empoasca* and/or *Amrasca* feeding on a composition containing that eHTP. As used herein in the context of an eHTP, an "enhanced Hemipteran inhibitory activity or "greater enhanced Hemipteran inhibitory activity" refers to any measurable increase in the inhibition of Hemipteran viability, growth, development, reproduction, feeding behavior, mating behavior and/or any measurable decrease in the adverse effects caused by Hemipteran feeding on a composition containing that eHTP relative to the corresponding inhibitory activity observed with any one or more of the scaffold proteins, including TIC807, Cry51Aa1 (SEQ ID NO:182), TIC853 (SEQ ID NO: 184), and/or AXMI-171 (SEQ ID NO:206) proteins. Likewise, "enhanced *Lygus, Empoasca* and/or *Amrasca* inhibitory activity" or "greater enhanced *Lygus, Empoasca* and/or *Amrasca* inhibitory activity" refers to any measurable increase in the inhibition, viability, growth, development, reproduction, feeding behavior, mating behavior and/or any measurable decrease in the adverse effects caused by the presence of one or more eHTP of the present invention in a composition or plant provided in the diet of *Lygus, Empoasca* and/or *Amrasca* relative to the corresponding inhibitory activity observed with an equivalent composition or plant containing only an applicable amount of one or more of the scaffold proteins, including but not limited to TIC807 (SEQ ID NO:2), Cry51Aa1 (SEQ ID NO:182), TIC853 (SEQ ID NO:184), and/or AXMI-171 (SEQ ID NO:206) proteins.

As used herein in the context of an eHTP, an "enhanced Lygus, Empoasca and/or Amrasca inhibitory spectrum" refers to any measurable increase in the inhibition of a specific Lygus spp., Empoasca spp. and/or Amrasca spp. viability, growth, development, reproduction, feeding behavior, mating behavior and/or any measurable decrease in the adverse effects caused by that Lygus spp., Empoasca spp. and/or Amrasca spp. feeding on a plant relative to the corresponding inhibition of that specific Lygus spp., Empoasca spp. and/or Amrasca spp. observed with the TIC807 protein. In certain embodiments, eHTP provided herein exhibit an enhanced Lygus inhibitory spectrum relative to TIC807 in that those eHTP's can provide increased inhibition of Lygus lineolaris.

An eHTP provided herein can exhibit from about 2 to about 260 fold greater Lygus, Empoasca and/or Amrasca inhibitory activity against a Lygus, Empoasca and/or Amrasca pest species than a protein of SEQ ID NO:2 (TIC807), SEQ ID NO:8 (TIC807 M2), SEQ ID NO:182 (Cry51Aa1), SEQ ID NO:184 (TIC853), and SEQ ID NO:206 (AXMI-171). An eHTP provided herein can exhibit from about 3, 4, 5, 7, 8, 10, 12, 15, 20, 25, 27, 30, 38, 46, 50, 52, 54, 66, 91, 122, 186, 243, or 262 fold greater Lygus, Empoasca and/or Amrasca inhibitory activity against a Lygus, Empoasca and/or Amrasca pest species than a protein of SEQ ID NO:2 (TIC807), SEQ ID NO:8 (TIC807 M2), SEQ ID NO:182 (Cry51Aa1), SEQ ID NO:184 (TIC853), and SEQ ID NO:206 (AXMI-171).

eHTP's can exhibit an enhanced target pest inhibitory spectrum and/or improved target pest inhibitory activity over SEQ ID NO:2 (TIC807), SEQ ID NO:8 (TIC807 M2), SEQ ID NO:182 (Cry51Aa1), SEQ ID NO:184 (TIC853), and/or a SEQ ID NO:206 (AXMI-171) by causing mortality:
  (i) at a dose of about 0.3 µg/mL to about 70 µg/mL against a Lygus hesperus insect species,
  (ii) at a dose of about 0.85 µg/mL to about 100 µg/mL against a Lygus lineolaris insect species,
  (iii) measuring at an LC50 value of about 0.3 to about 70 g/mL against Lygus hesperus, (iii)
  (iv) measuring at an LC50 value of about 0.85 to about 100 µg/mL against Lygus lineolaris, or
  (v) measuring at an LC50 value of more than two-fold lower the LC50 value of TIC807, SEQ ID NO:8, SEQ ID NO:182 (Cry51Aa1), SEQ ID NO:184 (TIC853), and/or a SEQ ID NO:206 (AXMI-171) against Lygus spp. Emrasca spp. and/or Amrasca spp., or
  (vi) at a dose of about 0.69 µg/mL to about 500 µg/mL against a Amrasca devastans or Empoasca fabae insect species, or
  (vii) measuring at an LC50 value of about 3.5 to about 15 g/mL against Amrasca devastans and/or Empoasca fabae.

Table 4A and 4B tabulate the exemplary eHTP's of the present invention with Amrasca and Lygus spp. mortality data. Mortality data available for Lygus spp. and Amrasca spp. are reported either as (a) a µg/mL LC50 value, or as (b) a % mortality at doses of about 1 to about 3 µg/mL for L. hesperus or about 100 µg/mL protein for L. lineolaris, and about 0.69 to 500 µg/mL for Amrasca devastans. The fold increased toxicity compared to TIC807 (SEQ ID NO:2) and TIC807 M2 (SEQ ID NO:8) is provided for exemplary eHTP's where LC50 values were determined.

The eHTP's of the present invention are particularly useful in controlling insects of the order Hemiptera compared to the scaffold proteins. Lygus lineolaris required high doses of TIC807 protein (e.g., in excess of 100 µg/mL) to elicit mortality. The dose response curve for one eHTP of the present invention TIC807 M8 (SEQ ID NO:16), an eHTP that exhibits remarkably improved toxic effects against both L. lineolaris and L. hesperus, but against L. lineolaris the eHTP exhibits a calculated LC50 value of 223 µg/mL. It has not been possible previously to achieve a protein concentration toxic dose that can elicit greater than 50% mortality against L. lineolaris species because providing significantly large doses of TIC807 and TIC807 M2 protein in excess of 1000 µg/mL in the diet has not been possible. Therefore, LC50 values against L. lineolaris for TIC807 and TIC807 M2 (SEQ ID NO:8) proteins were not determined, but rather estimated as greater than (>) 223 µg/mL (Sec Tables 1 and 3, Example 4, and FIG. 1B).

Iterative design refers to a semi-random approach for developing and selecting eHTP's including a combination of engineering, testing, and selecting (not necessarily in that order) (see Examples 1 through 4). The word "engineering" is intended to include identifying relevant residues to modify, cloning, and expressing eHTP's described herein. The word "testing" is intended to refer to comparing the Hemipteran activity of an eHTP to the activity of a scaffold protein such as TIC807 (SEQ ID NO:2), TIC807 M2 (SEQ ID NO:8), Cry51Aa1 (SEQ ID NO:182), and/or TIC853 (SEQ ID NO:184); or, comparing an eHTP of the present invention against another protein such as AXMI-171 (SEQ ID NO:206). The word "selecting" is intended to refer to the act of identifying improved variant proteins of the present invention, i.e., eHTP's, and the applicable amino acid residues for "engineering".

Iterative design includes the elucidation of the atomic structure of proteins of the present invention (for example, as set forth in FIG. 2) and the use of the atomic structure to guide and complement semi-random approaches of "selecting" amino acid residues to modify for "engineering", and in this case, has included the identification of amino acid residues at loops and at surface exposed regions of a folded insect inhibitory scaffold protein such as TIC807, TIC853, and Cry51Aa1 that can be modified to confer improvements to insect inhibitory spectrum and activity. Such amino acid residues at loops and at surface exposed regions are selected for "engineering". In this case, iterative design has included the identification of two different regions within the three dimensional structure of the scaffold protein that harbor an accumulation of relevant amino acid residues that, when modified to contain amino acid residues other than those appearing at those positions in the naturally occurring scaffold protein, result in one or more of the eHTP proteins of the present invention.

Initially the scaffold protein TIC807 (SEQ ID NO:2) used in this process of iterative design, and 267 different eHTP's were discovered that exhibited increased Lygus spp. inhibitory activity compared to the scaffold protein TIC807. TIC807 M8 (SEQ ID NO: 16) was discovered in early rounds of the design process. Subsequent rounds of iterative engineering-testing-selecting led to the discovery of other eHTP proteins that exhibited yet greater levels of toxicity against Lygus species and also exhibited a broader host range of toxic effects when compared to the scaffold protein. Seven variants (eHTP's) exhibited significantly higher levels of increased toxicity against both Lygus species (L.

hesperus and *L. lineolaris*) when compared to TIC807. LC50 values for these seven, and other, eHTP's constructed herein were determined against *Lygus hesperus* and *Lygus lineolaris* species and compared to LC50 values for scaffold proteins, particularly TIC807. The results are shown in Table 1, and FIG. 3 is a bar chart showing graphically the results observed as tabulated in Table 1.

TABLE 1

LC50 values of select eHTP's compared to TIC807

| SEQ ID NO: | Toxin | *Lygus hesperus* | | *Lygus lineolaris* | |
|---|---|---|---|---|---|
| | | LC50 value' (µg/mL) | Toxicity (fold increase) | LC50 value (µg/mL) | Toxicity (fold increase) |
| 2 | TIC807 | 73 | 1 | >223* | 1 |
| 6 | TIC807_M1 | 23 | 3 | 100 | ≥2 |
| 8 | TIC807_M2 | 5.9 | 12 | >223* | ~1 |
| 10 | TIC807_M3 | 2.9 | 25 | ND | — |
| 12 | TIC807_M4 | 2.4 | 30 | ND | — |
| 14 | TIC807_M5 | 1.1 | 66 | ND | — |
| 18 | TIC807_M6 | 1.45 | 50 | ND | — |
| 20 | TIC807_M7 | 1.4 | 52 | ND | — |
| 16 | TIC807_M8 | 0.8 | 91 | 223 | ≥1 |
| 28 | TIC807_M9 | 9.9 | 7 | 8.3 | ≥27 |
| 30 | TIC807_M10 | 0.6 | 122 | 4.8 | ≥46 |
| 32 | TIC807_M11 | 1.35 | 54 | 5.9 | ≥38 |
| 36 | TIC807_M12 | 0.4 | 182 | 1.2 | ≥186 |
| 34 | TIC807_M13 | 0.3 | 243 | 0.85 | ≥262 |

ND = Not Determined.
LC50 values are determined by presenting 8-10 different protein concentrations to a population of newly hatched *Lygus* nymphs, allowing nymphs to feed for 5 days, and then scoring for mortality over the dose range provided.
*Toxicity, displayed in terms of a multiple of increased activity compared to the level observed against *Lygus hesperus* using the observed LD50 for TIC807 as the baseline value of 1. Significantly large amounts of protein in excess of 1000 [µg/mL have not been possible to provide in *Lygus* diet in order to complete the high range of toxicity dose response to *Lygus lineolaris*. Therefore, an LC50 value was not determined for TIC807 or TIC807_M2. Instead, a 4-dose LC50 estimation in the low range was performed verifying that expected LC50 values for TIC807 and TIC807_M2 are greater than 223 [µg/mL.

With reference to Table 1, the iterative design process has provided a means for identifying proteins exhibiting improved toxic properties, not only to *Lygus hesperus*, but also to *Lygus lineolaris*.

Recombinant polynucleotide compositions that encode eHTP's are also provided. In certain embodiments, eHTP's can be expressed with recombinant DNA constructs in which a polynucleotide molecule with the open reading frame encoding the protein is operably linked to elements such as a promoter and any other regulatory element functional for expression in the system for which the construct is intended. For example, plant-functional promoters can be operably linked to an applicable eHTP coding sequence to enable expression of the protein in plants. Promoters functional in bacteria are also contemplated for use in expression cassettes. Promoters functional in an applicable bacterium, for example, in an *E. coli* or in a *Bacillus thuringiensis* species can be operably linked to the eHTP coding sequences for expression of the applicable protein in the applicable bacterial strain. Other useful elements that can be operably linked to the eHTP coding sequences include, but are not limited to, enhancers, introns, leaders, encoded protein immobilization tags (HIS-tag), encoded sub-cellular translocation peptides (i.e. plastid transit peptides, signal peptides), encoded polypeptide sites for post-translational modifying enzymes, ribosomal binding sites, and segments designed for use as RNAi triggers for suppression of one or more genes either in plants or in a particular target pest species.

Exemplary recombinant polynucleotide molecules provided herein include, but are not limited to, SEQ ID NO: 186, SEQ ID NO:187, SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO:198, SEQ ID NO: 199, SEQ ID NO:200, SEQ ID NO:35, and SEQ ID NO:201. These sequences encode the respective proteins each having the amino acid sequence as set forth in SEQ ID NO:4 (TIC807 4), SEQ ID NO:6 (TIC807 M1), SEQ ID NO:8 (TIC807 M2), SEQ ID NO:10 (TIC807 M3), SEQ ID NO:12 (TIC807 M4), SEQ ID NO:14 (TIC807 M5), SEQ ID NO:16 (TIC807 M8), SEQ ID NO:18 (TIC807 M6), SEQ ID NO:20 (TIC807 M7), SEQ ID NO:22 (TIC807 22), SEQ ID NO:24 (TIC807 24), SEQ ID NO:26 (TIC807 26), SEQ ID NO:28 (TIC807 M9), SEQ ID NO:30 (TIC807 M10), SEQ ID NO:32 (TIC807 M11), SEQ ID NO:36 (TIC807 M12), and SEQ ID NO:34 (TIC807 M13). Because of the redundancy of the genetic code, the codons of a recombinant polynucleotide molecule encoding for proteins of the present invention may be substituted for synonymous codons (also called a silent substitution); and are within the scope of the present invention. Recombinant polynucleotides encoding any of the eHTP's disclosed herein are thus provided.

A recombinant DNA construct comprising eHTP coding sequences can also further comprise a region of DNA that codes for one or more insect inhibitory agents which can be configured to be co-expressed along with a DNA sequence encoding an applicable eHTP, a protein different from an eHTP, or an insect or plant gene inhibitory dsRNA molecule. A recombinant DNA construct can be assembled so that all agents designed to be expressed from a particular construct are expressed from one promoter or so that separate agents are each under separate promoter control, or some combination thereof. The proteins of this invention can be expressed from a multi-gene expression system in which one or more proteins are expressed from a common nucleotide segment on which is also contained other open reading frames and/or promoters depending on the type of expression system selected.

Recombinant polynucleotide or recombinant DNA construct comprising an eHTP encoding sequence can be delivered to host cells by vectors, e.g., a plasmid, baculovirus, artificial chromosome, virion, cosmid, phagemid, phage, or viral vector. Such vectors can be used to achieve stable or transient expression of an eHTP encoding sequence in a host cell; and, if the case may be, subsequent expression to polypeptide. An exogenous recombinant polynucleotide or recombinant DNA construct that comprises an eHTP encoding sequence and that is introduced into a host cell is also referred to herein as a "transgene".

Also provided herewith are transgenic bacteria, transgenic plant cells, transgenic plants, and transgenic plant parts that contain any a recombinant polynucleotide (i.e. transgene) that expresses any one or more eHTP encoding sequence. It is intended that "bacterial cell" or "bacterium" can include, but are not limited to, an *Agrobacterium*, a *Bacillus*, an *Escherichia*, a *Salmonella*, a *Pseudomonas*, or a *Rhizobium* cell. It is intended that "plant cell" or "plant" include an alfalfa, almont, banana, barley, bean, bect, broccoli, cabbage, *brassica*, brinjal, carrot, cassava, castor, cauliflower, celery, chickpea, Chinese cabbage, celery, citrus, coconut, coffee, corn, clover, cotton, a cucurbit, cucumber, Douglas fir, eggplant, *eucalyptus*, flax, garlic, grape, guar, hops, leek, legumes, lettuce, Loblolly pine, millets, melons, nectarine, nut, oat, okra, olive, onion, ornamental, palm, pasture grass, *papaya*, pea, peach, peanut, pepper, pigeonpea, pine, potato, poplar, pumpkin, *Radiata* pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat plant cell or plant. In certain embodiments: transgenic plants and transgenic plant parts regenerated from a transgenic plant cell are provided; transgenic plants can be obtained from a transgenic seed; transgenic plant parts can be obtained by cutting, snapping, grinding or otherwise disassociating the part from the plant; the plant part can be a seed, a boll, a leaf, a flower, a stem, a root, or any portion thereof; and a transgenic plant part provided herein is a non-regenerable portion of a transgenic plant part. As used in this context, a "non-regenerable" portion of a transgenic plant part is a portion that can not be induced to form a whole plant or that can not be induced to form a whole plant that is capable of sexual and/or asexual reproduction. A non-regenerable portion of a plant part is a portion of a transgenic pollen, ovule, seed, boll, leaf, flower, stem, or root.

Also provided herein are methods of making transgenic plants that contain insect or *Lygus* and/or *Amrasca* inhibitory amounts of an eHTP. Such plants can be made by introducing a recombinant polynucleotide that encodes any of the eHTP proteins provided herein into a plant cell, and selecting a plant derived from said plant cell that expresses an insect or Hemipteran inhibitory amount of the eHTP's. Plants can be derived from the plant cells by regeneration, seed, pollen, or meristem transformation techniques.

Transgenic plants and host cells are provided that express an insect or Hemipteran inhibitory amount of the eHTP to control an insect or Hemipteran infestation. Any of the aforementioned plant species can be used for protecting a plant from insect or Hemipteran infestation provided herein as long as the plant is transformed with a polynucleotide construct designed to express the applicable eHTP.

Additional aspects of the invention include antibodies, kits, methods for detecting polynucleotides that encode eHTP's or distinguishing fragments thereof, or eHTP's or distinguishing fragments thereof, methods for identifying additional insect inhibitory members of the protein genus of the present invention, formulations and methods for controlling insect growth and/or infestation, and methods for providing such control to plants and other recipient hosts. Each composition, construct, cell, plant, formulation, method or kit provides for the industrial application of the proteins of the present invention, for example, by increasing plant productivity through the commercial use of any of these proteins to inhibit insects.

A plant product, other than a seed or a fruit or vegetable, is intended as a commodity or other products which move through commerce and are derived from a transgenic plant or transgenic plant part, in which the commodity or other products can be tracked through commerce by detecting nucleotide segments, RNA or proteins that corresponding to an eHTP of the present invention and are produced in or maintained in the plant or plant tissue or part from which the commodity or other product has been obtained. Such commodity or other products of commerce include, but are not limited to, plant parts, biomass, oil, meal, sugar, animal feed, flour, flakes, bran, lint, processed seed, and seed. Plant parts include but are not limited to a plant seed, boll, leaf, flower, stem, pollen, or root. In certain embodiments, the plant part is a non-regenerable portion of said seed, boll, leaf, flower, stem, pollen, or root. Cotton and flax plant bolls and non-regenerable portions thereof that contain the eHTP's are also provided.

Also provided herewith are processed plant products that contain a detectable amount of an eHTP, an insect inhibitory fragment thereof, or any distinguishing portion thereof. Without seeking to be limited by theory, it is believed that such processed plant products containing a detectable amount of one or more of the eHTP's provided herein can in certain embodiments exhibit reductions in undesirable microorganisms that can be transmitted by Hemiptera and/or reductions in the undesirable side products of such microorganisms. In certain embodiments, a distinguishing portion thereof can comprise any polypeptide of at least from about 20 to about 100 or more contiguous amino acids as set forth in SEQ ID NO:180, in particular in which the polypeptide does not contain a corresponding polypeptide of contiguous amino acids present in SEQ ID NO:2, SEQ ID NO:8, SEQ ID NO: 182, or SEQ ID NO: 184, and wherein the polypeptide comprises at least one amino acid substitution, addition, or deletion in the corresponding amino acid sequence as set forth in SEQ ID NO:2. Such substitutions, deletions or additions are those as set forth above in paragraph [0009].

Processed plant products are provided that contain a detectable amount of a recombinant polynucleotide encoding an eHTP, an eHTP or an insect inhibitory fragment thereof, or any distinguishing portion thereof. The processed product is selected from the group consisting of plant biomass, oil, meal, animal feed, flour, flakes, bran, lint, hulls, and processed seed.

Hemiptera infestations of crop plants are controlled by providing in the crop plants a recombinant polynucleotide sequence encoding one or more of the eHTP's of the present invention. Such transgenic crops produce or are treated to contain an insect or Hemiptera inhibitory amount of an applicable eHTP, and such crops are imbued with sufficient eHTP by (i) applying any composition comprising or encoding an eHTP to the plant or a seed that gives rise to the plant; and/or (ii) transforming the plant or a plant cell that gives rise to the seed and ultimately, the plant, with a polynucleotide encoding an eHTP. The plant may be a transiently or stably transformed transgenic plant comprising a transgene that expresses an insect or Hemiptera inhibitory amount of an eHTP. The plant may be a non-transgenic plant to which a composition comprising an eHTP has been applied. In such methods, the plant is a dicot plant, and more specifically may be a cotton, soybean or alfalfa plant. The Hemipteran insects include adults and nymphs, such as but not limited to the listing of bugs that is set forth above in paragraph [0020].

Preferably, the *Lygus* spp. is *Lygus hesperus* or *Lygus lineolaris*, the *Empoasca* spp. is *Empoasca fabae*, and the *Amrasca* spp. is *Amrasca devastans*.

Other features and advantages of the invention will be apparent from the following detailed description, examples, and claims.

EXAMPLES

In view of the foregoing, those of skill in the art should appreciate that changes can be made in the specific aspects which are disclosed and still obtain a like or similar result without departing from the spirit and scope of the invention. Thus, specific details disclosed herein are not to be interpreted as limiting. The U.S. Provisional Application Ser. No. 61/621,436 to which this application claims the benefit of priority, the Sequence Listing referenced in paragraph [0002], as well as all references material to the inventions disclosed and claimed, particularly references and published patent applications cited in this application, are incorporated herein by reference in their entirety.

Example 1: Iterative Engineering-Testing-Selecting Approach

This example illustrates the random, combinatorial, and inventive aspects of the iterative (also can be referred to as "recursive") engineering-testing-selecting approach used to identify and describe insect inhibitory proteins exhibiting Coleopteran and/or nematicidal activity or increased toxicity to Hemipteran insect species compared to TIC807 (SEQ ID NO:2). Several design approaches were employed to engineer for eHTP's with greater inhibitory activity against Lygus species; approaches that included but were not limited to semi-random modifications, directed modifications of variances in an alignment of TIC807 with other native Bt proteins, and structure/function assisted design. Numerous rounds of engineering and testing were conducted (both consecutively and concurrently) to select for TIC807 protein variants exhibiting increased toxicity. Design approaches were adjusted as data was collected. This iterative engineering-testing-selection approach also included, but was not limited to steps including cloning, expressing, purifying, and bioassay testing of TIC807 control protein compared to the eHTP's.

About 267 exemplary eHTP's having exhibited increased Lygus toxicity compared to TIC807 were obtained from more than 2000 groups of candidate eHTP's (i.e. "test" proteins) that were assayed for improved insect inhibitory activity. The actual total number of candidate eHTP's tested was much greater than 2000 because testing included recombinant nucleotide segments encoding a number of candidate eHTP's derived from library mutagenesis that were not sequenced in the selection process.

Protein stocks of various amounts and purity were prepared depending on the purpose of the test and the testing throughput desired. For example, lower quantity and lower purity protein preparations were prepared for screening higher numbers of variants in bioassay. Larger quantity and higher purity protein stocks were prepared for high-powered bioassays. Testing trended towards the high-powered bioassays as principally relevant residue positions of the improved variants were elucidated. Initially, about 2000 variants were tested on Lygus hesperus. Based on data from L. hesperus approximately 600 variants were designed and then further tested on Lygus lineolaris. Of these, about 267 variants (Table 4B) demonstrated increased toxicity against Lygus hesperus and/or Lygus lineolaris when compared to TIC807. These 267 variants included twenty-two (22) variants that were confirmed to demonstrate increased toxicity against both Lygus species. Further confirmation and dose response testing narrowed the selection to seven (7) variants that were subsequently characterized using an 8-dose replicated bioassay to determine LC50 values against both Lygus species.

The selection process included dynamic updates of testing data, constantly adjusting engineering approaches, and performing iterative rounds. Concurrently, labor intensive cloning, protein expression, protein purification, and bioassay experiments were employed test the candidate eHTP's.

Example 2: Engineering Approaches

Alignment Based Approaches

A multiple sequence alignment of protein members of Cry51: Cry51Aa1 (SEQ ID NO:182), TIC853 (SEQ ID NO:184), and TIC807 (SEQ ID NO:2) were used to identify regions of variability, e.g., positions 195 to 201 and positions 211 to 219, relative to SEQ ID NO:2 (TIC807). These regions were targeted for saturation mutagenesis through use of degenerate oligonucleotide primers encoding random amino acid residues in these regions. Construct libraries were prepared for subsequent protein expression in host cells.

A multiple sequence alignment of Cry51Aa1 (SEQ ID NO:182), TIC853 (SEQ ID NO:184), and TIC807 (SEQ ID NO:2) was used in combination with a BLOSUM 80 substitution matrix to calculate average pair-wise distances for each position variant to TIC807. Residue positions with lower average pair-wise distances were substituted with alternative amino acid residues using degenerate oligonucleotide primers encoding for alternative amino acid residues, e.g., G28X, G31X, F46X, E125X, F138X, F147X, S167X, Y216X, P218X, G234X, T247X, D268X, and T308X. Construct libraries were prepared for subsequent protein expression in host cells.

Scanning Approaches

Polynucleotide constructs were engineered to express a single Alanine substitution or a double Alanine substitution (Alanine-<parent residue>-Alanine) at every possible position over the full-length of SEQ ID NO:2 (TIC807). See Table 2 for a hypothetical example.

TABLE 2

A hypothetical example of single and double Alanine scans on a scaffold protein containing the amino acid sequence XXXXAXX.

| | Single Alanine Scan | Double Alanine Scan |
|---|---|---|
| 1 | AXXXaXX | AXAXaXX |
| 2 | XAXXaXX | XAXAaXX |
| 3 | XXAXaXX | XXAXSXX |
| 4 | XXXAaXX | XXXAaAX |
| 5 | XXXXSXX | XXXXSXA |
| 6 | XXXXaAX | — |
| 7 | XXXXaXA | — |

X = parent residue
a = parent residue is an Alanine residue
A = Modified to an Alanine residue
S = Modified to a Serine residue Where an Alanine residue was already present in TIC807, a Serine was substituted instead. Protein variants that exhibited increased toxicity compared to TIC807 were further tested by combination and saturation mutagenesis at those Alanine-substituted residues that conferred increased toxicity. Scanning approaches were also performed on improved combination variants having accumulated modifications from previous iterative rounds of engineering-testing-selecting, e. g., TIC807 M2 (SEQ ID NO:8) having mutations F46S, Y54H, S167R, S217N, and a contiguous triple deletion in residue range 196-201 was further engineered by an additional round of single Alanine substitutions to further improve upon the improved TIC807 M2. Principally relevant residues were identified and further tested by combination and saturation mutagenesis (e. g., A150X, E125X, E155X, F147X, I134X, N157X, Q149X, T133X, E135X, and N137X). Variants engineered by these combined approaches exhibited further improvements to increased toxicity compared to TIC807 and were further combined with other design approaches that took advantage of the atomic structure of TIC807 (SEQ ID NO:2).

Surface Exposed Residues

The atomic structure of proteins of the present invention was determined in the midst of the Iterative Engineering-Testing-Selecting approach; and, the relative solvent-accessibility (% SA) of each residue was determined using Molsoft's ICM-Browser (Molsoft L.L.C., 11199 Sorrento Valley Road, 5209, San Diego, CA 92121). Shown in Table 3 in columns (A) and (B), actual % SA was calculated for proteins having the respective amino acid sequences set forth as SEQ ID NO:185 (TIC807 L11M) and SEQ ID NO:8 (TIC807 M2). The predicted % SA for residues of TIC807 and TIC853 are listed in Table 3 in columns (A) and (C), respectively. Altogether, the % SA values reported in Table 3 are calculated as a percentage of the solvent-accessible surface area probed by a water molecule over the maximal solvent accessible area in standard extended conformation (Gly-XXX-Gly) for each residue in each position of the atomic structure. Table 3 aligns the residues of each protein by aligned residues in a Clustal W alignment. % SA greater than 100 can occur when maximal solvent accessible area in standard extended conformation (Gly-XXX-Gly) for each residue is less than the actual solvent accessible area probed by a water molecule. % SA greater than 100 are reported in the table as 100%.

Combined engineering-testing-selecting approaches described herein resulted in a number of principally relevant residues that accumulate in a surface patch ([2] of FIG. 2) of residues having a radius of about 9.2-12.2 Angstroms around the Cb atom of P219 of SEQ ID NO:2 (TIC807): V10, I14, N22, N23, G24, I25, Q26, G27, F30, Q38, I39, D40, T41, I43, S193, T194, E195, H196, Y197, S198, H199, Y200, S201, G202, Y203, P204, I205, L206, T207, W208, I209, S210, Y216, S217, G218, P219, F220, M221, S222, W223, Y224, F225, N239, and V244 of SEQ ID NO:2 (TIC807). At least half of these residues exhibit % SA values of greater or equal to fifteen (15).

TABLE 3

Relative % Solvent Accessability (SA) of Amino Acids of eHTP's & Scaffold Proteins.

| (A) TIC807_L11M (SEQ ID NO: 185) | | (B) TIC807_M2 (SEQ ID NO: 8) | | (C) TIC853 (SEQ ID NO: 184) | |
|---|---|---|---|---|---|
| Position and amino acid residue | Calculated % SA per residue | Position and amino acid residue | Calculated % SA per residue | Position and amino acid residue | Estimated % SA per residue |
| 2ALA | 82.1# | 2ALA | 64.8# | 2ALA | 60.9# |
| 3ILE | 23.3 | 3ILE | 28.9 | 3ILE | 24.3 |
| 4LEU | 26.4 | 4LEU | 31.9 | 4LEU | 27.9 |
| 5ASP | 26.0 | 5ASP | 22.7 | 5ASP | 29.9 |
| 6LEU | 1.0 | 6LEU | 3.4 | 6LEU | 3.7 |
| 7LYS | 25.1 | 7LYS | 16.2 | 7LYS | 17.1 |
| 8SER | 46.4# | 8SER | 37.6# | 8SER | 44.9# |
| 9LEU | 8.9 | 9LEU | 5.2 | 9LEU | 6.3 |
| 10VALP[1] | 0.3 | 10VAL | 0.6 | 10VAL | 0.0 |
| 11MET | 25.0 | 11LEU | 17.0 | 11LEU | 16.6 |
| 12ASN* | 49.8# | 12ASN | 43.2# | 12ASP | 39.7# |
| 13ALA | 0.0 | 13ALA | 0.0 | 13ALA | 0.0 |
| 14ILEP[1] | 0.0 | 14ILE | 0.0 | 14ILE | 0.0 |
| 15ASN | 23.7 | 15ASN | 24.9 | 15ASN | 19.2 |
| 16TYR | 29.5 | 16TYR | 47.1# | 16TYR | 52.5# |
| 17TRP | 14.1 | 17TRP | 18.2 | 17TRP | 20.1 |
| 18GLY | 4.3 | 18GLY | 1.4 | 18GLY | 1.0 |
| 19PRO | 63.6# | 19PRO | 57.3# | 19PRO | 59.0# |
| 20LYS | 57.3# | 20LYS | 77.2# | 20LYS | 100# |
| 21ASN | 36.3# | 21ASN | 28.4 | 21ASN | 61.5# |
| 22ASNP[1] | 16.9 | 22ASN | 10.1 | 22ASN | 15.2 |
| 23ASNP[1] | 0.3 | 23ASN | 0.8 | 23ASN | 0.0 |
| 24GLYP[1] | 42.0# | 24GLY | 43.2# | 24GLY | 43.3# |
| 25ILEP[1] | 10.1 | 25ILE | 13.8 | 25ILE | 7.6 |
| 26GLNP[1] | 92.4# | 26GLN | 86.2# | 26GLN | 94.7# |
| 27GLYP[1] | 62.0# | 27GLY | 73.9# | 27GLY | 62.8# |
| 28GLY | 49.0# | 28GLY | 50.6# | 28TYR | 47.7# |
| 29ASP | 66.0# | 29ASP | 68.1# | 29ASN | 80.7# |
| 30PHEP[1] | 4.5 | 30PHE | 4.1 | 30PHE | 1.5 |
| 31GLY | 37.2# | 31GLY | 41.4# | 31ASN | 61.1# |
| 32TYR | 25.2 | 32TYR | 25.3 | 32TYR | 21.5 |
| 33PRO | 70.7# | 33PRO | 76.0# | 33PRO | 78.5# |
| 34ILE | 4.8 | 34ILE | 5.5 | 34ILE | 2.6 |
| 35SER | 42.2# | 35SER | 29.1 | 35SER | 27.0 |
| 36GLU | 54.2# | 36GLU | 47.2# | 36GLU | 50.2# |
| 37LYS | 81.0# | 37LYS | 79.5# | 37ARG | 87.5# |
| 38GLNP[1] | 12.8 | 38GLN | 14.5# | 38GLN | 9.0 |
| 39ILEP[1] | 7.8 | 39ILE | 7.9 | 39ILE | 5.1 |
| 40ASPP[1] | 52.4# | 40ASP | 55.3# | 40ASP | 49.8# |
| 41THRP[1] | 0.3 | 41THR | 0.0 | 41THR | 0.2 |
| 42SER | 53.1# | 42SER | 56.0# | 42SER | 53.0# |
| 43ILEP[1] | 13.1 | 43ILE | 23.5 | 43ILE | 25.1 |
| 44ILE | 8.3 | 44ILE | 12.0 | 44ILE | 8.1 |
| 45THR | 30.7 | 45THR | 37.8# | 45THR | 45.7# |
| 46PHE* | 20.0 | 46SER | 43.7# | 46SER | 40.5# |
| 47THR | 48.1# | 47THR | 45.2# | 47THR | 43.7# |
| 48HIS | 73.5# | 48HIS | 65.3# | 48HIS | 78.3# |
| 49PRO | 9.4 | 49PRO | 12.6 | 49SER | 9.0 |
| 50ARG | 58.7# | 50ARG | 53.7# | 50ARG | 61.5# |
| 51LEU | 13.7 | 51LEU | 8.1 | 51LEU | 3.0 |
| 52ILE* | 32.4 | 52ILE | 31.5 | 52MET | 43.7# |
| 53PRO | 22.2 | 53PRO | 26.5 | 53PRO | 22.8 |
| 54TYR* | 52.7# | 54HIS | 42.2# | 54HIS | 45.5# |
| 55ASP | 57.5# | 55ASP | 59.2# | 55ASP | 55.5# |
| 56LEU | 15.0 | 56LEU | 18.6 | 56LEU | 15.1 |
| 57THR | 62.0# | 57THR | 73.2# | 57THR | 80.0# |
| 58ILE | 67.6# | 58ILE | 60.9# | 58ILE | 68.0# |
| 59PRO | 26.6 | 59PRO | 21.9 | 59PRO | 20.7 |
| 60GLN | 28.8 | 60GLN | 20.7 | 60GLN | 21.3 |
| 61ASN | 71.9# | 61ASN | 73.6# | 61ASN | 74.6# |
| 62LEU | 13.4 | 62LEU | 11.7 | 62LEU | 10.0 |
| 63GLU | 62.2# | 63GLU | 66.0# | 63GLU | 66.4# |
| 64THR | 51.2# | 64THR | 51.1# | 64THR | 49.0# |
| 65ILE | 46.1# | 65ILE | 41.5# | 65ILE | 38.4# |
| 66PHE | 27.0 | 66PHE | 26.3 | 66PHE | 29.6 |
| 67THR | 52.5# | 67THR | 55.5# | 67THR | 62.2# |
| 68THR* | 31.6 | 68THR | 35.8# | 68THR | 35.3 |
| 69THR | 54.3# | 69THR | 51.1# | 69THR | 50.3# |
| 70GLN* | 31.0 | 70GLN | 36.5# | 70GLN | 34.3 |
| 71VAL | 53.4# | 71VAL | 53.2# | 71VAL | 53.1# |
| 72LEU | 7.9 | 72LEU | 11.8 | 72LEU | 8.1 |
| 73THR | 40.5# | 73THR | 44.0# | 73THR | 47.0# |
| 74ASN | 0.6 | 74ASN | 0.0 | 74ASN | 0.0 |
| 75ASN | 69.8# | 75ASN | 63.2# | 75ASN | 65.9# |
| 76THR | 36.7# | 76THR | 40.5# | 76THR | 44.0# |
| 77ASP | 80.2# | 77ASP | 63.0# | 77ASP | 62.1# |
| 78LEU | 62.6# | 78LEU | 62.5# | 78VAL | 63.8# |
| 79GLN | 74.4# | 79GLN | 54.7# | 79GLN | 43.5# |
| 80GLN | 33.3 | 80GLN | 32.1 | 80GLN | 40.1# |
| 81SER | 81.0# | 81SER | 68.6# | 81SER | 75.2# |
| 82GLN | 19.0 | 82GLN | 23.9 | 82GLN | 24.6 |
| 83THR | 62.7# | 83THR | 63.6# | 83THR | 63.7# |
| 84VAL | 1.8 | 84VAL | 0.9 | 84VAL | 0.0 |
| 85SER | 50.8# | 85SER | 55.7# | 85SER | 54.0# |
| 86PHE | 7.2 | 86PHE | 5.8 | 86PHE | 4.0 |
| 87ALA* | 58.5# | 87ALA | 61.9# | 87SER | 68.0# |
| 88LYS | 30.5 | 88LYS | 30.6 | 88LYS | 32.6 |
| 89LYS | 69.8# | 89LYS | 67.8# | 89LYS | 67.9# |
| 90THR | 19.9 | 90THR | 23.1 | 90THR | 16.7 |
| 91THR | 54.1# | 91THR | 55.1# | 91THR | 48.1# |

TABLE 3-continued

Relative % Solvent Accessibility (SA) of Amino Acids of eHTP's & Scaffold Proteins.

| (A) TIC807_L11M (SEQ ID NO: 185) | | (B) TIC807_M2 (SEQ ID NO: 8) | | (C) TIC853 (SEQ ID NO: 184) | |
|---|---|---|---|---|---|
| Position and amino acid residue | Calculated % SA per residue | Position and amino acid residue | Calculated % SA per residue | Position and amino acid residue | Estimated % SA per residue |
| 92THR | 1.8 | 92THR | 1.8 | 92THR | 0.0 |
| 93THRP[2]* | 40.3# | 93THR | 36.4# | 93THR | 29.4 |
| 94THR | 0.0 | 94THR | 0.6 | 94THR | 0.2 |
| 95SERP[2]* | 14.4 | 95SER | 15.7 | 95SER | 18.1 |
| 96THR | 5.5 | 96THR | 1.5 | 96THR | 0.0 |
| 97SERP[2] | 16.6 | 97SER | 18.5 | 97SER | 29.9 |
| 98THR | 8.2 | 98THR | 5.9 | 98THR | 1.9 |
| 99THR | 41.8# | 99THR | 46.4# | 99THR | 49.3# |
| 100ASN | 37.7# | 100ASN | 34.1 | 100ASP | 20.1 |
| 101GLY | 1.0 | 101GLY | 1.9 | 101GLY | 0.0 |
| 102TRP | 3.6 | 102TRP | 10.4 | 102TRP | 6.6 |
| 103THR | 8.1 | 103THR | 8.1 | 103THR | 3.9 |
| 104GLU | 9.7 | 104GLU | 21.9 | 104GLU | 14.8 |
| 105GLY* | 35.3 | 105GLY | 46.8# | 105GLY | 31.4 |
| 106GLY | 57.0# | 106GLY | 68.6# | 106GLY | 61.8# |
| 107LYS | 52.4# | 107LYS | 57.2# | 107ARG | 54.6# |
| 108ILE | 61.8# | 108ILE | 63.5# | 108ILE | 67.1# |
| 109SER | 43.5# | 109SER | 47.9# | 109SER | 47.7# |
| 110ASP | 83.1# | 110ASP | 83.5# | 110ASP | 65.7# |
| 111THR | 43.4# | 111THR | 41.3# | 111THR | 39.9# |
| 112LEU | 26.7 | 112LEU | 29.6 | 112LEU | 31.3 |
| 113GLU | 53.8# | 113GLU | 64.1# | 113GLU | 62.5# |
| 114GLU | 34.8 | 114GLU | 30.9 | 114GLU | 32.6 |
| 115LYS | 62.2# | 115LYS | 55.2# | 115ASN | 54.6# |
| 116VAL | 6.4 | 116VAL | 8.6 | 116VAL | 10.4 |
| 117SER* | 46.6# | 117SER | 48.9# | 117SER | 51.2# |
| 118VAL | 0.9 | 118VAL | 2.5 | 118VAL | 1.3 |
| 119SER* | 20.2 | 119SER | 23.4 | 119SER | 23.7 |
| 120ILE | 0.8 | 120ILE | 0.3 | 120ILE | 0.0 |
| 121PRO | 5.9 | 121PRO | 10.7 | 121PRO | 8.0 |
| 122PHE | 0.2 | 122PHE | 1.4 | 122PHE | 0.3 |
| 123ILE | 19.1 | 123ILE | 20.8 | 123ILE | 18.3 |
| 124GLY | 4.3 | 124GLY | 6.2 | 124GLY | 3.3 |
| 125GLU* | 59.7# | 125GLU | 56.2# | 125ALA | 57.8# |
| 126GLY | 50.0# | 126GLY | 52.5# | 126GLY | 49.6# |
| 127GLY | 47.2# | 127GLY | 56.7# | 127GLY | 38.6# |
| 128GLY* | 34.7 | 128GLY | 30.3 | 128ALA | 23.0 |
| 129LYS | 68.8# | 129LYS | 73.9# | 129LYS | 78.4# |
| 130ASN | 16.2 | 130ASN | 14.6 | 130ASN | 10.1 |
| 131SER | 78.2# | 131SER | 77.9# | 131SER | 80.3# |
| 132THR | 9.8 | 132THR | 10.3 | 132THR | 12.3 |
| 133THR | 45.7# | 133THR | 42.0# | 133THR | 44.3# |
| 134ILE* | 1.1 | 134ILE | 0.8 | 134ILE | 0.0 |
| 135GLU* | 51.5# | 135GLU | 45.2# | 135GLU | 48.5# |
| 136ALA | 0.0 | 136ALA | 1.3 | 136ALA | 2.4 |
| 137ASN* | 18.1 | 137ASN | 15.5 | 137ASN | 15.6 |
| 138PHE* | 1.9 | 138PHE | 0.9 | 138VAL | 2.5 |
| 139ALA* | 2.8 | 139ALA | 6.3 | 139ALA | 4.1 |
| 140HIS | 2.3 | 140HIS | 2.1 | 140HIS | 0.0 |
| 141ASN | 5.3 | 141ASN | 6.5 | 141ASN | 2.8 |
| 142SER | 5.4 | 142SER | 4.4 | 142SER | 6.6 |
| 143SER | 7.7 | 143SER | 10.6 | 143SER | 7.0 |
| 144THR | 23.5 | 144THR | 17.3 | 144THR | 16.6 |
| 145THR* | 48.3# | 145THR | 52.7# | 145THR | 55.2# |
| 146THR | 50.2# | 146THR | 49.7# | 146THR | 53.6# |
| 147PHEP[2]* | 49.9# | 147PHE | 61.6# | 147SER | 51.7# |
| 148GLN* | 12.9 | 148GLN | 17.8 | 148GLN | 18.4 |
| 149GLNP[2] | 59.5# | 149GLN | 65.1# | 149GLN | 69.1# |
| 150ALA | 6.9 | 150ALA | 8.7 | 150ALA | 9.1 |
| 151SERP[2]* | 51.0# | 151SER | 51.7# | 151SER | 57.9# |
| 152THR | 9.9 | 152THR | 8.7 | 152THR | 12.3 |
| 153ASP* | 83.5# | 153ASP | 84.5# | 153GLU | 63.3# |
| 154ILE | 11.2 | 154ILE | 6.1 | 154ILE | 6.3 |
| 155GLU* | 49.5# | 155GLU | 63.9# | 155GLU | 49.7# |
| 156TRP | 1.7 | 156TRP | 3.8 | 156TRP | 1.8 |
| 157ASN* | 59.1# | 157ASN | 59.1# | 157ASN | 53.4# |
| 158ILE* | 13.1 | 158ILE | 5.9 | 158ILE | 0.8 |
| 159SER* | 60.2# | 159SER | 52.9# | 159SER | 52.2# |
| 160GLN | 29.2 | 160GLN | 19.3 | 160GLN | 9.3 |
| 161PRO | 54.0# | 161PRO | 63.6# | 161PRO | 62.6# |
| 162VAL | 0.6 | 162VAL | 4.0 | 162VAL | 2.4 |
| 163LEU | 53.8# | 163LEU | 56.6# | 163LEU | 64.5# |
| 164VAL | 0.0 | 164VAL | 0.0 | 164VAL | 0.0 |
| 165PRO | 22.8 | 165PRO | 22.1 | 165PRO | 26.9 |
| 166PRO | 30.7 | 166PRO | 36.1# | 166PRO | 39.7# |
| 167SER* | 31.0 | 167ARG | 32.8 | 167ARG | 36.7# |
| 168LYS | 18.2 | 168LYS | 18.5 | 168LYS | 19.9 |
| 169GLN | 17.4 | 169GLN | 15.1 | 169GLN | 10.7 |
| 170VAL | 0.0 | 170VAL | 0.0 | 170VAL | 0.0 |
| 171VAL | 13.2 | 171VAL | 13.8 | 171VAL | 12.2 |
| 172ALA | 0.0 | 172ALA | 0.0 | 172ALA | 0.0 |
| 173THR | 9.8 | 173THR | 9.2 | 173THR | 6.5 |
| 174LEU | 1.3 | 174LEU | 2.6 | 174LEU | 0.2 |
| 175VAL* | 17.2 | 175VAL | 17.8 | 175VAL | 13.4 |
| 176ILE | 0.0 | 176ILE | 0.0 | 176ILE | 0.0 |
| 177MET* | 7.0 | 177MET | 7.7 | 177MET | 17.3 |
| 178GLY | 1.6 | 178GLY | 0.5 | 178GLY | 0.0 |
| 179GLY | 15.9 | 179GLY | 22.2 | 179GLY | 16.5 |
| 180ASNP[2]* | 60.0# | 180ASN | 60.1# | 180ASP | 44.9# |
| 181PHE | 0.7 | 181PHE | 2.8 | 181PHE | 1.8 |
| 182THRP[2]* | 50.6# | 182THR | 44.3# | 182THR | 40.8# |
| 183ILE | 0.0 | 183ILE | 1.1 | 183VAL | 0.0 |
| 184PRO | 36.6# | 184PRO | 34.2 | 184PRO | 34.5 |
| 185MET | 4.4 | 185MET | 2.1 | 185MET | 1.8 |
| 186ASP | 52.4# | 186ASP | 23.5 | 186ASP | 20.3 |
| 187LEU* | 0.8 | 187LEU | 0.0 | 187LEU | 0.0 |
| 188MET | 25.9 | 188MET | 12.7 | 188ILE | 24.9 |
| 189THR | 1.4 | 189THR | 2.9 | 189THR | 0.5 |
| 190THR | 26.1 | 190THR | 26.2 | 190THR | 24.1 |
| 191ILE | 4.0 | 191ILE | 6.2 | 191ILE | 1.8 |
| 192ASP | 25.9 | 192ASP | 29.2 | 192ASP | 21.4 |
| 193SERP[2] | 7.4 | 193SER | 7.7 | 193SER | 2.7 |
| 194THRP[1] | 66.2# | 194THR | 60.2# | 194THR | 59.9# |
| 195GLUP[1] | 38.5# | 195GLU | 35.0 | 195GLN | 35.5# |
| 196HIS* | 37.7# | — | 100 | — | 100# |
| 197TYR* | 32.2 | — | 100# | — | 100# |
| 198SER* | 35.5# | — | 100# | — | 100# |
| 199HISP[1]* | 64.3# | 196HIS | 55.5# | 196HIS | 51.7# |
| 200TYRP[1]* | 85.3# | 197TYR | 56.2# | 197PHE | 45.8# |
| 201SERP[1]* | 50.3# | 198SER | 68.3# | 198THR | 64.5# |
| 202GLYP[1] | 32.8 | 199GLY | 50.0# | 199GLY | 51.1# |
| 203TYRP[1] | 21.5 | 200TYR | 22.6 | 200TYR | 26.0 |
| 204PROP[1] | 1.4 | 201PRO | 1.0 | 201PRO | 1.0 |
| 205ILEP[1] | 1.1 | 202ILE | 0.3 | 202ILE | 0.0 |
| 206LEUP[1] | 1.8 | 203LEU | 2.6 | 203LEU | 0.0 |
| 207THRP[1] | 0.0 | 204THR | 0.0 | 204THR | 0.0 |
| 208TRPP[1]* | 38.8# | 205TRP | 35.6# | 205TRP | 22.5 |
| 209ILEP[1] | 0.0 | 206ILE | 0.0 | 206ILE | 0.0 |
| 210SERP[1] | 22.5 | 207SER | 20.1 | 207GLU | 17.0 |
| 211SER | 3.1 | 208SER | 3.4 | 208ASN | 4.6 |
| 212PRO | 56.5# | 209PRO | 58.4# | 209PRO | 56.2# |
| 213ASP | 68.0# | 210ASP | 55.2# | 210GLU | 60.5# |
| 214ASN | 65.5# | 211ASN | 66.4# | 211HIS | 64.4# |
| 215SER | 67.2# | 212SER | 74.1# | 212ASN | 74.2# |
| 216TYRP[1] | 42.5# | 213TYR | 39.8# | 213VAL | 29.4 |
| 217SERP[1]* | 43.2# | 214ASN | 46.3# | 214ARG | 57.1# |
| 218GLYP[1] | 1.2 | 215GLY | 4.1 | 215GLY | 6.1 |
| 219PROP[1]* | 14.4 | 216PRO | 14.7 | 216ARG | 33.7 |
| 220PHEP[1] | 0.0 | 217PHE | 0.0 | 217PHE | 0.0 |
| 221METP[1] | 15.2 | 218MET | 16.1 | 218LEU | 8.4 |
| 222SERP[1] | 3.3 | 219SER | 3.3 | 210SER | 0.0 |
| 223TRPP[1]* | 35.6# | 220TRP | 34.3 | 220TRP | 42.5# |
| 224TYRP[1] | 13.5 | 221TYR | 15.9 | 221PHE | 11.3 |
| 225PHEP[1] | 0.9 | 222PHE | 1.4 | 222PHE | 0.0 |
| 226ALA | 15.9 | 223ALA | 13.1 | 223ALA | 7.8 |
| 227ASN | 40.7# | 224ASN | 41.9# | 224ASN | 43.2# |

TABLE 3-continued

Relative % Solvent Accessibility (SA) of Amino Acids of eHTP's & Scaffold Proteins.

| (A) TIC807_L11M (SEQ ID NO: 185) | | (B) TIC807_M2 (SEQ ID NO: 8) | | (C) TIC853 (SEQ ID NO: 184) | |
|---|---|---|---|---|---|
| Position and amino acid residue | Calculated % SA per residue | Position and amino acid residue | Calculated % SA per residue | Position and amino acid residue | Estimated % SA per residue |
| 228TRP | 9.0 | 225TRP | 8.9 | 225TRP | 7.3 |
| 229PRO | 56.3# | 226PRO | 61.5# | 226PRO | 65.5# |
| 230ASN | 67.6# | 227ASN | 67.3# | 227ASN | 67.3# |
| 231LEU | 21.1 | 228LEU | 16.1 | 228LEU | 16.1 |
| 232PRO | 23.7 | 229PRO | 23.0 | 229PRO | 23.6 |
| 233SER | 97.0# | 230SER | 95.8# | 230SER | 88.1# |
| 234GLY | 23.0 | 231GLY | 19.5 | 231GLU | 13.0 |
| 235PHE* | 8.3 | 232PHE | 9.0 | 232PHE | 6.1 |
| 236GLY | 26.1 | 233GLY | 18.3 | 233GLY | 28.5 |
| 237PRO | 72.6# | 234PRO | 70.8# | 234SER | 81.9# |
| 238LEU | 27.7 | 235LEU | 28.1 | 235LEU | 25.9 |
| 239ASN* | 33.2 | 236ASN | 26.5 | 236ASN | 42.2# |
| 240SER | 100# | 237SER | 100# | 237SER | 100# |
| 241ASP* | 62.2# | 238ASP | 61.7# | 238ASP | 55.2# |
| 242ASN | 15.1 | 239ASN | 20.8 | 239ASN | 21.7 |
| 243THR* | 3.3 | 240THR | 2.4 | 240THR | 2.6 |
| 244VAL* | 1.8 | 241VAL | 3.1 | 241ILE | 0.0 |
| 245THR* | 19.0 | 242THR | 23.8 | 242THR | 30.1 |
| 246TYR* | 8.6 | 243TYR | 4.8 | 243TYR | 0.4 |
| 247THR* | 36.8# | 244THR | 40.8# | 244LYS | 58.8# |
| 248GLY | 2.5 | 245GLY | 1.4 | 245GLY | 0.0 |
| 249SER* | 20.7 | 246SER | 23.9 | 246SER | 27.0 |
| 250VAL* | 6.0 | 247VAL | 1.4 | 247VAL | 0.0 |
| 251VALP[1]* | 32.6 | 248VAL | 30.0 | 248VAL | 29.7 |
| 252SER* | 0.0 | 249SER | 0.0 | 249SER | 0.0 |
| 253GLNP[1] | 40.2# | 250GLN | 37.6# | 250ARG | 51.3# |
| 254VAL | 1.2 | 251VAL | 1.5 | 251ILE | 2.7 |
| 255SERP[1] | 35.3 | 252SER | 37.3# | 252SER | 43.7# |
| 256ALA | 6.1 | 253ALA | 2.4 | 253ALA | 2.1 |
| 257GLY | 4.1 | 254GLY | 6.1 | 254GLY | 1.2 |
| 258VAL | 0.3 | 255VAL | 0.0 | 255VAL | 0.0 |
| 259TYR | 2.2 | 256TYR | 1.1 | 256TYR | 1.0 |
| 260ALA | 0.7 | 257ALA | 0.7 | 257ALA | 0.0 |
| 261THR | 9.2 | 258THR | 9.3 | 258THR | 5.0 |
| 262VAL | 3.6 | 259VAL | 1.5 | 259VAL | 0.2 |
| 263ARG | 26.6 | 260ARG | 29.8 | 260ARG | 26.9 |
| 264PHE | 0.5 | 261PHE | 3.8 | 261PHE | 1.5 |
| 265ASP | 6.9 | 262ASP | 7.2 | 262ASP | 10.8 |
| 266GLN | 5.6 | 263GLN | 5.8 | 263GLN | 2.6 |
| 267TYR | 16.1 | 264TYR | 14.5 | 264TYR | 12.4 |
| 268ASP | 29.8 | 265ASP | 31.4 | 265ALA | 19.3 |
| 269ILE | 25.4 | 266ILE | 18.2 | 266ILE | 14.5 |
| 270HIS | 85.5# | 267HIS | 72.2# | 267ASN | 92.0# |
| 271ASN | 43.4# | 268ASN | 46.9# | 268ASN | 64.0# |
| 272LEU | 40.3# | 269LEU | 43.1# | 269LEU | 39.8# |
| 273ARG* | 86.3# | 270ARG | 63.1# | 270ARG | 84.4# |
| 274THR* | 52.0# | 271THR | 66.1# | 271THR | 76.8# |
| 275ILE* | 41.0# | 272ILE | 37.9# | 272ILE | 32.4 |
| 276GLU | 47.9# | 273GLU | 50.1# | 273GLU | 53.0# |
| 277LYS | 49.8# | 274LYS | 47.2# | 274LYS | 70.2# |
| 278THR | 46.3# | 275THR | 51.2# | 275THR | 53.7# |
| 279TRP | 25.2 | 276TRP | 25.0 | 276TRP | 33.4 |
| 280TYR | 35.5 | 277TYR | 30.7 | 277TYR | 21.3 |
| 281ALA | 6.6 | 278ALA | 7.9 | 278ALA | 4.4 |
| 282ARG* | 77.6# | 279ARG | 80.6# | 279ARG | 86.1# |
| 283HIS | 45.2# | 280HIS | 36.6# | 280HIS | 35.8# |
| 284ALA | 0.8 | 281ALA | 0.8 | 281GLY | 0.6 |
| 285THR | 14.7 | 282THR | 8.6 | 282THR | 2.0 |
| 286LEU | 3.6 | 283LEU | 5.9 | 283LEU | 2.3 |
| 287HIS* | 8.4 | 284HIS | 16.5 | 284HIS | 11.9 |
| 288ASN | 40.4# | 285ASN | 43.9# | 285ASN | 38.7# |
| 289GLY | 61.0# | 286GLY | 53.5# | 286GLY | 61.1# |
| 290LYS | 61.7# | 287LYS | 61.6# | 287LYS | 73.8# |
| 291LYS | 68.4# | 288LYS | 66.2# | 288LYS | 51.9# |
| 292ILE | 19.2 | 289ILE | 19.5 | 289ILE | 21.0 |
| 293SER* | 40.3# | 290SER | 47.9# | 290SER | 45.7# |
| 294ILE | 3.4 | 291ILE | 4.8 | 291ILE | 5.1 |
| 295ASN* | 29.3 | 292ASN | 21.9 | 292ASN | 18.0 |
| 296ASN | 38.2# | 293ASN | 40.4# | 293ASN | 37.4# |
| 297VAL | 1.3 | 294VAL | 1.4 | 294VAL | 0.7 |
| 298THR | 10.1 | 295THR | 9.5# | 295THR | 4.3 |
| 299GLU* | 77.1# | 296GLU | 72.7# | 296GLU | 68.8# |
| 300MET* | 48.6# | 297MET | 46.4# | 297MET | 42.8# |
| 301ALA | 65.3# | 298ALA | 54.1# | 298ALA | 60.4# |
| 302PRO | 66.0# | 299PRO | 73.0# | 299PRO | 77.8# |
| 303THR* | 83.7# | 300THR | 85.8# | 300THR | 94.1# |
| 304SER | 77.4# | 301SER | 76.1# | 301SER | 84.9# |
| 305PRO* | 81.1# | 302PRO | 65.7# | 302PRO | 83.4# |
| 306ILE* | 78.1# | 303ILE | 81.6# | 303ILE | 91.3# |
| 307LYS | 81.9# | 304LYS | 99.3# | 304GLU | 100# |
| 308THR* | 89.4# | 305THR | 100# | 305ARG | 100# |
| 309ASN | 100# | 306ASN | 100# | 306ASN | 100# |

P1 designates an amino acid in surface patch [1] of FIG. 2.
P2 designates an amino acid in surface patch [2] of FIG. 2.
*designates one of the 72 principally relevant amino acids described herein (see FIG. 2). Shown are residues of TIC807_L11M, TIC807_M2, and TIC853 aligned by Clustal W. Numbers marked with # represent % SA of at least about 36%.

Receptor Binding

A surface patch ([1] of FIG. 2) of residues having % SA values greater than 36% or within about 3 residues of a residue having % SA greater than 36% in a radius of about 9.2-12.2 Angstroms from the Cb atom of S95 of SEQ ID NO:2 (TIC807) was identified as a region comprising residues of a TIC807 protein that can be substituted to provide for eHTP's that exhibit enhanced *Lygus* inhibitory spectrum and/or improved *Lygus* inhibitory activity. This surface patch region may be associated with target insect receptor binding activity; and, includes residues T93, S95, S97, F147, Q149, S151, N180, T182, V251, Q253, and S255 of SEQ ID NO:2 (TIC807). eHTP's can include, but are not limited to, one or more substitutions of surface patch 1 amino acid residues such as S95A, F147A, Q149E, and/or, V251A.

The combined engineering-testing-selecting approaches described herein identified residues located in surface patch 1 that can provide for eHTP's when substituted or otherwise modified. These residues may be important for productive binding of eHTP's to receptors in *Lygus* insect gut to provide for enhanced *Lygus* inhibitory spectrum and/or improved *Lygus* inhibitory activity when compared to TIC807. Modifications of the surface patch 1 amino acid residues that can provide for eHTP's include substitutions that provide aromatic groups and/or hydrogen-bonding groups which favoring binding to sugar groups found on glycosylated receptors of insects.

Membrane Binding

Certain amino acid residues located in beta-sheet regions of the protein were identified from the atomic structure of TIC807 and were substituted with aromatic residues. More specifically, amino acids L78, I123, H270, 8273, I275 of the folded TIC807 beta sheet regions were substituted with Phenylalanine, Tyrosine, or Tryptophan. Aromatic amino acid substitutions of 8273 and 1275 were amongst those residues that provided for an enhanced *Lygus* inhibitory spectrum and/or improved *Lygus* inhibitory activity (See Table 4, data for SEQ ID NOs:32, 34, 68, 92, and 122).

Amino acid side chains of residues in these positions may be likely to interact with the membrane of target insects.

Proteolytic Activation Sites

Glycine residues generally thought to be involved in proteolysis were substituted with Serines to alter proteolytic cleavage dynamics. The presence of a glycine residue in a loop region can impart more flexibility and therefore susceptibility to proteolysis, which can either increase insect inhibitory activity or decrease insect inhibitory activity. Residues in structurally identified loop regions were substituted with a glycine residue, and no improvements were observed. Positions in loops that were already glycines, (e.g. G18, G24, G27) were substituted with a serine, a small residue in an attempt to reduce proteolytic susceptibility, and no improvements were observed.

Combined Structure Design Approaches

The atomic structure of TIC807 (SEQ ID NO:2) was used to identify loop regions for library mutagenesis followed by testing of the engineered variants. A loop at amino acid positions 211-216 of SEQ ID NO:2 (TIC807) was library-mutagenized and tested. Consecutive loops in close proximity at amino acid positions 75-83, 161-167, and 267-276 of SEQ ID NO:2 (TIC807) was library-mutagenized and tested.

Analysis of the atomic structure of TIC807 suggests that a structural loop resides at residues 113-138 of SEQ ID NO:2, and variants were engineered to stabilize and destabilize the loop.

In another region spanning two beta-strands connected by a short loop, the two beta-strands exhibited an alternating pattern of hydrophobic and hydrophilic amino acid residues at positions 116 to 121 and at positions 133 to 138 relative to SEQ ID NO:2, characteristic of pore-forming loops. An expression library was engineered to modify both beta-strand segments replacing residues V116, V118, and I120 with respective combinations 116V/Y/L/H/F/D, 118V/Y/L/H/F/D, and 120I/D/F/H/L/NN/Y for a total of 288 possible variants in the library. This procedure was repeated for: residues S117, S119, and P121 with respective combinations 117S/A/D/E/G/K/N/R/T, 119S/A/D/E/G/K/N/R/T, and 121P/S/T for 243 potential variants; residues I133, A135, and F137 with respective combinations 133I/D/F/NN/Y, 135A/D/F/H/L/V/Y, and 137F/D/H/L/V/Y for 252 possible variants; and residues T134. E136, and N138 with respective combinations 134T/A/D/E/G/K/N/R/S. 136E/A/D/G/K/N/R/S/T. and 138N/A/D/G/S/T for 486 possible variants. An enhanced *Lygus* inhibitory spectrum and/or improved *Lygus* inhibitory activity was associated with certain of these substitutions as shown in Table 4.

Structure-Function Relationship

Altogether, more than 2000 clones (including mixed library clones) expressing variants of TIC807 were tested for enhanced *Lygus* inhibitory spectrum and/or improved *Lygus* inhibitory activity against *Lygus* spp. compared to TIC807. Semi-random modifications, directed modifications, and predictive structure-function modifications, including structure modeling, receptor binding potential, metal binding potential, oligomerization potential, uniformity of surface charge distribution, pore formation potential, ion channel function, and identification of surface exposed patches to with an objective of identifying eHTP's with an enhanced *Lygus* inhibitory spectrum and/or improved *Lygus* inhibitory activity compared to TIC807. These clones were expressed for bioassay testing.

Example 3: Protein Expression and Purification of TIC807, Including Variants and Fragments Control protein TIC807 is a protein of 309 amino acids in length that can be expressed in crystalline form in *Bacillus thuringiensis* (Bt) or aggregate form in *E. coli*. Test variants thereof were recombinantly expressed in Bt. An expression characteristic of TIC807 and variants of TIC807 is the predominant crystalline and aggregate forms extracted from Bt and *E. coli* cells, respectively. To test for *Lygus* bioactivity, test and control samples were made suitable for *Lygus* bioassay by solubilizing samples in 25 mM Sodium Carbonate buffer and removing unsolubilized materials by centrifugation. The amount of protein in test and control samples were measured using total protein methods, e.g.s, a Bradford assay, an ELISA method, or similar. Gel electrophoresis was used to determine the purity and stock concentration of the solubilized recombinant protein. C-terminal HIS-tagged TIC807 protein was engineered to facilitate detection, purification, and quantification of large amounts of TIC807 control protein. C-terminal HIS-tagged TIC807 and un-tagged TIC807 test samples were separately assayed and confirmed to have equivalent activity against *Lygus* (see Examples 4, 5, and 6).

Site-directed amino acid substitutions were made to TIC807 M13 (SEQ ID NO:34) to elevate expression of a soluble form. Inventors postulate that more readily soluble variants of the proteins of the present invention can facilitate expression and purification, e.g., expressed in *E. coli* host cells; and can increase insect inhibitory efficacy when expressed in plant host cells. Recombinant DNA constructs encoding TIC807 M13 (SEQ ID NO:34) were engineered three different ways to reflect three different variants: Relative to TIC807 M13, the modifications were for Variant #1: I58K and P59K, for Variant #2: S198K and G199K, and for Variant #3: S246R, V248E, and Q250R. Relative to TIC807 (SEQ ID NO:2), the modifications can be alternatively described as follows for Variant #1: I58K and P59K, for Variant #2: S201K and G202K, and for Variant #3: S249R, V251E, and Q253R; this positional difference is congruent due to a contiguous triple deletion of SEQ ID NO:2 (TIC807) in residue range 196-201 that is reflected in TIC807 M13 (SEQ ID NO:34). The four engineered recombinant DNA constructs were each cloned and expressed in *E. coli*. The soluble fraction from the four *E. coli* preparations were evaluated by coomassie-stained SDS-PAGE, which showed that TIC807 M13 (SEQ ID NO:34) was not detectable in the soluble fraction; but, in contrast, Variant #s 1, 2, and 3 were soluble. Similar amino acid substitutions either singly or in combination are made to proteins of the present invention to elevate their solubility in non-Bt or plant host cells. Recombinant DNA constructs were engineered to encode for and express TIC807 M13 variant #3 (renamed TIC807 M14; nucleotide SEQ ID NO:203 and amino acid SEQ ID NO:204). Prepared *E. coli* lysate was clarified, and the recombinant protein purified and enriched-for on a series of columns, including ion-exchange and gel filtration methods. Pooled protein fractions were quantified and determined to be active against *Lygus* insects (See Example 4, Table 4B).

Proteins of the present invention, including but not limited to proteins having the amino acid sequence as set forth as SEQ ID NO:28, SEQ ID NO:30, SEQ ID NO:32, or SEQ ID NO:36, are engineered to elevate expression of a soluble form when expressed in a host cell, e.g., expressed in Bt. *E. coli*, or in a plant cell or in a compartment of a plant cell. Engineering includes substituting a lysine amino acid residue at one or more of the following positions 58, 59, 198, 199, 201, or 202; or, a Glutamic acid at one or more of the following positions 198, 248, or 301; or, an Arginine at one or more of the following positions 246, 250, or 253.

The C-terminal region protrudes away from the monomeric core of the protein (See FIG. 2). A recombinant DNA construct was engineered to encode for and express a protein having the amino acid sequence of SEQ ID NO:202, which is a protein fragment (amino acids 1 to 301) of TIC807 M8 (SEQ ID NO:16); and, the expressed protein was purified, quantified, and determined active against *Lygus* insects (See Example 4, Table 4B). Recombinant DNA constructs were designed to encode for and express TIC807 fragments exhibiting varying truncations off of the C-terminus end of the proteins of the present invention at the respective TIC807 positions A281, G289, 5293, A301, and 5304. Protein fragments are engineered to encode for and express proteins having the amino acid sequences set forth as SEQ ID NO:28, SEQ ID NO:30, SEQ ID NO:32, SEQ ID NO:34, and SEQ ID NO:36; and, the expressed protein fragments are used as test samples against *Lygus* insects.

Example 4: Hemipteran Activity of Engineered Proteins

This example illustrates eHTP's to have improved insecticidal activity or enhanced insecticidal specificity against Hemipteran insects when provided in the diet of Hemipteran insects, including but not limited to members of the Heteroptera miridae, including the genus *Lygus*, e.g., *Lygus hesperus* and *Lygus lineolaris*, and the family Cicadellidae, including the genus *Amrasca*, e.g. *Amrasca devastans*, and *Empoasca*, e.g. *Empoasca fabae*. This example with Table 4B illustrates the feeding assay used to determine the enhanced *Lygus* inhibitory spectrum and/or improved *Lygus* inhibitory activity of a Bt expressed recombinant proteins of the present invention against both *Lygus hesperus* and *Lygus lineolaris*. Proteins expressed in recombinant bacterium host cells were solubilized in carbonate buffer and analyzed by SDS polyacrylamide gel electrophoresis (SDS-PAGE); and, protein concentrations determined by densitometry using bovine serum albumin (BSA) as a standard. Protein stock (2×) prepared this way were mixed with diet for feeding assays.

Feeding assays with the Hemipteran species *Lygus hesperus* and *Lygus lineolaris* were based on a 96 well microtiter plate format with *Lygus* diet encapsulated between stretched Parafilm® and Mylar sheets. Artificial diet was obtained from Bio-Sery® (Bio-Sery® Diet F9644B, Frenchtown, NJ). Autoclaved, boiling water (518 mL) was combined with 156.3 grams of Bio-Sery® diet F9644B in a surface-sterilized blender. The contents of four surface-sterilized chicken eggs were added and the mixture blended until smooth, then adjusted to one liter total volume and allowed to cool to room temperature, this being the 2× diet. Test samples were prepared by mixing in a 1:1 ratio of 2× diet and 2× sample. A sheet of Parafilm® (Pechiney Plastic Packing, Chicago, IL) was placed over a vacuum manifold designed for 96-well format (Analytical Research Systems, Gainesville, FL) and a vacuum of approximately −20 millimeters mercury was applied, sufficient to cause extrusion of the Parafilm® into the wells. Twenty to forty microliters of test sample were added to the Parafilm® extrusions. A sheet of Mylar film (Clear Lam Packaging, Inc., Elk Grove Village, IL) was placed over the sample filled Parafilm® extrusions and sealed with a tacking iron (Bienfang Sealector II, Hunt Corporation, Philadelphia, PA), thus forming diet filled Parafilm® sachets. These Parafilm® sachets were positioned over a flat-bottom 96-well plate containing *Lygus* eggs suspended in a dilute agarose solution. Upon hatching, *Lygus* nymphs feed on the diet by piercing the diet filled Parafilm® sachets. Alternatively, newly hatched *Lygus* nymphs instead of eggs were manually infested into each well. Stunting and mortality scores were determined on day 5 and compared to controls. Data were analyzed using J MP4 statistical software. For each protein at a test concentration, three populations of eight nymphs were subjected to this bioassay, and mortality scores reported in Table 4B.

For LC50 determinations listed in Table 1 and Table 4B, proteins were presented to newly hatched *Lygus* nymphs at 8-10 concentrations and the nymphs allowed to feed for 5 days before scoring for mortality over the dose range. For each concentration, three populations of eight nymphs were subjected to this bioassay, and all LC50 determinations in Table 1 and Table 4B were repeated at least once.

For LC50 estimations, proteins were presented to newly hatched *Lygus lineolaris* nymphs at 4 concentrations and the nymphs allowed to feed for 5 days before scoring for mortality over the dose range. *Lygus lineolaris* LC50 estimations were performed on TIC807 and TIC807 M2 because significantly large amounts of these proteins in excess of 1000 [μg/mL have not been possible to provide in *Lygus* diet in order to complete the high range of toxicity dose response to *Lygus lineolaris*; and therefore, an LC50 value was not determined for TIC807 or TIC807 M2. Instead, a 4-dose LC50 estimation in the low range was performed, and reported in Table 1 and Table 4B. The estimated *Lygus lineolaris* LC50 for TIC807 M14 is 4.4 μg/mL. For each concentration, three populations of eight nymphs were subjected to this bioassay.

This example with Tables 4A and 4B illustrate the feeding assay used to determine the enhanced inhibitory spectrum and/or improved inhibitory activity of a Bt expressed recombinant protein disclosed herein against *Amrasca devastans*. TIC807 variants with improved insecticidal activity or enhanced insecticidal specificity against *Lygus hesperus* and *Lygus lineolaris* exhibit improved insecticidal activity against *Amrasca devastans*.

TIC807, and TIC807-M13 were dissolved in 25 mM sodium carbonate buffer, pH 10. *Amrasca devastans* eggs were collected on Okra leaf and incubated in a petriplate containing 2% agar. Upon hatching the neonates were used for biossays using the diluted (1:5) *Lygus* diet. The proteins and diet were mixed at equal proportion (bringing final concentration of protein to 500 μg/mL) and dispensed into test arena. Untreated control was prepared by mixing the buffer with the diet. Individual neonates were infested into the test arena, the assays were incubated at 25° C. 60% RH. Twenty neonate nymphs were tested for each concentration, protein and in 2 replicates. A control was maintained with 25 mM Sodium Carbonate buffer, pH 10, in 1:5 diluted *Lygus* diet. Mortality of the insects was determined on the fifth day. Mortality values were calculated by the following formula: (% mortality in treatment−% mortality in control)/(100−% mortality in control)×100. Table 4A tabulates *Amrasca* activity for TIC807 and TIC807_M13 at 5 different concentrations.

TABLE 4A

TIC807 and TIC807_M13 Percent Mortality Directed to *Amrasca* species

| | | Mortality (%) | | | | |
|---|---|---|---|---|---|---|
| SEQ ID NO: | Protein Name | 500 µg/mL | 166.66 µg/mL | 55.55 µg/mL | 18.51 µg/mL | 6.17 µg/mL |
| 2 | TIC807 | 100% | 55.88% | 17.64% | 0 | 0 |
| 34 | TIC807_M13 | 100% | 88.23% | 73.52% | 44.11% | 26.47% |

LC50 values were determined for TIC807 and TIC807 M13 in a separate test, SEQ ID NO:2 (TIC807) exhibited a LC50 value of 116.79 µg/mL and LC90 of 437.27 µg/mL, SEQ ID NO:34 (TIC807 M13) exhibited a LC50 value of 7.59 µg/mL and LC90 value of 239.8 µg/mL.

A feeding assay as described for *Amrasca devastans* is used to test eHTP's for improved insecticidal activity and/or enhanced insecticidal specificity against *Empoasca fabae*. TIC807 variants with improved insecticidal activity or enhanced insecticidal specificity against *Lygus hesperus* and *Lygus lineolaris* exhibit improved insecticidal activity against *Empoasca fabae*.

The LC50 values of Cry51Aa1 (SEQ ID NO:182), for TIC807 (SEQ ID NO:2), TIC807_M2 (SEQ ID NO:8), TIC807 M10 (SEQ ID NO:30) and TIC807-M13 (SEQ ID NO:34) against *Lygus hesperus* and *Lygus lineolaris* were determined in one testset. TIC807_M2, TIC807_M10 and TIC807_M12 exhibit improved LC50 values compared to Cry51Aa1.

It should be apparent to those skilled in the art that variations to this procedure can exist that should not affect results.

TABLE 4B

Iterative engineering-testing-selecting of eHTP's against *Lygus* spp. resulted in 267 proteins with enhanced *Lygus* inhibitory spectrum and/or improved *Lygus* inhibitory activity against *Lygus* spp. compared to TIC807.

| | | Amino acid differences compared to TIC807 parent protein | | | *Lygus hesperus* | | | *Lygus lineolaris* | | |
|---|---|---|---|---|---|---|---|---|---|---|
| SEQ ID NO: | Protein Name | Amino acid difference(s) relative to SEQ ID NO: 2 (TIC807) | Amino acid difference(s) in the first patch | Amino acid difference(s) in the second patch | LC50 value (µg/mL) | fold increased toxicity (LC50) | % Mortality at about 1-3 µg/mL protein* | LC50 value (µg/mL) | fold increased toxicity (LC50) | % Mortality at about 100 µg/mL protein* |
| 2 | TIC807 | Parent | Parent | Parent | 73 | 1 | 0 | >223 | 1 | 0 |
| 6 | TIC807_M1 | F147A | F147A | None | 23 | 3 | ND | 100 | at least 2 | ND |
| 8 | TIC807_M2 | F46S, Y54H, S167R, S217N, then a contiguous triple deletion in residue range 196-201 | none | S217N, then a contiguous triple deletion in residue range 196-201 | 6.0 | 12 | 39 | >223 | — | 14 |
| 10 | TIC807_M3 | F46S, Y54H, T93A, S167R, S217N, then a contiguous triple deletion in residue range 196-201 | T93A | S217N, then a contiguous triple deletion in residue range 196-201 | 2.9 | 25 | 43 | ND | — | ND |
| 12 | TIC807_M4 | F46S, Y54H, S95A, S167R, S217N, then a contiguous triple deletion in residue range 196-201 | S95A | S217N, then a contiguous triple deletion in residue range 196-201 | 2.4 | 30 | 20 | ND | — | ND |
| 14 | TIC807_M5 | F46S, Y54H, F147A, S167R, S217N, then a contiguous triple deletion in residue range 196-201 | F147A | S217N, then a contiguous triple deletion in residue range 196-201 | 1.1 | 66 | 34 | ND | — | ND |
| 16 | TIC807_M8 | F46S, Y54H, S95A, F147A, S167R, S217N, then a contiguous triple deletion in residue range 196-201 | S95A, F147A | S217N, then a contiguous triple deletion in residue range 196-201 | 0.8 | 91 | ND | 223 | at least 1 | ND |
| 18 | TIC807_M6 | F46S, Y54H, T93A, F147A, S167R, S217N, then a contiguous triple deletion in residue range 196-201 | T93A, F147A | S217N, then a contiguous triple deletion in residue range 196-201 | 1.5 | 50 | ND | ND | — | ND |

TABLE 4B-continued

Iterative engineering-testing-selecting of eHTP's against *Lygus* spp. resulted in 267 proteins with enhanced *Lygus* inhibitory spectrum and/or improved *Lygus* inhibitory activity against *Lygus* spp. compared to TIC807.

| | | Amino acid differences compared to TIC807 parent protein | | | *Lygus hesperus* | | | *Lygus lineolaris* | | |
|---|---|---|---|---|---|---|---|---|---|---|
| | | | | | | | % Mortality | | | % Mortality |
| SEQ ID NO: | Protein Name | Amino acid difference(s) relative to SEQ ID NO: 2 (TIC807) | Amino acid difference(s) in the first patch | Amino acid difference(s) in the second patch | LC50 value (μg/mL) | fold increased toxicity (LC50) | at about 1-3 μg/mL protein* | LC50 value (μg/mL) | fold increased toxicity (LC50) | at about 100 μg/mL protein* |
| 20 | TIC807_M7 | F46S, Y54H, Q149E, S167R, S217N, then a contiguous triple deletion in residue range 196-201 | Q149E | S217N, then a contiguous triple deletion in residue range 196-201 | 1.4 | 52 | 62 | ND | — | 49 |
| 28 | TIC807_M9 | F46S, Y54H, S95A, F147A, S167R, P219R, then a contiguous triple deletion in residue range 196-201 | S95A, F147A | P219R, then a contiguous triple deletion in residue range 196-201 | 9.9 | 7 | ND | 8.3 | at least 27 | ND |
| 30 | TIC807_M10 | F46S, Y54H, S95A, F147A, S167R, P219R, V251A, then a contiguous triple deletion in residue range 196-201 | S95A, F147A, V251A | P219R, then a contiguous triple deletion in residue range 196-201 | 0.6 | 122 | ND | 4.8 | at least 46 | ND |
| 32 | TIC807_M11 | F46S, Y54H, S95A, F147A, S167R, P219R, R273W, then a contiguous triple deletion in residue range 196-201 | S95A, F147A | P219R, then a contiguous triple deletion in residue range 196-201 | 1.4 | 54 | ND | 5.9 | at least 38 | ND |
| 34 | TIC807_M13 | F46S, Y54H, S95A, F147S, Q149E, S167R, P219R, R273W, then a contiguous triple deletion in residue range 196-201 | S95A, F147A, Q149E | P219R, then a contiguous triple deletion in residue range 196-201 | 0.3 | 243 | ND | 0.85 | at least 262 | ND |
| 36 | TIC807_M12 | F46S, Y54H, S95A, F147A, S167R, P219R, N239A, V251A, then a contiguous triple deletion in residue range 196-201 | S95A, F147A, V251A | P219R, then a contiguous triple deletion in residue range 196-201 | 0.4 | 182 | ND | 1.2 | at least 186 | ND |
| 37 | TIC807_37 | TIC807_HYS_deletion | none | a contiguous triple deletion in HYSHYS residues (positions 196-201) | 22.4 | 3 | ND | ND | — | ND |
| 38 | TIC807_38 | F46S, Y54H, F138V, S167R, S217N, then a contiguous triple deletion in residue range 196-201 | none | S217N, then a contiguous triple deletion in residue range 196-201 | ND | — | 41 | ND | — | 44 |
| 39 | TIC807_39 | F46S, Y54H, S167R, S217N, H287F, then a contiguous triple deletion in residue range 196-201 | none | S217N, then a contiguous triple deletion in residue range 196-201 | ND | — | 57 | ND | — | 31 |
| 40 | TIC807_40 | F46S, I52M, Y54H, S167R, S217N, then a contiguous triple deletion in residue range 196-201 | none | S217N, then a contiguous triple deletion in residue range 196-201 | ND | — | 52 | ND | — | 36 |
| 41 | TIC807_41 | N12D, F46S, Y54H, S167R, S217N, then a contiguous triple deletion in residue range 196-201 | none | S217N, then a contiguous triple deletion in residue range 196-201 | ND | — | 52 | ND | — | 31 |
| 42 | TIC807_42 | F46S, Y54H, S167R, N180D, S217N, then a contiguous triple deletion in residue range 196-201 | N180D | S217N, then a contiguous triple deletion in residue range 196-201 | ND | — | 63 | ND | — | 50 |

TABLE 4B-continued

Iterative engineering-testing-selecting of eHTP's against *Lygus* spp. resulted in 267 proteins with enhanced
*Lygus* inhibitory spectrum and/or improved *Lygus* inhibitory activity against *Lygus* spp. compared to TIC807.

| | | Amino acid differences compared to TIC807 parent protein | | | *Lygus hesperus* | | | *Lygus lineolaris* | | |
|---|---|---|---|---|---|---|---|---|---|---|
| SEQ ID NO: | Protein Name | Amino acid difference(s) relative to SEQ ID NO: 2 (TIC807) | Amino acid difference(s) in the first patch | Amino acid difference(s) in the second patch | LC50 value (µg/mL) | fold increased toxicity (LC50) | % Mortality at about 1-3 µg/mL protein* | LC50 value (µg/mL) | fold increased toxicity (LC50) | % Mortality at about 100 µg/mL protein* |
| 43 | TIC807_43 | F46S, Y54H, S167R, then a contiguous triple deletion in residue range 196-201 | none | a contiguous triple deletion in HYSHYS residues (positions 196-201) | ND | — | 46 | ND | — | 87 |
| 44 | TIC807_44 | F46S, Y54H, S167R, S217N, P219R, then a contiguous triple deletion in residue range 196-201 | none | S217N, P219R, then a contiguous triple deletion in residue range 196-201 | ND | — | 30 | ND | — | 94 |
| 45 | TIC807_45 | F46S, Y54H, S159T, S167R, S217N, then a contiguous triple deletion in residue range 196-201 | none | S217N, then a contiguous triple deletion in residue range 196-201 | ND | — | 67 | ND | — | 21 |
| 46 | TIC807_46 | F46S, Y54H, S167R, S217N, T247K, then a contiguous triple deletion in residue range 196-201 | none | S217N, then a contiguous triple deletion in residue range 196-201 | ND | — | 52 | ND | — | 31 |
| 47 | TIC807_47 | F46S, Y54H, S167R, S217N, V244I, then a contiguous triple deletion in residue range 196-201 | none | S217N, then a contiguous triple deletion in residue range 196-201 | ND | — | 59 | ND | — | 31 |
| 48 | TIC807_48 | F46S, Y54H, S167R, S217N, V244I, T247K, then a contiguous triple deletion in residue range196-201 | none | S217N, then a contiguous triple deletion in residue range 196-201 | ND | — | 58 | ND | — | 34 |
| 49 | TIC807_49 | F46S, Y54H, S167R, S217N, W223Y, then a contiguous triple deletion in residue range 196-201 | none | S217N, W223Y, then a contiguous triple deletion in residue range 196-201 | ND | — | 17 | ND | — | 13 |
| 50 | TIC807_50 | F46S, Y54H, S167R, S217N, Y246F, then a contiguous triple deletion in residue range 196-201 | none | S217N, then a contiguous triple deletion in residue range 196-201 | ND | — | 48 | ND | — | 19 |
| 51 | TIC807_51 | F46S, Y54H, F147A, G128A, S167R, S217N, then a contiguous triple deletion in residue range 196-201 | F147A | S217N, then a contiguous triple deletion in residue range 196-201 | ND | — | 77 | ND | — | ND |
| 52 | TIC807_52 | F46S, Y54H, F147A, S167R, S217N, M300A, then a contiguous triple deletion in residue range 196-201 | F147A | S217N, then a contiguous triple deletion in residue range 196-201 | ND | — | 73 | ND | — | ND |
| 53 | TIC807_53 | F46S, Y54H, F147A, S167R, S217N, S293A, then a contiguous triple deletion in residue range 196-201 | F147A | S217N, then a contiguous triple deletion in residue range 196-201 | ND | — | 73 | ND | — | ND |
| 54 | TIC807_54 | F46S, Y54H, F147A, S167R, S217N, H287A, then a contiguous triple deletion in residue range 196-201 | F147A | S217N, then a contiguous triple deletion in residue range 196-201 | ND | — | 67 | ND | — | ND |

TABLE 4B-continued

Iterative engineering-testing-selecting of eHTP's against *Lygus* spp. resulted in 267 proteins with enhanced
*Lygus* inhibitory spectrum and/or improved *Lygus* inhibitory activity against *Lygus* spp. compared to TIC807.

| | | Amino acid differences compared to TIC807 parent protein | | | *Lygus hesperus* | | | *Lygus lineolaris* | | |
|---|---|---|---|---|---|---|---|---|---|---|
| | | | | | | | % Mortality | | | % Mortality |
| SEQ ID NO: | Protein Name | Amino acid difference(s) relative to SEQ ID NO: 2 (TIC807) | Amino acid difference(s) in the first patch | Amino acid difference(s) in the second patch | LC50 value (μg/mL) | fold increased toxicity (LC50) | at about 1-3 μg/mL protein* | LC50 value (μg/mL) | fold increased toxicity (LC50) | at about 100 μg/mL protein* |
| 55 | TIC807_55 | F46S, Y54H, F147A, S167R, S217N, T274A, then a contiguous triple deletion in residue range 196-201 | F147A | S217N, then a contiguous triple deletion in residue range 196-201 | ND | — | 65 | ND | — | ND |
| 56 | TIC807_56 | F46S, Y54H, F147A, S167R, S217N, R282A, then a contiguous triple deletion in residue range 196-201 | F147A | S217N, then a contiguous triple deletion in residue range 196-201 | ND | — | 64 | ND | — | ND |
| 57 | TIC807_57 | F46S, Y54H, T93A, S167R, S217N, T308A, then a contiguous triple deletion in residue range 196-201 | T93A | S217N, then a contiguous triple deletion in residue range 196-201 | ND | — | 63 | ND | — | ND |
| 58 | TIC807_58 | F46S, Y54H, Q70A, T93A, S167R, S217N, then a contiguous triple deletion in residue range 196-201 | T93A | S217N, then a contiguous triple deletion in residue range 196-201 | ND | — | 61 | ND | — | ND |
| 59 | TIC807_59 | F46S, Y54H, E125A, F147A, S167R, S217N, then a contiguous triple deletion in residue range 196-201 | F147A | S217N, then a contiguous triple deletion in residue range 196-201 | ND | — | 61 | ND | — | ND |
| 60 | TIC807_60 | F46S, Y54H, F147A, S167R, S217N, T247A, then a contiguous triple deletion in residue range 196-201 | F147A | S217N, then a contiguous triple deletion in residue range 196-201 | ND | — | 61 | ND | — | ND |
| 61 | TIC807_61 | F46S, Y54H, T93A, S167R, S217N, P305A, then a contiguous triple deletion in residue range 196-201 | T93A | S217N, then a contiguous triple deletion in residue range 196-201 | ND | — | 59 | ND | — | ND |
| 62 | TIC807_62 | F46S, Y54H, F147A, S167R, S217N, I306A, then a contiguous triple deletion in residue range 196-201 | F147A | S217N, then a contiguous triple deletion in residue range 196-201 | ND | — | 57 | ND | — | ND |
| 63 | TIC807_63 | F46S, Y54H, T93A, S167R, S217N, R282A, then a contiguous triple deletion in residue range 196-201 | T93A | S217N, then a contiguous triple deletion in residue range 196-201 | ND | — | 56 | ND | — | ND |
| 64 | TIC807_64 | F46S, Y54H, T93A, S167R, S217N, T308A, then a contiguous triple deletion in residue range 196-201 | T93A | S217N, then a contiguous triple deletion in residue range 196-201 | ND | — | 55 | ND | — | ND |
| 65 | TIC807_65 | F46S, Y54H, T93A, S167R, S217N, M300A, then a contiguous triple deletion in residue range 196-201 | T93A | S217N, then a contiguous triple deletion in residue range 196-201 | ND | — | 55 | ND | — | ND |

TABLE 4B-continued

Iterative engineering-testing-selecting of eHTP's against *Lygus* spp. resulted in 267 proteins with enhanced *Lygus* inhibitory spectrum and/or improved *Lygus* inhibitory activity against *Lygus* spp. compared to TIC807.

| | | Amino acid differences compared to TIC807 parent protein | | | *Lygus hesperus* | | | *Lygus lineolaris* | | |
|---|---|---|---|---|---|---|---|---|---|---|
| | | | | | | | % Mortality | | | % Mortality |
| SEQ ID NO: | Protein Name | Amino acid difference(s) relative to SEQ ID NO: 2 (TIC807) | Amino acid difference(s) in the first patch | Amino acid difference(s) in the second patch | LC50 value (μg/mL) | fold increased toxicity (LC50) | at about 1-3 μg/mL protein* | LC50 value (μg/mL) | fold increased toxicity (LC50) | at about 100 μg/mL protein* |
| 66 | TIC807_66 | F46S, Y54H, T93A, S167R, S217N, H287A, then a contiguous triple deletion in residue range 196-201 | T93A | S217N, then a contiguous triple deletion in residue range 196-201 | ND | — | 53 | ND | — | ND |
| 67 | TIC807_67 | F46S, Y54H, S95A, S167R, S217N, M300A, then a contiguous triple deletion in residue range 196-201 | S95A | S217N, then a contiguous triple deletion in residue range 196-201 | ND | — | 52 | ND | — | ND |
| 68 | TIC807_68 | F46S, Y54H, F147A, S167R, S217N, I275A, then a contiguous triple deletion in residue range 196-201 | F147A | S217N, then a contiguous triple deletion in residue range 196-201 | ND | — | 52 | ND | — | ND |
| 69 | TIC807_69 | F46S, Y54H, S95A, S167R, S217N, T247A, then a contiguous triple deletion in residue range 196-201 | S95A | S217N, then a contiguous triple deletion in residue range 196-201 | ND | — | 51 | ND | — | ND |
| 70 | TIC807_70 | F46S, Y54H, F147A, S167R, V175A, S217N, then a contiguous triple deletion in residue range 196-201 | F147A | S217N, then a contiguous triple deletion in residue range 196-201 | ND | — | 50 | ND | — | ND |
| 71 | TIC807_71 | F46S, Y54H, F147A, S159A, S167R, S217N, then a contiguous triple deletion in residue range 196-201 | F147A | S217N, then a contiguous triple deletion in residue range 196-201 | ND | — | 50 | ND | — | ND |
| 72 | TIC807_72 | F46S, Y54H, S95A, F147A, S167R, S217N, then a contiguous triple deletion in residue range 196-201 | S95A, F147A | S217N, then a contiguous triple deletion in residue range 196-201 | ND | — | 48 | ND | — | ND |
| 73 | TIC807_73 | F46S, Y54H, F147A, S167R, L187A, S217N, then a contiguous triple deletion in residue range 196-201 | F147A | S217N, then a contiguous triple deletion in residue range 196-201 | ND | — | 47 | ND | — | ND |
| 74 | TIC807_74 | F46S, Y54H, T93A, S167R, T182A, S217N, then a contiguous triple deletion in residue range 196-201 | T93A | S217N, then a contiguous triple deletion in residue range 196-201 | ND | — | 47 | ND | — | ND |
| 75 | TIC807_75 | F46S, Y54H, F147A, S167R, S217N, T245A, then a contiguous triple deletion in residue range 196-201 | F147A | S217N, then a contiguous triple deletion in residue range 196-201 | ND | — | 46 | ND | — | ND |
| 76 | TIC807_76 | F46S, Y54H, T93A, S167R, S217N, S249A, then a contiguous triple deletion in residue range 196-201 | T93A | S217N, then a contiguous triple deletion in residue range 196-201 | ND | — | 46 | ND | — | ND |

TABLE 4B-continued

Iterative engineering-testing-selecting of eHTP's against *Lygus* spp. resulted in 267 proteins with enhanced *Lygus* inhibitory spectrum and/or improved *Lygus* inhibitory activity against *Lygus* spp. compared to TIC807.

| | | Amino acid differences compared to TIC807 parent protein | | | *Lygus hesperus* | | | *Lygus lineolaris* | | |
|---|---|---|---|---|---|---|---|---|---|---|
| SEQ ID NO: | Protein Name | Amino acid difference(s) relative to SEQ ID NO: 2 (TIC807) | Amino acid difference(s) in the first patch | Amino acid difference(s) in the second patch | LC50 value (µg/mL) | fold increased toxicity (LC50) | % Mortality at about 1-3 µg/mL protein* | LC50 value (µg/mL) | fold increased toxicity (LC50) | % Mortality at about 100 µg/mL protein* |
| 77 | TIC807_77 | F46S, Y54H, T93A, Q149A, S167R, S217N, then a contiguous triple deletion in residue range 196-201 | T93A, Q149A | S217N, then a contiguous triple deletion in residue range 196-201 | ND | — | 45 | ND | — | ND |
| 78 | TIC807_78 | F46S, Y54H, T93A, S151A, S167R, S217N, then a contiguous triple deletion in residue range 196-201 | T93A, S151A | S217N, then a contiguous triple deletion in residue range 196-201 | ND | — | 45 | ND | — | ND |
| 79 | TIC807_79 | F46S, Y54H, Q70A, F147A, S167R, S217N, then a contiguous triple deletion in residue range 196-201 | F147A | S217N, then a contiguous triple deletion in residue range 196-201 | ND | — | 45 | ND | — | ND |
| 80 | TIC807_80 | F46S, Y54H, S95A, Q148A, S167R, S217N, then a contiguous triple deletion in residue range 196-201 | S95A | S217N, then a contiguous triple deletion in residue range 196-201 | ND | — | 44 | ND | — | ND |
| 81 | TIC807_81 | F46S, Y54H, T93A, S167R, S217N, T274A, then a contiguous triple deletion in residue range 196-201 | T93A | S217N, then a contiguous triple deletion in residue range 196-201 | ND | — | 44 | ND | — | ND |
| 82 | TIC807_82 | F46S, Y54H, T93A, S167R, S217N, then a contiguous triple deletion in residue range 196-201 | T93A | S217N, then a contiguous triple deletion in residue range 196-201 | ND | — | 43 | ND | — | ND |
| 83 | TIC807_83 | F46S, Y54H, T93A, S167R, M177A, S217N, then a contiguous triple deletion in residue range 196-201 | T93A | S217N, then a contiguous triple deletion in residue range 196-201 | ND | — | 42 | ND | — | ND |
| 84 | TIC807_84 | F46S, Y54H, S95A, S167R, S217N, V250A, then a contiguous triple deletion in residue range 196-201 | S95A | S217N, then a contiguous triple deletion in residue range 196-201 | ND | — | 42 | ND | — | ND |
| 85 | TIC807_85 | F46S, Y54H, T93A, E155A, S167R, S217N, then a contiguous triple deletion in residue range 196-201 | T93A | S217N, then a contiguous triple deletion in residue range 196-201 | ND | — | 42 | ND | — | ND |
| 86 | TIC807_86 | F46S, Y54H, I134A, F147A, S167R, S217N, then a contiguous triple deletion in residue range 196-201 | F147A | S217N, then a contiguous triple deletion in residue range 196-201 | ND | — | 41 | ND | — | ND |
| 87 | TIC807_87 | F46S, Y54H, T93A, S167R, S217N, T245A, then a contiguous triple deletion in residue range 196-201 | T93A | S217N, then a contiguous triple deletion in residue range 196-201 | ND | — | 41 | ND | — | ND |

TABLE 4B-continued

Iterative engineering-testing-selecting of eHTP's against *Lygus* spp. resulted in 267 proteins with enhanced *Lygus* inhibitory spectrum and/or improved *Lygus* inhibitory activity against *Lygus* spp. compared to TIC807.

| | | Amino acid differences compared to TIC807 parent protein | | | *Lygus hesperus* | | | *Lygus lineolaris* | | |
|---|---|---|---|---|---|---|---|---|---|---|
| | | | | | | | % Mortality | | | % Mortality |
| SEQ ID NO: | Protein Name | Amino acid difference(s) relative to SEQ ID NO: 2 (TIC807) | Amino acid difference(s) in the first patch | Amino acid difference(s) in the second patch | LC50 value (μg/mL) | fold increased toxicity (LC50) | at about 1-3 μg/mL protein* | LC50 value (μg/mL) | fold increased toxicity (LC50) | at about 100 μg/mL protein* |
| 88 | TIC807_88 | F46S, Y54H, T93A, S167R, S217N, then a contiguous triple deletion in residue range 196-201 followed by a S198A | T93A | S217N, then a contiguous triple deletion in residue range 196-201 followed by S198A | ND | — | 40 | ND | — | ND |
| 89 | TIC807_89 | F46S, Y54H, F147A, S167R, S217N, N295A, then a contiguous triple deletion in residue range 196-201 | F147A | S217N, then a contiguous triple deletion in residue range 196-201 | ND | — | 40 | ND | — | ND |
| 90 | TIC807_90 | F46S, Y54H, A87S, F147A, S167R, S217N, then a contiguous triple deletion in residue range 196-201 | F147A | S217N, then a contiguous triple deletion in residue range 196-201 | ND | — | 38 | ND | — | ND |
| 91 | TIC807_91 | F46S, Y54H, F147A, S167R, S217N, S249A, then a contiguous triple deletion in residue range 196-201 | F147A | S217N, then a contiguous triple deletion in residue range 196-201 | ND | — | 38 | ND | — | ND |
| 92 | TIC807_92 | F46S, Y54H, S95A, S167R, S217N, I275A, then a contiguous triple deletion in residue range 196-201 | S95A | S217N, then a contiguous triple deletion in residue range 196-201 | ND | — | 37 | ND | — | ND |
| 93 | TIC807_93 | F46S, Y54H, T93A, A139S, S167R, S217N, then a contiguous triple deletion in residue range 196-201 | T93A | S217N, then a contiguous triple deletion in residue range 196-201 | ND | — | 37 | ND | — | ND |
| 94 | TIC807_94 | F46S, Y54H, F147A, S167R, S217N, P305A, then a contiguous triple deletion in residue range 196-201 | F147A | S217N, then a contiguous triple deletion in residue range 196-201 | ND | — | 36 | ND | — | ND |
| 95 | TIC807_95 | F46S, Y54H, F147A, S167R, S217N, then a contiguous triple deletion in residue range 196-201 followed by a S198A | F147A | S217N, then a contiguous triple deletion in residue range 196-201 followed by S198A | ND | — | 36 | ND | — | ND |
| 96 | TIC807_96 | F46S, Y54H, F147A, S167R, S217N, S252A, then a contiguous triple deletion in residue range 196-201 | F147A | S217N, then a contiguous triple deletion in residue range 196-201 | ND | — | 36 | ND | — | ND |
| 97 | TIC807_97 | F46S, Y54H, T93A, F147A, S167R, S217N, then a contiguous triple deletion in residue range 196-201 | T93A, F147A | S217N, then a contiguous triple deletion in residue range 196-201 | ND | — | 36 | ND | — | ND |
| 98 | TIC807_98 | F46S, Y54H, F147A, S167R, S217N, V250A, then a contiguous triple deletion in residue range 196-201 | F147A | S217N, then a contiguous triple deletion in residue range 196-201 | ND | — | 36 | ND | — | ND |

TABLE 4B-continued

Iterative engineering-testing-selecting of eHTP's against *Lygus* spp. resulted in 267 proteins with enhanced *Lygus* inhibitory spectrum and/or improved *Lygus* inhibitory activity against *Lygus* spp. compared to TIC807.

| | | Amino acid differences compared to TIC807 parent protein | | | | *Lygus hesperus* | | | *Lygus lineolaris* | |
|---|---|---|---|---|---|---|---|---|---|---|
| SEQ ID NO: | Protein Name | Amino acid difference(s) relative to SEQ ID NO: 2 (TIC807) | Amino acid difference(s) in the first patch | Amino acid difference(s) in the second patch | LC50 value (μg/mL) | fold increased toxicity (LC50) | % Mortality at about 1-3 μg/mL protein* | LC50 value (μg/mL) | fold increased toxicity (LC50) | % Mortality at about 100 μg/mL protein* |
| 99 | TIC807_99 | F46S, Y54H, F147A, S167R, S217N, T243A, then a contiguous triple deletion in residue range 196-201 | F147A | S217N, then a contiguous triple deletion in residue range 196-201 | ND | — | 35 | ND | — | ND |
| 100 | TIC807_100 | F46S, Y54H, F147A, S167R, S217N, then a contiguous triple deletion in residue range 196-201 followed by a Y197A | F147A | S217N, then a contiguous triple deletion in residue range 196-201 followed by a Y197A | ND | — | 35 | ND | — | ND |
| 101 | TIC807_101 | F46S, Y54H, S95A, S167R, S217N, N295A, then a contiguous triple deletion in residue range 196-201 | S95A | S217N, then a contiguous triple deletion in residue range 196-201 | ND | — | 35 | ND | — | ND |
| 102 | TIC807_102 | F46S, Y54H, F147A, S167R, S217N, then a contiguous triple deletion in residue range 196-201 | F147A | S217N, then a contiguous triple deletion in residue range 196-201 | ND | — | 34 | ND | — | ND |
| 103 | TIC807_103 | F46S, Y54H, F147A, S167R, S217N, E299A, then a contiguous triple deletion in residue range 196-201 | F147A | S217N, then a contiguous triple deletion in residue range 196-201 | ND | — | 32 | ND | — | ND |
| 104 | TIC807_104 | F46S, Y54H, S95A, S167R, S217N, R282A, then a contiguous triple deletion in residue range 196-201 | S95A | S217N, then a contiguous triple deletion in residue range 196-201 | ND | — | 32 | ND | — | ND |
| 105 | TIC807_105 | F46S, Y54H, T93A, S167R, S217N, I306A, then a contiguous triple deletion in residue range 196-201 | T93A | S217N, then a contiguous triple deletion in residue range 196-201 | ND | — | 32 | ND | — | ND |
| 106 | TIC807_106 | F46S, Y54H, S95A, S167R, S217N, S249A, then a contiguous triple deletion in residue range 196-201 | S95A | S217N, then a contiguous triple deletion in residue range 196-201 | ND | — | 30 | ND | — | ND |
| 107 | TIC807_107 | F46S, Y54H, A87S, T93A, S167R, S217N, then a contiguous triple deletion in residue range 196-201 | T93A | S217N, then a contiguous triple deletion in residue range 196-201 | ND | — | 30 | ND | — | ND |
| 108 | TIC807_108 | F46S, Y54H, T93A, S159A, S167R, S217N, then a contiguous triple deletion in residue range 196-201 | T93A | S217N, then a contiguous triple deletion in residue range 196-201 | ND | — | 29 | ND | — | ND |
| 109 | TIC807_109 | F46S, Y54H, F147A, S167R, S217N, T303A, then a contiguous triple deletion in residue range 196-201 | F147A | S217N, then a contiguous triple deletion in residue range 196-201 | ND | — | 28 | ND | — | ND |

TABLE 4B-continued

Iterative engineering-testing-selecting of eHTP's against *Lygus* spp. resulted in 267 proteins with enhanced *Lygus* inhibitory spectrum and/or improved *Lygus* inhibitory activity against *Lygus* spp. compared to TIC807.

| | | Amino acid differences compared to TIC807 parent protein | | | *Lygus hesperus* | | | *Lygus lineolaris* | | |
|---|---|---|---|---|---|---|---|---|---|---|
| | | | | | LC50 value (μg/mL) | fold increased toxicity (LC50) | % Mortality at about 1-3 μg/mL protein* | LC50 value (μg/mL) | fold increased toxicity (LC50) | % Mortality at about 100 μg/mL protein* |
| SEQ ID NO: | Protein Name | Amino acid difference(s) relative to SEQ ID NO: 2 (TIC807) | Amino acid difference(s) in the first patch | Amino acid difference(s) in the second patch | | | | | | |
| 110 | TIC807_110 | F46S, Y54H, T93A, Q148A, S167R, S217N, then a contiguous triple deletion in residue range 196-201 | T93A | S217N, then a contiguous triple deletion in residue range 196-201 | ND | — | 27 | ND | — | ND |
| 111 | TIC807_111 | F46S, Y54H, S95A, S167R, V175N, S217N, then a contiguous triple deletion in residue range 196-201 | S95A | S217N, then a contiguous triple deletion in residue range 196-201 | ND | — | 27 | ND | — | ND |
| 112 | TIC807_112 | F46S, Y54H, F147A, S167R, S217N, D241A, then a contiguous triple deletion in residue range 196-201 | F147A | S217N, then a contiguous triple deletion in residue range 196-201 | ND | — | 27 | ND | — | ND |
| 113 | TIC807_113 | F46S, Y54H, S95A, F147A, S167R, S217N, then a contiguous triple deletion in residue range 196-201 | S95A, F147A | S217N, then a contiguous triple deletion in residue range 196-201 | ND | — | 26 | ND | — | ND |
| 114 | TIC807_114 | F46S, Y54H, F147A, S167R, M177A, S217N, then a contiguous triple deletion in residue range 196-201 | F147A | S217N, then a contiguous triple deletion in residue range 196-201 | ND | — | 26 | ND | — | ND |
| 115 | TIC807_115 | F46S, Y54H, F147A, S167R, S217N, M300A, then a contiguous triple deletion in residue range 196-201 | F147A | S217N, then a contiguous triple deletion in residue range 196-201 | ND | — | 26 | ND | — | ND |
| 116 | TIC807_116 | F46S, Y54H, S95A, S167R, S217N, P305A, then a contiguous triple deletion in residue range 196-201 | S95A | S217N, then a contiguous triple deletion in residue range 196-201 | ND | — | 26 | ND | — | ND |
| 117 | TIC807_117 | F46S, Y54H, F147A, S167R, S217N, then a contiguous triple deletion in residue range 196-201 followed by H196A | F147A | S217N, then a contiguous triple deletion in residue range 196-201 followed by H196A | ND | — | 25 | ND | — | ND |
| 118 | TIC807_118 | F46S, Y54H, A139S, F147A, S167R, S217N, then a contiguous triple deletion in residue range 196-201 | F147A | S217N, then a contiguous triple deletion in residue range 196-201 | ND | — | 25 | ND | — | ND |
| 119 | TIC807_119 | F46S, Y54H, T93A, S167R, S217N, N295A, then a contiguous triple deletion in residue range 196-201 | T93A | S217N, then a contiguous triple deletion in residue range 196-201 | ND | — | 25 | ND | — | ND |
| 120 | TIC807_120 | F46S, Y54H, T93A, T145A, S167R, S217N, then a contiguous triple deletion in residue range 196-201 | T93A | S217N, then a contiguous triple deletion in residue range 196-201 | ND | — | 24 | ND | — | ND |

TABLE 4B-continued

Iterative engineering-testing-selecting of eHTP's against *Lygus* spp. resulted in 267 proteins with enhanced *Lygus* inhibitory spectrum and/or improved *Lygus* inhibitory activity against *Lygus* spp. compared to TIC807.

| SEQ ID NO: | Protein Name | Amino acid differences compared to TIC807 parent protein | | | *Lygus hesperus* | | | *Lygus lineolaris* | | |
|---|---|---|---|---|---|---|---|---|---|---|
| | | Amino acid difference(s) relative to SEQ ID NO: 2 (TIC807) | Amino acid difference(s) in the first patch | Amino acid difference(s) in the second patch | LC50 value (µg/mL) | fold increased toxicity (LC50) | % Mortality at about 1-3 µg/mL protein* | LC50 value (µg/mL) | fold increased toxicity (LC50) | % Mortality at about 100 µg/mL protein* |
| 121 | TIC807_121 | F46S, Y54H, S117A, F147A, S167R, S217N, then a contiguous triple deletion in residue range 196-201 | F147A | S217N, then a contiguous triple deletion in residue range 196-201 | ND | — | 24 | ND | — | ND |
| 122 | TIC807_122 | F46S, Y54H, T93A, S167R, S217N, I275A, then a contiguous triple deletion in residue range 196-201 | T93A | S217N, then a contiguous triple deletion in residue range 196-201 | ND | — | 23 | ND | — | ND |
| 123 | TIC807_123 | F46S, Y54H, S95A, S167R, S217N, H287A, then a contiguous triple deletion in residue range 196-201 | S95A | S217N, then a contiguous triple deletion in residue range 196-201 | ND | — | 23 | ND | — | ND |
| 124 | TIC807_124 | F46S, Y54H, S95A, G105A, S167R, S217N, then a contiguous triple deletion in residue range 196-201 | S95A | S217N, then a contiguous triple deletion in residue range 196-201 | ND | — | 21 | ND | — | ND |
| 125 | TIC807_125 | F46S, Y54H, S95A, S167R, S217N, then a contiguous triple deletion in residue range 196-201 | S95A | S217N, then a contiguous triple deletion in residue range 196-201 | ND | — | 20 | ND | — | ND |
| 126 | TIC807_126 | F46S, Y54H, S95A, I134A, S167R, S217N, then a contiguous triple deletion in residue range 196-201 | S95A | S217N, then a contiguous triple deletion in residue range 196-201 | ND | — | 20 | ND | — | ND |
| 127 | TIC807_127 | F46S, Y54H, T93A, S167R, S217N, M300A, then a contiguous triple deletion in residue range 196-201 | T93A | S217N, then a contiguous triple deletion in residue range 196-201 | ND | — | 20 | ND | — | ND |
| 128 | TIC807_128 | F46S, Y54H, T93A, S167R, S217N, T303A, then a contiguous triple deletion in residue range 196-201 | T93A | S217N, then a contiguous triple deletion in residue range 196-201 | ND | — | 18 | ND | — | ND |
| 129 | TIC807_129 | F46S, Y54H, T93A, A150S, S167R, S217N, then a contiguous triple deletion in residue range 196-201 | T93A | S217N, then a contiguous triple deletion in residue range 196-201 | ND | — | 18 | ND | — | ND |
| 130 | TIC807_130 | F46S, Y54H, S95A, E155A, S167R, S217N, then a contiguous triple deletion in residue range 196-201 | S95A | S217N, then a contiguous triple deletion in residue range 196-201 | ND | — | 18 | ND | — | ND |
| 131 | TIC807_131 | F46S, Y54H, T93A, T145A, S167R, S217N, then a contiguous triple deletion in residue range 196-201 | T93A | S217N, then a contiguous triple deletion in residue range 196-201 | ND | — | 17 | ND | — | ND |

TABLE 4B-continued

Iterative engineering-testing-selecting of eHTP's against *Lygus* spp. resulted in 267 proteins with enhanced *Lygus* inhibitory spectrum and/or improved *Lygus* inhibitory activity against *Lygus* spp. compared to TIC807.

| | | Amino acid differences compared to TIC807 parent protein | | | *Lygus hesperus* | | | *Lygus lineolaris* | | |
|---|---|---|---|---|---|---|---|---|---|---|
| | | | | | | | % Mortality | | | % Mortality |
| SEQ ID NO: | Protein Name | Amino acid difference(s) relative to SEQ ID NO: 2 (TIC807) | Amino acid difference(s) in the first patch | Amino acid difference(s) in the second patch | LC50 value (µg/mL) | fold increased toxicity (LC50) | at about 1-3 µg/mL protein* | LC50 value (µg/mL) | fold increased toxicity (LC50) | at about 100 µg/mL protein* |
| 132 | TIC807_132 | F46S, Y54H, S95A, S167R, W208A, S217N, then a contiguous triple deletion in residue range 196-201 | S95A | W208A, S217N, then a contiguous triple deletion in residue range 196-201 | ND | — | 17 | ND | — | ND |
| 133 | TIC807_133 | F46S, Y54H, S95A, S167R, T182A, S217N, then a contiguous triple deletion in residue range 196-201 | S95A, T182A | S217N, then a contiguous triple deletion in residue range 196-201 | ND | — | 17 | ND | — | ND |
| 134 | TIC807_134 | F46S, Y54H, T93A, S167R, S217N, T243A, then a contiguous triple deletion in residue range 196-201 | T93A | S217N, then a contiguous triple deletion in residue range 196-201 | ND | — | 17 | ND | — | ND |
| 135 | TIC807_135 | F46S, Y54H, S95A, S167R, S217N, I306A, then a contiguous triple deletion in residue range 196-201 | S95A | S217N, then a contiguous triple deletion in residue range 196-201 | ND | — | 16 | ND | — | ND |
| 136 | TIC807_136 | F46S, Y54H, S95A, S117A, S167R, S217N, then a contiguous triple deletion in residue range 196-201 | S95A | S217N, then a contiguous triple deletion in residue range 196-201 | ND | — | 16 | ND | — | ND |
| 137 | TIC807_137 | F46S, Y54H, T93A, S119A, S167R, S217N, then a contiguous triple deletion in residue range 196-201 | T93A | S217N, then a contiguous triple deletion in residue range 196-201 | ND | — | 15 | ND | — | ND |
| 138 | TIC807_138 | F46S, Y54H, T68A, F147A, S167R, S217N, then a contiguous triple deletion in residue range 196-201 | F147A | S217N, then a contiguous triple deletion in residue range 196-201 | ND | — | 15 | ND | — | ND |
| 139 | TIC807_139 | F46S, Y54H, G105A, F147A, S167R, S217N, then a contiguous triple deletion in residue range 196-201 | F147A | S217N, then a contiguous triple deletion in residue range 196-201 | ND | — | 15 | ND | — | ND |
| 140 | TIC807_140 | F46S, Y54H, S95A, E125A, S167R, S217N, then a contiguous triple deletion in residue range 196-201 | S95A | S217N, then a contiguous triple deletion in residue range 196-201 | ND | — | 15 | ND | — | ND |
| 141 | TIC807_141 | F46S, Y54H, T93A, E155A, S167R, S217N, then a contiguous triple deletion in residue range 196-201 | T93A | S217N, then a contiguous triple deletion in residue range 196-201 | ND | — | 14 | ND | — | ND |
| 142 | TIC807_142 | F46S, Y54H, T93A, S167R, S217N, P305A, then a contiguous triple deletion in residue range 196-201 | T93A | S217N, then a contiguous triple deletion in residue range 196-201 | ND | — | 14 | ND | — | ND |

TABLE 4B-continued

Iterative engineering-testing-selecting of eHTP's against *Lygus* spp. resulted in 267 proteins with enhanced *Lygus* inhibitory spectrum and/or improved *Lygus* inhibitory activity against *Lygus* spp. compared to TIC807.

| | | Amino acid differences compared to TIC807 parent protein | | | *Lygus hesperus* | | | *Lygus lineolaris* | | |
|---|---|---|---|---|---|---|---|---|---|---|
| | | | | | | | % Mortality | | | % Mortality |
| SEQ ID NO: | Protein Name | Amino acid difference(s) relative to SEQ ID NO: 2 (TIC807) | Amino acid difference(s) in the first patch | Amino acid difference(s) in the second patch | LC50 value (µg/mL) | fold increased toxicity (LC50) | at about 1-3 µg/mL protein* | LC50 value (µg/mL) | fold increased toxicity (LC50) | at about 100 µg/mL protein* |
| 143 | TIC807_143 | F46S, Y54H, S95A, S167R, M177A, S217N, then a contiguous triple deletion in residue range 196-201 | S95A | S217N, then a contiguous triple deletion in residue range 196-201 | ND | — | 13 | ND | — | ND |
| 144 | TIC807_144 | F46S, Y54H, T93A, S167R, S217N, then a contiguous triple deletion in residue range 196-201 followed by H196A | T93A | S217N, then a contiguous triple deletion in residue range 196-201 followed by H196A | ND | — | 13 | ND | — | ND |
| 145 | TIC807_145 | F46S, Y54H, T93A, D153A, S167R, S217N, then a contiguous triple deletion in residue range 196-201-T93A-D153A | T93A | S217N, then a contiguous triple deletion in residue range 196-201 | ND | — | 11 | ND | — | ND |
| 146 | TIC807_146 | F46S, Y54H, F147A, S167R, S217N, W208A, then a contiguous triple deletion in residue range 196-201 | F147A | W208A, S217N, then a contiguous triple deletion in residue range 196-201 | ND | — | 10 | ND | — | ND |
| 147 | TIC807_147 | F46S, Y54H, T93A, S167R, S217N, I306A, then a contiguous triple deletion in residue range 196-201 | T93A | S217N, then a contiguous triple deletion in residue range 196-201 | ND | — | 9 | ND | — | ND |
| 148 | TIC807_148 | F46S, Y54H, S95A, S167R, S217N, then a contiguous triple deletion in residue range 196-201 followed by H196A | S95A | S217N, then a contiguous triple deletion in residue range 196-201 followed by H196A | ND | — | 9 | ND | — | ND |
| 149 | TIC807_149 | F46S, Y54H, S95A, Q149A, S167R, S217N, then a contiguous triple deletion in residue range 196-201 | S95A, Q149A | S217N, then a contiguous triple deletion in residue range 196-201 | ND | — | 9 | ND | — | ND |
| 150 | TIC807_150 | F46S, Y54H, S95A, S167R, S217N, S293A, then a contiguous triple deletion in residue range 196-201 | S95A | S217N, then a contiguous triple deletion in residue range 196-201 | ND | — | 8 | ND | — | ND |
| 151 | TIC807_151 | F46S, Y54H, S95A, A150S, S167R, S217N, then a contiguous triple deletion in residue range 196-201 | S95A | S217N, then a contiguous triple deletion in residue range 196-201 | ND | — | 8 | ND | — | ND |
| 152 | TIC807_152 | F46S, Y54H, S119A, F147A, S167R, S217N, then a contiguous triple deletion in residue range 196-201 | F147A | S217N, then a contiguous triple deletion in residue range 196-201 | ND | — | 7 | ND | — | ND |
| 153 | TIC807_153 | F46S, Y54H, S95A, S167A, S217N, then a contiguous triple deletion in residue range 196-201 | S95A | S217N, then a contiguous triple deletion in residue range 196-201 | ND | — | 7 | ND | — | ND |

TABLE 4B-continued

Iterative engineering-testing-selecting of eHTP's against *Lygus* spp. resulted in 267 proteins with enhanced *Lygus* inhibitory spectrum and/or improved *Lygus* inhibitory activity against *Lygus* spp. compared to TIC807.

| | | Amino acid differences compared to TIC807 parent protein | | | | *Lygus hesperus* | | | *Lygus lineolaris* | |
|---|---|---|---|---|---|---|---|---|---|---|
| | | | | | | | | % Mortality | | % Mortality |
| SEQ ID NO: | Protein Name | Amino acid difference(s) relative to SEQ ID NO: 2 (TIC807) | Amino acid difference(s) in the first patch | Amino acid difference(s) in the second patch | LC50 value (µg/mL) | fold increased toxicity (LC50) | at about 1-3 µg/mL protein* | LC50 value (µg/mL) | fold increased toxicity (LC50) | at about 100 µg/mL protein* |
| 154 | TIC807_154 | F46S, Y54H, F147A, I158A, S167R, S217N, then a contiguous triple deletion in residue range 196-201 | F147A | S217N, then a contiguous triple deletion in residue range 196-201 | ND | — | 7 | ND | — | ND |
| 155 | TIC807_155 | F46S, Y54H, S95A, S167R, S217N, M300A, then a contiguous triple deletion in residue range 196-201 | S95A | S217N, then a contiguous triple deletion in residue range 196-201 | ND | — | 7 | ND | — | ND |
| 156 | TIC807_156 | F46S, Y54H, F147A, T182A, S167R, S217N, then a contiguous triple deletion in residue range 196-201 | F147A, T182A | S217N, then a contiguous triple deletion in residue range 196-201 | ND | — | 6 | ND | — | ND |
| 157 | TIC807_157 | F46S, Y54H, F147A, S167R, S217N, F235A, then a contiguous triple deletion in residue range 196-201 | F147A | S217N, then a contiguous triple deletion in residue range 196-201 | ND | — | 5 | ND | — | ND |
| 158 | TIC807_158 | F46S, Y54H, F147A, S167R, S217N, then a contiguous triple deletion in residue range 196-201 | F147A | S217N, then a contiguous triple deletion in residue range 196-201 | ND | — | 5 | ND | — | ND |
| 159 | TIC807_159 | F46S, Y54H, T93A, S167R, S217N, D241A, then a contiguous triple deletion in residue range 196-201 | T93A | S217N, then a contiguous triple deletion in residue range 196-201 | ND | — | 5 | ND | — | ND |
| 160 | TIC807_160 | F46S, Y54H, S95A, S167R, S217N, T274A, then a contiguous triple deletion in residue range 196-201 | S95A | S217N, then a contiguous triple deletion in residue range 196-201 | ND | — | 4 | ND | — | ND |
| 161 | TIC807_161 | F46S, Y54H, T93A, Q148A, S167R, S217N, then a contiguous triple deletion in residue range 196-201 | T93A | S217N, then a contiguous triple deletion in residue range 196-201 | ND | — | 4 | ND | — | ND |
| 162 | TIC807_162 | F46S, Y54H, S95A, S167R, S217N, D241A, then a contiguous triple deletion in residue range 196-201 | S95A | S217N, then a contiguous triple deletion in residue range 196-201 | ND | — | 4 | ND | — | ND |
| 163 | TIC807_163 | F46S, Y54H, S95A, E155A, S167R, S217N, then a contiguous triple deletion in residue range 196-201 | S95A | S217N, then a contiguous triple deletion in residue range 196-201 | ND | — | 4 | ND | — | ND |
| 164 | TIC807_164 | F46S, Y54H, T93A, S167R, L187A, S217N, then a contiguous triple deletion in residue range 196-201 | T93A | S217N, then a contiguous triple deletion in residue range 196-201 | ND | — | 4 | ND | — | ND |

TABLE 4B-continued

Iterative engineering-testing-selecting of eHTP's against *Lygus* spp. resulted in 267 proteins with enhanced *Lygus* inhibitory spectrum and/or improved *Lygus* inhibitory activity against *Lygus* spp. compared to TIC807.

| | | Amino acid differences compared to TIC807 parent protein | | | *Lygus hesperus* | | | *Lygus lineolaris* | | |
|---|---|---|---|---|---|---|---|---|---|---|
| | | | | | | | % Mortality | | | % Mortality |
| SEQ ID NO: | Protein Name | Amino acid difference(s) relative to SEQ ID NO: 2 (TIC807) | Amino acid difference(s) in the first patch | Amino acid difference(s) in the second patch | LC50 value (μg/mL) | fold increased toxicity (LC50) | at about 1-3 μg/mL protein* | LC50 value (μg/mL) | fold increased toxicity (LC50) | at about 100 μg/mL protein* |
| 165 | TIC807_165 | F46S, Y54H, T93A, S167R, S217N, T303A, then a contiguous triple deletion in residue range 196-201 | T93A | S217N, then a contiguous triple deletion in residue range 196-201 | ND | — | 4 | ND | — | ND |
| 166 | TIC807_166 | F46S, Y54H, T93A, E155A, S167R, S217N, then a contiguous triple deletion in residue range 196-201 | T93A | S217N, then a contiguous triple deletion in residue range 196-201 | ND | — | 3 | ND | — | ND |
| 167 | TIC807_167 | F46S, Y54H, T93A, D153A, S167R, S217N, then a contiguous triple deletion in residue range 196-201 | T93A | S217N, then a contiguous triple deletion in residue range 196-201 | ND | — | 3 | ND | — | ND |
| 168 | TIC807_168 | F46S, Y54H, T93A, I134A, S167R, S217N, then a contiguous triple deletion in residue range 196-201 | T93A | S217N, then a contiguous triple deletion in residue range 196-201 | ND | — | 3 | ND | — | ND |
| 169 | TIC807_169 | N137T | none | None | ND | — | 44* | ND | — | ND |
| 169 | TIC807_169 | E135S | none | None | ND | — | 20* | ND | — | ND |
| 169 | TIC807_169 | N137T, E135S | none | None | ND | — | 34* | ND | — | ND |
| 169 | TIC807_169 | E135T, N137D | none | None | ND | — | 16* | ND | — | ND |
| 169 | TIC807_169 | T133E | none | None | ND | — | 60* | ND | — | ND |
| 169 | TIC807_169 | E135A, N137G | none | None | ND | — | 50* | ND | — | ND |
| 170 | TIC807_170 | E125C | none | None | ND | — | 12 | ND | — | ND |
| 170 | TIC807_170 | E125H | none | None | ND | — | 38 | ND | — | ND |
| 170 | TIC807_170 | E125R | none | None | ND | — | 14 | ND | — | ND |
| 170 | TIC807_170 | E125F | none | None | ND | — | 33 | ND | — | ND |
| 170 | TIC807_170 | E125S | none | None | ND | — | 24 | ND | — | ND |
| 170 | TIC807_170 | E125Q | none | None | ND | — | 21 | ND | — | ND |
| 170 | TIC807_170 | E125K | none | None | ND | — | 20 | ND | — | ND |
| 170 | TIC807_170 | E125T | none | None | ND | — | 33 | ND | — | ND |
| 170 | TIC807_170 | E125N | none | None | ND | — | 19 | ND | — | ND |
| 170 | TIC807_170 | E125A | none | None | ND | — | 41 | ND | — | ND |
| 170 | TIC807_170 | E125L | none | None | ND | — | 13 | ND | — | ND |
| 170 | TIC807_170 | E125V | none | None | ND | — | 14 | ND | — | ND |
| 170 | TIC807_170 | E125M | none | None | ND | — | 13 | ND | — | ND |
| 170 | TIC807_170 | E125D | none | None | ND | — | 15 | ND | — | ND |
| 170 | TIC807_170 | E125Y | none | None | ND | — | 38 | ND | — | ND |
| 171 | TIC807_171 | T133E | none | None | ND | — | 23 | ND | — | ND |
| 171 | TIC807_171 | T133Y | none | None | ND | — | 17 | ND | — | ND |
| 171 | TIC807_171 | T133W | none | None | ND | — | 13 | ND | — | ND |
| 172 | TIC807_172 | I134V | none | None | ND | — | 18 | ND | — | ND |
| 172 | TIC807_172 | I134L | none | None | ND | — | 10 | ND | — | ND |
| 172 | TIC807_172 | I134F | none | None | ND | — | 18 | ND | — | ND |
| 172 | TIC807_172 | I134K | none | None | ND | — | 13 | ND | — | ND |
| 172 | TIC807_172 | I134C | none | None | ND | — | 30 | ND | — | ND |
| 172 | TIC807_172 | I134M | none | None | ND | — | 33 | ND | — | ND |
| 173 | TIC807_173 | E135V | none | None | ND | — | 13 | ND | — | ND |
| 173 | TIC807_173 | E135W | none | None | ND | — | 13 | ND | — | ND |
| 173 | TIC807_173 | E135T | none | None | ND | — | 39 | ND | — | ND |
| 174 | TIC807_174 | N137H | none | None | ND | — | 42 | ND | — | ND |
| 174 | TIC807_174 | N137Y | none | None | ND | — | 17 | ND | — | ND |
| 174 | TIC807_174 | N137T | none | None | ND | — | 31 | ND | — | ND |
| 174 | TIC807_174 | N137E | none | None | ND | — | 32 | ND | — | ND |
| 174 | TIC807_174 | N137S | none | None | ND | — | 24 | ND | — | ND |
| 174 | TIC807_174 | N137A | none | None | ND | — | 24 | ND | — | ND |
| 174 | TIC807_174 | N137Q | none | None | ND | — | 21 | ND | — | ND |
| 174 | TIC807_174 | N137G | none | None | ND | — | 18 | ND | — | ND |
| 174 | TIC807_174 | N137I | none | None | ND | — | 10 | ND | — | ND |

TABLE 4B-continued

Iterative engineering-testing-selecting of eHTP's against *Lygus* spp. resulted in 267 proteins with enhanced *Lygus* inhibitory spectrum and/or improved *Lygus* inhibitory activity against *Lygus* spp. compared to TIC807.

| | | Amino acid differences compared to TIC807 parent protein | | | | *Lygus hesperus* | | | *Lygus lineolaris* | |
|---|---|---|---|---|---|---|---|---|---|---|
| | | | | | | | % Mortality | | | % Mortality |
| SEQ ID NO: | Protein Name | Amino acid difference(s) relative to SEQ ID NO: 2 (TIC807) | Amino acid difference(s) in the first patch | Amino acid difference(s) in the second patch | LC50 value (µg/mL) | fold increased toxicity (LC50) | at about 1-3 µg/mL protein* | LC50 value (µg/mL) | fold increased toxicity (LC50) | at about 100 µg/mL protein* |
| 174 | TIC807_174 | N137W | none | None | ND | — | 17 | ND | — | ND |
| 174 | TIC807_174 | N137K | none | None | ND | — | 66 | ND | — | ND |
| 174 | TIC807_174 | N137C | none | None | ND | — | 19 | ND | — | ND |
| 174 | TIC807_174 | N137M | none | None | ND | — | 41 | ND | — | ND |
| 174 | TIC807_174 | N137D | none | None | ND | — | 69 | ND | — | ND |
| 174 | TIC807_174 | N137F | none | None | ND | — | 13 | ND | — | ND |
| 174 | TIC807_174 | N137R | none | None | ND | — | 37 | ND | — | ND |
| 175 | TIC807_175 | F147V | F147V | None | ND | — | 87 | ND | — | ND |
| 175 | TIC807_175 | F147T | F147T | None | ND | — | 68 | ND | — | ND |
| 175 | TIC807_175 | F147C | F147C | None | ND | — | 74 | ND | — | ND |
| 175 | TIC807_175 | F147L | F147L | None | ND | — | 62 | ND | — | ND |
| 175 | TIC807_175 | F147D | F147D | None | ND | — | 51 | ND | — | ND |
| 175 | TIC807_175 | F147A | F147A | None | ND | — | 57 | ND | — | ND |
| 175 | TIC807_175 | F147G | F147G | None | ND | — | 56 | ND | — | ND |
| 175 | TIC807_175 | F147E | F147E | None | ND | — | 50 | ND | — | ND |
| 175 | TIC807_175 | F147I | F147I | None | ND | — | 69 | ND | — | ND |
| 175 | TIC807_175 | F147Y | F147Y | None | ND | — | 67 | ND | — | ND |
| 175 | TIC807_175 | F147M | F147M | None | ND | — | 64 | ND | — | ND |
| 175 | TIC807_175 | F147N | F147N | None | ND | — | 64 | ND | — | ND |
| 175 | TIC807_175 | F147Q | F147Q | None | ND | — | 50 | ND | — | ND |
| 175 | TIC807_175 | F147H | F147H | None | ND | — | 60 | ND | — | ND |
| 175 | TIC807_175 | F147R | F147R | None | ND | — | 20 | ND | — | ND |
| 175 | TIC807_175 | F147W | F147W | None | ND | — | 82 | ND | — | ND |
| 175 | TIC807_175 | F147P | F147P | None | ND | — | 7 | ND | — | ND |
| 176 | TIC807_176 | Q149D | Q149D | None | ND | — | 92 | ND | — | ND |
| 176 | TIC807_176 | Q149E | Q149E | None | ND | — | 89 | ND | — | ND |
| 176 | TIC807_176 | Q149C | Q149C | None | ND | — | 87 | ND | — | ND |
| 176 | TIC807_176 | Q149A | Q149A | None | ND | — | 76 | ND | — | ND |
| 176 | TIC807_176 | Q149F | Q149F | None | ND | — | 54 | ND | — | ND |
| 177 | TIC807_177 | A150S | none | None | ND | — | 34 | ND | — | ND |
| 177 | TIC807_177 | A150L | none | None | ND | — | 24 | ND | — | ND |
| 177 | TIC807_177 | A150V | none | None | ND | — | 25 | ND | — | ND |
| 177 | TIC807_177 | A150G | none | None | ND | — | 28 | ND | — | ND |
| 177 | TIC807_177 | A150D | none | None | ND | — | 19 | ND | — | ND |
| 177 | TIC807_177 | A150W | none | None | ND | — | 13 | ND | — | ND |
| 177 | TIC807_177 | A150E | none | None | ND | — | 24 | ND | — | ND |
| 177 | TIC807_177 | A150N | none | None | ND | — | 18 | ND | — | ND |
| 177 | TIC807_177 | A150Y | none | None | ND | — | 11 | ND | — | ND |
| 177 | TIC807_177 | A150F | none | None | ND | — | 11 | ND | — | ND |
| 177 | TIC807_177 | A150P | none | None | ND | — | 11 | ND | — | ND |
| 177 | TIC807_177 | A150K | none | None | ND | — | 17 | ND | — | ND |
| 177 | TIC807_177 | A150T | none | None | ND | — | 17 | ND | — | ND |
| 177 | TIC807_177 | A150Q | none | None | ND | — | 11 | ND | — | ND |
| 177 | TIC807_177 | A150R | none | None | ND | — | 11 | ND | — | ND |
| 178 | TIC807_178 | E155C | none | None | ND | — | 82 | ND | — | ND |
| 178 | TIC807_178 | E155I | none | None | ND | — | 36 | ND | — | ND |
| 178 | TIC807_178 | E155K | none | None | ND | — | 28 | ND | — | ND |
| 178 | TIC807_178 | E155D | none | None | ND | — | 22 | ND | — | ND |
| 178 | TIC807_178 | E155H | none | None | ND | — | 22 | ND | — | ND |
| 178 | TIC807_178 | E155Y | none | None | ND | — | 16 | ND | — | ND |
| 178 | TIC807_178 | E155Q | none | None | ND | — | 16 | ND | — | ND |
| 178 | TIC807_178 | E155L | none | None | ND | — | 15 | ND | — | ND |
| 178 | TIC807_178 | E155N | none | None | ND | — | 14 | ND | — | ND |
| 178 | TIC807_178 | E155T | none | None | ND | — | 13 | ND | — | ND |
| 178 | TIC807_178 | E155A | none | None | ND | — | 11 | ND | — | ND |
| 178 | TIC807_178 | E155F | none | None | ND | — | 7 | ND | — | ND |
| 178 | TIC807_178 | E155R | none | None | ND | — | 6 | ND | — | ND |
| 178 | TIC807_178 | E155M | none | None | ND | — | 6 | ND | — | ND |
| 178 | TIC807_178 | E155P | none | None | ND | — | 5 | ND | — | ND |
| 178 | TIC807_178 | E155W | none | None | ND | — | 5 | ND | — | ND |
| 178 | TIC807_178 | E155S | none | None | ND | — | 4 | ND | — | ND |
| 178 | TIC807_178 | E155V | none | None | ND | — | 4 | ND | — | ND |
| 179 | TIC807_179 | N157C | none | None | ND | — | 86 | ND | — | ND |
| 179 | TIC807_179 | N157D | none | None | ND | — | 64 | ND | — | ND |
| 179 | TIC807_179 | N157W | none | None | ND | — | 52 | ND | — | ND |
| 179 | TIC807_179 | N157Y | none | None | ND | — | 39 | ND | — | ND |

TABLE 4B-continued

Iterative engineering-testing-selecting of eHTP's against *Lygus* spp. resulted in 267 proteins with enhanced *Lygus* inhibitory spectrum and/or improved *Lygus* inhibitory activity against *Lygus* spp. compared to TIC807.

| | | Amino acid differences compared to TIC807 parent protein | | | *Lygus hesperus* | | | *Lygus lineolaris* | | |
|---|---|---|---|---|---|---|---|---|---|---|
| | | | | | | | % Mortality | | | % Mortality |
| SEQ ID NO: | Protein Name | Amino acid difference(s) relative to SEQ ID NO: 2 (TIC807) | Amino acid difference(s) in the first patch | Amino acid difference(s) in the second patch | LC50 value (µg/mL) | fold increased toxicity (LC50) | at about 1-3 µg/mL protein* | LC50 value (µg/mL) | fold increased toxicity (LC50) | at about 100 µg/mL protein* |
| 179 | TIC807_179 | N157M | none | None | ND | — | 22 | ND | — | ND |
| 179 | TIC807_179 | N157A | none | None | ND | — | 22 | ND | — | ND |
| 179 | TIC807_179 | N157F | none | None | ND | — | 20 | ND | — | ND |
| 179 | TIC807_179 | N157V | none | None | ND | — | 18 | ND | — | ND |
| 179 | TIC807_179 | N157L | none | None | ND | — | 18 | ND | — | ND |
| 179 | TIC807_179 | N157P | none | None | ND | — | 18 | ND | — | ND |
| 179 | TIC807_179 | N157E | none | None | ND | — | 17 | ND | — | ND |
| 179 | TIC807_179 | N157T | none | None | ND | — | 8 | ND | — | ND |
| 179 | TIC807_179 | N157G | none | None | ND | — | 7 | ND | — | ND |
| 179 | TIC807_179 | N157I | none | None | ND | — | 7 | ND | — | ND |
| 179 | TIC807_179 | N157R | none | None | ND | — | 6 | ND | — | ND |
| 202 | TIC807_M8_d5C | F46S, Y54H, S95A, F147A, S167R, S217N, then a five amino acid deletion at 305-309, then a contiguous triple deletion in residue range 196-201 | S95A, F147A | S217N, then a contiguous triple deletion in residue range 196-201 | ND | — | 92* | ND | — | ND |
| 204 | TIC807_M14 | F46S, Y54H, S95A, F147A, Q149E, S167R, P219R, S249R, V251E, Q253R, R273W, then a contiguous triple deletion in residue range 196-201 | S95A, F147A, Q149E, V251E, Q253R | P219R, then a contiguous triple deletion in residue range 196-201 | ND | — | — | ND | — | 60* |

ND = Not Determined;
*tested at about 5 µg/mL.

Example 5: Insect Inhibitory Activities of Protein Members of the Present Invention Proteins of the present invention, such as but not limited to TIC807 M1 (SEQ ID NO:6), TIC807 M2 (SEQ ID NO:8), TIC807 M3 (SEQ ID NO:10), TIC807 M4 (SEQ ID NO:12), TIC807 M5 (SEQ ID NO:14), TIC807 M6 (SEQ ID NO:16), TIC807 M7 (SEQ ID NO:18), TIC807 M8 (SEQ ID NO:20), TIC807 M9 (SEQ ID NO:22), TIC807 M14 (SEQ ID NO:32), TIC807 M15 (SEQ ID NO:34), and TIC807 M16 (SEQ ID NO:36), are prepared and tested for bioactivity against pests of plants other than from *Lygus*.

Proteins TIC807 M10 (SEQ ID NO:24), TIC807 M11 (SEQ ID NO:26), TIC807 M12 (SEQ ID NO:28), and TIC807 M13 (SEQ ID NO:30) were prepared and tested for bioactivity against pests from the order Lepidoptera, Coleoptera, Heteroptera, and Homoptera. Protein TIC807 M5 (SEQ ID NO:14) was prepared and tested for bioactivity against Coleopteran pests. Bioassays were conducted to evaluate the effects of these proteins on insects as shown in Table 5. Feeding assays were conducted on an artificial diet containing the insecticidal protein. The insecticidal protein was prepared as described in example 3 and topically applied using an insect-specific artificial diet, depending on the insect being tested. The toxin was suspended in a buffer and applied at a rate of 500 µg/mL of sample per well, and in the case of TIC807 M5 of 1000 µg/mL, and then allowed to dry. Mean stunting scores and population mortalities were determined on three populations of 8 insects per insect species tested. Results were expressed as positive (+) for insect reactions such as stunting and mortality that were statistically significant compared to the untreated control. Results were expressed as negative (−) if the insects were similar to the UTC, that is, feeding diet to which the above buffer only has been applied.

TABLE 5 eHTP's demonstrate additional insect inhibitory activities against pests other than *Lygus* spp.

| Protein | µg/mL | CPB | WCR | ECB | SWCB | CEW | FAW | SGSB | NBSB | GPA |
|---|---|---|---|---|---|---|---|---|---|---|
| UTC | 0 | − | − | − | − | − | − | − | − | − |
| TIC807 M5 | 1000 | + | − | ND | ND | ND | ND | ND | ND | ND |
| TIC807 M10 | 500 | − | − | − | − | − | − | − | − | − |
| TIC807 M11 | 500 | + | − | − | − | − | − | − | − | − |

TABLE 5-continued eHTP's demonstrate additional insect inhibitory activities against pests other than *Lygus* spp.

| Protein | µg/mL | CPB | WCR | ECB | SWCB | CEW | FAW | SGSB | NBSB | GPA |
|---|---|---|---|---|---|---|---|---|---|---|
| TIC807 M12 | 500 | − | − | − | − | − | − | − | − | − |
| TIC807 M13 | 500 | + | − | − | − | − | − | − | − | − |

UTC = UnTreated Control;
ND = Not Determined
CPB = Colorado potato beetle (*Leptinotarsa decemlineata*);
WCR = western corn rootworm (*Diabrotica virgifera*);
ECB = European corn borer (*Ostrinia nubilalis*); southwestern corn borer (*Diatraea grandiosella*);
CEW = corn earworm (*Helicoverpa zea*);
FAW = Fall armyworm (*Spodoptera frugiperda*);
SGSB = southern green stink bug (*Nezara virudula*);
NBSB = neotropical brown stink bug (*Euschistus heros*);
GPA = Green peach aphid (*Myzus persicae*).

The proteins of the present invention are also tested for bioactivity against a pest from the phylum Nematoda.

Example 6: Plants Expressing Proteins of the Present Invention Exhibit Insect Inhibitory Activity This example illustrates expression of proteins of the present invention in plants, and demonstrates that cotton plants expressing proteins of the present invention exhibit insect inhibitory activity.

Polynucleotide segments for use in expression of the proteins of the present invention in plants are made according to the methods set forth in U.S. Pat. No. 7,741,118. For example, toxin proteins having the amino acid sequence as set forth in SEQ ID NO:4 (TIC807 4), SEQ ID NO:6 (TIC807 M1), SEQ ID NO:8 (TIC807 M2), SEQ ID NO: 10 (TIC807 M3), SEQ ID NO: 12 (TIC807 M4), SEQ ID NO:14 (TIC807 M5), SEQ ID NO:16 (TIC807 M8), SEQ ID NO:18 (TIC807 M6). SEQ ID NO:20 (TIC807 M7), SEQ ID NO:22 (TIC807 22), SEQ ID NO:24 (TIC807 24), SEQ ID NO:26 (TIC807 26), SEQ ID NO:28 (TIC807 M9), SEQ ID NO:30 (TIC807 M10), SEQ ID NO:32 (TIC807 M11), and SEQ ID NO:34 (TIC807 M13), are expressed from polynucleotide segments designed for use in plants and encoding the proteins of the present invention, including the polynucleotide sequences as set forth in SEQ ID NO:186, SEQ ID NO: 187, SEQ ID NO: 188, SEQ ID NO:189, SEQ ID NO:190, SEQ ID NO:191, SEQ ID NO:192, SEQ ID NO:193, SEQ ID NO:194, SEQ ID NO: 195, SEQ ID NO: 196, SEQ ID NO: 197, SEQ ID NO: 198, SEQ ID NO: 199. SEQ ID NO:200, and SEQ ID NO:201, respectively.

It is intended that polynucleotide segments (or polynucleotide molecules) encoding each of the variant proteins or insect inhibitory fragments thereof, be used alone or in combination with each other, or in combination with other insect inhibitory proteins or insect inhibitory agents such as dsRNA mediated gene suppression molecules. Such combinations designed to work in synergistic or compatible mechanism with the proteins of the present invention. The intention of these combinations is to achieve plants and plant cells protected from pest, particularly insect pest, infestation. The specific variant proteins within the scope of the invention include the proteins corresponding to SEQ ID NOs listed in Table 4B and described throughout the application as filed.

Polynucleotide segments from SEQ ID NO: 188 (encodes for TIC807 M2, SEQ ID NO:8) and from SEQ ID NO:192 (encodes for TIC807 M8, SEQ ID NO:16) were each recombinantly engineered into expression constructs for cotton transformation.

Transgenic cotton plants (recombinant cotton plants) were produced and tested for efficacy. Regenerated (RO) transgenic plants were selected that were low in copy number and high in expression of the respective variant protein, as determined by various quantitative and semi-quantitative methods, e.g. PCR. ELISAs and Westerns. Expression levels in RO cotton leaf tissue typically ranged from 0.5 to 500 ppm fresh weight. RO plants expressing high levels of protein were transferred to soil and selfed. Thirty seed from each of the selfed RO plants were planted and progeny homozygous for the transgene were grown to flowering. Eleven to 18 plants per 4 to 5 events per each construct of this example were tested for efficacy against *Lygus* (Tables 6A, 6B, and 6C). The untransformed cotton cultivar, plants from the pooled negative segregate population (progeny not containing the transgene), and plants expressing TIC807 parent protein served as negative controls. A branch of a flowering stage cotton plant was enclosed in a mesh bag made from breathable plastic 'pollination' sleeves (Vilutis and Co. Inc., Frankfort, IL), and multiple branches set up in similar fashion. Each mesh bag was secured at the stem using a twist tie. About 4-6 *Lygus hesperus* nymphs (<24 hours post-hatch) were placed into a 1.4 ml conical tube (Matrix Technologies Corp., NH). The branch inside a mesh bag was infested with nymphs by sliding the uncapped conical tube into the mesh bag. Insects were allowed to feed for a period of 10-11 days before all surviving insects in the mesh bag were collected on dry ice. Survivors were weighed to obtain a gross mass. Percent mortality and mean survivor mass were calculated. Missing insects were included in the mortality percent mortality calculation. As shown in Tables 6A, 6B, and 6C, cotton plants expressing the variant proteins TIC807 M2 and TIC807 M8 significantly impacted the growth and development of *Lygus hesperus* nymphs. Based on these results, these plants, seed, expression constructs were advanced for further development.

TABLE 6A

Mean % mortality determined from flowering stage *Lygus* feeding assays with cotton plants expressing the variant TIC807 proteins TIC807 M2 and TIC807 M8.

| Plant Event ID | Protein | N | Mean % Mortality | Std Dev | SEM | Lo 95% | Up 95% | Mortality t group |
|---|---|---|---|---|---|---|---|---|
| 64 | TIC807 M8 | 18 | 78.889 | 19.967 | 4.706 | 68.959 | 88.818 | A |
| 49 | TIC807 M8 | 18 | 75.556 | 22.288 | 5.253 | 64.472 | 86.639 | A |
| 91 | TIC807 M2 | 18 | 74.444 | 20.356 | 4.798 | 64.321 | 84.567 | A |
| 20 | TIC807 M8 | 18 | 73.333 | 19.403 | 4.573 | 63.685 | 82.982 | A |
| 15 | TIC807 M8 | 18 | 66.667 | 25.668 | 6.050 | 53.902 | 79.431 | AB |
| 58 | TIC807 M2 | 18 | 65.556 | 19.166 | 4.517 | 56.025 | 75.086 | AB |
| 48 | TIC807 M2 | 18 | 64.444 | 21.206 | 4.998 | 53.899 | 74.990 | AB |
| 19 | TIC807 M2 | 18 | 53.333 | 25.668 | 6.050 | 40.569 | 66.098 | BC |
| 68 | TIC807 M2 | 18 | 47.778 | 25.795 | 6.080 | 34.950 | 60.605 | C |
| Negative | | 24 | 41.667 | 22.001 | 4.491 | 32.376 | 50.957 | C |

TABLE 6B

Mean Instar determined from flowering stage *Lygus* feeding assays with cotton plants expressing the variant TIC807 proteins TIC807 M2 and TIC807 M8.

| Plant Event ID | Construct | N | Mean Instar | Std Dev | SEM | Lo 95% | Up 95% | Instar t group |
|---|---|---|---|---|---|---|---|---|
| 64 | TIC807 M8 | 11 | 3.636 | 0.552 | 0.166 | 3.266 | 4.007 | C |
| 68 | TIC807 M2 | 16 | 3.949 | 0.803 | 0.201 | 3.521 | 4.377 | BC |
| 48 | TIC807 M2 | 16 | 4.042 | 0.604 | 0.151 | 3.720 | 4.364 | BC |
| 58 | TIC807 M2 | 17 | 4.069 | 0.802 | 0.194 | 3.657 | 4.481 | BC |
| 15 | TIC807 M8 | 15 | 4.094 | 0.747 | 0.193 | 3.681 | 4.508 | BC |
| 19 | TIC807 M2 | 17 | 4.100 | 0.698 | 0.169 | 3.741 | 4.459 | BC |
| 91 | TIC807 M2 | 12 | 4.125 | 0.829 | 0.239 | 3.598 | 4.652 | ABC |
| 49 | TIC807 M8 | 12 | 4.139 | 0.762 | 0.220 | 3.655 | 4.623 | ABC |
| 20 | TIC807 M8 | 14 | 4.298 | 0.918 | 0.245 | 3.768 | 4.828 | AB |
| Negative | | 24 | 4.599 | 0.774 | 0.158 | 4.273 | 4.926 | A |

TABLE 6C

Mean Survival Mass determined from flowering stage *Lygus* feeding assays with cotton plants expressing the variant TIC807 proteins TIC807 M2 and TIC807 M8.

| Plant Event ID | Construct | N | Mean Survival Mass | Std Dev | SEM | Lo 95% | Up 95% | Survivor Mass t group |
|---|---|---|---|---|---|---|---|---|
| 64 | TIC807 M8 | 11 | 2.315 | 1.489 | 0.449 | 1.314 | 3.315 | C |
| 68 | TIC807 M2 | 16 | 3.548 | 1.325 | 0.331 | 2.843 | 4.254 | B |
| 58 | TIC807 M2 | 17 | 3.561 | 1.348 | 0.327 | 2.868 | 4.255 | B |
| 48 | TIC807 M2 | 16 | 3.596 | 1.436 | 0.359 | 2.831 | 4.362 | B |
| 91 | TIC807 M2 | 12 | 3.775 | 1.775 | 0.512 | 2.647 | 4.902 | AB |
| 49 | TIC807 M8 | 12 | 3.837 | 2.135 | 0.616 | 2.481 | 5.193 | AB |
| 19 | TIC807 M2 | 17 | 3.908 | 1.467 | 0.356 | 3.154 | 4.662 | AB |
| 20 | TIC807 M8 | 14 | 3.918 | 1.950 | 0.521 | 2.792 | 5.044 | AB |
| 15 | TIC807 M8 | 15 | 3.937 | 1.906 | 0.492 | 2.881 | 4.993 | AB |
| Negative | | 24 | 4.735 | 1.179 | 0.241 | 4.237 | 5.233 | A |

Std Dev = standard deviation
SEM = Standard error on the mean
Lo 95% = Lower limit at 95% confidence interval
Up 95% = Upper limit at 95% confidence interval
T grouping = Using a least significant difference test,
F value = 101.1756,
df = 15, 44,
Pr < 0.0001

In another example, cotton plants from five transgenic events expressing TIC807 M11 were tested in a field trial having natural *Lygus* infestation pressures. These plants demonstrated field efficacy compared to the non-transgenic recipient line (DP393 germplasm used for transformation). The average number of *Lygus lineolaris* insects on five plants per event was significantly lower than the average number of *Lygus lineolaris* insects on plants from the non-transgenic control. Seed cotton yield from plants from the five events was statistically comparable to seed cotton yield of the non-transgenic control, e.g. season-long square retention.

In another similar field trial, cotton plants from seven transgenic events expressing TIC807 M10 demonstrated field efficacy compared to the non-transgenic control. The average number of *Lygus lineolaris* insects on five plants per event was significantly lower than the average number of *Lygus lineolaris* insects on plants from the non-transgenic control. Seed cotton yield from plants from three of the seven events was statistically higher than to seed cotton yield of the non-transgenic control.

In another example, cotton plants from thirty-four transgenic events expressing TIC807 M13 demonstrated growth chamber efficacy compared to the non-transgenic control. Mesh bags were placed around the whole cotton plants at flowering stage (instead of just around single branches described earlier in this example). Five plants per event were evaluated and the average number of *Lygus lineolaris* insects recovered (nymphs to adults to $2^{nd}$ generation *Lygus*) per plant was significantly lower than the average number of *Lygus lineolaris* insects per non-transgenic plant.

Similar experiments are performed with plants expressing proteins listed in Table 1 and in Tables 4A and 4B.

Example 7: Tissue from Alfalfa Plants Expressing Proteins of the Present Invention Exhibit Insect Inhibitory Activity This example illustrates expression of proteins of the present invention in alfalfa plants, and demonstrates that tissue from alfalfa plants expressing proteins of the present invention exhibit insect inhibitory activity.

Polynucleotide segment from SEQ ID NO:192 (encodes for TIC807 M8, SEQ ID NO:16) was recombinantly engineered into three differently configured expression constructs for alfalfa transformation. For purposes of data reporting, the three recombinant constructs are coded [ER], [ES], and [ET].

Transgenic alfalfa plants (recombinant alfalfa plants) were recovered from transformants that were outcrossed and then selfed. Recombinant alfalfa plants were selected that were low in copy number and high in TIC807 expression as determined by RT-PCR and semi-quantitative Western methods, respectively. Alfalfa plant tissue from ten separate events were pooled, lyophilized, ground, and resuspended in stock buffer, 25 mM NaCarb, pH10.5. Plant tissue from Alfalfa having no TIC807 M8 expressing transgene was prepared for use as control. Stock preparations were serially diluted 100, 300, and 900 fold for incorporation into *Lygus* diet. Using the feeding assay method of Example 4, mortality and stunting scores were determined on day 5 and compared to controls (See Tables 7A and 7B; data were analyzed using JMP4 statistical software). For each test sample and each dilution, three populations of eight nymphs were subjected to this bioassay. Stunting scores correspond to visual mass ratings where 0=no difference to negative control, 1=about 25% less mass, 2=about 50% less mass, and 3=about 75% less mass. The average of the stunting scores for each population of eight nymphs is reported.

TABLE 7A

Mean % mortality determined from *Lygus* feeding assays with diet incorporated with tissue from alfalfa plants expressing the variant TIC807 protein TIC807 M8.

| Construct | Sample Source | Dilution fold | Mean Stunting Score | Std Dev | SEM | Lower 95% | Upper 95% | t Grouping |
|---|---|---|---|---|---|---|---|---|
| [ER] TIC807 M8 | Pooled Alfalfa tissue from 10 events per construct | 100 | 2.00 | 0.00 | 0.00 | 2.00 | 2.00 | CD |
|  |  | 300 | 0.00 | 0.00 | 0.00 | 0.00 | 0.00 | E |
|  |  | 900 | 0.00 | 0.00 | 0.00 | 0.00 | 0.00 | E |
| [ES] TIC807 M8 |  | 100 | 3.00 | 0.00 | 0.00 | 3.00 | 3.00 | A |
|  |  | 300 | 2.33 | 0.58 | 0.33 | 0.90 | 3.77 | BC |
|  |  | 900 | 0.00 | 0.00 | 0.00 | 0.00 | 0.00 | E |
| [ET] TIC807 M8 |  | 100 | 2.67 | 0.58 | 0.33 | 1.23 | 4.10 | AB |
|  |  | 300 | 1.67 | 0.58 | 0.33 | 0.23 | 3.10 | D |
|  |  | 900 | 0.00 | 0.00 | 0.00 | 0.00 | 0.00 | E |
| None | Control Alfalfa | 100 | 2.00 | 0.00 | 0.00 | 2.00 | 2.00 | CD |
|  |  | 300 | 0.00 | 0.00 | 0.00 | 0.00 | 0.00 | E |
|  |  | 900 | 0.00 | 0.00 | 0.00 | 0.00 | 0.00 | E |
| No Alfalfa incorporated in the diet |  | 0 | 0.00 | 0.00 | 0.00 | 0.00 | 0.00 | E |

TABLE 7B

Mean stunting determined from *Lygus* feeding assays with diet incorporated with tissue from alfalfa plants expressing the variant TIC807 protein TIC807 M8.

| Construct | Sample Source | Dilution fold | Mean Percent mortality | Std Dev | SEM | Lower 95% | Upper 95% | t Grouping |
|---|---|---|---|---|---|---|---|---|
| [ER] TIC807 M8 | Pooled Alfalfa tissue from 10 events per construct | 100 | 4.17 | 7.22 | 4.17 | −13.76 | 22.09 | CD |
|  |  | 300 | 0.00 | 0.00 | 0.00 | 0.00 | 0.00 | CD |
|  |  | 900 | 13.10 | 12.54 | 7.24 | −18.06 | 44.25 | CD |
| [ES] TIC807 M8 |  | 100 | 56.55 | 6.27 | 3.62 | 40.97 | 72.12 | AB |
|  |  | 300 | 41.67 | 19.09 | 11.02 | −5.77 | 89.10 | B |
|  |  | 900 | 0.00 | 0.00 | 0.00 | 0.00 | 0.00 | CD |
| [ET] TIC807 M8 |  | 100 | 64.88 | 19.91 | 11.50 | 15.42 | 114.34 | A |
|  |  | 300 | 16.67 | 19.09 | 11.02 | −30.77 | 64.10 | C |
|  |  | 900 | 12.50 | 12.50 | 7.22 | −18.55 | 43.55 | CD |

TABLE 7B-continued

Mean stunting determined from Lygus feeding assays with diet incorporated with tissue from alfalfa plants expressing the variant TIC807 protein TIC807 M8.

| Construct | Sample Source | Dilution fold | Mean Percent mortality | Std Dev | SEM | Lower 95% | Upper 95% | t Grouping |
|---|---|---|---|---|---|---|---|---|
| None | Control Alfalfa | | 12.50 | 12.50 | 7.22 | −18.55 | 43.55 | CD |
| | | | 0.00 | 0.00 | 0.00 | 0.00 | 0.00 | CD |
| | | | 8.33 | 14.43 | 8.33 | −27.52 | 44.19 | CD |
| No Alfalfa incorporated in the diet | | 0 | 2.50 | 7.01 | 1.81 | −1.38 | 6.38 | D |

Example 8: Plants Co-Expressing an eHTP and a Second Insect Inhibitory Protein Exhibiting *Lygus* Species Inhibitory Activity Protein samples were prepared containing various mixtures of TIC1415 and TIC807_M13 and tested in bioassay. The TIC1415 protein and other *Lygus* inhibitory proteins are described in PCT Patent Application Publication No. WO 2012/139004. Sample mixtures were fed to *Lygus lineolaris* using bioactivity assay. TIC1415 protein alone and TIC807_M13 alone were also prepared as positive controls. Buffer was used as negative control. Samples from all three types of preparations exhibited mortality against *Lygus lineolaris* and survivors were stunted. Mortality and stunting scores were significant compared to bioactivity scores of insects fed with buffer (see Table 8A). The data suggests that there are no antagonistic effects. Additional bioassay tests are performed on mixtures to demonstrate synergistic and/or additive effects.

TABLE 8A

Bioassay data for protein mix: TIC1415 combined with TIC807_M13

| SAMPLE | TIC1415 (μg/mL) | TIC807_M13 (μg/mL) | Mean Population mortality | T Grouping on mort | Mean stuntingt score | T Grouping on stunting |
|---|---|---|---|---|---|---|
| TIC1415 + TIC807_M13 | 4.35 | 1 | 21.79 | AB* | 0.60 | AB* |
| TIC1415 + TIC807_M13 | 2.175 | 1 | 20.36 | B* | 0.60 | AB* |
| TIC1415 + TIC807_M13 | 1.0875 | 1 | 12.50 | BC | 0.60 | AB* |
| TIC1415 + TIC807_M13 | 4.35 | 0.5 | 32.50 | A* | 0.80 | A* |
| TIC1415 + TIC807_M13 | 1.75 | 0.265 | 7.86 | CD | 0.40 | ABC |
| TIC1415 + TIC807_M13 | 0.875 | 0.265 | 0.00 | D | 0.00 | C |
| TIC1415 + TIC807_M13 | 0.4375 | 0.265 | 5.36 | CD | 0.00 | C |
| TIC1415 + TIC807_M13 | 4.35 | 0.25 | 13.21 | BC | 0.40 | ABC |
| TIC1415 + TIC807_M13 | 1.75 | 0.1325 | 0.00 | D | 0.00 | C |
| TIC1415 + TIC807_M13 | 1.75 | 0.06625 | 0.00 | D | 0.00 | C |
| TIC1415 | 4.35 | 0 | 12.50 | BC | 0.40 | ABC |
| TIC1415 | 1.75 | 0 | 7.86 | CD | 0.00 | C |
| TIC807_M13 | 0 | 1 | 0.00 | D | 0.20 | BC |
| TIC807_M13 | 0 | 0.265 | 2.50 | CD | 0.00 | C |
| Buffer (negative) | 0 | 0 | 0.00 | D | 0.00 | C |

Average (mean) of 5 populations of 8 nymphs per population.

Stunting scores correspond to visual mass ratings where 0 = no difference to negative control, 1 = about 25% less mass, 2 = about 50% less mass, and 3 = about 75% less mass. The average of the stunting scores for each population of eight nymphs is reported.

*At 95% confidence interval.

Cotton plants comprising events with transgenic DNA were designed to co-express respective proteins TIC1415 and TIC807_M13. Such plants were evaluated in a caged whole plant assay infested with *Lygus lineolaris*. Five plants each from ten events were caged and infested with 2 pairs of male and female *L. lineolaris* per plant. The assay was incubated in a growth chamber under normal environmental conditions for cotton plant development for 21 days. DP393 negative control plants were grown in similar manner. At the end of the 3 week period. *Lygus* of various stages of development were counted. The mean number per plant of *Lygus hesperus* insects at each stage in development were calculated (see Table 8B).

TABLE 8B

In-planta data for for protein mix: TIC1415 combined with TIC807_M13

| Constru. | Event | N | Mean 3rd Instar or < | Mean 4th Instar Nymph | Mean 5th Instar Nymph | Mean Live 2nd Gen. Adults | Mean Total 2nd Gen. *Lygus* | SEM | Tukey Groupi |
|---|---|---|---|---|---|---|---|---|---|
| 12 | 021 | 5 | 0.00 | 0.00 | 0.00 | 0.00 | 0.00 | 0.00 | B |
| | 625 | 5 | 0.20 | 0.20 | 0.20 | 0.00 | 0.60 | 0.24 | B |
| | 830 | 5 | 2.20 | 0.20 | 0.00 | 0.00 | 2.40 | 1.12 | AB |
| | 890 | 5 | 4.40 | 0.00 | 0.20 | 0.00 | 4.60 | 2.62 | AB |
| | 521 | 5 | 4.60 | 0.60 | 0.00 | 0.00 | 5.20 | 4.27 | AB |
| | 980 | 5 | 3.40 | 1.20 | 1.20 | 0.00 | 5.80 | 4.86 | AB |
| 13 | 426 | 5 | 0.00 | 0.00 | 0.00 | 0.00 | 0.00 | 0.00 | B |
| | 611 | 5 | 0.60 | 0.00 | 0.00 | 0.00 | 0.60 | 0.60 | B |
| | 999 | 5 | 0.40 | 0.00 | 0.40 | 0.00 | 0.80 | 0.37 | B |
| | 356 | 5 | 6.20 | 0.00 | 0.40 | 0.00 | 6.60 | 4.73 | AB |
| Inbred | DP393 (Negative) | 10 | 7.00 | 2.50 | 0.80 | 0.00 | 10.30 | 3.75 | A |

What is claimed is:

1. An insect inhibitory recombinant polypeptide comprising the amino acid sequence as set forth in SEQ ID NO: 12.

2. The insect inhibitory recombinant polypeptide of claim 1, wherein the polypeptide exhibits inhibitory activity against an insect species of the order Hemiptera.

3. The insect inhibitory recombinant polypeptide of claim 2, wherein the Hemipteran species is selected from the group consisting of a *Lygus* sp., an Emrasca sp., and an *Amrasca* sp.

4. The insect inhibitory recombinant polypeptide of claim 2, wherein the Hemipteran species is selected from the group consisting of *Lygus Hesperus, Lygus lineolaris,* and *Amrasca devastans.*

5. A polynucleotide encoding the insect inhibitory recombinant polypeptide of claim 1.

6. The polynucleotide of claim 5, wherein the polynucleotide comprises the nucleotide sequence as set forth in SEQ ID NO: 11.

7. A host cell comprising the polynucleotide of claim 5, wherein the host cell is selected from the group consisting of a bacterial host cell and a plant host cell.

8. The host cell of claim 7, wherein the bacterial host cell is selected from the group consisting of *Agrobacterium, Rhizobium, Bacillus, Escherichia, Pseudomonas,* and *Salmonella; and wherein the Bacillus* species is a *Bacillus thuringiensis,* and the *Escherichia* is an *Escherichia coli.*

9. The host cell of claim 7, wherein the plant host cell is selected from the group consisting of a monocot cell and a dicot cell.

10. An insect inhibitory composition comprising the insect inhibitory recombinant polypeptide of claim 1.

11. The composition of claim 10, wherein the composition is prepared by lyophilization, extraction, filtration, or centrifugation.

12. The insect inhibitory composition of claim 10, further comprising at least one insect inhibitory agent different from the insect inhibitory recombinant polypeptide.

13. The insect inhibitory composition of claim 12, wherein the at least one insect inhibitory agent is selected from the group consisting of an insect inhibitory protein, an insect inhibitory dsRNA molecule, and an insect inhibitory chemistry.

14. The insect inhibitory composition of claim 12, wherein the at least one insect inhibitory agent exhibits activity against one or more pest species of the order Lepidoptera, Coleoptera, Hemiptera, or Homoptera.

15. A seed comprising the polynucleotide of claim 5.

16. The seed of claim 15, wherein the polynucleotide comprises the sequence as set forth in SEQ ID NO: 11.

17. A method of controlling a Hemipteran pest, the method comprising presenting the Hemipteran pest with an inhibitory amount of the insect inhibitory recombinant polypeptide of claim 1.

18. The method of claim 17, wherein said presenting is via expressing the insect inhibitory recombinant polypeptide in a cotton plant.

19. A transgenic plant cell, plant, or plant part comprising the insect inhibitory recombinant polypeptide of claim 1.

20. A method of controlling a Hemipteran pest, comprising exposing the Hemipteran pest to the transgenic plant cell, plant or plant part of claim 19, wherein the plant cell, plant or plant part expresses a Hemipteran inhibitory amount of the insect inhibitory recombinant polypeptide.

21. A commodity product obtained from the plant cell, plant, or plant part of claim 19, wherein the commodity product comprises a detectable amount of the insect inhibitory recombinant polypeptide, wherein the commodity product is selected from the group consisting of plant biomass, oil, meal, animal feed, flour, flakes, bran, lint, hulls, and processed seed.

22. A method of producing a seed, the method comprising:
  a. planting at least one seed comprising a polynucleotide encoding the insect inhibitory recombinant polypeptide of claim 1;
  b. growing at least one plant from the at least one seed; and
  c. harvesting a seed from the at least one plant, wherein the harvested seed comprises the polynucleotide encoding the insect inhibitory recombinant polypeptide.

* * * * *

SEQUENCE LISTING

```
Sequence total quantity: 206
SEQ ID NO: 1            moltype = DNA  length = 927
FEATURE                 Location/Qualifiers
misc_feature            1..927
                        note = A sequence representing a recombinant polynucleotide
                         derived from a native gene from a Bacillus thuringiensis
                         (Bt) species encoding a TIC807 protein.
source                  1..927
                        mol_type = other DNA
                        organism = Bacillus thuringiensis
SEQUENCE: 1
atggctatcc tagaccttaa gtccctcgtg ctgaacgcca ttaactactg gggccctaag  60
aacaacaacg gcatccaggg cggtgacttc ggctacccca tctctgagaa gcagatcgac  120
actagcatca ttaccttcac ccaccctcgc ttgatcccct acgatcttac tatcccgcag  180
aaccttgaga ccatcttcac cacaacgcag gtgctcacca ataacactga cctccagcaa  240
tcccagaccg tgagctttgc gaagaagacc actaccacga cctcaactag cacgaccaac  300
ggttggacag aaggaggcaa gatcagcgac acgctggagg agaaagtttc ggttagcatt  360
ccgttcatcg gtgagggtgg cgggaagaac tcgactacca tagaggccaa cttcgcacac  420
aactctagca ccactacctt ccagcaagca agcactgaca ttgagtggaa cattagccaa  480
ccggtgctgg ttcctccctc taaacaagtt gtcgcgaccc ttgtgatcat gggaggcaac  540
tttaccatcc ctatggactt gatgaccacg attgatagta cagagcacta ctcccactac  600
tccggttacc ctatcctcac ctggatctcg tccccagata actcttactc cggtcccttt  660
atgtcatggt actttgcaaa ctggcctaac cttccgagtg gattcggccc actgaatagt  720
gataacacgg tcacatacac tggctctgtc gtgtcccaag tttcggccgg tgtctacgct  780
accgtccggt tcgatcagta tgacattcac aatctccgta ctatcgagaa gacttggtat  840
gctcgccatg cgacgctgca taatggcaag aagatttcta tcaacaatgt cacggaaatg  900
gctccaacat cccctatcaa gacaaat                                      927

SEQ ID NO: 2            moltype = AA  length = 309
FEATURE                 Location/Qualifiers
REGION                  1..309
                        note = engineered
REGION                  1..309
                        note = TIC807
REGION                  1..309
                        note = The amino acid sequence translation of of the open
                         reading frame of SEQ ID NO: 1 from nucleotides 1 through
```

```
                              927.
source                        1..309
                              mol_type = protein
                              organism = synthetic construct
SEQUENCE: 2
MAILDLKSLV LNAINYWGPK NNNGIQGGDF GYPISEKQID TSIITFTHPR LIPYDLTIPQ    60
NLETIFTTTQ VLTNNTDLQQ SQTVSFAKKT TTTTSTSTTN GWTEGGKISD TLEEKVSVSI   120
PFIGEGGGKN STTIEANFAH NSSTTTFQQA STDIEWNISQ PVLVPPSKQV VATLVIMGGN   180
FTIPMDLMTT IDSTEHYSHY SGYPILTWIS SPDNSYSGPF MSWYFANWPN LPSGFGPLNS   240
DNTVTYTGSV VSQVSAGVYA TVRFDQYDIH NLRTIEKTWY ARHATLHNGK KISINNVTEM   300
APTSPIKTN                                                          309

SEQ ID NO: 3                  moltype = DNA  length = 927
FEATURE                       Location/Qualifiers
misc_feature                  1..927
                              note = engineered
misc_feature                  1..927
                              note = A nucleotide sequence encoding SEQ ID NO: 4 with an
                               open reading frame from 1 to 927.
source                        1..927
                              mol_type = other DNA
                              organism = synthetic construct
SEQUENCE: 3
atggctatcc tagaccttaa gtccctcgtg ctgaacgcca ttaactactg gggccctaag    60
aacaacaacg gcatccaggg cggtgacttc ggctacccca tctctgagaa gcagatcgac   120
actagcatca ttaccttcac ccaccctcgc ttgatccctt acgatcttac tatcccgcag   180
aaccttgaga ccatcttcac cacaacgcag gtgctcacca ataacactga cctccagcaa   240
tcccagaccg tgagctttgc gaagaagacc actaccacga cctcaactag cacgaccaac   300
ggttggacag aaggaggcaa gatcagcgac acgctgaggg agaaagtttc ggttagcatt   360
ccgttcatcg gtgcgggtgg cgggaagaac tcgactacca tagaggccaa cttcgcacac   420
aactctagca ccactacctt ccagcaagca agcactgaca ttgagtggaa cattagccaa   480
ccggtgctgg ttcctccctc taaacaagtt gtcgcgaccc ttgtgatcat gggaggcaac   540
tttaccatcc ctatggactt gatgaccacg attgatagta cagagcacta ctcccactac   600
tccggttacc ctatcctcac ctggatctcg tccccagata actcttactc cggtcccttt   660
atgtcatggt actttgcaaa ctggcctaac cttccgagtg gattcggccc actgaatagt   720
gataacacgg tcacatacac tggctctgtc gtgtcccaag tttcggccgg tgtctacgct   780
accgtccggt tcgatcagta tgacattcac aatctccgta ctatcgagaa gacttggtat   840
gctcgccatg cgacgctgca taatgggcaa gaagatttcta tcaacaatgt cacggaaatg   900
gctccaacat cccctatcaa gacaaat                                      927

SEQ ID NO: 4                  moltype = AA  length = 309
FEATURE                       Location/Qualifiers
REGION                        1..309
                              note = engineered
REGION                        1..309
                              note = The amino acid sequence translation of of the open
                               reading frame set forth as SEQ ID NO: 3.
source                        1..309
                              mol_type = protein
                              organism = synthetic construct
SEQUENCE: 4
MAILDLKSLV LNAINYWGPK NNNGIQGGDF GYPISEKQID TSIITFTHPR LIPYDLTIPQ    60
NLETIFTTTQ VLTNNTDLQQ SQTVSFAKKT TTTTSTSTTN GWTEGGKISD TLEEKVSVSI   120
PFIGAGGGKN STTIEANFAH NSSTTTFQQA STDIEWNISQ PVLVPPSKQV VATLVIMGGN   180
FTIPMDLMTT IDSTEHYSHY SGYPILTWIS SPDNSYSGPF MSWYFANWPN LPSGFGPLNS   240
DNTVTYTGSV VSQVSAGVYA TVRFDQYDIH NLRTIEKTWY ARHATLHNGK KISINNVTEM   300
APTSPIKTN                                                          309

SEQ ID NO: 5                  moltype = DNA  length = 927
FEATURE                       Location/Qualifiers
misc_feature                  1..927
                              note = engineered
misc_feature                  1..927
                              note = A nucleotide sequence encoding SEQ ID NO: 6 with an
                               open reading frame from 1 to 927.
source                        1..927
                              mol_type = other DNA
                              organism = synthetic construct
SEQUENCE: 5
atggctatcc tagaccttaa gtccctcgtg ctgaacgcca ttaactactg gggccctaag    60
aacaacaacg gcatccaggg cggtgacttc ggctacccca tctctgagaa gcagatcgac   120
actagcatca ttaccttcac ccaccctcgc ttgatccctt acgatcttac tatcccgcag   180
aaccttgaga ccatcttcac cacaacgcag gtgctcacca ataacactga cctccagcaa   240
tcccagaccg tgagctttgc gaagaagacc actaccacga cctcaactag cacgaccaac   300
ggttggacag aaggaggcaa gatcagcgac acgctgaggg agaaagtttc ggttagcatt   360
ccgttcatcg gtgagggtgg cgggaagaac tcgactacca tagaggccaa cttcgcacac   420
aactctagca ccactaccgc ccagcaagca agcactgaca ttgagtggaa cattagccaa   480
ccggtgctgg ttcctccctc taaacaagtt gtcgcgaccc ttgtgatcat gggaggcaac   540
tttaccatcc ctatggactt gatgaccacg attgatagta cagagcacta ctcccactac   600
```

```
tccggttacc ctatcctcac ctggatctcg tccccagata actcttactc cggtcccttt    660
atgtcatggt actttgcaaa ctggcctaac cttccgagtg gattcggccc actgaatagt    720
gataacacgg tcacatacac tggctctgtc gtgtcccaag tttcggccgg tgtctacgct    780
accgtccggt tcgatcagta tgacattcac aatctccgta ctatcgagaa acttggtat     840
gctcgccatg cgacgctgca taatggcaag aagatttcta tcaacaatgt cacggaaatg    900
gctccaacat cccctatcaa gacaaat                                        927
```

| | | |
|---|---|---|
| SEQ ID NO: 6 | moltype = AA   length = 309 | |
| FEATURE | Location/Qualifiers | |
| REGION | 1..309 | |
| | note = engineered | |
| REGION | 1..309 | |
| | note = The amino acid sequence translation of the open reading frame set forth as SEQ ID NO: 5. | |
| source | 1..309 | |
| | mol_type = protein | |
| | organism = synthetic construct | |

```
SEQUENCE: 6
MAILDLKSLV LNAINYWGPK NNNGIQGGDF GYPISEKQID TSIITFTHPR LIPYDLTIPQ     60
NLETIFTTTQ VLTNNTDLQQ SQTVSFAKKT TTTTSTSTTN GWTEGGKISD TLEEKVSVSI    120
PFIGEGGGKN STTIEANFAH NSSTTTAQQA STDIEWNISQ PVLVPPSKQV VATLVIMGGN    180
FTIPMDLMTT IDSTEHYSHY SGYPILTWIS SPDNSYSGPF MSWYFANWPN LPSGFGPLNS    240
DNTVTYTGSV VSQVSAGVYA TVRFDQYDIH NLRTIEKTWY ARHATLHNGK KISINNVTEM    300
APTSPIKTN                                                            309
```

| | | |
|---|---|---|
| SEQ ID NO: 7 | moltype = DNA   length = 918 | |
| FEATURE | Location/Qualifiers | |
| misc_feature | 1..918 | |
| | note = engineered | |
| misc_feature | 1..918 | |
| | note = A nucleotide sequence encoding SEQ ID NO: 8 with an open reading frame from 1 to 918. | |
| source | 1..918 | |
| | mol_type = other DNA | |
| | organism = synthetic construct | |

```
SEQUENCE: 7
atggctatcc tagacttaa gtccctcgtg ctgaacgcca ttaactactg gggccctaag     60
aacaacaacg gcatccaggg cggtgacttc ggctaccccc tctctgagaa gcagatcgac    120
actagcatca ttacctccac ccaccctcgc ttgatcccca acgatcttac tatcccgcag    180
aaccttgaga ccatcttcac cacaacgcag gtgctcacca ataacactga cctccagcaa    240
tcccagaccg tgagctttgc gaagaagacc actaccacga cctcaactag cacgaccaac    300
ggttggacag aaggaggcaa gatcagcgac acgctggagg agaaagtttc ggttagcatt    360
ccgttcatcg gtgagggtgg cgggaagaac tcgactacta gaggccaa cttcgccac      420
aactctagca ccactacctt ccagcaagca agcactgaca ttgagtggaa cattagccaa    480
ccggtccttg tgcctccccg caaacaggtt gttgccactc tcgttatcat gggtggcaac    540
ttcactattc ctatggatct tatgactacc attgactcta ctgagcacta ctctggctac    600
cccattctca cttggatctc ttctcctgac aatagctacc acggtccatt catgtcatgg    660
tacttcgcta actggccgaa tctcccttct ggctttggtc ctcttaactc tgataacact    720
gtgacctaca ctggctctgt cgtcagtcag gtctctgccg gtgtgtacgc aactgttcgc    780
ttcgatcagt atgacatcca taatctcagg actattgaga gacctggta cgctcgtcat    840
gcgacgcttc acaacggcaa gaagatcagc atcaataacg tgacagaaat ggcccctacc    900
agcccgatca agactaac                                                  918
```

| | | |
|---|---|---|
| SEQ ID NO: 8 | moltype = AA   length = 306 | |
| FEATURE | Location/Qualifiers | |
| REGION | 1..306 | |
| | note = engineered | |
| REGION | 1..306 | |
| | note = TIC807M2 | |
| REGION | 1..306 | |
| | note = The amino acid sequence translation of the open reading frame set forth as SEQ ID NO: 7. | |
| source | 1..306 | |
| | mol_type = protein | |
| | organism = synthetic construct | |

```
SEQUENCE: 8
MAILDLKSLV LNAINYWGPK NNNGIQGGDF GYPISEKQID TSIITSTHPR LIPHDLTIPQ     60
NLETIFTTTQ VLTNNTDLQQ SQTVSFAKKT TTTTSTSTTN GWTEGGKISD TLEEKVSVSI    120
PFIGEGGGKN STTIEANFAH NSSTTTFQQA STDIEWNISQ PVLVPPRKQV VATLVIMGGN    180
FTIPMDLMTT IDSTEHYSGY PILTWISSPD NSYNGPFMSW YFANWPNLPS GFGPLNSDNT    240
VTYTGSVVSQ VSAGVYATVR FDQYDIHNLR TIEKTWYARH ATLHNGKKIS INNVTEMAPT    300
SPIKTN                                                               306
```

| | | |
|---|---|---|
| SEQ ID NO: 9 | moltype = DNA   length = 918 | |
| FEATURE | Location/Qualifiers | |
| misc_feature | 1..918 | |
| | note = engineered | |
| misc_feature | 1..918 | |
| | note = A nucleotide sequence encoding SEQ ID NO: 10 with an | |

```
                              open reading frame from 1 to 918.
source                        1..918
                              mol_type = other DNA
                              organism = synthetic construct
SEQUENCE: 9
atggctatcc tagaccttaa gtccctcgtg ctgaacgcca ttaactactg gggccctaag   60
aacaacaacg gcatccaggg cggtgacttc ggctacccca tctctgagaa gcagatcgac  120
actagcatca ttacctccac ccaccctcgc ttgatccccc acgatcttac tatcccgcag  180
aaccttgaga ccatcttcac cacaaacgca gtgctcacca ataacactga cctccagcaa  240
tcccagaccg tgagctttgc gaagaagacc actaccgcga cctcaactag cacgaccaac  300
ggttggacag aaggaggcaa gatcagcgac acgctggagg agaaagtttc ggttagcatt  360
ccgttcatcg gtgagggtgg cgggaagaac tcgactacca tagaggccaa cttcgcacac  420
aactctagca ccactacctt ccagcaagca agcactgaca ttgagtggaa cattagccaa  480
ccggtccttg tgcctccccg caaacaggtt gttgccactc tcgttatcat gggtggcaac  540
ttcactattc ctatggatct tatgactacc attgactcta ctgagcacta ctctggctac  600
cccattctca cttggatctc ttctcctgac aatagctaca acggtccatt catgtcatgg  660
tacttcgcta actggccgaa tctcccttct ggctttggtc ctcttaactc tgataacact  720
gtgacctaca ctggctctgt cgtcagtcag gtctctgcca gtgtgtacgc aactgttcgc  780
ttcgatcagt atgacatcca taatctcagg actattgaga agacctggta cgctcgtcat  840
gcgacgcttc acaacggcaa gaagatcagc atcaataacg tgacagaaat ggcccctacc  900
agcccgatca agactaac                                                918

SEQ ID NO: 10             moltype = AA   length = 306
FEATURE                   Location/Qualifiers
REGION                    1..306
                          note = engineered
REGION                    1..306
                          note = The amino acid sequence translation of the open
                           reading frame set forth as SEQ ID NO: 9.
source                    1..306
                          mol_type = protein
                          organism = synthetic construct
SEQUENCE: 10
MAILDLKSLV LNAINYWGPK NNNGIQGGDF GYPISEKQID TSIITSTHPR LIPHDLTIPQ   60
NLETIFTTTQ VLTNNTDLQQ SQTVSFAKKT TTATSTSTTN GWTEGGKISD TLEEKVSVSI  120
PFIGEGGGKN STTIEANFAH NSSTTTFQQA STDIEWNISQ PVLVPPRKQV VATLVIMGGN  180
FTIPMDLMTT IDSTEHYSGY PILTWISSPD NSYNGPFMSW YFANWPNLPS GFGPLNSDNT  240
VTYTGSVVSQ VSAGVYATVR FDQYDIHNLR TIEKTWYARH ATLHNGKKIS INNVTEMAPT  300
SPIKTN                                                             306

SEQ ID NO: 11             moltype = DNA   length = 918
FEATURE                   Location/Qualifiers
misc_feature              1..918
                          note = engineered
misc_feature              1..918
                          note = A nucleotide sequence encoding SEQ ID NO: 12 with an
                           open reading frame from 1 to 918.
source                    1..918
                          mol_type = other DNA
                          organism = synthetic construct
SEQUENCE: 11
atggctatcc tagaccttaa gtccctcgtg ctgaacgcca ttaactactg gggccctaag   60
aacaacaacg gcatccaggg cggtgacttc ggctacccca tctctgagaa gcagatcgac  120
actagcatca ttacctccac ccaccctcgc ttgatccccc acgatcttac tatcccgcag  180
aaccttgaga ccatcttcac cacaaacgca gtgctcacca ataacactga cctccagcaa  240
tcccagaccg tgagctttgc gaagaagacc actaccacga ccgcaactag cacgaccaac  300
ggttggacag aaggaggcaa gatcagcgac acgctggagg agaaagtttc ggttagcatt  360
ccgttcatcg gtgagggtgg cgggaagaac tcgactacca tagaggccaa cttcgcacac  420
aactctagca ccactacctt ccagcaagca agcactgaca ttgagtggaa cattagccaa  480
ccggtccttg tgcctccccg caaacaggtt gttgccactc tcgttatcat gggtggcaac  540
ttcactattc ctatggatct tatgactacc attgactcta ctgagcacta ctctggctac  600
cccattctca cttggatctc ttctcctgac aatagctaca acggtccatt catgtcatgg  660
tacttcgcta actggccgaa tctcccttct ggctttggtc ctcttaactc tgataacact  720
gtgacctaca ctggctctgt cgtcagtcag gtctctgcca gtgtgtacgc aactgttcgc  780
ttcgatcagt atgacatcca taatctcagg actattgaga agacctggta cgctcgtcat  840
gcgacgcttc acaacggcaa gaagatcagc atcaataacg tgacagaaat ggcccctacc  900
agcccgatca agactaac                                                918

SEQ ID NO: 12             moltype = AA   length = 306
FEATURE                   Location/Qualifiers
REGION                    1..306
                          note = engineered
REGION                    1..306
                          note = The amino acid sequence translation of the open
                           reading frame set forth as SEQ ID NO: 11.
source                    1..306
                          mol_type = protein
                          organism = synthetic construct
SEQUENCE: 12
```

```
MAILDLKSLV LNAINYWGPK NNNGIQGGDF GYPISEKQID TSIITSTHPR LIPHDLTIPQ    60
NLETIFTTTQ VLTNNTDLQQ SQTVSFAKKT TTTTATSTTN GWTEGGKISD TLEEKVSVSI   120
PFIGEGGGKN STTIEANFAH NSSTTTFQQA STDIEWNISQ PVLVPPRKQV VATLVIMGGN   180
FTIPMDLMTT IDSTEHYSGY PILTWISSPD NSYNGPFMSW YFANWPNLPS GFGPLNSDNT   240
VTYTGSVVSQ VSAGVYATVR FDQYDIHNLR TIEKTWYARH ATLHNGKKIS INNVTEMAPT   300
SPIKTN                                                              306

SEQ ID NO: 13           moltype = DNA  length = 918
FEATURE                 Location/Qualifiers
misc_feature            1..918
                        note = engineered
misc_feature            1..918
                        note = A nucleotide sequence encoding SEQ ID NO: 14 with an
                         open reading frame from 1 to 918.
source                  1..918
                        mol_type = other DNA
                        organism = synthetic construct
SEQUENCE: 13
atggctatcc tagaccttaa gtccctcgtg ctgaacgcca ttaactactg gggccctaag    60
aacaacaacg gcatccaggg cggtgacttc ggctacccca tctctgagaa gcagatcgac   120
actagcatca ttacctccac ccaccctcgc ttgatccccc acgatcttac tatcccgcag   180
aaccttgaga ccatcttcac cacaacgcag gtgctcacaa ataacactga cctccagcaa   240
tcccagaccg tgagctttgc gaagaagacc actaccacga cctcaactag cacgaccaac   300
ggttggacag aaggaggcaa gatcagcgac acgctggagg agaaagtttc ggttagcatt   360
ccgttcatcg gtgagggtgg cgggaagaac tcgactacca tagaggccaa cttcgcacac   420
aactctagca ccactaccgc ccagcaagca agcactgaca ttgagtggaa cattagcaaa   480
ccggtccttg tgcctccccg caaacaggtt gttgccactc tcgttatcat gggtggcaac   540
ttcactattc ctatggatct tatgactacc attgactcta ctgagcacta ctctggctac   600
cccattctca cttggatctc ttctcctgac aatagctaca acggtccatt catgtcatgg   660
tacttcgcta actggccgaa tctcccttct ggctttggtc ctcttaactc tgataacact   720
gtgacctaca ctggctctgt cgtcagtcag gtctctgccg gtgtgtacgc aactgttcgc   780
ttcgatcagt atgacatcca taatctcagg actattgaga gacctggta cgctcgtcat   840
gcgacgcttc acaacggcaa gaagatcagc atcaataacg tgacagaaat ggcccctacc   900
agcccgatca agactaac                                                 918

SEQ ID NO: 14           moltype = AA  length = 306
FEATURE                 Location/Qualifiers
REGION                  1..306
                        note = engineered
REGION                  1..306
                        note = The amino acid sequence translation of the open
                         reading frame set forth as SEQ ID NO: 13.
source                  1..306
                        mol_type = protein
                        organism = synthetic construct
SEQUENCE: 14
MAILDLKSLV LNAINYWGPK NNNGIQGGDF GYPISEKQID TSIITSTHPR LIPHDLTIPQ    60
NLETIFTTTQ VLTNNTDLQQ SQTVSFAKKT TTTTSTSTTN GWTEGGKISD TLEEKVSVSI   120
PFIGEGGGKN STTIEANFAH NSSTTTAQQA STDIEWNISQ PVLVPPRKQV VATLVIMGGN   180
FTIPMDLMTT IDSTEHYSGY PILTWISSPD NSYNGPFMSW YFANWPNLPS GFGPLNSDNT   240
VTYTGSVVSQ VSAGVYATVR FDQYDIHNLR TIEKTWYARH ATLHNGKKIS INNVTEMAPT   300
SPIKTN                                                              306

SEQ ID NO: 15           moltype = DNA  length = 918
FEATURE                 Location/Qualifiers
misc_feature            1..918
                        note = engineered
misc_feature            1..918
                        note = A nucleotide sequence encoding SEQ ID NO: 16 with an
                         open reading frame from 1 to 918.
source                  1..918
                        mol_type = other DNA
                        organism = synthetic construct
SEQUENCE: 15
atggctatcc tagaccttaa gtccctcgtg ctgaacgcca ttaactactg gggccctaag    60
aacaacaacg gcatccaggg cggtgacttc ggctacccca tctctgagaa gcagatcgac   120
actagcatca ttacctccac ccaccctcgc ttgatccccc acgatcttac tatcccgcag   180
aaccttgaga ccatcttcac cacaacgcag gtgctcacaa ataacactga cctccagcaa   240
tcccagaccg tgagctttgc gaagaagacc actaccacga ccgcaactag cacgaccaac   300
ggttggacag aaggaggcaa gatcagcgac acgctggagg agaaagtttc ggttagcatt   360
ccgttcatcg gtgagggtgg cgggaagaac tcgactacca tagaggccaa cttcgcacac   420
aactctagca ccactaccgc ccagcaagca agcactgaca ttgagtggaa cattagcaaa   480
ccggtccttg tgcctccccg caaacaggtt gttgccactc tcgttatcat gggtggcaac   540
ttcactattc ctatggatct tatgactacc attgactcta ctgagcacta ctctggctac   600
cccattctca cttggatctc ttctcctgac aatagctaca acggtccatt catgtcatgg   660
tacttcgcta actggccgaa tctcccttct ggctttggtc ctcttaactc tgataacact   720
gtgacctaca ctggctctgt cgtcagtcag gtctctgccg gtgtgtacgc aactgttcgc   780
ttcgatcagt atgacatcca taatctcagg actattgaga gacctggta cgctcgtcat   840
gcgacgcttc acaacggcaa gaagatcagc atcaataacg tgacagaaat ggcccctacc   900
```

```
agcccgatca agactaac                                                     918

SEQ ID NO: 16              moltype = AA  length = 306
FEATURE                    Location/Qualifiers
REGION                     1..306
                           note = engineered
REGION                     1..306
                           note = TIC807M8
REGION                     1..306
                           note = The amino acid sequence translation of the open
                            reading frame set forth as SEQ ID NO: 15.
source                     1..306
                           mol_type = protein
                           organism = synthetic construct
SEQUENCE: 16
MAILDLKSLV LNAINYWGPK NNNGIQGGDF GYPISEKQID TSIITSTHPR LIPHDLTIPQ    60
NLETIFTTTQ VLTNNTDLQQ SQTVSFAKKT TTTTATSTTN GWTEGGKISD TLEEKVSVSI   120
PFIGEGGGKN STTIEANFAH NSSTTTAQQA STDIEWNISQ PVLVPPRKQV VATLVIMGGN   180
FTIPMDLMTT IDSTEHYSGY PILTWISSPD NSYNGPFMSW YFANWPNLPS GFGPLNSDNT   240
VTYTGSVVSQ VSAGVYATVR FDQYDIHNLR TIEKTWYARH ATLHNGKKIS INNVTEMAPT   300
SPIKTN                                                              306

SEQ ID NO: 17              moltype = DNA  length = 918
FEATURE                    Location/Qualifiers
misc_feature               1..918
                           note = engineered
misc_feature               1..918
                           note = A nucleotide sequence encoding SEQ ID NO: 18 with an
                            open reading frame from 1 to 918.
source                     1..918
                           mol_type = other DNA
                           organism = synthetic construct
SEQUENCE: 17
atggctatcc tagaccttaa gtccctcgtg ctgaacgcca ttaactactg gggccctaag    60
aacaacaacg gcatccaggg cggtgacttc ggctacccca tctctgagaa gcagatcgac   120
actagcatca ttacctccac ccaccctcgc ttgatccccc acgatcttac tatcccgcag   180
aaccttgaga ccatcttcac cacaacgcag gtgctcacca ataacactga cctccagcaa   240
tcccagaccg tgagctttgc gaagaagacc actaccgcga cctcaactag cacgaccaac   300
ggttggacag aaggaggcaa gatcagcgac acgctgaagg agaaagtttc ggttagcatt   360
ccgttcatcg gtgagggtgg cgggaagaac tcgactacca tagaggccaa cttcgcacac   420
aactctagca ccactaccgc ccagcaagca agcactgaca ttgagtggaa cattagcaa   480
ccggtccttg tgcctcccg caaacaggtt gttgccactc tcgttatcat gggtggcaac   540
ttcactattc ctatggatct tatgactacc attgactcta ctgagcacta tctctggcta   600
cccattctca cttggatctc ttctcctgac aatagctaca acgtccatt catgtcatgg   660
tacttcgcta actggccgaa tctcccttct ggctttggtc ctcttaactc tgataacact   720
gtgacctaca ctggctctgt cgtcagtcag gtctctgccg gtgtgtacgc aactgttcgc   780
ttcgatcagt atgacatcca taatctcagg actattgaga agacctggta cgctcgtcat   840
gcgacgcttc acaacggcaa gaagatcagc atcaataacg tgacagaaat ggcccctacc   900
agcccgatca agactaac                                                 918

SEQ ID NO: 18              moltype = AA  length = 306
FEATURE                    Location/Qualifiers
REGION                     1..306
                           note = engineered
REGION                     1..306
                           note = The amino acid sequence translation of the open
                            reading frame set forth as SEQ ID NO: 17.
source                     1..306
                           mol_type = protein
                           organism = synthetic construct
SEQUENCE: 18
MAILDLKSLV LNAINYWGPK NNNGIQGGDF GYPISEKQID TSIITSTHPR LIPHDLTIPQ    60
NLETIFTTTQ VLTNNTDLQQ SQTVSFAKKT TTATSTSTTN GWTEGGKISD TLEEKVSVSI   120
PFIGEGGGKN STTIEANFAH NSSTTTAQQA STDIEWNISQ PVLVPPRKQV VATLVIMGGN   180
FTIPMDLMTT IDSTEHYSGY PILTWISSPD NSYNGPFMSW YFANWPNLPS GFGPLNSDNT   240
VTYTGSVVSQ VSAGVYATVR FDQYDIHNLR TIEKTWYARH ATLHNGKKIS INNVTEMAPT   300
SPIKTN                                                              306

SEQ ID NO: 19              moltype = DNA  length = 918
FEATURE                    Location/Qualifiers
misc_feature               1..918
                           note = engineered
misc_feature               1..918
                           note = A nucleotide sequence encoding SEQ ID NO: 20 with an
                            open reading frame from 1 to 918.
source                     1..918
                           mol_type = other DNA
                           organism = synthetic construct
SEQUENCE: 19
```

```
atggctatcc tagaccttaa gtccctcgtg ctgaacgcca ttaactactg gggccctaag   60
aacaacaacg gcatccaggg cggtgacttc ggctacccca tctctgagaa gcagatcgac  120
actagcatca ttacctccac ccaccctcgc ttgatccccc acgatcttac tatcccgcag  180
aaccttgaga ccatcttcac cacaacgcag gtgctcacca ataacactga cctccagcaa  240
tcccagaccg tgagctttgc gaagaagacc actaccacga cctcaactag cacgaccaac  300
ggttggacag aaggaggcaa gatcagcgac acgctggagg agaaagtttc ggttagcatt  360
ccgttcatcg gtgagggtgg cgggaagaac tcgactacca tagaggccaa cttcgcacac  420
aactctagca ccactacctt ccaggaggca agcactgaca ttgagtggaa cattagccaa  480
ccggtccttg tgcctccccg caaacaggtt gttgccactc tcgttatcat gggtggcaac  540
ttcactattc ctatggatct tatgactacc attgactcta ctgagcacta ctctggctac  600
cccattctca cttggatctc ttctcctgac aatagctaca acggtccatt catgtcatgg  660
tacttcgcta actggccgaa tctcccttct ggctttggtc ctcttaactc tgataacact  720
gtgacctaca ctggctctgt cgtcagtcag gtctctgccg gtgtgtacgc aactgttcgc  780
ttcgatcagt atgacatcca taatctcagg actattgaga gacctggta cgctcgtcat  840
gcgacgcttc acaacggcaa gaagatcagc atcaataacg tgacagaaat ggcccctacc  900
agcccgatca agactaac                                                918

SEQ ID NO: 20        moltype = AA   length = 306
FEATURE              Location/Qualifiers
REGION               1..306
                     note = engineered
REGION               1..306
                     note = The amino acid sequence translation of the open
                     reading frame set forth as SEQ ID NO: 19.
source               1..306
                     mol_type = protein
                     organism = synthetic construct
SEQUENCE: 20
MAILDLKSLV LNAINYWGPK NNNGIQGGDF GYPISEKQID TSIITSTHPR LIPHDLTIPQ   60
NLETIFTTTQ VLTNNTDLQQ SQTVSFAKKT TTTSTSTTN GWTEGGKISD TLEEKVSVSI  120
PFIGEGGGKN STTIEANFAH NSSTTTFQEA STDIEWNISQ PVLVPPRKQV VATLVIMGGN  180
FTIPMDLMTT IDSTEHYSGY PILTWISSPD NSYNGPFMSW YFANWPNLPS GFGPLNSDNT  240
VTYTGSVVSQ VSAGVYATVR FDQYDIHNLR TIEKTWYARH ATLHNGKKIS INNVTEMAPT  300
SPIKTN                                                             306

SEQ ID NO: 21        moltype = DNA   length = 918
FEATURE              Location/Qualifiers
misc_feature         1..918
                     note = engineered
misc_feature         1..918
                     note = A nucleotide sequence encoding SEQ ID NO: 22 with an
                     open reading frame from 1 to 918.
source               1..918
                     mol_type = other DNA
                     organism = synthetic construct
SEQUENCE: 21
atggctatcc tagaccttaa gtccctcgtg ctgaacgcca ttaactactg gggccctaag   60
aacaacaacg gcatccaggg cggtgacttc ggctacccca tctctgagaa gcagatcgac  120
actagcatca ttacctccac ccaccctcgc ttgatccccc acgatcttac tatcccgcag  180
aaccttgaga ccatcttcac cacaacgcag gtgctcacca ataacactga cctccagcaa  240
tcccagaccg tgagctttgc gaagaagacc actaccacga cctcaactag cacgaccaac  300
ggttggacag aaggaggcaa gatcagcgac acgctggagg agaaagtttc ggttagcatt  360
ccgttcatcg gtgagggtgg cgggaagaac tcgactacca tagaggccaa cttcgcacac  420
aactctagca ccactacctt ccaggcagca agcactgaca ttgagtggaa cattagccaa  480
ccggtccttg tgcctccccg caaacaggtt gttgccactc tcgttatcat gggtggcaac  540
ttcactattc ctatggatct tatgactacc attgactcta ctgagcacta ctctggctac  600
cccattctca cttggatctc ttctcctgac aatagctaca acggtccatt catgtcatgg  660
tacttcgcta actggccgaa tctcccttct ggctttggtc ctcttaactc tgataacact  720
gtgacctaca ctggctctgt cgtcagtcag gtctctgccg gtgtgtacgc aactgttcgc  780
ttcgatcagt atgacatcca taatctcagg actattgaga gacctggta cgctcgtcat  840
gcgacgcttc acaacggcaa gaagatcagc atcaataacg tgacagaaat ggcccctacc  900
agcccgatca agactaac                                                918

SEQ ID NO: 22        moltype = AA   length = 306
FEATURE              Location/Qualifiers
REGION               1..306
                     note = engineered
REGION               1..306
                     note = The amino acid sequence translation of the open
                     reading frame set forth as SEQ ID NO: 21.
source               1..306
                     mol_type = protein
                     organism = synthetic construct
SEQUENCE: 22
MAILDLKSLV LNAINYWGPK NNNGIQGGDF GYPISEKQID TSIITSTHPR LIPHDLTIPQ   60
NLETIFTTTQ VLTNNTDLQQ SQTVSFAKKT TTATSTSTTN GWTEGGKISD TLEEKVSVSI  120
PFIGEGGGKN STTIEANFAH NSSTTTFQEA STDIEWNISQ PVLVPPRKQV VATLVIMGGN  180
FTIPMDLMTT IDSTEHYSGY PILTWISSPD NSYNGPFMSW YFANWPNLPS GFGPLNSDNT  240
VTYTGSVVSQ VSAGVYATVR FDQYDIHNLR TIEKTWYARH ATLHNGKKIS INNVTEMAPT  300
```

```
SPIKTN                                                                        306

SEQ ID NO: 23           moltype = DNA  length = 918
FEATURE                 Location/Qualifiers
misc_feature            1..918
                        note = engineered
misc_feature            1..918
                        note = A nucleotide sequence encoding SEQ ID NO: 24 with an
                        open reading frame from 1 to 918.
source                  1..918
                        mol_type = other DNA
                        organism = synthetic construct
SEQUENCE: 23
atggctatcc tagacettaa gtccctcgtg ctgaacgcca ttaactactg gggccctaag    60
aacaacaacg gcatccaggg cggtgacttc ggctacccca tctctgagaa gcagatcgac   120
actagcatca ttacctccac ccaccctcgc ttgatcccce acgatcttac tatccegcag   180
aaccttgaga ccatcttcac cacaacgcag gtgctcacca ataacactga cctccagcaa   240
tcccagaccg tgagctttgc gaagaagacc actaccgcga cctcaactag cacgaccaac   300
ggttggacag aaggaggcaa gatcagcgac acgctggagg agaaagtttc ggttagcatt   360
ccgttcatcg gtgagggtgg cgggaagaac tcgactacca tagaggccaa cttcgcacac   420
aactctagca ccactacctt ccaggaggca agcactgaca ttgagtggaa cattagccaa   480
ccggtccttg tgcctccccg caaacaggtt gttgccactc tcgttatcat gggtggcaac   540
ttcactattc ctatggatct tatgactacc attgactcta ctgagcacta ctctggctac   600
cccattctca cttggatctc ttctcctgac aatagctaca acgtccatt  catgtcatgg   660
tacttcgcta actggccgaa tctcccttct ggctttggtc ctcttaactc tgataacact   720
gtgacctaca ctggctctgt cgtcagtcag gtctctgccg gtgtgtacgc aactgttcgc   780
ttcgatcagt atgacatcca taatctcagg actattgaga gacctggta  cgctcgtcat   840
gcgacgcttc acaacggcaa gaagatcagc atcaataacg tgacagaaat ggcccctacc   900
agcccgatca agactaac                                                918

SEQ ID NO: 24           moltype = AA  length = 306
FEATURE                 Location/Qualifiers
REGION                  1..306
                        note = engineered
REGION                  1..306
                        note = The amino acid sequence translation of the open
                        reading frame set forth as SEQ ID NO: 23.
source                  1..306
                        mol_type = protein
                        organism = synthetic construct
SEQUENCE: 24
MAILDLKSLV LNAINYWGPK NNNGIQGGDF GYPISEKQID TSIITSTHPR LIPHDLTIPQ    60
NLETIFTTTQ VLTNNTDLQQ SQTVSFAKKT TTATSTSTTN GWTEGGKISD TLEEKVSVSI   120
PFIGEGGGKN STTIEANFAH NSSTTTFQEA STDIEWNISQ PVLVPPRKQV VATLVIMGGN   180
FTIPMDLMTT IDSTEHYSGY PILTWISSPD NSYNGPFMSW YFANWPNLPS GFGPLNSDNT   240
VTYTGSVVSQ VSAGVYATVR FDQYDIHNLR TIEKTWYARH ATLHNGKKIS INNVTEMAPT   300
SPIKTN                                                              306

SEQ ID NO: 25           moltype = DNA  length = 918
FEATURE                 Location/Qualifiers
misc_feature            1..918
                        note = engineered
misc_feature            1..918
                        note = A nucleotide sequence encoding SEQ ID NO: 26 with an
                        open reading frame from 1 to 918.
source                  1..918
                        mol_type = other DNA
                        organism = synthetic construct
SEQUENCE: 25
atggctatcc tagacettaa gtccctcgtg ctgaacgcca ttaactactg gggccctaag    60
aacaacaacg gcatccaggg cggtgacttc ggctacccca tctctgagaa gcagatcgac   120
actagcatca ttacctccac ccaccctcgc ttgatcccce acgatcttac tatccegcag   180
aaccttgaga ccatcttcac cacaacgcag gtgctcacca ataacactga cctccagcaa   240
tcccagaccg tgagctttgc gaagaagacc actaccgcga ccgcaactag cacgaccaac   300
ggttggacag aaggaggcaa gatcagcgac acgctggagg agaaagtttc ggttagcatt   360
ccgttcatcg gtgagggtgg cgggaagaac tcgactacca tagaggccaa cttcgcacac   420
aactctagca ccactaccgc ccagcaagca agcactgaca ttgagtggaa cattagccaa   480
ccggtccttg tgcctccccg caaacaggtt gttgccactc tcgttatcat gggtggcaac   540
ttcactattc ctatggatct tatgactacc attgactcta ctgagcacta ctctggctac   600
cccattctca cttggatctc ttctcctgac aatagctaca gcggtccatt catgtcatgg   660
tacttcgcta actggccgaa tctcccttct ggctttggtc ctcttaactc tgataacact   720
gtgacctaca ctggctctgt cgtcagtcag gtctctgccg gtgtgtacgc aactgttcgc   780
ttcgatcagt atgacatcca taatctcagg actattgaga gacctggta  cgctcgtcat   840
gcgacgcttc acaacggcaa gaagatcagc atcaataacg tgacagaaat ggcccctacc   900
agcccgatca agactaac                                                918

SEQ ID NO: 26           moltype = AA  length = 306
FEATURE                 Location/Qualifiers
REGION                  1..306
```

```
                        note = engineered
REGION                  1..306
                        note = The amino acid sequence translation of the open
                        reading frame set forth as SEQ ID NO: 25.
source                  1..306
                        mol_type = protein
                        organism = synthetic construct
SEQUENCE: 26
MAILDLKSLV LNAINYWGPK NNNGIQGGDF GYPISEKQID TSIITSTHPR LIPHDLTIPQ    60
NLETIFTTTQ VLTNNTDLQQ SQTVSFAKKT TTTTATSTTN GWTEGGKISD TLEEKVSVSI   120
PFIGEGGGKN STTIEANFAH NSSTTTAQQA STDIEWNISQ PVLVPPRKQV VATLVIMGGN   180
FTIPMDLMTT IDSTEHYSGY PILTWISSPD NSYSGPFMSW YFANWPNLPS GFGPLNSDNT   240
VTYTGSVVSQ VSAGVYATVR FDQYDIHNLR TIEKTWYARH ATLHNGKKIS INNVTEMAPT   300
SPIKTN                                                             306

SEQ ID NO: 27           moltype = DNA   length = 918
FEATURE                 Location/Qualifiers
misc_feature            1..918
                        note = engineered
misc_feature            1..918
                        note = A nucleotide sequence encoding SEQ ID NO: 28 with an
                        open reading frame from 1 to 918.
source                  1..918
                        mol_type = other DNA
                        organism = synthetic construct
SEQUENCE: 27
atggctatcc tagaccttaa gtccctcgtg ctgaacgcca ttaactactg gggccctaag    60
aacaacaacg gcatccaggg cggtgacttc ggctacccca tctctgagaa gcagatcgac   120
actagcatca ttacctccac ccaccctcgc ttgatccccc acgatcttac tatcccgcag   180
aaccttgaga ccatcttcac cacaacgcag gtgctcacca ataacactga cctccagcaa   240
tcccagaccg tgagctttgc gaagaagacc actaccacga ccgcaactag cacgaccaac   300
ggttggacaa aggaggcaa gatcagcgac acgctggagg agaaagtttc ggttagcatt   360
ccgttcatcg gtgagggtgg cgggaagaac tcgactacca tagaggccaa cttcgcacac   420
aactctagca ccactaccgc cagcaagca agcactacag ttgagtggaa cattagcaa   480
ccggtccttg tgcctccccg caaacaggtt gttgccactc tcgttatcat gggtggcaac   540
ttcactattc ctatggatct tatgactacc attgactcta ctgagcacta ctctggctac   600
cccattctca cttggatctc ttctcctgac aatagctaca cgcgtcgatt catgtcatgg   660
tacttcgcta actggccgaa tctcccttct ggctttggtc ctcttaactc tgataacact   720
gtgacctaca ctggctctgt cgtcagtcag gtctctgccg gtgtgtacgc aactgttcgc   780
ttcgatcagt atgacatcca taatctcagg actattgaga agacctggta cgctcgtcat   840
gcgacgcttc acaacggcaa gaagatcagc atcaataacg tgacagaaat ggcccctacc   900
agcccgatca agactaac                                                918

SEQ ID NO: 28           moltype = AA   length = 306
FEATURE                 Location/Qualifiers
REGION                  1..306
                        note = engineered
REGION                  1..306
                        note = The amino acid sequence translation of the open
                        reading frame set forth as SEQ ID NO: 27.
source                  1..306
                        mol_type = protein
                        organism = synthetic construct
SEQUENCE: 28
MAILDLKSLV LNAINYWGPK NNNGIQGGDF GYPISEKQID TSIITSTHPR LIPHDLTIPQ    60
NLETIFTTTQ VLTNNTDLQQ SQTVSFAKKT TTTTATSTTN GWTEGGKISD TLEEKVSVSI   120
PFIGEGGGKN STTIEANFAH NSSTTTAQQA STDIEWNISQ PVLVPPRKQV VATLVIMGGN   180
FTIPMDLMTT IDSTEHYSGY PILTWISSPD NSYSGRFMSW YFANWPNLPS GFGPLNSDNT   240
VTYTGSVVSQ VSAGVYATVR FDQYDIHNLR TIEKTWYARH ATLHNGKKIS INNVTEMAPT   300
SPIKTN                                                             306

SEQ ID NO: 29           moltype = DNA   length = 918
FEATURE                 Location/Qualifiers
misc_feature            1..918
                        note = engineered
misc_feature            1..918
                        note = A nucleotide sequence encoding SEQ ID NO: 30 with an
                        open reading frame from 1 to 918.
source                  1..918
                        mol_type = other DNA
                        organism = synthetic construct
SEQUENCE: 29
atggctatcc tagaccttaa gtccctcgtg ctgaacgcca ttaactactg gggccctaag    60
aacaacaacg gcatccaggg cggtgacttc ggctacccca tctctgagaa gcagatcgac   120
actagcatca ttacctccac ccaccctcgc ttgatccccc acgatcttac tatcccgcag   180
aaccttgaga ccatcttcac cacaacgcag gtgctcacca ataacactga cctccagcaa   240
tcccagaccg tgagctttgc gaagaagacc actaccacga ccgcaactag cacgaccaac   300
ggttggacaa aggaggcaa gatcagcgac acgctggagg agaaagtttc ggttagcatt   360
ccgttcatcg gtgagggtgg cgggaagaac tcgactacca tagaggccaa cttcgcacac   420
```

```
aactctagca ccactaccgc ccagcaagca agcactgaca ttgagtggaa cattagccaa    480
ccggtccttg tgcctcccg caaacaggtt gttgccactc tcgttatcat gggtggcaac    540
ttcactattc ctatggatct tatgactacc attgactcta ctgagcacta ctctggctac   600
cccattctca cttggatctc ttctcctgac aatagctaca gcggtcgatt catgtcatgg   660
tacttcgcta actggccgaa tctcccttct ggctttggtc ctcttaactc tgataacact   720
gtgacctaca ctggctctgt cgccagtcag gtctctgccg gtgtgtacgc aactgttcgc   780
ttcgatcagt atgacatcca taatctcagg actattgaga gacctggta cgctcgtcat    840
gcgacgcttc acaacggcaa gaagatcagc atcaataacg tgacagaaat ggcccctacc   900
agcccgatca agactaac                                                 918

SEQ ID NO: 30           moltype = AA  length = 306
FEATURE                 Location/Qualifiers
REGION                  1..306
                        note = engineered
REGION                  1..306
                        note = TIC807M10
REGION                  1..306
                        note = The amino acid sequence translation of the open
                        reading frame set forth as SEQ ID NO: 29.
source                  1..306
                        mol_type = protein
                        organism = synthetic construct
SEQUENCE: 30
MAILDLKSLV LNAINYWGPK NNNGIQGGDF GYPISEKQID TSIITSTHPR LIPHDLTIPQ    60
NLETIFTTTQ VLTNNTDLQQ SQTVSFAKKT TTTTATSTTN GWTEGGKISD TLEEKVSVSI   120
PFIGEGGGKN STTIEANFAH NSSTTTAQQA STDIEWNISQ PVLVPPRKQV VATLVIMGGN   180
FTIPMDLMTT IDSTEHYSGY PILTWISSPD NSYSGRFMSW YFANWPNLPS GFGPLNSDNT   240
VTYTGSVASQ VSAGVYATVR FDQYDIHNLR TIEKTWYARH ATLHNGKKIS INNVTEMAPT   300
SPIKTN                                                              306

SEQ ID NO: 31           moltype = DNA  length = 918
FEATURE                 Location/Qualifiers
misc_feature            1..918
                        note = engineered
misc_feature            1..918
                        note = A nucleotide sequence encoding SEQ ID NO: 32 with an
                        open reading frame from 1 to 918.
source                  1..918
                        mol_type = other DNA
                        organism = synthetic construct
SEQUENCE: 31
atggctatcc tagaccttaa gtccctcgtg ctgaacgcca ttaactactg gggccctaag    60
aacaacaacg gcatccaggg cggtgacttc ggctacccca tctctgagaa gcagatcgac   120
actagcatca ttacctccac ccaccctcgc ttgatccccc acgatcttac tatcccgcag   180
aaccttgaga ccatcttcac cacaacgcag gtgctcacca ataacactga cctcagcaa    240
tcccagaccg tgagctttgc gaagaagacc actaccacga ccgcaactag cacgaccaac   300
ggttggacag aaggaggcaa gatcagcgac acgctggagg agaaagtttc ggttagcatt   360
ccgttcatcg gtgagggtgg cgggaagaac tcgactacca tagaggccaa cttcgcacac   420
aactctagca ccactaccgc ccagcaagca agcactgaca ttgagtggaa cattagccaa   480
ccggtccttg tgcctcccg caaacaggtt gttgccactc tcgttatcat gggtggcaac    540
ttcactattc ctatggatct tatgactacc attgactcta ctgagcacta ctctggctac   600
cccattctca cttggatctc ttctcctgac aatagctaca gcggtcgatt catgtcatgg   660
tacttcgcta actggccgaa tctcccttct ggctttggtc ctcttaactc tgataacact   720
gtgacctaca ctggctctgt cgtcagtcag gtctctgccg gtgtgtacgc aactgttcgc   780
ttcgatcagt atgacatcca taatctctgg actattgaga gacctggta cgctcgtcat    840
gcgacgcttc acaacggcaa gaagatcagc atcaataacg tgacagaaat ggcccctacc   900
agcccgatca agactaac                                                 918

SEQ ID NO: 32           moltype = AA  length = 306
FEATURE                 Location/Qualifiers
REGION                  1..306
                        note = engineered
REGION                  1..306
                        note = The amino acid sequence translation of the open
                        reading frame set forth as SEQ ID NO: 31.
source                  1..306
                        mol_type = protein
                        organism = synthetic construct
SEQUENCE: 32
MAILDLKSLV LNAINYWGPK NNNGIQGGDF GYPISEKQID TSIITSTHPR LIPHDLTIPQ    60
NLETIFTTTQ VLTNNTDLQQ SQTVSFAKKT TTTTATSTTN GWTEGGKISD TLEEKVSVSI   120
PFIGEGGGKN STTIEANFAH NSSTTTAQQA STDIEWNISQ PVLVPPRKQV VATLVIMGGN   180
FTIPMDLMTT IDSTEHYSGY PILTWISSPD NSYSGRFMSW YFANWPNLPS GFGPLNSDNT   240
VTYTGSVVSQ VSAGVYATVR FDQYDIHNLW TIEKTWYARH ATLHNGKKIS INNVTEMAPT   300
SPIKTN                                                              306

SEQ ID NO: 33           moltype = DNA  length = 918
FEATURE                 Location/Qualifiers
misc_feature            1..918
```

|  |  |  |
|---|---|---|
| | note = engineered | |
| misc_feature | 1..918 | |
| | note = A nucleotide sequence encoding SEQ ID NO: 34 with an open reading frame from 1 to 918. | |
| source | 1..918 | |
| | mol_type = other DNA | |
| | organism = synthetic construct | |

SEQUENCE: 33

```
atggctatcc tagaccttaa gtccctcgtg ctgaacgcca ttaactactg gggccctaag   60
aacaacaacg gcatccaggg cggtgacttc ggctacccca tctctgagaa gcagatcgac  120
actagcatca ttacctccac ccaccctcgc ttgatccccc acgatcttac tatcccgcag  180
aaccttgaga ccatcttcac cacaacgcag gtgctcacca ataacactga cctccagcaa  240
tcccagaccg tgagctttgc gaagaagacc actaccacga ccgcaactag cacgaccaac  300
ggttggacag aaggaggcaa gatcagcgac acgctggacg agaaagtttc ggttagcatc  360
ccgttcatcg gtgagggtgg cgggaagaac tcgactacca tagaggccaa cttcgcacac  420
aactctagca ccactacctc ccaggaagca agcactgaca ttgagtggaa cattagccaa  480
ccggtccttg tgcctccccg caaacaggtt gttgccactc tcgttatcat gggtggcaac  540
ttcactattc ctatggatct tatgactacc attgactcta ctgagcacta ctctggctat  600
cccattctca cttggatctc ttctcctgac aatagctaca gcggtcgatt catgtcatgg  660
tacttcgcta actggccgaa tctcccttct ggctttggtc ctcttaactc tgataacact  720
gtgacctaca ctggctctgt cgtcagtcag gtctctgccg gtgtgtacgc aactgttcgc  780
ttcgatcagt atgacatcca taatctctgg actattgaga gacctggta cgctcgtcat  840
gcgacgcttc acaacggcaa gaagatcagc atcaataacg tgacagaaat ggcccctacc  900
agcccgatca agactaac                                                918
```

|  |  |
|---|---|
| SEQ ID NO: 34 | moltype = AA   length = 306 |
| FEATURE | Location/Qualifiers |
| REGION | 1..306 |
| | note = engineered |
| REGION | 1..306 |
| | note = TIC807M13 |
| REGION | 1..306 |
| | note = The amino acid sequence translation of the open reading frame set forth as SEQ ID NO: 33. |
| source | 1..306 |
| | mol_type = protein |
| | organism = synthetic construct |

SEQUENCE: 34

```
MAILDLKSLV LNAINYWGPK NNNGIQGGDF GYPISEKQID TSIITSTHPR LIPHDLTIPQ   60
NLETIFTTTQ VLTNNTDLQQ SQTVSFAKKT TTTTATSTTN GWTEGGKISD TLEEKVSVSI  120
PFIGEGGGKN STTIEANFAH NSSTTTSQEA STDIEWNISQ PVLVPPRKQV VATLVIMGGN  180
FTIPMDLMTT IDSTEHYSGY PILTWISSPD NSYSGRFMSW YFANWPNLPS GFGPLNSDNT  240
VTYTGSVVSQ VSAGVYATVR FDQYDIHNLW TIEKTWYARH ATLHNGKKIS INNVTEMAPT  300
SPIKTN                                                             306
```

|  |  |
|---|---|
| SEQ ID NO: 35 | moltype = DNA  length = 918 |
| FEATURE | Location/Qualifiers |
| misc_feature | 1..918 |
| | note = engineered |
| misc_feature | 1..918 |
| | note = A nucleotide sequence encoding SEQ ID NO: 36 with an open reading frame from 1 to 918. |
| source | 1..918 |
| | mol_type = other DNA |
| | organism = synthetic construct |

SEQUENCE: 35

```
atggctatcc tagaccttaa gtccctcgtg ctgaacgcca ttaactactg gggccctaag   60
aacaacaacg gcatccaggg cggtgacttc ggctacccca tctctgagaa gcagatcgac  120
actagcatca ttacctccac ccaccctcgc ttgatccccc acgatcttac tatcccgcag  180
aaccttgaga ccatcttcac cacaacgcag gtgctcacca ataacactga cctccagcaa  240
tcccagaccg tgagctttgc gaagaagacc actaccacga ccgcaactag cacgaccaac  300
ggttggacag aaggaggcaa gatcagcgac acgctggagg agaaagtttc ggttagcatt  360
ccgttcatcg gtgagggtgg cgggaagaac tcgactacca tagaggccaa cttcgcacac  420
aactctagca ccactaccgc ccagcaagca agcactgaca ttgagtggaa cattagccaa  480
ccggtccttg tgcctccccg caaacaggtt gttgccactc tcgttatcat gggtggcaac  540
ttcactattc ctatggatct tatgactacc attgactcta ctgagcacta ctctggctac  600
cccattctca cttggatctc ttctcctgac aatagctaca gcggtcgatt catgtcatgg  660
tacttcgcta actggccgaa tctcccttct ggctttggtc ctcttgcctc tgataacact  720
gtgacctaca ctggctctgt cgccagtcag gtctctgccg gtgtgtacgc aactgttcgc  780
ttcgatcagt atgacatcca taatctcagg actattgaga gacctggta cgctcgtcat  840
gcgacgcttc acaacggcaa gaagatcagc atcaataacg tgacagaaat ggcccctacc  900
agcccgatca agactaac                                                918
```

|  |  |
|---|---|
| SEQ ID NO: 36 | moltype = AA   length = 306 |
| FEATURE | Location/Qualifiers |
| REGION | 1..306 |
| | note = engineered |
| REGION | 1..306 |
| | note = The amino acid sequence translation of the open |

```
                         reading frame set forth as SEQ ID NO: 35.
source                   1..306
                         mol_type = protein
                         organism = synthetic construct
SEQUENCE: 36
MAILDLKSLV LNAINYWGPK NNNGIQGGDF GYPISEKQID TSIITSTHPR LIPHDLTIPQ    60
NLETIFTTTQ VLTNNTDLQQ SQTVSFAKKT TTTTATSTTN GWTEGGKISD TLEEKVSVSI   120
PFIGEGGGKN STTIEANFAH NSSTTTAQQA STDIEWNISQ PVLVPPRKQV VATLVIMGGN   180
FTIPMDLMTT IDSTEHYSGY PILTWISSPD NSYSGRFMSW YFANWPNLPS GFGPLASDNT   240
VTYTGSVASQ VSAGVYATVR FDQYDIHNLR TIEKTWYARH ATLHNGKKIS INNVTEMAPT   300
SPIKTN                                                               306

SEQ ID NO: 37            moltype = AA   length = 306
FEATURE                  Location/Qualifiers
REGION                   1..306
                         note = engineered
source                   1..306
                         mol_type = protein
                         organism = synthetic construct
SEQUENCE: 37
MAILDLKSLV LNAINYWGPK NNNGIQGGDF GYPISEKQID TSIITFTHPR LIPYDLTIPQ    60
NLETIFTTTQ VLTNNTDLQQ SQTVSFAKKT TTTTSTSTTN GWTEGGKISD TLEEKVSVSI   120
PFIGEGGGKN STTIEANFAH NSSTTTFQQA STDIEWNISQ PVLVPPSKQV VATLVIMGGN   180
FTIPMDLMTT IDSTEHYSGY PILTWISSPD NSYSGPFMSW YFANWPNLPS GFGPLNSDNT   240
VTYTGSVVSQ VSAGVYATVR FDQYDIHNLR TIEKTWYARH ATLHNGKKIS INNVTEMAPT   300
SPIKTN                                                               306

SEQ ID NO: 38            moltype = AA   length = 306
FEATURE                  Location/Qualifiers
REGION                   1..306
                         note = engineered
source                   1..306
                         mol_type = protein
                         organism = synthetic construct
SEQUENCE: 38
MAILDLKSLV LNAINYWGPK NNNGIQGGDF GYPISEKQID TSIITSTHPR LIPHDLTIPQ    60
NLETIFTTTQ VLTNNTDLQQ SQTVSFAKKT TTTTSTSTTN GWTEGGKISD TLEEKVSVSI   120
PFIGEGGGKN STTIEANVAH NSSTTTFQQA STDIEWNISQ PVLVPPRKQV VATLVIMGGN   180
FTIPMDLMTT IDSTEHYSGY PILTWISSPD NSYNGPFMSW YFANWPNLPS GFGPLNSDNT   240
VTYTGSVVSQ VSAGVYATVR FDQYDIHNLR TIEKTWYARH ATLHNGKKIS INNVTEMAPT   300
SPIKTN                                                               306

SEQ ID NO: 39            moltype = AA   length = 306
FEATURE                  Location/Qualifiers
REGION                   1..306
                         note = engineered
source                   1..306
                         mol_type = protein
                         organism = synthetic construct
SEQUENCE: 39
MAILDLKSLV LNAINYWGPK NNNGIQGGDF GYPISEKQID TSIITSTHPR LIPHDLTIPQ    60
NLETIFTTTQ VLTNNTDLQQ SQTVSFAKKT TTTTSTSTTN GWTEGGKISD TLEEKVSVSI   120
PFIGEGGGKN STTIEANFAH NSSTTTFQQA STDIEWNISQ PVLVPPRKQV VATLVIMGGN   180
FTIPMDLMTT IDSTEHYSGY PILTWISSPD NSYNGPFMSW YFANWPNLPS GFGPLNSDNT   240
VTYTGSVVSQ VSAGVYATVR FDQYDIHNLR TIEKTWYARH ATLFNGKKIS INNVTEMAPT   300
SPIKTN                                                               306

SEQ ID NO: 40            moltype = AA   length = 306
FEATURE                  Location/Qualifiers
REGION                   1..306
                         note = engineered
source                   1..306
                         mol_type = protein
                         organism = synthetic construct
SEQUENCE: 40
MAILDLKSLV LNAINYWGPK NNNGIQGGDF GYPISEKQID TSIITSTHPR LMPHDLTIPQ    60
NLETIFTTTQ VLTNNTDLQQ SQTVSFAKKT TTTTSTSTTN GWTEGGKISD TLEEKVSVSI   120
PFIGEGGGKN STTIEANFAH NSSTTTFQQA STDIEWNISQ PVLVPPRKQV VATLVIMGGN   180
FTIPMDLMTT IDSTEHYSGY PILTWISSPD NSYNGPFMSW YFANWPNLPS GFGPLNSDNT   240
VTYTGSVVSQ VSAGVYATVR FDQYDIHNLR TIEKTWYARH ATLHNGKKIS INNVTEMAPT   300
SPIKTN                                                               306

SEQ ID NO: 41            moltype = AA   length = 306
FEATURE                  Location/Qualifiers
REGION                   1..306
                         note = engineered
source                   1..306
                         mol_type = protein
                         organism = synthetic construct
```

```
SEQUENCE: 41
MAILDLKSLV LDAINYWGPK NNNGIQGGDF GYPISEKQID TSIITSTHPR LIPHDLTIPQ    60
NLETIFTTTQ VLTNNTDLQQ SQTVSFAKKT TTTTSTSTTN GWTEGGKISD TLEEKVSVSI   120
PFIGEGGGKN STTIEANFAH NSSTTTFQQA STDIEWNISQ PVLVPPRKQV VATLVIMGGN   180
FTIPMDLMTT IDSTEHYSGY PILTWISSPD NSYNGPFMSW YFANWPNLPS GFGPLNSDNT   240
VTYTGSVVSQ VSAGVYATVR FDQYDIHNLR TIEKTWYARH ATLHNGKKIS INNVTEMAPT   300
SPIKTN                                                              306

SEQ ID NO: 42           moltype = AA   length = 306
FEATURE                 Location/Qualifiers
REGION                  1..306
                        note = engineered
source                  1..306
                        mol_type = protein
                        organism = synthetic construct
SEQUENCE: 42
MAILDLKSLV LNAINYWGPK NNNGIQGGDF GYPISEKQID TSIITSTHPR LIPHDLTIPQ    60
NLETIFTTTQ VLTNNTDLQQ SQTVSFAKKT TTTTSTSTTN GWTEGGKISD TLEEKVSVSI   120
PFIGEGGGKN STTIEANFAH NSSTTTFQQA STDIEWNISQ PVLVPPRKQV VATLVIMGGD   180
FTIPMDLMTT IDSTEHYSGY PILTWISSPD NSYNGPFMSW YFANWPNLPS GFGPLNSDNT   240
VTYTGSVVSQ VSAGVYATVR FDQYDIHNLR TIEKTWYARH ATLHNGKKIS INNVTEMAPT   300
SPIKTN                                                              306

SEQ ID NO: 43           moltype = AA   length = 306
FEATURE                 Location/Qualifiers
REGION                  1..306
                        note = engineered
source                  1..306
                        mol_type = protein
                        organism = synthetic construct
SEQUENCE: 43
MAILDLKSLV LNAINYWGPK NNNGIQGGDF GYPISEKQID TSIITSTHPR LIPHDLTIPQ    60
NLETIFTTTQ VLTNNTDLQQ SQTVSFAKKT TTTTSTSTTN GWTEGGKISD TLEEKVSVSI   120
PFIGEGGGKN STTIEANFAH NSSTTTFQQA STDIEWNISQ PVLVPPRKQV VATLVIMGGN   180
FTIPMDLMTT IDSTEHYSGY PILTWISSPD NSYSGPFMSW YFANWPNLPS GFGPLNSDNT   240
VTYTGSVVSQ VSAGVYATVR FDQYDIHNLR TIEKTWYARH ATLHNGKKIS INNVTEMAPT   300
SPIKTN                                                              306

SEQ ID NO: 44           moltype = AA   length = 306
FEATURE                 Location/Qualifiers
REGION                  1..306
                        note = engineered
source                  1..306
                        mol_type = protein
                        organism = synthetic construct
SEQUENCE: 44
MAILDLKSLV LNAINYWGPK NNNGIQGGDF GYPISEKQID TSIITSTHPR LIPHDLTIPQ    60
NLETIFTTTQ VLTNNTDLQQ SQTVSFAKKT TTTTSTSTTN GWTEGGKISD TLEEKVSVSI   120
PFIGEGGGKN STTIEANFAH NSSTTTFQQA STDIEWNISQ PVLVPPRKQV VATLVIMGGN   180
FTIPMDLMTT IDSTEHYSGY PILTWISSPD NSYNGRFMSW YFANWPNLPS GFGPLNSDNT   240
VTYTGSVVSQ VSAGVYATVR FDQYDIHNLR TIEKTWYARH ATLHNGKKIS INNVTEMAPT   300
SPIKTN                                                              306

SEQ ID NO: 45           moltype = AA   length = 306
FEATURE                 Location/Qualifiers
REGION                  1..306
                        note = engineered
source                  1..306
                        mol_type = protein
                        organism = synthetic construct
SEQUENCE: 45
MAILDLKSLV LNAINYWGPK NNNGIQGGDF GYPISEKQID TSIITSTHPR LIPHDLTIPQ    60
NLETIFTTTQ VLTNNTDLQQ SQTVSFAKKT TTTTSTSTTN GWTEGGKISD TLEEKVSVSI   120
PFIGEGGGKN STTIEANFAH NSSTTTFQQA STDIEWNITQ PVLVPPRKQV VATLVIMGGN   180
FTIPMDLMTT IDSTEHYSGY PILTWISSPD NSYNGPFMSW YFANWPNLPS GFGPLNSDNT   240
VTYTGSVVSQ VSAGVYATVR FDQYDIHNLR TIEKTWYARH ATLHNGKKIS INNVTEMAPT   300
SPIKTN                                                              306

SEQ ID NO: 46           moltype = AA   length = 306
FEATURE                 Location/Qualifiers
REGION                  1..306
                        note = engineered
source                  1..306
                        mol_type = protein
                        organism = synthetic construct
SEQUENCE: 46
MAILDLKSLV LNAINYWGPK NNNGIQGGDF GYPISEKQID TSIITSTHPR LIPHDLTIPQ    60
NLETIFTTTQ VLTNNTDLQQ SQTVSFAKKT TTTTSTSTTN GWTEGGKISD TLEEKVSVSI   120
PFIGEGGGKN STTIEANFAH NSSTTTFQQA STDIEWNISQ PVLVPPRKQV VATLVIMGGN   180
```

```
FTIPMDLMTT IDSTEHYSGY PILTWISSPD NSYNGPFMSW YFANWPNLPS GFGPLNSDNT   240
VTYKGSVVSQ VSAGVYATVR FDQYDIHNLR TIEKTWYARH ATLHNGKKIS INNVTEMAPT   300
SPIKTN                                                             306

SEQ ID NO: 47           moltype = AA   length = 306
FEATURE                 Location/Qualifiers
REGION                  1..306
                        note = engineered
source                  1..306
                        mol_type = protein
                        organism = synthetic construct
SEQUENCE: 47
MAILDLKSLV LNAINYWGPK NNNGIQGGDF GYPISEKQID TSIITSTHPR LIPHDLTIPQ   60
NLETIFTTTQ VLTNNTDLQQ SQTVSFAKKT TTTTSTSTTN GWTEGGKISD TLEEKVSVSI   120
PFIGEGGGKN STTIEANFAH NSSTTTFQQA STDIEWNISQ PVLVPPRKQV VATLVIMGGN   180
FTIPMDLMTT IDSTEHYSGY PILTWISSPD NSYNGPFMSW YFANWPNLPS GFGPLNSDNT   240
ITYTGSVVSQ VSAGVYATVR FDQYDIHNLR TIEKTWYARH ATLHNGKKIS INNVTEMAPT   300
SPIKTN                                                             306

SEQ ID NO: 48           moltype = AA   length = 306
FEATURE                 Location/Qualifiers
REGION                  1..306
                        note = engineered
source                  1..306
                        mol_type = protein
                        organism = synthetic construct
SEQUENCE: 48
MAILDLKSLV LNAINYWGPK NNNGIQGGDF GYPISEKQID TSIITSTHPR LIPHDLTIPQ   60
NLETIFTTTQ VLTNNTDLQQ SQTVSFAKKT TTTTSTSTTN GWTEGGKISD TLEEKVSVSI   120
PFIGEGGGKN STTIEANFAH NSSTTTFQQA STDIEWNISQ PVLVPPRKQV VATLVIMGGN   180
FTIPMDLMTT IDSTEHYSGY PILTWISSPD NSYNGPFMSW YFANWPNLPS GFGPLNSDNT   240
ITYKGSVVSQ VSAGVYATVR FDQYDIHNLR TIEKTWYARH ATLHNGKKIS INNVTEMAPT   300
SPIKTN                                                             306

SEQ ID NO: 49           moltype = AA   length = 306
FEATURE                 Location/Qualifiers
REGION                  1..306
                        note = engineered
source                  1..306
                        mol_type = protein
                        organism = synthetic construct
SEQUENCE: 49
MAILDLKSLV LNAINYWGPK NNNGIQGGDF GYPISEKQID TSIITSTHPR LIPHDLTIPQ   60
NLETIFTTTQ VLTNNTDLQQ SQTVSFAKKT TTTTSTSTTN GWTEGGKISD TLEEKVSVSI   120
PFIGEGGGKN STTIEANFAH NSSTTTFQQA STDIEWNISQ PVLVPPRKQV VATLVIMGGN   180
FTIPMDLMTT IDSTEHYSGY PILTWISSPD NSYNGPFMSY YFANWPNLPS GFGPLNSDNT   240
VTYTGSVVSQ VSAGVYATVR FDQYDIHNLR TIEKTWYARH ATLHNGKKIS INNVTEMAPT   300
SPIKTN                                                             306

SEQ ID NO: 50           moltype = AA   length = 306
FEATURE                 Location/Qualifiers
REGION                  1..306
                        note = engineered
source                  1..306
                        mol_type = protein
                        organism = synthetic construct
SEQUENCE: 50
MAILDLKSLV LNAINYWGPK NNNGIQGGDF GYPISEKQID TSIITSTHPR LIPHDLTIPQ   60
NLETIFTTTQ VLTNNTDLQQ SQTVSFAKKT TTTTSTSTTN GWTEGGKISD TLEEKVSVSI   120
PFIGEGGGKN STTIEANFAH NSSTTTFQQA STDIEWNISQ PVLVPPRKQV VATLVIMGGN   180
FTIPMDLMTT IDSTEHYSGY PILTWISSPD NSYNGPFMSW YFANWPNLPS GFGPLNSDNT   240
VTFTGSVVSQ VSAGVYATVR FDQYDIHNLR TIEKTWYARH ATLHNGKKIS INNVTEMAPT   300
SPIKTN                                                             306

SEQ ID NO: 51           moltype = AA   length = 306
FEATURE                 Location/Qualifiers
REGION                  1..306
                        note = engineered
source                  1..306
                        mol_type = protein
                        organism = synthetic construct
SEQUENCE: 51
MAILDLKSLV LNAINYWGPK NNNGIQGGDF GYPISEKQID TSIITSTHPR LIPHDLTIPQ   60
NLETIFTTTQ VLTNNTDLQQ SQTVSFAKKT TTTTSTSTTN GWTEGGKISD TLEEKVSVSI   120
PFIGEGGAKN STTIEANFAH NSSTTTAQQA STDIEWNISQ PVLVPPRKQV VATLVIMGGN   180
FTIPMDLMTT IDSTEHYSGY PILTWISSPD NSYNGPFMSW YFANWPNLPS GFGPLNSDNT   240
VTYTGSVVSQ VSAGVYATVR FDQYDIHNLR TIEKTWYARH ATLHNGKKIS INNVTEMAPT   300
SPIKTN                                                             306
```

```
SEQ ID NO: 52              moltype = AA  length = 306
FEATURE                    Location/Qualifiers
REGION                     1..306
                           note = engineered
source                     1..306
                           mol_type = protein
                           organism = synthetic construct
SEQUENCE: 52
MAILDLKSLV LNAINYWGPK NNNGIQGGDF GYPISEKQID TSIITSTHPR LIPHDLTIPQ   60
NLETIFTTTQ VLTNNTDLQQ SQTVSFAKKT TTTTSTSTTN GWTEGGKISD TLEEKVSVSI  120
PFIGEGGGKN STTIEANFAH NSSTTTAQQA STDIEWNISQ PVLVPPRKQV VATLVIMGGN  180
FTIPMDLMTT IDSTEHYSGY PILTWISSPD NSYNGPFMSW YFANWPNLPS GFGPLNSDNT  240
VTYTGSVVSQ VSAGVYATVR FDQYDIHNLR TIEKTWYARH ATLHNGKKIS INNVTEAAPT  300
SPIKTN                                                             306

SEQ ID NO: 53              moltype = AA  length = 306
FEATURE                    Location/Qualifiers
REGION                     1..306
                           note = engineered
source                     1..306
                           mol_type = protein
                           organism = synthetic construct
SEQUENCE: 53
MAILDLKSLV LNAINYWGPK NNNGIQGGDF GYPISEKQID TSIITSTHPR LIPHDLTIPQ   60
NLETIFTTTQ VLTNNTDLQQ SQTVSFAKKT TTTTSTSTTN GWTEGGKISD TLEEKVSVSI  120
PFIGEGGGKN STTIEANFAH NSSTTTAQQA STDIEWNISQ PVLVPPRKQV VATLVIMGGN  180
FTIPMDLMTT IDSTEHYSGY PILTWISSPD NSYNGPFMSW YFANWPNLPS GFGPLNSDNT  240
VTYTGSVVSQ VSAGVYATVR FDQYDIHNLR TIEKTWYARH ATLHNGKKIA INNVTEMAPT  300
SPIKTN                                                             306

SEQ ID NO: 54              moltype = AA  length = 306
FEATURE                    Location/Qualifiers
REGION                     1..306
                           note = engineered
source                     1..306
                           mol_type = protein
                           organism = synthetic construct
SEQUENCE: 54
MAILDLKSLV LNAINYWGPK NNNGIQGGDF GYPISEKQID TSIITSTHPR LIPHDLTIPQ   60
NLETIFTTTQ VLTNNTDLQQ SQTVSFAKKT TTTTSTSTTN GWTEGGKISD TLEEKVSVSI  120
PFIGEGGGKN STTIEANFAH NSSTTTAQQA STDIEWNISQ PVLVPPRKQV VATLVIMGGN  180
FTIPMDLMTT IDSTEHYSGY PILTWISSPD NSYNGPFMSW YFANWPNLPS GFGPLNSDNT  240
VTYTGSVVSQ VSAGVYATVR FDQYDIHNLR TIEKTWYARH ATLANGKKIS INNVTEMAPT  300
SPIKTN                                                             306

SEQ ID NO: 55              moltype = AA  length = 306
FEATURE                    Location/Qualifiers
REGION                     1..306
                           note = engineered
source                     1..306
                           mol_type = protein
                           organism = synthetic construct
SEQUENCE: 55
MAILDLKSLV LNAINYWGPK NNNGIQGGDF GYPISEKQID TSIITSTHPR LIPHDLTIPQ   60
NLETIFTTTQ VLTNNTDLQQ SQTVSFAKKT TTTTSTSTTN GWTEGGKISD TLEEKVSVSI  120
PFIGEGGGKN STTIEANFAH NSSTTTAQQA STDIEWNISQ PVLVPPRKQV VATLVIMGGN  180
FTIPMDLMTT IDSTEHYSGY PILTWISSPD NSYNGPFMSW YFANWPNLPS GFGPLNSDNT  240
VTYTGSVVSQ VSAGVYATVR FDQYDIHNLR AIEKTWYARH ATLHNGKKIS INNVTEMAPT  300
SPIKTN                                                             306

SEQ ID NO: 56              moltype = AA  length = 306
FEATURE                    Location/Qualifiers
REGION                     1..306
                           note = engineered
source                     1..306
                           mol_type = protein
                           organism = synthetic construct
SEQUENCE: 56
MAILDLKSLV LNAINYWGPK NNNGIQGGDF GYPISEKQID TSIITSTHPR LIPHDLTIPQ   60
NLETIFTTTQ VLTNNTDLQQ SQTVSFAKKT TTTTSTSTTN GWTEGGKISD TLEEKVSVSI  120
PFIGEGGGKN STTIEANFAH NSSTTTAQQA STDIEWNISQ PVLVPPRKQV VATLVIMGGN  180
FTIPMDLMTT IDSTEHYSGY PILTWISSPD NSYNGPFMSW YFANWPNLPS GFGPLNSDNT  240
VTYTGSVVSQ VSAGVYATVR FDQYDIHNLR TIEKTWYAAH ATLHNGKKIS INNVTEMAPT  300
SPIKTN                                                             306

SEQ ID NO: 57              moltype = AA  length = 306
FEATURE                    Location/Qualifiers
REGION                     1..306
                           note = engineered
```

```
source                      1..306
                            mol_type = protein
                            organism = synthetic construct
SEQUENCE: 57
MAILDLKSLV LNAINYWGPK NNNGIQGGDF GYPISEKQID TSIITSTHPR LIPHDLTIPQ   60
NLETIFTTTQ VLTNNTDLQQ SQTVSFAKKT TTATSTSTTN GWTEGGKISD TLEEKVSVSI  120
PFIGEGGGKN STTIEANFAH NSSTTTFQQA STDIEWNISQ PVLVPPRKQV VATLVIMGGN  180
FTIPMDLMTT IDSTEHYSGY PILTWISSPD NSYNGPFMSW YFANWPNLPS GFGPLNSDNT  240
VTYTGSVVSQ VSAGVYATVR FDQYDIHNLR TIEKTWYARH ATLHNGKKIS INNVTEMAPT  300
SPIKAN                                                             306

SEQ ID NO: 58               moltype = AA  length = 306
FEATURE                     Location/Qualifiers
REGION                      1..306
                            note = engineered
source                      1..306
                            mol_type = protein
                            organism = synthetic construct
SEQUENCE: 58
MAILDLKSLV LNAINYWGPK NNNGIQGGDF GYPISEKQID TSIITSTHPR LIPHDLTIPQ   60
NLETIFTTTA VLTNNTDLQQ SQTVSFAKKT TTATSTSTTN GWTEGGKISD TLEEKVSVSI  120
PFIGEGGGKN STTIEANFAH NSSTTTFQQA STDIEWNISQ PVLVPPRKQV VATLVIMGGN  180
FTIPMDLMTT IDSTEHYSGY PILTWISSPD NSYNGPFMSW YFANWPNLPS GFGPLNSDNT  240
VTYTGSVVSQ VSAGVYATVR FDQYDIHNLR TIEKTWYARH ATLHNGKKIS INNVTEMAPT  300
SPIKTN                                                             306

SEQ ID NO: 59               moltype = AA  length = 306
FEATURE                     Location/Qualifiers
REGION                      1..306
                            note = engineered
source                      1..306
                            mol_type = protein
                            organism = synthetic construct
SEQUENCE: 59
MAILDLKSLV LNAINYWGPK NNNGIQGGDF GYPISEKQID TSIITSTHPR LIPHDLTIPQ   60
NLETIFTTTQ VLTNNTDLQQ SQTVSFAKKT TTTTSTSTTN GWTEGGKISD TLEEKVSVSI  120
PFIGAGGGKN STTIEANFAH NSSTTTAQQA STDIEWNISQ PVLVPPRKQV VATLVIMGGN  180
FTIPMDLMTT IDSTEHYSGY PILTWISSPD NSYNGPFMSW YFANWPNLPS GFGPLNSDNT  240
VTYTGSVVSQ VSAGVYATVR FDQYDIHNLR TIEKTWYARH ATLHNGKKIS INNVTEMAPT  300
SPIKTN                                                             306

SEQ ID NO: 60               moltype = AA  length = 306
FEATURE                     Location/Qualifiers
REGION                      1..306
                            note = engineered
source                      1..306
                            mol_type = protein
                            organism = synthetic construct
SEQUENCE: 60
MAILDLKSLV LNAINYWGPK NNNGIQGGDF GYPISEKQID TSIITSTHPR LIPHDLTIPQ   60
NLETIFTTTQ VLTNNTDLQQ SQTVSFAKKT TTTTSTSTTN GWTEGGKISD TLEEKVSVSI  120
PFIGEGGGKN STTIEANFAH NSSTTTAQQA STDIEWNISQ PVLVPPRKQV VATLVIMGGN  180
FTIPMDLMTT IDSTEHYSGY PILTWISSPD NSYNGPFMSW YFANWPNLPS GFGPLNSDNT  240
VTYAGSVVSQ VSAGVYATVR FDQYDIHNLR TIEKTWYARH ATLHNGKKIS INNVTEMAPT  300
SPIKTN                                                             306

SEQ ID NO: 61               moltype = AA  length = 306
FEATURE                     Location/Qualifiers
REGION                      1..306
                            note = engineered
source                      1..306
                            mol_type = protein
                            organism = synthetic construct
SEQUENCE: 61
MAILDLKSLV LNAINYWGPK NNNGIQGGDF GYPISEKQID TSIITSTHPR LIPHDLTIPQ   60
NLETIFTTTQ VLTNNTDLQQ SQTVSFAKKT TTATSTSTTN GWTEGGKISD TLEEKVSVSI  120
PFIGEGGGKN STTIEANFAH NSSTTTFQQA STDIEWNISQ PVLVPPRKQV VATLVIMGGN  180
FTIPMDLMTT IDSTEHYSGY PILTWISSPD NSYNGPFMSW YFANWPNLPS GFGPLNSDNT  240
VTYTGSVVSQ VSAGVYATVR FDQYDIHNLR TIEKTWYARH ATLHNGKKIS INNVTEMAPT  300
SAIKTN                                                             306

SEQ ID NO: 62               moltype = AA  length = 306
FEATURE                     Location/Qualifiers
REGION                      1..306
                            note = engineered
source                      1..306
                            mol_type = protein
                            organism = synthetic construct
SEQUENCE: 62
```

```
MAILDLKSLV LNAINYWGPK NNNGIQGGDF GYPISEKQID TSIITSTHPR LIPHDLTIPQ    60
NLETIFTTTQ VLTNNTDLQQ SQTVSFAKKT TTTTSTSTTN GWTEGGKISD TLEEKVSVSI   120
PFIGEGGGKN STTIEANFAH NSSTTTAQQA STDIEWNISQ PVLVPPRKQV VATLVIMGGN   180
FTIPMDLMTT IDSTEHYSGY PILTWISSPD NSYNGPFMSW YFANWPNLPS GFGPLNSDNT   240
VTYTGSVVSQ VSAGVYATVR FDQYDIHNLR TIEKTWYARH ATLHNGKKIS INNVTEMAPT   300
SPAKTN                                                             306

SEQ ID NO: 63           moltype = AA  length = 306
FEATURE                 Location/Qualifiers
REGION                  1..306
                        note = engineered
source                  1..306
                        mol_type = protein
                        organism = synthetic construct
SEQUENCE: 63
MAILDLKSLV LNAINYWGPK NNNGIQGGDF GYPISEKQID TSIITSTHPR LIPHDLTIPQ    60
NLETIFTTTQ VLTNNTDLQQ SQTVSFAKKT TTATSTSTTN GWTEGGKISD TLEEKVSVSI   120
PFIGEGGGKN STTIEANFAH NSSTTTFQQA STDIEWNISQ PVLVPPRKQV VATLVIMGGN   180
FTIPMDLMTT IDSTEHYSGY PILTWISSPD NSYNGPFMSW YFANWPNLPS GFGPLNSDNT   240
VTYTGSVVSQ VSAGVYATVR FDQYDIHNLR TIEKTWYAAH ATLHNGKKIS INNVTEMAPT   300
SPIKTN                                                             306

SEQ ID NO: 64           moltype = AA  length = 306
FEATURE                 Location/Qualifiers
REGION                  1..306
                        note = engineered
source                  1..306
                        mol_type = protein
                        organism = synthetic construct
SEQUENCE: 64
MAILDLKSLV LNAINYWGPK NNNGIQGGDF GYPISEKQID TSIITSTHPR LIPHDLTIPQ    60
NLETIFTTTQ VLTNNTDLQQ SQTVSFAKKT TTATSTSTTN GWTEGGKISD TLEEKVSVSI   120
PFIGEGGGKN STTIEANFAH NSSTTTFQQA STDIEWNISQ PVLVPPRKQV VATLVIMGGN   180
FTIPMDLMTT IDSTEHYSGY PILTWISSPD NSYNGPFMSW YFANWPNLPS GFGPLNSDNT   240
VTYTGSVVSQ VSAGVYATVR FDQYDIHNLR TIEKTWYARH ATLHNGKKIS INNVTEMAPT   300
SPIKAN                                                             306

SEQ ID NO: 65           moltype = AA  length = 306
FEATURE                 Location/Qualifiers
REGION                  1..306
                        note = engineered
source                  1..306
                        mol_type = protein
                        organism = synthetic construct
SEQUENCE: 65
MAILDLKSLV LNAINYWGPK NNNGIQGGDF GYPISEKQID TSIITSTHPR LIPHDLTIPQ    60
NLETIFTTTQ VLTNNTDLQQ SQTVSFAKKT TTATSTSTTN GWTEGGKISD TLEEKVSVSI   120
PFIGEGGGKN STTIEANFAH NSSTTTFQQA STDIEWNISQ PVLVPPRKQV VATLVIMGGN   180
FTIPMDLMTT IDSTEHYSGY PILTWISSPD NSYNGPFMSW YFANWPNLPS GFGPLNSDNT   240
VTYTGSVVSQ VSAGVYATVR FDQYDIHNLR TIEKTWYARH ATLHNGKKIS INNVTEAAPT   300
SPIKTN                                                             306

SEQ ID NO: 66           moltype = AA  length = 306
FEATURE                 Location/Qualifiers
REGION                  1..306
                        note = engineered
source                  1..306
                        mol_type = protein
                        organism = synthetic construct
SEQUENCE: 66
MAILDLKSLV LNAINYWGPK NNNGIQGGDF GYPISEKQID TSIITSTHPR LIPHDLTIPQ    60
NLETIFTTTQ VLTNNTDLQQ SQTVSFAKKT TTATSTSTTN GWTEGGKISD TLEEKVSVSI   120
PFIGEGGGKN STTIEANFAH NSSTTTFQQA STDIEWNISQ PVLVPPRKQV VATLVIMGGN   180
FTIPMDLMTT IDSTEHYSGY PILTWISSPD NSYNGPFMSW YFANWPNLPS GFGPLNSDNT   240
VTYTGSVVSQ VSAGVYATVR FDQYDIHNLR TIEKTWYARH ATLANGKKIS INNVTEMAPT   300
SPIKTN                                                             306

SEQ ID NO: 67           moltype = AA  length = 306
FEATURE                 Location/Qualifiers
REGION                  1..306
                        note = engineered
source                  1..306
                        mol_type = protein
                        organism = synthetic construct
SEQUENCE: 67
MAILDLKSLV LNAINYWGPK NNNGIQGGDF GYPISEKQID TSIITSTHPR LIPHDLTIPQ    60
NLETIFTTTQ VLTNNTDLQQ SQTVSFAKKT TTTTATSTTN GWTEGGKISD TLEEKVSVSI   120
PFIGEGGGKN STTIEANFAH NSSTTTFQQA STDIEWNISQ PVLVPPRKQV VATLVIMGGN   180
FTIPMDLMTT IDSTEHYSGY PILTWISSPD NSYNGPFMSW YFANWPNLPS GFGPLNSDNT   240
```

```
VTYTGSVVSQ VSAGVYATVR FDQYDIHNLR TIEKTWYARH ATLHNGKKIS INNVTEAAPT    300
SPIKTN                                                              306

SEQ ID NO: 68           moltype = AA  length = 306
FEATURE                 Location/Qualifiers
REGION                  1..306
                        note = engineered
source                  1..306
                        mol_type = protein
                        organism = synthetic construct
SEQUENCE: 68
MAILDLKSLV LNAINYWGPK NNNGIQGGDF GYPISEKQID TSIITSTHPR LIPHDLTIPQ     60
NLETIFTTTQ VLTNNTDLQQ SQTVSFAKKT TTTTSTSTTN GWTEGGKISD TLEEKVSVSI    120
PFIGEGGGKN STTIEANFAH NSSTTTAQQA STDIEWNISQ PVLVPPRKQV VATLVIMGGN    180
FTIPMDLMTT IDSTEHYSGY PILTWISSPD NSYNGPFMSW YFANWPNLPS GFGPLNSDNT    240
VTYTGSVVSQ VSAGVYATVR FDQYDIHNLR TAEKTWYARH ATLHNGKKIS INNVTEMAPT    300
SPIKTN                                                              306

SEQ ID NO: 69           moltype = AA  length = 306
FEATURE                 Location/Qualifiers
REGION                  1..306
                        note = engineered
source                  1..306
                        mol_type = protein
                        organism = synthetic construct
SEQUENCE: 69
MAILDLKSLV LNAINYWGPK NNNGIQGGDF GYPISEKQID TSIITSTHPR LIPHDLTIPQ     60
NLETIFTTTQ VLTNNTDLQQ SQTVSFAKKT TTTTATSTTN GWTEGGKISD TLEEKVSVSI    120
PFIGEGGGKN STTIEANFAH NSSTTTFQQA STDIEWNISQ PVLVPPRKQV VATLVIMGGN    180
FTIPMDLMTT IDSTEHYSGY PILTWISSPD NSYNGPFMSW YFANWPNLPS GFGPLNSDNT    240
VTYAGSVVSQ VSAGVYATVR FDQYDIHNLR TIEKTWYARH ATLHNGKKIS INNVTEMAPT    300
SPIKTN                                                              306

SEQ ID NO: 70           moltype = AA  length = 306
FEATURE                 Location/Qualifiers
REGION                  1..306
                        note = engineered
source                  1..306
                        mol_type = protein
                        organism = synthetic construct
SEQUENCE: 70
MAILDLKSLV LNAINYWGPK NNNGIQGGDF GYPISEKQID TSIITSTHPR LIPHDLTIPQ     60
NLETIFTTTQ VLTNNTDLQQ SQTVSFAKKT TTTTSTSTTN GWTEGGKISD TLEEKVSVSI    120
PFIGEGGGKN STTIEANFAH NSSTTTAQQA STDIEWNISQ PVLVPPRKQV VATLAIMGGN    180
FTIPMDLMTT IDSTEHYSGY PILTWISSPD NSYNGPFMSW YFANWPNLPS GFGPLNSDNT    240
VTYTGSVVSQ VSAGVYATVR FDQYDIHNLR TIEKTWYARH ATLHNGKKIS INNVTEMAPT    300
SPIKTN                                                              306

SEQ ID NO: 71           moltype = AA  length = 306
FEATURE                 Location/Qualifiers
REGION                  1..306
                        note = engineered
source                  1..306
                        mol_type = protein
                        organism = synthetic construct
SEQUENCE: 71
MAILDLKSLV LNAINYWGPK NNNGIQGGDF GYPISEKQID TSIITSTHPR LIPHDLTIPQ     60
NLETIFTTTQ VLTNNTDLQQ SQTVSFAKKT TTTTSTSTTN GWTEGGKISD TLEEKVSVSI    120
PFIGEGGGKN STTIEANFAH NSSTTTAQQA STDIEWNIAQ PVLVPPRKQV VATLVIMGGN    180
FTIPMDLMTT IDSTEHYSGY PILTWISSPD NSYNGPFMSW YFANWPNLPS GFGPLNSDNT    240
VTYTGSVVSQ VSAGVYATVR FDQYDIHNLR TIEKTWYARH ATLHNGKKIS INNVTEMAPT    300
SPIKTN                                                              306

SEQ ID NO: 72           moltype = AA  length = 306
FEATURE                 Location/Qualifiers
REGION                  1..306
                        note = engineered
source                  1..306
                        mol_type = protein
                        organism = synthetic construct
SEQUENCE: 72
MAILDLKSLV LNAINYWGPK NNNGIQGGDF GYPISEKQID TSIITSTHPR LIPHDLTIPQ     60
NLETIFTTTQ VLTNNTDLQQ SQTVSFAKKT TTTTATSTTN GWTEGGKISD TLEEKVSVSI    120
PFIGEGGGKN STTIEANFAH NSSTTTAQQA STDIEWNISQ PVLVPPRKQV VATLVIMGGN    180
FTIPMDLMTT IDSTEHYSGY PILTWISSPD NSYNGPFMSW YFANWPNLPS GFGPLNSDNT    240
VTYTGSVVSQ VSAGVYATVR FDQYDIHNLR TIEKTWYARH ATLHNGKKIS INNVTEMAPT    300
SPIKTN                                                              306

SEQ ID NO: 73           moltype = AA  length = 306
```

```
FEATURE                 Location/Qualifiers
REGION                  1..306
                        note = engineered
source                  1..306
                        mol_type = protein
                        organism = synthetic construct
SEQUENCE: 73
MAILDLKSLV LNAINYWGPK NNNGIQGGDF GYPISEKQID TSIITSTHPR LIPHDLTIPQ    60
NLETIFTTTQ VLTNNTDLQQ SQTVSFAKKT TTTTSTSTTN GWTEGGKISD TLEEKVSVSI   120
PFIGEGGGKN STTIEANFAH NSSTTTAQQA STDIEWNISQ PVLVPPRKQV VATLVIMGGN   180
FTIPMDAMTT IDSTEHYSGY PILTWISSPD NSYNGPFMSW YFANWPNLPS GFGPLNSDNT   240
VTYTGSVVSQ VSAGVYATVR FDQYDIHNLR TIEKTWYARH ATLHNGKKIS INNVTEMAPT   300
SPIKTN                                                              306

SEQ ID NO: 74           moltype = AA  length = 306
FEATURE                 Location/Qualifiers
REGION                  1..306
                        note = engineered
source                  1..306
                        mol_type = protein
                        organism = synthetic construct
SEQUENCE: 74
MAILDLKSLV LNAINYWGPK NNNGIQGGDF GYPISEKQID TSIITSTHPR LIPHDLTIPQ    60
NLETIFTTTQ VLTNNTDLQQ SQTVSFAKKT TTATSTSTTN GWTEGGKISD TLEEKVSVSI   120
PFIGEGGGKN STTIEANFAH NSSTTTFQQA STDIEWNISQ PVLVPPRKQV VATLVIMGGN   180
FAIPMDLMTT IDSTEHYSGY PILTWISSPD NSYNGPFMSW YFANWPNLPS GFGPLNSDNT   240
VTYTGSVVSQ VSAGVYATVR FDQYDIHNLR TIEKTWYARH ATLHNGKKIS INNVTEMAPT   300
SPIKTN                                                              306

SEQ ID NO: 75           moltype = AA  length = 306
FEATURE                 Location/Qualifiers
REGION                  1..306
                        note = engineered
source                  1..306
                        mol_type = protein
                        organism = synthetic construct
SEQUENCE: 75
MAILDLKSLV LNAINYWGPK NNNGIQGGDF GYPISEKQID TSIITSTHPR LIPHDLTIPQ    60
NLETIFTTTQ VLTNNTDLQQ SQTVSFAKKT TTTTSTSTTN GWTEGGKISD TLEEKVSVSI   120
PFIGEGGGKN STTIEANFAH NSSTTTAQQA STDIEWNISQ PVLVPPRKQV VATLVIMGGN   180
FTIPMDLMTT IDSTEHYSGY PILTWISSPD NSYNGPFMSW YFANWPNLPS GFGPLNSDNT   240
VAYTGSVVSQ VSAGVYATVR FDQYDIHNLR TIEKTWYARH ATLHNGKKIS INNVTEMAPT   300
SPIKTN                                                              306

SEQ ID NO: 76           moltype = AA  length = 306
FEATURE                 Location/Qualifiers
REGION                  1..306
                        note = engineered
source                  1..306
                        mol_type = protein
                        organism = synthetic construct
SEQUENCE: 76
MAILDLKSLV LNAINYWGPK NNNGIQGGDF GYPISEKQID TSIITSTHPR LIPHDLTIPQ    60
NLETIFTTTQ VLTNNTDLQQ SQTVSFAKKT TTATSTSTTN GWTEGGKISD TLEEKVSVSI   120
PFIGEGGGKN STTIEANFAH NSSTTTFQQA STDIEWNISQ PVLVPPRKQV VATLVIMGGN   180
FTIPMDLMTT IDSTEHYSGY PILTWISSPD NSYNGPFMSW YFANWPNLPS GFGPLNSDNT   240
VTYTGAVVSQ VSAGVYATVR FDQYDIHNLR TIEKTWYARH ATLHNGKKIS INNVTEMAPT   300
SPIKTN                                                              306

SEQ ID NO: 77           moltype = AA  length = 306
FEATURE                 Location/Qualifiers
REGION                  1..306
                        note = engineered
source                  1..306
                        mol_type = protein
                        organism = synthetic construct
SEQUENCE: 77
MAILDLKSLV LNAINYWGPK NNNGIQGGDF GYPISEKQID TSIITSTHPR LIPHDLTIPQ    60
NLETIFTTTQ VLTNNTDLQQ SQTVSFAKKT TTATSTSTTN GWTEGGKISD TLEEKVSVSI   120
PFIGEGGGKN STTIEANFAH NSSTTTFQAA STDIEWNISQ PVLVPPRKQV VATLVIMGGN   180
FTIPMDLMTT IDSTEHYSGY PILTWISSPD NSYNGPFMSW YFANWPNLPS GFGPLNSDNT   240
VTYTGSVVSQ VSAGVYATVR FDQYDIHNLR TIEKTWYARH ATLHNGKKIS INNVTEMAPT   300
SPIKTN                                                              306

SEQ ID NO: 78           moltype = AA  length = 306
FEATURE                 Location/Qualifiers
REGION                  1..306
                        note = engineered
source                  1..306
```

```
                        mol_type = protein
                        organism = synthetic construct
SEQUENCE: 78
MAILDLKSLV LNAINYWGPK NNNGIQGGDF GYPISEKQID TSIITSTHPR LIPHDLTIPQ   60
NLETIFTTTQ VLTNNTDLQQ SQTVSFAKKT TTATSTSTTN GWTEGGKISD TLEEKVSVSI  120
PFIGEGGGKN STTIEANFAH NSSTTTFQQA ATDIEWNISQ PVLVPPRKQV VATLVIMGGN  180
FTIPMDLMTT IDSTEHYSGY PILTWISSPD NSYNGPFMSW YFANWPNLPS GFGPLNSDNT  240
VTYTGSVVSQ VSAGVYATVR FDQYDIHNLR TIEKTWYARH ATLHNGKKIS INNVTEMAPT  300
SPIKTN                                                            306

SEQ ID NO: 79           moltype = AA  length = 306
FEATURE                 Location/Qualifiers
REGION                  1..306
                        note = engineered
source                  1..306
                        mol_type = protein
                        organism = synthetic construct
SEQUENCE: 79
MAILDLKSLV LNAINYWGPK NNNGIQGGDF GYPISEKQID TSIITSTHPR LIPHDLTIPQ   60
NLETIFTTTA VLTNNTDLQQ SQTVSFAKKT TTTTSTSTTN GWTEGGKISD TLEEKVSVSI  120
PFIGEGGGKN STTIEANFAH NSSTTTAQQA STDIEWNISQ PVLVPPRKQV VATLVIMGGN  180
FTIPMDLMTT IDSTEHYSGY PILTWISSPD NSYNGPFMSW YFANWPNLPS GFGPLNSDNT  240
VTYTGSVVSQ VSAGVYATVR FDQYDIHNLR TIEKTWYARH ATLHNGKKIS INNVTEMAPT  300
SPIKTN                                                            306

SEQ ID NO: 80           moltype = AA  length = 306
FEATURE                 Location/Qualifiers
REGION                  1..306
                        note = engineered
source                  1..306
                        mol_type = protein
                        organism = synthetic construct
SEQUENCE: 80
MAILDLKSLV LNAINYWGPK NNNGIQGGDF GYPISEKQID TSIITSTHPR LIPHDLTIPQ   60
NLETIFTTTQ VLTNNTDLQQ SQTVSFAKKT TTTATSTTTN GWTEGGKISD TLEEKVSVSI  120
PFIGEGGGKN STTIEANFAH NSSTTTFAQA STDIEWNISQ PVLVPPRKQV VATLVIMGGN  180
FTIPMDLMTT IDSTEHYSGY PILTWISSPD NSYNGPFMSW YFANWPNLPS GFGPLNSDNT  240
VTYTGSVVSQ VSAGVYATVR FDQYDIHNLR TIEKTWYARH ATLHNGKKIS INNVTEMAPT  300
SPIKTN                                                            306

SEQ ID NO: 81           moltype = AA  length = 306
FEATURE                 Location/Qualifiers
REGION                  1..306
                        note = engineered
source                  1..306
                        mol_type = protein
                        organism = synthetic construct
SEQUENCE: 81
MAILDLKSLV LNAINYWGPK NNNGIQGGDF GYPISEKQID TSIITSTHPR LIPHDLTIPQ   60
NLETIFTTTQ VLTNNTDLQQ SQTVSFAKKT TTATSTSTTN GWTEGGKISD TLEEKVSVSI  120
PFIGEGGGKN STTIEANFAH NSSTTTFQQA STDIEWNISQ PVLVPPRKQV VATLVIMGGN  180
FTIPMDLMTT IDSTEHYSGY PILTWISSPD NSYNGPFMSW YFANWPNLPS GFGPLNSDNT  240
VTYTGSVVSQ VSAGVYATVR FDQYDIHNLR AIEKTWYARH ATLHNGKKIS INNVTEMAPT  300
SPIKTN                                                            306

SEQ ID NO: 82           moltype = AA  length = 306
FEATURE                 Location/Qualifiers
REGION                  1..306
                        note = engineered
source                  1..306
                        mol_type = protein
                        organism = synthetic construct
SEQUENCE: 82
MAILDLKSLV LNAINYWGPK NNNGIQGGDF GYPISEKQID TSIITSTHPR LIPHDLTIPQ   60
NLETIFTTTQ VLTNNTDLQQ SQTVSFAKKT TTATSTSTTN GWTEGGKISD TLEEKVSVSI  120
PFIGEGGGKN STTIEANFAH NSSTTTFQQA STDIEWNISQ PVLVPPRKQV VATLVIMGGN  180
FTIPMDLMTT IDSTEHYSGY PILTWISSPD NSYNGPFMSW YFANWPNLPS GFGPLNSDNT  240
VTYTGSVVSQ VSAGVYATVR FDQYDIHNLR TIEKTWYARH ATLHNGKKIS INNVTEMAPT  300
SPIKTN                                                            306

SEQ ID NO: 83           moltype = AA  length = 306
FEATURE                 Location/Qualifiers
REGION                  1..306
                        note = engineered
source                  1..306
                        mol_type = protein
                        organism = synthetic construct
SEQUENCE: 83
MAILDLKSLV LNAINYWGPK NNNGIQGGDF GYPISEKQID TSIITSTHPR LIPHDLTIPQ   60
```

```
NLETIFTTTQ VLTNNTDLQQ SQTVSFAKKT TTATSTSTTN GWTEGGKISD TLEEKVSVSI    120
PFIGEGGGKN STTIEANFAH NSSTTTFQQA STDIEWNISQ PVLVPPRKQV VATLVIAGGN    180
FTIPMDLMTT IDSTEHYSGY PILTWISSPD NSYNGPFMSW YFANWPNLPS GFGPLNSDNT    240
VTYTGSVVSQ VSAGVYATVR FDQYDIHNLR TIEKTWYARH ATLHNGKKIS INNVTEMAPT    300
SPIKTN                                                               306

SEQ ID NO: 84           moltype = AA  length = 306
FEATURE                 Location/Qualifiers
REGION                  1..306
                        note = engineered
source                  1..306
                        mol_type = protein
                        organism = synthetic construct
SEQUENCE: 84
MAILDLKSLV LNAINYWGPK NNNGIQGGDF GYPISEKQID TSIITSTHPR LIPHDLTIPQ    60
NLETIFTTTQ VLTNNTDLQQ SQTVSFAKKT TTTTATSTTN GWTEGGKISD TLEEKVSVSI    120
PFIGEGGGKN STTIEANFAH NSSTTTFQQA STDIEWNISQ PVLVPPRKQV VATLVIMGGN    180
FTIPMDLMTT IDSTEHYSGY PILTWISSPD NSYNGPFMSW YFANWPNLPS GFGPLNSDNT    240
VTYTGSAVSQ VSAGVYATVR FDQYDIHNLR TIEKTWYARH ATLHNGKKIS INNVTEMAPT    300
SPIKTN                                                               306

SEQ ID NO: 85           moltype = AA  length = 306
FEATURE                 Location/Qualifiers
REGION                  1..306
                        note = engineered
source                  1..306
                        mol_type = protein
                        organism = synthetic construct
SEQUENCE: 85
MAILDLKSLV LNAINYWGPK NNNGIQGGDF GYPISEKQID TSIITSTHPR LIPHDLTIPQ    60
NLETIFTTTQ VLTNNTDLQQ SQTVSFAKKT TTATSTSTTN GWTEGGKISD TLEEKVSVSI    120
PFIGEGGGKN STTIEANFAH NSSTTTFQQA STDIAWNISQ PVLVPPRKQV VATLVIMGGN    180
FTIPMDLMTT IDSTEHYSGY PILTWISSPD NSYNGPFMSW YFANWPNLPS GFGPLNSDNT    240
VTYTGSVVSQ VSAGVYATVR FDQYDIHNLR TIEKTWYARH ATLHNGKKIS INNVTEMAPT    300
SPIKTN                                                               306

SEQ ID NO: 86           moltype = AA  length = 306
FEATURE                 Location/Qualifiers
REGION                  1..306
                        note = engineered
source                  1..306
                        mol_type = protein
                        organism = synthetic construct
SEQUENCE: 86
MAILDLKSLV LNAINYWGPK NNNGIQGGDF GYPISEKQID TSIITSTHPR LIPHDLTIPQ    60
NLETIFTTTQ VLTNNTDLQQ SQTVSFAKKT TTTTSTSTTN GWTEGGKISD TLEEKVSVSI    120
PFIGEGGGKN STTAEANFAH NSSTTTAQQA STDIEWNISQ PVLVPPRKQV VATLVIMGGN    180
FTIPMDLMTT IDSTEHYSGY PILTWISSPD NSYNGPFMSW YFANWPNLPS GFGPLNSDNT    240
VTYTGSVVSQ VSAGVYATVR FDQYDIHNLR TIEKTWYARH ATLHNGKKIS INNVTEMAPT    300
SPIKTN                                                               306

SEQ ID NO: 87           moltype = AA  length = 306
FEATURE                 Location/Qualifiers
REGION                  1..306
                        note = engineered
source                  1..306
                        mol_type = protein
                        organism = synthetic construct
SEQUENCE: 87
MAILDLKSLV LNAINYWGPK NNNGIQGGDF GYPISEKQID TSIITSTHPR LIPHDLTIPQ    60
NLETIFTTTQ VLTNNTDLQQ SQTVSFAKKT TTATSTSTTN GWTEGGKISD TLEEKVSVSI    120
PFIGEGGGKN STTIEANFAH NSSTTTFQQA STDIEWNISQ PVLVPPRKQV VATLVIMGGN    180
FTIPMDLMTT IDSTEHYSGY PILTWISSPD NSYNGPFMSW YFANWPNLPS GFGPLNSDNT    240
VAYTGSVVSQ VSAGVYATVR FDQYDIHNLR TIEKTWYARH ATLHNGKKIS INNVTEMAPT    300
SPIKTN                                                               306

SEQ ID NO: 88           moltype = AA  length = 306
FEATURE                 Location/Qualifiers
REGION                  1..306
                        note = engineered
source                  1..306
                        mol_type = protein
                        organism = synthetic construct
SEQUENCE: 88
MAILDLKSLV LNAINYWGPK NNNGIQGGDF GYPISEKQID TSIITSTHPR LIPHDLTIPQ    60
NLETIFTTTQ VLTNNTDLQQ SQTVSFAKKT TTATSTSTTN GWTEGGKISD TLEEKVSVSI    120
PFIGEGGGKN STTIEANFAH NSSTTTFQQA STDIEWNISQ PVLVPPRKQV VATLVIMGGN    180
FTIPMDLMTT IDSTEHYAGY PILTWISSPD NSYNGPFMSW YFANWPNLPS GFGPLNSDNT    240
VTYTGSVVSQ VSAGVYATVR FDQYDIHNLR TIEKTWYARH ATLHNGKKIS INNVTEMAPT    300
```

```
SPIKTN                                                              306

SEQ ID NO: 89           moltype = AA  length = 306
FEATURE                 Location/Qualifiers
REGION                  1..306
                        note = engineered
source                  1..306
                        mol_type = protein
                        organism = synthetic construct
SEQUENCE: 89
MAILDLKSLV LNAINYWGPK NNNGIQGGDF GYPISEKQID TSIITSTHPR LIPHDLTIPQ    60
NLETIFTTTQ VLTNNTDLQQ SQTVSFAKKT TTTTSTSTTN GWTEGGKISD TLEEKVSVSI   120
PFIGEGGGKN STTIEANFAH NSSTTTAQQA STDIEWNISQ PVLVPPRKQV VATLVIMGGN   180
FTIPMDLMTT IDSTEHYSGY PILTWISSPD NSYNGPFMSW YFANWPNLPS GFGPLNSDNT   240
VTYTGSVVSQ VSAGVYATVR FDQYDIHNLR TIEKTWYARH ATLHNGKKIS IANVTEMAPT   300
SPIKTN                                                              306

SEQ ID NO: 90           moltype = AA  length = 306
FEATURE                 Location/Qualifiers
REGION                  1..306
                        note = engineered
source                  1..306
                        mol_type = protein
                        organism = synthetic construct
SEQUENCE: 90
MAILDLKSLV LNAINYWGPK NNNGIQGGDF GYPISEKQID TSIITSTHPR LIPHDLTIPQ    60
NLETIFTTTQ VLTNNTDLQQ SQTVSFSKKT TTTTSTSTTN GWTEGGKISD TLEEKVSVSI   120
PFIGEGGGKN STTIEANFAH NSSTTTAQQA STDIEWNISQ PVLVPPRKQV VATLVIMGGN   180
FTIPMDLMTT IDSTEHYSGY PILTWISSPD NSYNGPFMSW YFANWPNLPS GFGPLNSDNT   240
VTYTGSVVSQ VSAGVYATVR FDQYDIHNLR TIEKTWYARH ATLHNGKKIS INNVTEMAPT   300
SPIKTN                                                              306

SEQ ID NO: 91           moltype = AA  length = 306
FEATURE                 Location/Qualifiers
REGION                  1..306
                        note = engineered
source                  1..306
                        mol_type = protein
                        organism = synthetic construct
SEQUENCE: 91
MAILDLKSLV LNAINYWGPK NNNGIQGGDF GYPISEKQID TSIITSTHPR LIPHDLTIPQ    60
NLETIFTTTQ VLTNNTDLQQ SQTVSFAKKT TTTTSTSTTN GWTEGGKISD TLEEKVSVSI   120
PFIGEGGGKN STTIEANFAH NSSTTTAQQA STDIEWNISQ PVLVPPRKQV VATLVIMGGN   180
FTIPMDLMTT IDSTEHYSGY PILTWISSPD NSYNGPFMSW YFANWPNLPS GFGPLNSDNT   240
VTYTGAVVSQ VSAGVYATVR FDQYDIHNLR TIEKTWYARH ATLHNGKKIS INNVTEMAPT   300
SPIKTN                                                              306

SEQ ID NO: 92           moltype = AA  length = 306
FEATURE                 Location/Qualifiers
REGION                  1..306
                        note = engineered
source                  1..306
                        mol_type = protein
                        organism = synthetic construct
SEQUENCE: 92
MAILDLKSLV LNAINYWGPK NNNGIQGGDF GYPISEKQID TSIITSTHPR LIPHDLTIPQ    60
NLETIFTTTQ VLTNNTDLQQ SQTVSFAKKT TTTTATSTTN GWTEGGKISD TLEEKVSVSI   120
PFIGEGGGKN STTIEANFAH NSSTTTFQQA STDIEWNISQ PVLVPPRKQV VATLVIMGGN   180
FTIPMDLMTT IDSTEHYSGY PILTWISSPD NSYNGPFMSW YFANWPNLPS GFGPLNSDNT   240
VTYTGSVVSQ VSAGVYATVR FDQYDIHNLR TAEKTWYARH ATLHNGKKIS INNVTEMAPT   300
SPIKTN                                                              306

SEQ ID NO: 93           moltype = AA  length = 306
FEATURE                 Location/Qualifiers
REGION                  1..306
                        note = engineered
source                  1..306
                        mol_type = protein
                        organism = synthetic construct
SEQUENCE: 93
MAILDLKSLV LNAINYWGPK NNNGIQGGDF GYPISEKQID TSIITSTHPR LIPHDLTIPQ    60
NLETIFTTTQ VLTNNTDLQQ SQTVSFAKKT TTATSTSTTN GWTEGGKISD TLEEKVSVSI   120
PFIGEGGGKN STTIEANFSH NSSTTTFQQA STDIEWNISQ PVLVPPRKQV VATLVIMGGN   180
FTIPMDLMTT IDSTEHYSGY PILTWISSPD NSYNGPFMSW YFANWPNLPS GFGPLNSDNT   240
VTYTGSVVSQ VSAGVYATVR FDQYDIHNLR TIEKTWYARH ATLHNGKKIS INNVTEMAPT   300
SPIKTN                                                              306

SEQ ID NO: 94           moltype = AA  length = 306
FEATURE                 Location/Qualifiers
```

```
REGION                    1..306
                          note = engineered
source                    1..306
                          mol_type = protein
                          organism = synthetic construct
SEQUENCE: 94
MAILDLKSLV LNAINYWGPK NNNGIQGGDF GYPISEKQID TSIITSTHPR LIPHDLTIPQ     60
NLETIFTTTQ VLTNNTDLQQ SQTVSFAKKT TTTTSTSTTN GWTEGGKISD TLEEKVSVSI    120
PFIGEGGGKN STTIEANFAH NSSTTTAQQA STDIEWNISQ PVLVPPRKQV VATLVIMGGN    180
FTIPMDLMTT IDSTEHYSGY PILTWISSPD NSYNGPFMSW YFANWPNLPS GFGPLNSDNT    240
VTYTGSVVSQ VSAGVYATVR FDQYDIHNLR TIEKTWYARH ATLHNGKKIS INNVTEMAPT    300
SAIKTN                                                               306

SEQ ID NO: 95             moltype = AA   length = 306
FEATURE                   Location/Qualifiers
REGION                    1..306
                          note = engineered
source                    1..306
                          mol_type = protein
                          organism = synthetic construct
SEQUENCE: 95
MAILDLKSLV LNAINYWGPK NNNGIQGGDF GYPISEKQID TSIITSTHPR LIPHDLTIPQ     60
NLETIFTTTQ VLTNNTDLQQ SQTVSFAKKT TTTTSTSTTN GWTEGGKISD TLEEKVSVSI    120
PFIGEGGGKN STTIEANFAH NSSTTTAQQA STDIEWNISQ PVLVPPRKQV VATLVIMGGN    180
FTIPMDLMTT IDSTEHYAGY PILTWISSPD NSYNGPFMSW YFANWPNLPS GFGPLNSDNT    240
VTYTGSVVSQ VSAGVYATVR FDQYDIHNLR TIEKTWYARH ATLHNGKKIS INNVTEMAPT    300
SPIKTN                                                               306

SEQ ID NO: 96             moltype = AA   length = 306
FEATURE                   Location/Qualifiers
REGION                    1..306
                          note = engineered
source                    1..306
                          mol_type = protein
                          organism = synthetic construct
SEQUENCE: 96
MAILDLKSLV LNAINYWGPK NNNGIQGGDF GYPISEKQID TSIITSTHPR LIPHDLTIPQ     60
NLETIFTTTQ VLTNNTDLQQ SQTVSFAKKT TTTTSTSTTN GWTEGGKISD TLEEKVSVSI    120
PFIGEGGGKN STTIEANFAH NSSTTTAQQA STDIEWNISQ PVLVPPRKQV VATLVIMGGN    180
FTIPMDLMTT IDSTEHYSGY PILTWISSPD NSYNGPFMSW YFANWPNLPS GFGPLNSDNT    240
VTYTGSVVAQ VSAGVYATVR FDQYDIHNLR TIEKTWYARH ATLHNGKKIS INNVTEMAPT    300
SPIKTN                                                               306

SEQ ID NO: 97             moltype = AA   length = 306
FEATURE                   Location/Qualifiers
REGION                    1..306
                          note = engineered
source                    1..306
                          mol_type = protein
                          organism = synthetic construct
SEQUENCE: 97
MAILDLKSLV LNAINYWGPK NNNGIQGGDF GYPISEKQID TSIITSTHPR LIPHDLTIPQ     60
NLETIFTTTQ VLTNNTDLQQ SQTVSFAKKT TTATSTSTTN GWTEGGKISD TLEEKVSVSI    120
PFIGEGGGKN STTIEANFAH NSSTTTAQQA STDIEWNISQ PVLVPPRKQV VATLVIMGGN    180
FTIPMDLMTT IDSTEHYSGY PILTWISSPD NSYNGPFMSW YFANWPNLPS GFGPLNSDNT    240
VTYTGSVVSQ VSAGVYATVR FDQYDIHNLR TIEKTWYARH ATLHNGKKIS INNVTEMAPT    300
SPIKTN                                                               306

SEQ ID NO: 98             moltype = AA   length = 306
FEATURE                   Location/Qualifiers
REGION                    1..306
                          note = engineered
source                    1..306
                          mol_type = protein
                          organism = synthetic construct
SEQUENCE: 98
MAILDLKSLV LNAINYWGPK NNNGIQGGDF GYPISEKQID TSIITSTHPR LIPHDLTIPQ     60
NLETIFTTTQ VLTNNTDLQQ SQTVSFAKKT TTTTSTSTTN GWTEGGKISD TLEEKVSVSI    120
PFIGEGGGKN STTIEANFAH NSSTTTAQQA STDIEWNISQ PVLVPPRKQV VATLVIMGGN    180
FTIPMDLMTT IDSTEHYSGY PILTWISSPD NSYNGPFMSW YFANWPNLPS GFGPLNSDNT    240
VTYTGSAVSQ VSAGVYATVR FDQYDIHNLR TIEKTWYARH ATLHNGKKIS INNVTEMAPT    300
SPIKTN                                                               306

SEQ ID NO: 99             moltype = AA   length = 306
FEATURE                   Location/Qualifiers
REGION                    1..306
                          note = engineered
source                    1..306
                          mol_type = protein
```

```
                           organism = synthetic construct
SEQUENCE: 99
MAILDLKSLV LNAINYWGPK NNNGIQGGDF GYPISEKQID TSIITSTHPR LIPHDLTIPQ       60
NLETIFTTTQ VLTNNTDLQQ SQTVSFAKKT TTTTSTSTTN GWTEGGKISD TLEEKVSVSI      120
PFIGEGGGKN STTIEANFAH NSSTTTAQQA STDIEWNISQ PVLVPPRKQV VATLVIMGGN      180
FTIPMDLMTT IDSTEHYSGY PILTWISSPD NSYNGPFMSW YFANWPNLPS GFGPLNSDNA      240
VTYTGSVVSQ VSAGVYATVR FDQYDIHNLR TIEKTWYARH ATLHNGKKIS INNVTEMAPT      300
SPIKTN                                                                306

SEQ ID NO: 100          moltype = AA  length = 306
FEATURE                 Location/Qualifiers
REGION                  1..306
                        note = engineered
source                  1..306
                        mol_type = protein
                        organism = synthetic construct
SEQUENCE: 100
MAILDLKSLV LNAINYWGPK NNNGIQGGDF GYPISEKQID TSIITSTHPR LIPHDLTIPQ       60
NLETIFTTTQ VLTNNTDLQQ SQTVSFAKKT TTTTSTSTTN GWTEGGKISD TLEEKVSVSI      120
PFIGEGGGKN STTIEANFAH NSSTTTAQQA STDIEWNISQ PVLVPPRKQV VATLVIMGGN      180
FTIPMDLMTT IDSTEHASGY PILTWISSPD NSYNGPFMSW YFANWPNLPS GFGPLNSDNT      240
VTYTGSVVSQ VSAGVYATVR FDQYDIHNLR TIEKTWYARH ATLHNGKKIS INNVTEMAPT      300
SPIKTN                                                                306

SEQ ID NO: 101          moltype = AA  length = 306
FEATURE                 Location/Qualifiers
REGION                  1..306
                        note = engineered
source                  1..306
                        mol_type = protein
                        organism = synthetic construct
SEQUENCE: 101
MAILDLKSLV LNAINYWGPK NNNGIQGGDF GYPISEKQID TSIITSTHPR LIPHDLTIPQ       60
NLETIFTTTQ VLTNNTDLQQ SQTVSFAKKT TTTTATSTTN GWTEGGKISD TLEEKVSVSI      120
PFIGEGGGKN STTIEANFAH NSSTTTFQQA STDIEWNISQ PVLVPPRKQV VATLVIMGGN      180
FTIPMDLMTT IDSTEHYSGY PILTWISSPD NSYNGPFMSW YFANWPNLPS GFGPLNSDNT      240
VTYTGSVVSQ VSAGVYATVR FDQYDIHNLR TIEKTWYARH ATLHNGKKIS IANVTEMAPT      300
SPIKTN                                                                306

SEQ ID NO: 102          moltype = AA  length = 306
FEATURE                 Location/Qualifiers
REGION                  1..306
                        note = engineered
source                  1..306
                        mol_type = protein
                        organism = synthetic construct
SEQUENCE: 102
MAILDLKSLV LNAINYWGPK NNNGIQGGDF GYPISEKQID TSIITSTHPR LIPHDLTIPQ       60
NLETIFTTTQ VLTNNTDLQQ SQTVSFAKKT TTTTSTSTTN GWTEGGKISD TLEEKVSVSI      120
PFIGEGGGKN STTIEANFAH NSSTTTAQQA STDIEWNISQ PVLVPPRKQV VATLVIMGGN      180
FTIPMDLMTT IDSTEHYSGY PILTWISSPD NSYNGPFMSW YFANWPNLPS GFGPLNSDNT      240
VTYTGSVVSQ VSAGVYATVR FDQYDIHNLR TIEKTWYARH ATLHNGKKIS INNVTEMAPT      300
SPIKTN                                                                306

SEQ ID NO: 103          moltype = AA  length = 306
FEATURE                 Location/Qualifiers
REGION                  1..306
                        note = engineered
source                  1..306
                        mol_type = protein
                        organism = synthetic construct
SEQUENCE: 103
MAILDLKSLV LNAINYWGPK NNNGIQGGDF GYPISEKQID TSIITSTHPR LIPHDLTIPQ       60
NLETIFTTTQ VLTNNTDLQQ SQTVSFAKKT TTTTSTSTTN GWTEGGKISD TLEEKVSVSI      120
PFIGEGGGKN STTIEANFAH NSSTTTAQQA STDIEWNISQ PVLVPPRKQV VATLVIMGGN      180
FTIPMDLMTT IDSTEHYSGY PILTWISSPD NSYNGPFMSW YFANWPNLPS GFGPLNSDNT      240
VTYTGSVVSQ VSAGVYATVR FDQYDIHNLR TIEKTWYARH ATLHNGKKIS INNVTAMAPT      300
SPIKTN                                                                306

SEQ ID NO: 104          moltype = AA  length = 306
FEATURE                 Location/Qualifiers
REGION                  1..306
                        note = engineered
source                  1..306
                        mol_type = protein
                        organism = synthetic construct
SEQUENCE: 104
MAILDLKSLV LNAINYWGPK NNNGIQGGDF GYPISEKQID TSIITSTHPR LIPHDLTIPQ       60
NLETIFTTTQ VLTNNTDLQQ SQTVSFAKKT TTTTATSTTN GWTEGGKISD TLEEKVSVSI      120
```

```
PFIGEGGGKN STTIEANFAH NSSTTTFQQA STDIEWNISQ PVLVPPRKQV VATLVIMGGN    180
FTIPMDLMTT IDSTEHYSGY PILTWISSPD NSYNGPFMSW YFANWPNLPS GFGPLNSDNT    240
VTYTGSVVSQ VSAGVYATVR FDQYDIHNLR TIEKTWYAAH ATLHNGKKIS INNVTEMAPT    300
SPIKTN                                                              306

SEQ ID NO: 105          moltype = AA   length = 306
FEATURE                 Location/Qualifiers
REGION                  1..306
                        note = engineered
source                  1..306
                        mol_type = protein
                        organism = synthetic construct
SEQUENCE: 105
MAILDLKSLV LNAINYWGPK NNNGIQGGDF GYPISEKQID TSIITSTHPR LIPHDLTIPQ    60
NLETIFTTTQ VLTNNTDLQQ SQTVSFAKKT TTATSTSTTN GWTEGGKISD TLEEKVSVSI    120
PFIGEGGGKN STTIEANFAH NSSTTTFQQA STDIEWNISQ PVLVPPRKQV VATLVIMGGN    180
FTIPMDLMTT IDSTEHYSGY PILTWISSPD NSYNGPFMSW YFANWPNLPS GFGPLNSDNT    240
VTYTGSVVSQ VSAGVYATVR FDQYDIHNLR TIEKTWYARH ATLHNGKKIS INNVTEMAPT    300
SPAKTN                                                              306

SEQ ID NO: 106          moltype = AA   length = 306
FEATURE                 Location/Qualifiers
REGION                  1..306
                        note = engineered
source                  1..306
                        mol_type = protein
                        organism = synthetic construct
SEQUENCE: 106
MAILDLKSLV LNAINYWGPK NNNGIQGGDF GYPISEKQID TSIITSTHPR LIPHDLTIPQ    60
NLETIFTTTQ VLTNNTDLQQ SQTVSFAKKT TTTTATSTTN GWTEGGKISD TLEEKVSVSI    120
PFIGEGGGKN STTIEANFAH NSSTTTFQQA STDIEWNISQ PVLVPPRKQV VATLVIMGGN    180
FTIPMDLMTT IDSTEHYSGY PILTWISSPD NSYNGPFMSW YFANWPNLPS GFGPLNSDNT    240
VTYTGAVVSQ VSAGVYATVR FDQYDIHNLR TIEKTWYARH ATLHNGKKIS INNVTEMAPT    300
SPIKTN                                                              306

SEQ ID NO: 107          moltype = AA   length = 306
FEATURE                 Location/Qualifiers
REGION                  1..306
                        note = engineered
source                  1..306
                        mol_type = protein
                        organism = synthetic construct
SEQUENCE: 107
MAILDLKSLV LNAINYWGPK NNNGIQGGDF GYPISEKQID TSIITSTHPR LIPHDLTIPQ    60
NLETIFTTTQ VLTNNTDLQQ SQTVSFSKKT TTATSTSTTN GWTEGGKISD TLEEKVSVSI    120
PFIGEGGGKN STTIEANFAH NSSTTTFQQA STDIEWNISQ PVLVPPRKQV VATLVIMGGN    180
FTIPMDLMTT IDSTEHYSGY PILTWISSPD NSYNGPFMSW YFANWPNLPS GFGPLNSDNT    240
VTYTGSVVSQ VSAGVYATVR FDQYDIHNLR TIEKTWYARH ATLHNGKKIS INNVTEMAPT    300
SPIKTN                                                              306

SEQ ID NO: 108          moltype = AA   length = 306
FEATURE                 Location/Qualifiers
REGION                  1..306
                        note = engineered
source                  1..306
                        mol_type = protein
                        organism = synthetic construct
SEQUENCE: 108
MAILDLKSLV LNAINYWGPK NNNGIQGGDF GYPISEKQID TSIITSTHPR LIPHDLTIPQ    60
NLETIFTTTQ VLTNNTDLQQ SQTVSFAKKT TTATSTSTTN GWTEGGKISD TLEEKVSVSI    120
PFIGEGGGKN STTIEANFAH NSSTTTFQQA STDIEWNIAQ PVLVPPRKQV VATLVIMGGN    180
FTIPMDLMTT IDSTEHYSGY PILTWISSPD NSYNGPFMSW YFANWPNLPS GFGPLNSDNT    240
VTYTGSVVSQ VSAGVYATVR FDQYDIHNLR TIEKTWYARH ATLHNGKKIS INNVTEMAPT    300
SPIKTN                                                              306

SEQ ID NO: 109          moltype = AA   length = 306
FEATURE                 Location/Qualifiers
REGION                  1..306
                        note = engineered
source                  1..306
                        mol_type = protein
                        organism = synthetic construct
SEQUENCE: 109
MAILDLKSLV LNAINYWGPK NNNGIQGGDF GYPISEKQID TSIITSTHPR LIPHDLTIPQ    60
NLETIFTTTQ VLTNNTDLQQ SQTVSFAKKT TTTTSTSTTN GWTEGGKISD TLEEKVSVSI    120
PFIGEGGGKN STTIEANFAH NSSTTTAQQA STDIEWNISQ PVLVPPRKQV VATLVIMGGN    180
FTIPMDLMTT IDSTEHYSGY PILTWISSPD NSYNGPFMSW YFANWPNLPS GFGPLNSDNT    240
VTYTGSVVSQ VSAGVYATVR FDQYDIHNLR TIEKTWYARH ATLHNGKKIS INNVTEMAPA    300
SPIKTN                                                              306
```

```
SEQ ID NO: 110          moltype = AA  length = 306
FEATURE                 Location/Qualifiers
REGION                  1..306
                        note = engineered
source                  1..306
                        mol_type = protein
                        organism = synthetic construct
SEQUENCE: 110
MAILDLKSLV LNAINYWGPK NNNGIQGGDF GYPISEKQID TSIITSTHPR LIPHDLTIPQ   60
NLETIFTTTQ VLTNNTDLQQ SQTVSFAKKT TTATSTSTTN GWTEGGKISD TLEEKVSVSI  120
PFIGEGGGKN STTIEANFAH NSSTTTFAQA STDIEWNISQ PVLVPPRKQV VATLVIMGGN  180
FTIPMDLMTT IDSTEHYSGY PILTWISSPD NSYNGPFMSW YFANWPNLPS GFGPLNSDNT  240
VTYTGSVVSQ VSAGVYATVR FDQYDIHNLR TIEKTWYARH ATLHNGKKIS INNVTEMAPT  300
SPIKTN                                                            306

SEQ ID NO: 111          moltype = AA  length = 306
FEATURE                 Location/Qualifiers
REGION                  1..306
                        note = engineered
source                  1..306
                        mol_type = protein
                        organism = synthetic construct
SEQUENCE: 111
MAILDLKSLV LNAINYWGPK NNNGIQGGDF GYPISEKQID TSIITSTHPR LIPHDLTIPQ   60
NLETIFTTTQ VLTNNTDLQQ SQTVSFAKKT TTTTATSTTN GWTEGGKISD TLEEKVSVSI  120
PFIGEGGGKN STTIEANFAH NSSTTTFQQA STDIEWNISQ PVLVPPRKQV VATLAIMGGN  180
FTIPMDLMTT IDSTEHYSGY PILTWISSPD NSYNGPFMSW YFANWPNLPS GFGPLNSDNT  240
VTYTGSVVSQ VSAGVYATVR FDQYDIHNLR TIEKTWYARH ATLHNGKKIS INNVTEMAPT  300
SPIKTN                                                            306

SEQ ID NO: 112          moltype = AA  length = 306
FEATURE                 Location/Qualifiers
REGION                  1..306
                        note = engineered
source                  1..306
                        mol_type = protein
                        organism = synthetic construct
SEQUENCE: 112
MAILDLKSLV LNAINYWGPK NNNGIQGGDF GYPISEKQID TSIITSTHPR LIPHDLTIPQ   60
NLETIFTTTQ VLTNNTDLQQ SQTVSFAKKT TTTTSTSTTN GWTEGGKISD TLEEKVSVSI  120
PFIGEGGGKN STTIEANFAH NSSTTTAQQA STDIEWNISQ PVLVPPRKQV VATLVIMGGN  180
FTIPMDLMTT IDSTEHYSGY PILTWISSPD NSYNGPFMSW YFANWPNLPS GFGPLNSANT  240
VTYTGSVVSQ VSAGVYATVR FDQYDIHNLR TIEKTWYARH ATLHNGKKIS INNVTEMAPT  300
SPIKTN                                                            306

SEQ ID NO: 113          moltype = AA  length = 306
FEATURE                 Location/Qualifiers
REGION                  1..306
                        note = engineered
source                  1..306
                        mol_type = protein
                        organism = synthetic construct
SEQUENCE: 113
MAILDLKSLV LNAINYWGPK NNNGIQGGDF GYPISEKQID TSIITSTHPR LIPHDLTIPQ   60
NLETIFTTTQ VLTNNTDLQQ SQTVSFAKKT TTTATSTTN GWTEGGKISD TLEEKVSVSI   120
PFIGEGGGKN STTIEANFAH NSSTTTAQQA STDIEWNISQ PVLVPPRKQV VATLVIMGGN  180
FTIPMDLMTT IDSTEHYSGY PILTWISSPD NSYNGPFMSW YFANWPNLPS GFGPLNSDNT  240
VTYTGSVVSQ VSAGVYATVR FDQYDIHNLR TIEKTWYARH ATLHNGKKIS INNVTEMAPT  300
SPIKTN                                                            306

SEQ ID NO: 114          moltype = AA  length = 306
FEATURE                 Location/Qualifiers
REGION                  1..306
                        note = engineered
source                  1..306
                        mol_type = protein
                        organism = synthetic construct
SEQUENCE: 114
MAILDLKSLV LNAINYWGPK NNNGIQGGDF GYPISEKQID TSIITSTHPR LIPHDLTIPQ   60
NLETIFTTTQ VLTNNTDLQQ SQTVSFAKKT TTTTSTSTTN GWTEGGKISD TLEEKVSVSI  120
PFIGEGGGKN STTIEANFAH NSSTTTAQQA STDIEWNISQ PVLVPPRKQV VATLVIAGGN  180
FTIPMDLMTT IDSTEHYSGY PILTWISSPD NSYNGPFMSW YFANWPNLPS GFGPLNSDNT  240
VTYTGSVVSQ VSAGVYATVR FDQYDIHNLR TIEKTWYARH ATLHNGKKIS INNVTEMAPT  300
SPIKTN                                                            306

SEQ ID NO: 115          moltype = AA  length = 306
FEATURE                 Location/Qualifiers
REGION                  1..306
```

```
                              note = engineered
source                        1..306
                              mol_type = protein
                              organism = synthetic construct
SEQUENCE: 115
MAILDLKSLV LNAINYWGPK NNNGIQGGDF GYPISEKQID TSIITSTHPR LIPHDLTIPQ     60
NLETIFTTTQ VLTNNTDLQQ SQTVSFAKKT TTTTSTSTTN GWTEGGKISD TLEEKVSVSI    120
PFIGEGGGKN STTIEANFAH NSSTTTAQQA STDIEWNISQ PVLVPPRKQV VATLVIMGGN    180
FTIPMDLMTT IDSTEHYSGY PILTWISSPD NSYNGPFMSW YFANWPNLPS GFGPLNSDNT    240
VTYTGSVVSQ VSAGVYATVR FDQYDIHNLR TIEKTWYARH ATLHNGKKIS INNVTEAAPT    300
SPIKTN                                                               306

SEQ ID NO: 116          moltype = AA  length = 306
FEATURE                 Location/Qualifiers
REGION                  1..306
                        note = engineered
source                  1..306
                        mol_type = protein
                        organism = synthetic construct
SEQUENCE: 116
MAILDLKSLV LNAINYWGPK NNNGIQGGDF GYPISEKQID TSIITSTHPR LIPHDLTIPQ     60
NLETIFTTTQ VLTNNTDLQQ SQTVSFAKKT TTTTATSTTN GWTEGGKISD TLEEKVSVSI    120
PFIGEGGGKN STTIEANFAH NSSTTTFQQA STDIEWNISQ PVLVPPRKQV VATLVIMGGN    180
FTIPMDLMTT IDSTEHYSGY PILTWISSPD NSYNGPFMSW YFANWPNLPS GFGPLNSDNT    240
VTYTGSVVSQ VSAGVYATVR FDQYDIHNLR TIEKTWYARH ATLHNGKKIS INNVTEMAPT    300
SAIKTN                                                               306

SEQ ID NO: 117          moltype = AA  length = 306
FEATURE                 Location/Qualifiers
REGION                  1..306
                        note = engineered
source                  1..306
                        mol_type = protein
                        organism = synthetic construct
SEQUENCE: 117
MAILDLKSLV LNAINYWGPK NNNGIQGGDF GYPISEKQID TSIITSTHPR LIPHDLTIPQ     60
NLETIFTTTQ VLTNNTDLQQ SQTVSFAKKT TTTTSTSTTN GWTEGGKISD TLEEKVSVSI    120
PFIGEGGGKN STTIEANFAH NSSTTTAQQA STDIEWNISQ PVLVPPRKQV VATLVIMGGN    180
FTIPMDLMTT IDSTEAYSGY PILTWISSPD NSYNGPFMSW YFANWPNLPS GFGPLNSDNT    240
VTYTGSVVSQ VSAGVYATVR FDQYDIHNLR TIEKTWYARH ATLHNGKKIS INNVTEMAPT    300
SPIKTN                                                               306

SEQ ID NO: 118          moltype = AA  length = 306
FEATURE                 Location/Qualifiers
REGION                  1..306
                        note = engineered
source                  1..306
                        mol_type = protein
                        organism = synthetic construct
SEQUENCE: 118
MAILDLKSLV LNAINYWGPK NNNGIQGGDF GYPISEKQID TSIITSTHPR LIPHDLTIPQ     60
NLETIFTTTQ VLTNNTDLQQ SQTVSFAKKT TTTTSTSTTN GWTEGGKISD TLEEKVSVSI    120
PFIGEGGGKN STTIEANFSH NSSTTTAQQA STDIEWNISQ PVLVPPRKQV VATLVIMGGN    180
FTIPMDLMTT IDSTEHYSGY PILTWISSPD NSYNGPFMSW YFANWPNLPS GFGPLNSDNT    240
VTYTGSVVSQ VSAGVYATVR FDQYDIHNLR TIEKTWYARH ATLHNGKKIS INNVTEMAPT    300
SPIKTN                                                               306

SEQ ID NO: 119          moltype = AA  length = 306
FEATURE                 Location/Qualifiers
REGION                  1..306
                        note = engineered
source                  1..306
                        mol_type = protein
                        organism = synthetic construct
SEQUENCE: 119
MAILDLKSLV LNAINYWGPK NNNGIQGGDF GYPISEKQID TSIITSTHPR LIPHDLTIPQ     60
NLETIFTTTQ VLTNNTDLQQ SQTVSFAKKT TTATSTSTTN GWTEGGKISD TLEEKVSVSI    120
PFIGEGGGKN STTIEANFAH NSSTTTFQQA STDIEWNISQ PVLVPPRKQV VATLVIMGGN    180
FTIPMDLMTT IDSTEHYSGY PILTWISSPD NSYNGPFMSW YFANWPNLPS GFGPLNSDNT    240
VTYTGSVVSQ VSAGVYATVR FDQYDIHNLR TIEKTWYARH ATLHNGKKIS IANVTEMAPT    300
SPIKTN                                                               306

SEQ ID NO: 120          moltype = AA  length = 306
FEATURE                 Location/Qualifiers
REGION                  1..306
                        note = engineered
source                  1..306
                        mol_type = protein
                        organism = synthetic construct
```

```
SEQUENCE: 120
MAILDLKSLV LNAINYWGPK NNNGIQGGDF GYPISEKQID TSIITSTHPR LIPHDLTIPQ    60
NLETIFTTTQ VLTNNTDLQQ SQTVSFAKKT TTATSTSTTN GWTEGGKISD TLEEKVSVSI   120
PFIGEGGGKN STTIEANFAH NSSTATFQQA STDIEWNISQ PVLVPPRKQV VATLVIMGGN   180
FTIPMDLMTT IDSTEHYSGY PILTWISSPD NSYNGPFMSW YFANWPNLPS GFGPLNSDNT   240
VTYTGSVVSQ VSAGVYATVR FDQYDIHNLR TIEKTWYARH ATLHNGKKIS INNVTEMAPT   300
SPIKTN                                                              306

SEQ ID NO: 121          moltype = AA   length = 306
FEATURE                 Location/Qualifiers
REGION                  1..306
                        note = engineered
source                  1..306
                        mol_type = protein
                        organism = synthetic construct
SEQUENCE: 121
MAILDLKSLV LNAINYWGPK NNNGIQGGDF GYPISEKQID TSIITSTHPR LIPHDLTIPQ    60
NLETIFTTTQ VLTNNTDLQQ SQTVSFAKKT TTTTSTSTTN GWTEGGKISD TLEEKVAVSI   120
PFIGEGGGKN STTIEANFAH NSSTTTAQQA STDIEWNISQ PVLVPPRKQV VATLVIMGGN   180
FTIPMDLMTT IDSTEHYSGY PILTWISSPD NSYNGPFMSW YFANWPNLPS GFGPLNSDNT   240
VTYTGSVVSQ VSAGVYATVR FDQYDIHNLR TIEKTWYARH ATLHNGKKIS INNVTEMAPT   300
SPIKTN                                                              306

SEQ ID NO: 122          moltype = AA   length = 306
FEATURE                 Location/Qualifiers
REGION                  1..306
                        note = engineered
source                  1..306
                        mol_type = protein
                        organism = synthetic construct
SEQUENCE: 122
MAILDLKSLV LNAINYWGPK NNNGIQGGDF GYPISEKQID TSIITSTHPR LIPHDLTIPQ    60
NLETIFTTTQ VLTNNTDLQQ SQTVSFAKKT TTATSTSTTN GWTEGGKISD TLEEKVSVSI   120
PFIGEGGGKN STTIEANFAH NSSTTTFQQA STDIEWNISQ PVLVPPRKQV VATLVIMGGN   180
FTIPMDLMTT IDSTEHYSGY PILTWISSPD NSYNGPFMSW YFANWPNLPS GFGPLNSDNT   240
VTYTGSVVSQ VSAGVYATVR FDQYDIHNLR TAEKTWYARH ATLHNGKKIS INNVTEMAPT   300
SPIKTN                                                              306

SEQ ID NO: 123          moltype = AA   length = 306
FEATURE                 Location/Qualifiers
REGION                  1..306
                        note = engineered
source                  1..306
                        mol_type = protein
                        organism = synthetic construct
SEQUENCE: 123
MAILDLKSLV LNAINYWGPK NNNGIQGGDF GYPISEKQID TSIITSTHPR LIPHDLTIPQ    60
NLETIFTTTQ VLTNNTDLQQ SQTVSFAKKT TTTTATSTTN GWTEGGKISD TLEEKVSVSI   120
PFIGEGGGKN STTIEANFAH NSSTTTFQQA STDIEWNISQ PVLVPPRKQV VATLVIMGGN   180
FTIPMDLMTT IDSTEHYSGY PILTWISSPD NSYNGPFMSW YFANWPNLPS GFGPLNSDNT   240
VTYTGSVVSQ VSAGVYATVR FDQYDIHNLR TIEKTWYARH ATLANGKKIS INNVTEMAPT   300
SPIKTN                                                              306

SEQ ID NO: 124          moltype = AA   length = 306
FEATURE                 Location/Qualifiers
REGION                  1..306
                        note = engineered
source                  1..306
                        mol_type = protein
                        organism = synthetic construct
SEQUENCE: 124
MAILDLKSLV LNAINYWGPK NNNGIQGGDF GYPISEKQID TSIITSTHPR LIPHDLTIPQ    60
NLETIFTTTQ VLTNNTDLQQ SQTVSFAKKT TTTTATSTTN GWTEAGKISD TLEEKVSVSI   120
PFIGEGGGKN STTIEANFAH NSSTTTFQQA STDIEWNISQ PVLVPPRKQV VATLVIMGGN   180
FTIPMDLMTT IDSTEHYSGY PILTWISSPD NSYNGPFMSW YFANWPNLPS GFGPLNSDNT   240
VTYTGSVVSQ VSAGVYATVR FDQYDIHNLR TIEKTWYARH ATLHNGKKIS INNVTEMAPT   300
SPIKTN                                                              306

SEQ ID NO: 125          moltype = AA   length = 306
FEATURE                 Location/Qualifiers
REGION                  1..306
                        note = engineered
source                  1..306
                        mol_type = protein
                        organism = synthetic construct
SEQUENCE: 125
MAILDLKSLV LNAINYWGPK NNNGIQGGDF GYPISEKQID TSIITSTHPR LIPHDLTIPQ    60
NLETIFTTTQ VLTNNTDLQQ SQTVSFAKKT TTTATSTTTN GWTEGGKISD TLEEKVSVSI   120
PFIGEGGGKN STTIEANFAH NSSTTTFQQA STDIEWNISQ PVLVPPRKQV VATLVIMGGN   180
```

```
FTIPMDLMTT IDSTEHYSGY PILTWISSPD NSYNGPFMSW YFANWPNLPS GFGPLNSDNT    240
VTYTGSVVSQ VSAGVYATVR FDQYDIHNLR TIEKTWYARH ATLHNGKKIS INNVTEMAPT    300
SPIKTN                                                              306

SEQ ID NO: 126         moltype = AA   length = 306
FEATURE                Location/Qualifiers
REGION                 1..306
                       note = engineered
source                 1..306
                       mol_type = protein
                       organism = synthetic construct
SEQUENCE: 126
MAILDLKSLV LNAINYWGPK NNNGIQGGDF GYPISEKQID TSIITSTHPR LIPHDLTIPQ     60
NLETIFTTTQ VLTNNTDLQQ SQTVSFAKKT TTTTATSTTN GWTEGGKISD TLEEKVSVSI    120
PFIGEGGGKN STTAEANFAH NSSTTTFQQA STDIEWNISQ PVLVPPRKQV VATLVIMGGN    180
FTIPMDLMTT IDSTEHYSGY PILTWISSPD NSYNGPFMSW YFANWPNLPS GFGPLNSDNT    240
VTYTGSVVSQ VSAGVYATVR FDQYDIHNLR TIEKTWYARH ATLHNGKKIS INNVTEMAPT    300
SPIKTN                                                              306

SEQ ID NO: 127         moltype = AA   length = 306
FEATURE                Location/Qualifiers
REGION                 1..306
                       note = engineered
source                 1..306
                       mol_type = protein
                       organism = synthetic construct
SEQUENCE: 127
MAILDLKSLV LNAINYWGPK NNNGIQGGDF GYPISEKQID TSIITSTHPR LIPHDLTIPQ     60
NLETIFTTTQ VLTNNTDLQQ SQTVSFAKKT TTATSTSTTN GWTEGGKISD TLEEKVSVSI    120
PFIGEGGGKN STTIEANFAH NSSTTTFQQA STDIEWNISQ PVLVPPRKQV VATLVIMGGN    180
FTIPMDLMTT IDSTEHYSGY PILTWISSPD NSYNGPFMSW YFANWPNLPS GFGPLNSDNT    240
VTYTGSVVSQ VSAGVYATVR FDQYDIHNLR TIEKTWYARH ATLHNGKKIS INNVTEAAPT    300
SPIKTN                                                              306

SEQ ID NO: 128         moltype = AA   length = 306
FEATURE                Location/Qualifiers
REGION                 1..306
                       note = engineered
source                 1..306
                       mol_type = protein
                       organism = synthetic construct
SEQUENCE: 128
MAILDLKSLV LNAINYWGPK NNNGIQGGDF GYPISEKQID TSIITSTHPR LIPHDLTIPQ     60
NLETIFTTTQ VLTNNTDLQQ SQTVSFAKKT TTATSTSTTN GWTEGGKISD TLEEKVSVSI    120
PFIGEGGGKN STTIEANFAH NSSTTTFQQA STDIEWNISQ PVLVPPRKQV VATLVIMGGN    180
FTIPMDLMTT IDSTEHYSGY PILTWISSPD NSYNGPFMSW YFANWPNLPS GFGPLNSDNT    240
VTYTGSVVSQ VSAGVYATVR FDQYDIHNLR TIEKTWYARH ATLHNGKKIS INNVTEMAPA    300
SPIKTN                                                              306

SEQ ID NO: 129         moltype = AA   length = 306
FEATURE                Location/Qualifiers
REGION                 1..306
                       note = engineered
source                 1..306
                       mol_type = protein
                       organism = synthetic construct
SEQUENCE: 129
MAILDLKSLV LNAINYWGPK NNNGIQGGDF GYPISEKQID TSIITSTHPR LIPHDLTIPQ     60
NLETIFTTTQ VLTNNTDLQQ SQTVSFAKKT TTATSTSTTN GWTEGGKISD TLEEKVSVSI    120
PFIGEGGGKN STTIEANFAH NSSTTTFQQS STDIEWNISQ PVLVPPRKQV VATLVIMGGN    180
FTIPMDLMTT IDSTEHYSGY PILTWISSPD NSYNGPFMSW YFANWPNLPS GFGPLNSDNT    240
VTYTGSVVSQ VSAGVYATVR FDQYDIHNLR TIEKTWYARH ATLHNGKKIS INNVTEMAPT    300
SPIKTN                                                              306

SEQ ID NO: 130         moltype = AA   length = 306
FEATURE                Location/Qualifiers
REGION                 1..306
                       note = engineered
source                 1..306
                       mol_type = protein
                       organism = synthetic construct
SEQUENCE: 130
MAILDLKSLV LNAINYWGPK NNNGIQGGDF GYPISEKQID TSIITSTHPR LIPHDLTIPQ     60
NLETIFTTTQ VLTNNTDLQQ SQTVSFAKKT TTTTATSTTN GWTEGGKISD TLEEKVSVSI    120
PFIGEGGGKN STTIEANFAH NSSTTTFQQA STDIAWNISQ PVLVPPRKQV VATLVIMGGN    180
FTIPMDLMTT IDSTEHYSGY PILTWISSPD NSYNGPFMSW YFANWPNLPS GFGPLNSDNT    240
VTYTGSVVSQ VSAGVYATVR FDQYDIHNLR TIEKTWYARH ATLHNGKKIS INNVTEMAPT    300
SPIKTN                                                              306
```

| SEQ ID NO: 131 | moltype = AA   length = 306 |
| --- | --- |
| FEATURE | Location/Qualifiers |
| REGION | 1..306 |
| | note = engineered |
| source | 1..306 |
| | mol_type = protein |
| | organism = synthetic construct |

SEQUENCE: 131
```
MAILDLKSLV LNAINYWGPK NNNGIQGGDF GYPISEKQID TSIITSTHPR LIPHDLTIPQ   60
NLETIFTTTQ VLTNNTDLQQ SQTVSFAKKT TTATSTSTTN GWTEGGKISD TLEEKVSVSI  120
PFIGEGGGKN STTIEANFAH NSSTATFQQA STDIEWNISQ PVLVPPRKQV VATLVIMGGN  180
FTIPMDLMTT IDSTEHYSGY PILTWISSPD NSYNGPFMSW YFANWPNLPS GFGPLNSDNT  240
VTYTGSVVSQ VSAGVYATVR FDQYDIHNLR TIEKTWYARH ATLHNGKKIS INNVTEMAPT  300
SPIKTN                                                            306
```

| SEQ ID NO: 132 | moltype = AA   length = 306 |
| --- | --- |
| FEATURE | Location/Qualifiers |
| REGION | 1..306 |
| | note = engineered |
| source | 1..306 |
| | mol_type = protein |
| | organism = synthetic construct |

SEQUENCE: 132
```
MAILDLKSLV LNAINYWGPK NNNGIQGGDF GYPISEKQID TSIITSTHPR LIPHDLTIPQ   60
NLETIFTTTQ VLTNNTDLQQ SQTVSFAKKT TTTTATSTTN GWTEGGKISD TLEEKVSVSI  120
PFIGEGGGKN STTIEANFAH NSSTTTFQQA STDIEWNISQ PVLVPPRKQV VATLVIMGGN  180
FTIPMDLMTT IDSTEHYSGY PILTAISSPD NSYNGPFMSW YFANWPNLPS GFGPLNSDNT  240
VTYTGSVVSQ VSAGVYATVR FDQYDIHNLR TIEKTWYARH ATLHNGKKIS INNVTEMAPT  300
SPIKTN                                                            306
```

| SEQ ID NO: 133 | moltype = AA   length = 306 |
| --- | --- |
| FEATURE | Location/Qualifiers |
| REGION | 1..306 |
| | note = engineered |
| source | 1..306 |
| | mol_type = protein |
| | organism = synthetic construct |

SEQUENCE: 133
```
MAILDLKSLV LNAINYWGPK NNNGIQGGDF GYPISEKQID TSIITSTHPR LIPHDLTIPQ   60
NLETIFTTTQ VLTNNTDLQQ SQTVSFAKKT TTTTATSTTN GWTEGGKISD TLEEKVSVSI  120
PFIGEGGGKN STTIEANFAH NSSTTTFQQA STDIEWNISQ PVLVPPRKQV VATLVIMGGN  180
FAIPMDLMTT IDSTEHYSGY PILTWISSPD NSYNGPFMSW YFANWPNLPS GFGPLNSDNT  240
VTYTGSVVSQ VSAGVYATVR FDQYDIHNLR TIEKTWYARH ATLHNGKKIS INNVTEMAPT  300
SPIKTN                                                            306
```

| SEQ ID NO: 134 | moltype = AA   length = 306 |
| --- | --- |
| FEATURE | Location/Qualifiers |
| REGION | 1..306 |
| | note = engineered |
| source | 1..306 |
| | mol_type = protein |
| | organism = synthetic construct |

SEQUENCE: 134
```
MAILDLKSLV LNAINYWGPK NNNGIQGGDF GYPISEKQID TSIITSTHPR LIPHDLTIPQ   60
NLETIFTTTQ VLTNNTDLQQ SQTVSFAKKT TTATSTSTTN GWTEGGKISD TLEEKVSVSI  120
PFIGEGGGKN STTIEANFAH NSSTTTFQQA STDIEWNISQ PVLVPPRKQV VATLVIMGGN  180
FTIPMDLMTT IDSTEHYSGY PILTWISSPD NSYNGPFMSW YFANWPNLPS GFGPLNSDNA  240
VTYTGSVVSQ VSAGVYATVR FDQYDIHNLR TIEKTWYARH ATLHNGKKIS INNVTEMAPT  300
SPIKTN                                                            306
```

| SEQ ID NO: 135 | moltype = AA   length = 306 |
| --- | --- |
| FEATURE | Location/Qualifiers |
| REGION | 1..306 |
| | note = engineered |
| source | 1..306 |
| | mol_type = protein |
| | organism = synthetic construct |

SEQUENCE: 135
```
MAILDLKSLV LNAINYWGPK NNNGIQGGDF GYPISEKQID TSIITSTHPR LIPHDLTIPQ   60
NLETIFTTTQ VLTNNTDLQQ SQTVSFAKKT TTTTATSTTN GWTEGGKISD TLEEKVSVSI  120
PFIGEGGGKN STTIEANFAH NSSTTTFQQA STDIEWNISQ PVLVPPRKQV VATLVIMGGN  180
FTIPMDLMTT IDSTEHYSGY PILTWISSPD NSYNGPFMSW YFANWPNLPS GFGPLNSDNT  240
VTYTGSVVSQ VSAGVYATVR FDQYDIHNLR TIEKTWYARH ATLHNGKKIS INNVTEMAPT  300
SPAKTN                                                            306
```

| SEQ ID NO: 136 | moltype = AA   length = 306 |
| --- | --- |
| FEATURE | Location/Qualifiers |
| REGION | 1..306 |
| | note = engineered |

```
source                  1..306
                        mol_type = protein
                        organism = synthetic construct
SEQUENCE: 136
MAILDLKSLV LNAINYWGPK NNNGIQGGDF GYPISEKQID TSIITSTHPR LIPHDLTIPQ    60
NLETIFTTTQ VLTNNTDLQQ SQTVSFAKKT TTTTATSTTN GWTEGGKISD TLEEKVAVSI   120
PFIGEGGGKN STTIEANFAH NSSTTTFQQA STDIEWNISQ PVLVPPRKQV VATLVIMGGN   180
FTIPMDLMTT IDSTEHYSGY PILTWISSPD NSYNGPFMSW YFANWPNLPS GFGPLNSDNT   240
VTYTGSVVSQ VSAGVYATVR FDQYDIHNLR TIEKTWYARH ATLHNGKKIS INNVTEMAPT   300
SPIKTN                                                              306

SEQ ID NO: 137          moltype = AA  length = 306
FEATURE                 Location/Qualifiers
REGION                  1..306
                        note = engineered
source                  1..306
                        mol_type = protein
                        organism = synthetic construct
SEQUENCE: 137
MAILDLKSLV LNAINYWGPK NNNGIQGGDF GYPISEKQID TSIITSTHPR LIPHDLTIPQ    60
NLETIFTTTQ VLTNNTDLQQ SQTVSFAKKT TTATSTSTTN GWTEGGKISD TLEEKVSVAI   120
PFIGEGGGKN STTIEANFAH NSSTTTFQQA STDIEWNISQ PVLVPPRKQV VATLVIMGGN   180
FTIPMDLMTT IDSTEHYSGY PILTWISSPD NSYNGPFMSW YFANWPNLPS GFGPLNSDNT   240
VTYTGSVVSQ VSAGVYATVR FDQYDIHNLR TIEKTWYARH ATLHNGKKIS INNVTEMAPT   300
SPIKTN                                                              306

SEQ ID NO: 138          moltype = AA  length = 306
FEATURE                 Location/Qualifiers
REGION                  1..306
                        note = engineered
source                  1..306
                        mol_type = protein
                        organism = synthetic construct
SEQUENCE: 138
MAILDLKSLV LNAINYWGPK NNNGIQGGDF GYPISEKQID TSIITSTHPR LIPHDLTIPQ    60
NLETIFTATQ VLTNNTDLQQ SQTVSFAKKT TTTTSTSTTN GWTEGGKISD TLEEKVSVSI   120
PFIGEGGGKN STTIEANFAH NSSTTTAQQA STDIEWNISQ PVLVPPRKQV VATLVIMGGN   180
FTIPMDLMTT IDSTEHYSGY PILTWISSPD NSYNGPFMSW YFANWPNLPS GFGPLNSDNT   240
VTYTGSVVSQ VSAGVYATVR FDQYDIHNLR TIEKTWYARH ATLHNGKKIS INNVTEMAPT   300
SPIKTN                                                              306

SEQ ID NO: 139          moltype = AA  length = 306
FEATURE                 Location/Qualifiers
REGION                  1..306
                        note = engineered
source                  1..306
                        mol_type = protein
                        organism = synthetic construct
SEQUENCE: 139
MAILDLKSLV LNAINYWGPK NNNGIQGGDF GYPISEKQID TSIITSTHPR LIPHDLTIPQ    60
NLETIFTTTQ VLTNNTDLQQ SQTVSFAKKT TTTTSTSTTN GWTEAGKISD TLEEKVSVSI   120
PFIGEGGGKN STTIEANFAH NSSTTTAQQA STDIEWNISQ PVLVPPRKQV VATLVIMGGN   180
FTIPMDLMTT IDSTEHYSGY PILTWISSPD NSYNGPFMSW YFANWPNLPS GFGPLNSDNT   240
VTYTGSVVSQ VSAGVYATVR FDQYDIHNLR TIEKTWYARH ATLHNGKKIS INNVTEMAPT   300
SPIKTN                                                              306

SEQ ID NO: 140          moltype = AA  length = 306
FEATURE                 Location/Qualifiers
REGION                  1..306
                        note = engineered
source                  1..306
                        mol_type = protein
                        organism = synthetic construct
SEQUENCE: 140
MAILDLKSLV LNAINYWGPK NNNGIQGGDF GYPISEKQID TSIITSTHPR LIPHDLTIPQ    60
NLETIFTTTQ VLTNNTDLQQ SQTVSFAKKT TTTTATSTTN GWTEGGKISD TLEEKVSVSI   120
PFIGAGGGKN STTIEANFAH NSSTTTFQQA STDIEWNISQ PVLVPPRKQV VATLVIMGGN   180
FTIPMDLMTT IDSTEHYSGY PILTWISSPD NSYNGPFMSW YFANWPNLPS GFGPLNSDNT   240
VTYTGSVVSQ VSAGVYATVR FDQYDIHNLR TIEKTWYARH ATLHNGKKIS INNVTEMAPT   300
SPIKTN                                                              306

SEQ ID NO: 141          moltype = AA  length = 306
FEATURE                 Location/Qualifiers
REGION                  1..306
                        note = engineered
source                  1..306
                        mol_type = protein
                        organism = synthetic construct
SEQUENCE: 141
```

```
MAILDLKSLV LNAINYWGPK NNNGIQGGDF GYPISEKQID TSIITSTHPR LIPHDLTIPQ   60
NLETIFTTTQ VLTNNTDLQQ SQTVSFAKKT TTATSTSTTN GWTEGGKISD TLEEKVSVSI  120
PFIGEGGGKN STTIEANFAH NSSTTTFQQA STDIAWNISQ PVLVPPRKQV VATLVIMGGN  180
FTIPMDLMTT IDSTEHYSGY PILTWISSPD NSYNGPFMSW YFANWPNLPS GFGPLNSDNT  240
VTYTGSVVSQ VSAGVYATVR FDQYDIHNLR TIEKTWYARH ATLHNGKKIS INNVTEMAPT  300
SPIKTN                                                             306

SEQ ID NO: 142          moltype = AA  length = 306
FEATURE                 Location/Qualifiers
REGION                  1..306
                        note = engineered
source                  1..306
                        mol_type = protein
                        organism = synthetic construct
SEQUENCE: 142
MAILDLKSLV LNAINYWGPK NNNGIQGGDF GYPISEKQID TSIITSTHPR LIPHDLTIPQ   60
NLETIFTTTQ VLTNNTDLQQ SQTVSFAKKT TTATSTSTTN GWTEGGKISD TLEEKVSVSI  120
PFIGEGGGKN STTIEANFAH NSSTTTFQQA STDIEWNISQ PVLVPPRKQV VATLVIMGGN  180
FTIPMDLMTT IDSTEHYSGY PILTWISSPD NSYNGPFMSW YFANWPNLPS GFGPLNSDNT  240
VTYTGSVVSQ VSAGVYATVR FDQYDIHNLR TIEKTWYARH ATLHNGKKIS INNVTEMAPT  300
SAIKTN                                                             306

SEQ ID NO: 143          moltype = AA  length = 306
FEATURE                 Location/Qualifiers
REGION                  1..306
                        note = engineered
source                  1..306
                        mol_type = protein
                        organism = synthetic construct
SEQUENCE: 143
MAILDLKSLV LNAINYWGPK NNNGIQGGDF GYPISEKQID TSIITSTHPR LIPHDLTIPQ   60
NLETIFTTTQ VLTNNTDLQQ SQTVSFAKKT TTTTATSTTN GWTEGGKISD TLEEKVSVSI  120
PFIGEGGGKN STTIEANFAH NSSTTTFQQA STDEWNISQ PVLVPPRKQV VATLVIAGGN   180
FTIPMDLMTT IDSTEHYSGY PILTWISSPD NSYNGPFMSW YFANWPNLPS GFGPLNSDNT  240
VTYTGSVVSQ VSAGVYATVR FDQYDIHNLR TIEKTWYARH ATLHNGKKIS INNVTEMAPT  300
SPIKTN                                                             306

SEQ ID NO: 144          moltype = AA  length = 306
FEATURE                 Location/Qualifiers
REGION                  1..306
                        note = engineered
source                  1..306
                        mol_type = protein
                        organism = synthetic construct
SEQUENCE: 144
MAILDLKSLV LNAINYWGPK NNNGIQGGDF GYPISEKQID TSIITSTHPR LIPHDLTIPQ   60
NLETIFTTTQ VLTNNTDLQQ SQTVSFAKKT TTATSTSTTN GWTEGGKISD TLEEKVSVSI  120
PFIGEGGGKN STTIEANFAH NSSTTTFQQA STDIEWNISQ PVLVPPRKQV VATLVIMGGN  180
FTIPMDLMTT IDSTEAYSGY PILTWISSPD NSYNGPFMSW YFANWPNLPS GFGPLNSDNT  240
VTYTGSVVSQ VSAGVYATVR FDQYDIHNLR TIEKTWYARH ATLHNGKKIS INNVTEMAPT  300
SPIKTN                                                             306

SEQ ID NO: 145          moltype = AA  length = 306
FEATURE                 Location/Qualifiers
REGION                  1..306
                        note = engineered
source                  1..306
                        mol_type = protein
                        organism = synthetic construct
SEQUENCE: 145
MAILDLKSLV LNAINYWGPK NNNGIQGGDF GYPISEKQID TSIITSTHPR LIPHDLTIPQ   60
NLETIFTTTQ VLTNNTDLQQ SQTVSFAKKT TTATSTSTTN GWTEGGKISD TLEEKVSVSI  120
PFIGEGGGKN STTIEANFAH NSSTTTFQQA STAIEWNISQ PVLVPPRKQV VATLVIMGGN  180
FTIPMDLMTT IDSTEHYSGY PILTWISSPD NSYNGPFMSW YFANWPNLPS GFGPLNSDNT  240
VTYTGSVVSQ VSAGVYATVR FDQYDIHNLR TIEKTWYARH ATLHNGKKIS INNVTEMAPT  300
SPIKTN                                                             306

SEQ ID NO: 146          moltype = AA  length = 306
FEATURE                 Location/Qualifiers
REGION                  1..306
                        note = engineered
source                  1..306
                        mol_type = protein
                        organism = synthetic construct
SEQUENCE: 146
MAILDLKSLV LNAINYWGPK NNNGIQGGDF GYPISEKQID TSIITSTHPR LIPHDLTIPQ   60
NLETIFTTTQ VLTNNTDLQQ SQTVSFAKKT TTTTSTSTTN GWTEGGKISD TLEEKVSVSI  120
PFIGEGGGKN STTIEANFAH NSSTTTAQQA STDIEWNISQ PVLVPPRKQV VATLVIMGGN  180
FTIPMDLMTT IDSTEHYSGY PILTAISSPD NSYNGPFMSW YFANWPNLPS GFGPLNSDNT  240
```

```
VTYTGSVVSQ VSAGVYATVR FDQYDIHNLR TIEKTWYARH ATLHNGKKIS INNVTEMAPT    300
SPIKTN                                                              306

SEQ ID NO: 147          moltype = AA   length = 306
FEATURE                 Location/Qualifiers
REGION                  1..306
                        note = engineered
source                  1..306
                        mol_type = protein
                        organism = synthetic construct
SEQUENCE: 147
MAILDLKSLV LNAINYWGPK NNNGIQGGDF GYPISEKQID TSIITSTHPR LIPHDLTIPQ    60
NLETIFTTTQ VLTNNTDLQQ SQTVSFAKKT TTATSTSTTN GWTEGGKISD TLEEKVSVSI    120
PFIGEGGGKN STTIEANFAH NSSTTTFQQA STDIEWNISQ PVLVPPRKQV VATLVIMGGN    180
FTIPMDLMTT IDSTEHYSGY PILTWISSPD NSYNGPFMSW YFANWPNLPS GFGPLNSDNT    240
VTYTGSVVSQ VSAGVYATVR FDQYDIHNLR TIEKTWYARH ATLHNGKKIS INNVTEMAPT    300
SPAKTN                                                              306

SEQ ID NO: 148          moltype = AA   length = 306
FEATURE                 Location/Qualifiers
REGION                  1..306
                        note = engineered
source                  1..306
                        mol_type = protein
                        organism = synthetic construct
SEQUENCE: 148
MAILDLKSLV LNAINYWGPK NNNGIQGGDF GYPISEKQID TSIITSTHPR LIPHDLTIPQ    60
NLETIFTTTQ VLTNNTDLQQ SQTVSFAKKT TTTTATSTTN GWTEGGKISD TLEEKVSVSI    120
PFIGEGGGKN STTIEANFAH NSSTTTFQQA STDIEWNISQ PVLVPPRKQV VATLVIMGGN    180
FTIPMDLMTT IDSTEAYSGY PILTWISSPD NSYNGPFMSW YFANWPNLPS GFGPLNSDNT    240
VTYTGSVVSQ VSAGVYATVR FDQYDIHNLR TIEKTWYARH ATLHNGKKIS INNVTEMAPT    300
SPIKTN                                                              306

SEQ ID NO: 149          moltype = AA   length = 306
FEATURE                 Location/Qualifiers
REGION                  1..306
                        note = engineered
source                  1..306
                        mol_type = protein
                        organism = synthetic construct
SEQUENCE: 149
MAILDLKSLV LNAINYWGPK NNNGIQGGDF GYPISEKQID TSIITSTHPR LIPHDLTIPQ    60
NLETIFTTTQ VLTNNTDLQQ SQTVSFAKKT TTTTATSTTN GWTEGGKISD TLEEKVSVSI    120
PFIGEGGGKN STTIEANFAH NSSTTTFQAA STDIEWNISQ PVLVPPRKQV VATLVIMGGN    180
FTIPMDLMTT IDSTEHYSGY PILTWISSPD NSYNGPFMSW YFANWPNLPS GFGPLNSDNT    240
VTYTGSVVSQ VSAGVYATVR FDQYDIHNLR TIEKTWYARH ATLHNGKKIS INNVTEMAPT    300
SPIKTN                                                              306

SEQ ID NO: 150          moltype = AA   length = 306
FEATURE                 Location/Qualifiers
REGION                  1..306
                        note = engineered
source                  1..306
                        mol_type = protein
                        organism = synthetic construct
SEQUENCE: 150
MAILDLKSLV LNAINYWGPK NNNGIQGGDF GYPISEKQID TSIITSTHPR LIPHDLTIPQ    60
NLETIFTTTQ VLTNNTDLQQ SQTVSFAKKT TTTTATSTTN GWTEGGKISD TLEEKVSVSI    120
PFIGEGGGKN STTIEANFAH NSSTTTFQQA STDIEWNISQ PVLVPPRKQV VATLVIMGGN    180
FTIPMDLMTT IDSTEHYSGY PILTWISSPD NSYNGPFMSW YFANWPNLPS GFGPLNSDNT    240
VTYTGSVVSQ VSAGVYATVR FDQYDIHNLR TIEKTWYARH ATLHNGKKIA INNVTEMAPT    300
SPIKTN                                                              306

SEQ ID NO: 151          moltype = AA   length = 306
FEATURE                 Location/Qualifiers
REGION                  1..306
                        note = engineered
source                  1..306
                        mol_type = protein
                        organism = synthetic construct
SEQUENCE: 151
MAILDLKSLV LNAINYWGPK NNNGIQGGDF GYPISEKQID TSIITSTHPR LIPHDLTIPQ    60
NLETIFTTTQ VLTNNTDLQQ SQTVSFAKKT TTTTATSTTN GWTEGGKISD TLEEKVSVSI    120
PFIGEGGGKN STTIEANFAH NSSTTTFQQS STDIEWNISQ PVLVPPRKQV VATLVIMGGN    180
FTIPMDLMTT IDSTEHYSGY PILTWISSPD NSYNGPFMSW YFANWPNLPS GFGPLNSDNT    240
VTYTGSVVSQ VSAGVYATVR FDQYDIHNLR TIEKTWYARH ATLHNGKKIS INNVTEMAPT    300
SPIKTN                                                              306

SEQ ID NO: 152          moltype = AA   length = 306
```

```
FEATURE                 Location/Qualifiers
REGION                  1..306
                        note = engineered
source                  1..306
                        mol_type = protein
                        organism = synthetic construct
SEQUENCE: 152
MAILDLKSLV LNAINYWGPK NNNGIQGGDF GYPISEKQID TSIITSTHPR LIPHDLTIPQ    60
NLETIFTTTQ VLTNNTDLQQ SQTVSFAKKT TTTTSTSTTN GWTEGGKISD TLEEKVSVAI   120
PFIGEGGGKN STTIEANFAH NSSTTTAQQA STDIEWNISQ PVLVPPRKQV VATLVIMGGN   180
FTIPMDLMTT IDSTEHYSGY PILTWISSPD NSYNGPFMSW YFANWPNLPS GFGPLNSDNT   240
VTYTGSVVSQ VSAGVYATVR FDQYDIHNLR TIEKTWYARH ATLHNGKKIS INNVTEMAPT   300
SPIKTN                                                              306

SEQ ID NO: 153          moltype = AA   length = 306
FEATURE                 Location/Qualifiers
REGION                  1..306
                        note = engineered
source                  1..306
                        mol_type = protein
                        organism = synthetic construct
SEQUENCE: 153
MAILDLKSLV LNAINYWGPK NNNGIQGGDF GYPISEKQID TSIITSTHPR LIPHDLTIPQ    60
NLETIFTTTQ VLTNNTDLQQ SQTVSFAKKT TTTTATSTTN GWTEGGKISD TLEEKVSVSI   120
PFIGEGGGKN STTIEANFAH NSSTTTFQQA STDIEWNISQ PVLVPPAKQV VATLVIMGGN   180
FTIPMDLMTT IDSTEHYSGY PILTWISSPD NSYNGPFMSW YFANWPNLPS GFGPLNSDNT   240
VTYTGSVVSQ VSAGVYATVR FDQYDIHNLR TIEKTWYARH ATLHNGKKIS INNVTEMAPT   300
SPIKTN                                                              306

SEQ ID NO: 154          moltype = AA   length = 306
FEATURE                 Location/Qualifiers
REGION                  1..306
                        note = engineered
source                  1..306
                        mol_type = protein
                        organism = synthetic construct
SEQUENCE: 154
MAILDLKSLV LNAINYWGPK NNNGIQGGDF GYPISEKQID TSIITSTHPR LIPHDLTIPQ    60
NLETIFTTTQ VLTNNTDLQQ SQTVSFAKKT TTTTSTSTTN GWTEGGKISD TLEEKVSVSI   120
PFIGEGGGKN STTIEANFAH NSSTTTAQQA STDIEWNASQ PVLVPPRKQV VATLVIMGGN   180
FTIPMDLMTT IDSTEHYSGY PILTWISSPD NSYNGPFMSW YFANWPNLPS GFGPLNSDNT   240
VTYTGSVVSQ VSAGVYATVR FDQYDIHNLR TIEKTWYARH ATLHNGKKIS INNVTEMAPT   300
SPIKTN                                                              306

SEQ ID NO: 155          moltype = AA   length = 306
FEATURE                 Location/Qualifiers
REGION                  1..306
                        note = engineered
source                  1..306
                        mol_type = protein
                        organism = synthetic construct
SEQUENCE: 155
MAILDLKSLV LNAINYWGPK NNNGIQGGDF GYPISEKQID TSIITSTHPR LIPHDLTIPQ    60
NLETIFTTTQ VLTNNTDLQQ SQTVSFAKKT TTTTATSTTN GWTEGGKISD TLEEKVSVSI   120
PFIGEGGGKN STTIEANFAH NSSTTTFQQA STDIEWNISQ PVLVPPRKQV VATLVIMGGN   180
FTIPMDLMTT IDSTEHYSGY PILTWISSPD NSYNGPFMSW YFANWPNLPS GFGPLNSDNT   240
VTYTGSVVSQ VSAGVYATVR FDQYDIHNLR TIEKTWYARH ATLHNGKKIS INNVTEAAPT   300
SPIKTN                                                              306

SEQ ID NO: 156          moltype = AA   length = 306
FEATURE                 Location/Qualifiers
REGION                  1..306
                        note = engineered
source                  1..306
                        mol_type = protein
                        organism = synthetic construct
SEQUENCE: 156
MAILDLKSLV LNAINYWGPK NNNGIQGGDF GYPISEKQID TSIITSTHPR LIPHDLTIPQ    60
NLETIFTTTQ VLTNNTDLQQ SQTVSFAKKT TTTTSTSTTN GWTEGGKISD TLEEKVSVSI   120
PFIGEGGGKN STTIEANFAH NSSTTTAQQA STDIEWNISQ PVLVPPRKQV VATLVIMGGN   180
FAIPMDLMTT IDSTEHYSGY PILTWISSPD NSYNGPFMSW YFANWPNLPS GFGPLNSDNT   240
VTYTGSVVSQ VSAGVYATVR FDQYDIHNLR TIEKTWYARH ATLHNGKKIS INNVTEMAPT   300
SPIKTN                                                              306

SEQ ID NO: 157          moltype = AA   length = 306
FEATURE                 Location/Qualifiers
REGION                  1..306
                        note = engineered
source                  1..306
```

```
                            mol_type = protein
                            organism = synthetic construct
SEQUENCE: 157
MAILDLKSLV LNAINYWGPK NNNGIQGGDF GYPISEKQID TSIITSTHPR LIPHDLTIPQ    60
NLETIFTTTQ VLTNNTDLQQ SQTVSFAKKT TTTTSTSTTN GWTEGGKISD TLEEKVSVSI   120
PFIGEGGGKN STTIEANFAH NSSTTTAQQA STDIEWNISQ PVLVPPRKQV VATLVIMGGN   180
FTIPMDLMTT IDSTEHYSGY PILTWISSPD NSYNGPFMSW YFANWPNLPS GAGPLNSDNT   240
VTYTGSVVSQ VSAGVYATVR FDQYDIHNLR TIEKTWYARH ATLHNGKKIS INNVTEMAPT   300
SPIKTN                                                              306

SEQ ID NO: 158          moltype = AA  length = 306
FEATURE                 Location/Qualifiers
REGION                  1..306
                        note = engineered
source                  1..306
                        mol_type = protein
                        organism = synthetic construct
SEQUENCE: 158
MAILDLKSLV LNAINYWGPK NNNGIQGGDF GYPISEKQID TSIITSTHPR LIPHDLTIPQ    60
NLETIFTTTQ VLTNNTDLQQ SQTVSFAKKT TTTTSTSTTN GWTEGGKISD TLEEKVSVSI   120
PFIGEGGGKN STTIEANFAH NSSTTTAQQA STDIEWNISQ PVLVPPAKQV VATLVIMGGN   180
FTIPMDLMTT IDSTEHYSGY PILTWISSPD NSYNGPFMSW YFANWPNLPS GFGPLNSDNT   240
VTYTGSVVSQ VSAGVYATVR FDQYDIHNLR TIEKTWYARH ATLHNGKKIS INNVTEMAPT   300
SPIKTN                                                              306

SEQ ID NO: 159          moltype = AA  length = 306
FEATURE                 Location/Qualifiers
REGION                  1..306
                        note = engineered
source                  1..306
                        mol_type = protein
                        organism = synthetic construct
SEQUENCE: 159
MAILDLKSLV LNAINYWGPK NNNGIQGGDF GYPISEKQID TSIITSTHPR LIPHDLTIPQ    60
NLETIFTTTQ VLTNNTDLQQ SQTVSFAKKT TTATSTSTTN GWTEGGKISD TLEEKVSVSI   120
PFIGEGGGKN STTIEANFAH NSSTTTFQQA STDIEWNISQ PVLVPPRKQV VATLVIMGGN   180
FTIPMDLMTT IDSTEHYSGY PILTWISSPD NSYNGPFMSW YFANWPNLPS GFGPLNSANT   240
VTYTGSVVSQ VSAGVYATVR FDQYDIHNLR TIEKTWYARH ATLHNGKKIS INNVTEMAPT   300
SPIKTN                                                              306

SEQ ID NO: 160          moltype = AA  length = 306
FEATURE                 Location/Qualifiers
REGION                  1..306
                        note = engineered
source                  1..306
                        mol_type = protein
                        organism = synthetic construct
SEQUENCE: 160
MAILDLKSLV LNAINYWGPK NNNGIQGGDF GYPISEKQID TSIITSTHPR LIPHDLTIPQ    60
NLETIFTTTQ VLTNNTDLQQ SQTVSFAKKT TTTTATSTTN GWTEGGKISD TLEEKVSVSI   120
PFIGEGGGKN STTIEANFAH NSSTTTFQQA STDIEWNISQ PVLVPPRKQV VATLVIMGGN   180
FTIPMDLMTT IDSTEHYSGY PILTWISSPD NSYNGPFMSW YFANWPNLPS GFGPLNSDNT   240
VTYTGSVVSQ VSAGVYATVR FDQYDIHNLR AIEKTWYARH ATLHNGKKIS INNVTEMAPT   300
SPIKTN                                                              306

SEQ ID NO: 161          moltype = AA  length = 306
FEATURE                 Location/Qualifiers
REGION                  1..306
                        note = engineered
source                  1..306
                        mol_type = protein
                        organism = synthetic construct
SEQUENCE: 161
MAILDLKSLV LNAINYWGPK NNNGIQGGDF GYPISEKQID TSIITSTHPR LIPHDLTIPQ    60
NLETIFTTTQ VLTNNTDLQQ SQTVSFAKKT TTATSTSTTN GWTEGGKISD TLEEKVSVSI   120
PFIGEGGGKN STTIEANFAH NSSTTTFAQA STDIEWNISQ PVLVPPRKQV VATLVIMGGN   180
FTIPMDLMTT IDSTEHYSGY PILTWISSPD NSYNGPFMSW YFANWPNLPS GFGPLNSDNT   240
VTYTGSVVSQ VSAGVYATVR FDQYDIHNLR TIEKTWYARH ATLHNGKKIS INNVTEMAPT   300
SPIKTN                                                              306

SEQ ID NO: 162          moltype = AA  length = 306
FEATURE                 Location/Qualifiers
REGION                  1..306
                        note = engineered
source                  1..306
                        mol_type = protein
                        organism = synthetic construct
SEQUENCE: 162
MAILDLKSLV LNAINYWGPK NNNGIQGGDF GYPISEKQID TSIITSTHPR LIPHDLTIPQ    60
```

```
NLETIFTTTQ VLTNNTDLQQ SQTVSFAKKT TTTTATSTTN GWTEGGKISD TLEEKVSVSI      120
PFIGEGGGKN STTIEANFAH NSSTTTFQQA STDIEWNISQ PVLVPPRKQV VATLVIMGGN      180
FTIPMDLMTT IDSTEHYSGY PILTWISSPD NSYNGPFMSW YFANWPNLPS GFGPLNSANT      240
VTYTGSVVSQ VSAGVYATVR FDQYDIHNLR TIEKTWYARH ATLHNGKKIS INNVTEMAPT      300
SPIKTN                                                                306

SEQ ID NO: 163          moltype = AA  length = 306
FEATURE                 Location/Qualifiers
REGION                  1..306
                        note = engineered
source                  1..306
                        mol_type = protein
                        organism = synthetic construct
SEQUENCE: 163
MAILDLKSLV LNAINYWGPK NNNGIQGGDF GYPISEKQID TSIITSTHPR LIPHDLTIPQ      60
NLETIFTTTQ VLTNNTDLQQ SQTVSFAKKT TTTTATSTTN GWTEGGKISD TLEEKVSVSI      120
PFIGEGGGKN STTIEANFAH NSSTTTFQQA STDIAWNISQ PVLVPPRKQV VATLVIMGGN      180
FTIPMDLMTT IDSTEHYSGY PILTWISSPD NSYNGPFMSW YFANWPNLPS GFGPLNSDNT      240
VTYTGSVVSQ VSAGVYATVR FDQYDIHNLR TIEKTWYARH ATLHNGKKIS INNVTEMAPT      300
SPIKTN                                                                306

SEQ ID NO: 164          moltype = AA  length = 306
FEATURE                 Location/Qualifiers
REGION                  1..306
                        note = engineered
source                  1..306
                        mol_type = protein
                        organism = synthetic construct
SEQUENCE: 164
MAILDLKSLV LNAINYWGPK NNNGIQGGDF GYPISEKQID TSIITSTHPR LIPHDLTIPQ      60
NLETIFTTTQ VLTNNTDLQQ SQTVSFAKKT TTATSTSTTN GWTEGGKISD TLEEKVSVSI      120
PFIGEGGGKN STTIEANFAH NSSTTTFQQA STDIEWNISQ PVLVPPRKQV VATLVIMGGN      180
FTIPMDAMTT IDSTEHYSGY PILTWISSPD NSYNGPFMSW YFANWPNLPS GFGPLNSDNT      240
VTYTGSVVSQ VSAGVYATVR FDQYDIHNLR TIEKTWYARH ATLHNGKKIS INNVTEMAPT      300
SPIKTN                                                                306

SEQ ID NO: 165          moltype = AA  length = 306
FEATURE                 Location/Qualifiers
REGION                  1..306
                        note = engineered
source                  1..306
                        mol_type = protein
                        organism = synthetic construct
SEQUENCE: 165
MAILDLKSLV LNAINYWGPK NNNGIQGGDF GYPISEKQID TSIITSTHPR LIPHDLTIPQ      60
NLETIFTTTQ VLTNNTDLQQ SQTVSFAKKT TTATSTSTTN GWTEGGKISD TLEEKVSVSI      120
PFIGEGGGKN STTIEANFAH NSSTTTFQQA STDIEWNISQ PVLVPPRKQV VATLVIMGGN      180
FTIPMDLMTT IDSTEHYSGY PILTWISSPD NSYNGPFMSW YFANWPNLPS GFGPLNSDNT      240
VTYTGSVVSQ VSAGVYATVR FDQYDIHNLR TIEKTWYARH ATLHNGKKIS INNVTEMAPA      300
SPIKTN                                                                306

SEQ ID NO: 166          moltype = AA  length = 306
FEATURE                 Location/Qualifiers
REGION                  1..306
                        note = engineered
source                  1..306
                        mol_type = protein
                        organism = synthetic construct
SEQUENCE: 166
MAILDLKSLV LNAINYWGPK NNNGIQGGDF GYPISEKQID TSIITSTHPR LIPHDLTIPQ      60
NLETIFTTTQ VLTNNTDLQQ SQTVSFAKKT TTATSTSTTN GWTEGGKISD TLEEKVSVSI      120
PFIGEGGGKN STTIEANFAH NSSTTTFQQA STDIAWNISQ PVLVPPRKQV VATLVIMGGN      180
FTIPMDLMTT IDSTEHYSGY PILTWISSPD NSYNGPFMSW YFANWPNLPS GFGPLNSDNT      240
VTYTGSVVSQ VSAGVYATVR FDQYDIHNLR TIEKTWYARH ATLHNGKKIS INNVTEMAPT      300
SPIKTN                                                                306

SEQ ID NO: 167          moltype = AA  length = 306
FEATURE                 Location/Qualifiers
REGION                  1..306
                        note = engineered
source                  1..306
                        mol_type = protein
                        organism = synthetic construct
SEQUENCE: 167
MAILDLKSLV LNAINYWGPK NNNGIQGGDF GYPISEKQID TSIITSTHPR LIPHDLTIPQ      60
NLETIFTTTQ VLTNNTDLQQ SQTVSFAKKT TTTTATSTTN GWTEGGKISD TLEEKVSVSI      120
PFIGEGGGKN STTIEANFAH NSSTTTFQQA STAIEWNISQ PVLVPPRKQV VATLVIMGGN      180
FTIPMDLMTT IDSTEHYSGY PILTWISSPD NSYNGPFMSW YFANWPNLPS GFGPLNSDNT      240
VTYTGSVVSQ VSAGVYATVR FDQYDIHNLR TIEKTWYARH ATLHNGKKIS INNVTEMAPT      300
```

```
SPIKTN                                                            306

SEQ ID NO: 168            moltype = AA  length = 306
FEATURE                   Location/Qualifiers
REGION                    1..306
                          note = engineered
source                    1..306
                          mol_type = protein
                          organism = synthetic construct
SEQUENCE: 168
MAILDLKSLV LNAINYWGPK NNNGIQGGDF GYPISEKQID TSIITSTHPR LIPHDLTIPQ  60
NLETIFTTTQ VLTNNTDLQQ SQTVSFAKKT TTATSTSTTN GWTEGGKISD TLEEKVSVSI  120
PFIGEGGGKN STTAEANFAH NSSTTTFQQA STDIEWNISQ PVLVPPRKQV VATLVIMGGN  180
FTIPMDLMTT IDSTEHYSGY PILTWISSPD NSYNGPFMSW YFANWPNLPS GFGPLNSDNT  240
VTYTGSVVSQ VSAGVYATVR FDQYDIHNLR TIEKTWYARH ATLHNGKKIS INNVTEMAPT  300
SPIKTN                                                            306

SEQ ID NO: 169            moltype = AA  length = 306
FEATURE                   Location/Qualifiers
REGION                    1..306
                          note = engineered
VARIANT                   133
                          note = is not T
VARIANT                   135
                          note = is not E
VARIANT                   137
                          note = is not N
source                    1..306
                          mol_type = protein
                          organism = synthetic construct
SEQUENCE: 169
MAILDLKSLV LNAINYWGPK NNNGIQGGDF GYPISEKQID TSIITSTHPR LIPHDLTIPQ  60
NLETIFTTTQ VLTNNTDLQQ SQTVSFAKKT TTATSTSTTN GWTEGGKISD TLEEKVSVSI  120
PFIGEGGGKN STXIXAXFAH NSSTTTFQQA STDIEWNISQ PVLVPPRKQV VATLVIMGGN  180
FTIPMDLMTT IDSTEHYSGY PILTWISSPD NSYNGPFMSW YFANWPNLPS GFGPLNSDNT  240
VTYTGSVVSQ VSAGVYATVR FDQYDIHNLR TIEKTWYARH ATLHNGKKIS INNVTEMAPT  300
SPIKTN                                                            306

SEQ ID NO: 170            moltype = AA  length = 309
FEATURE                   Location/Qualifiers
REGION                    1..309
                          note = engineered
VARIANT                   125
                          note = is not E
source                    1..309
                          mol_type = protein
                          organism = synthetic construct
SEQUENCE: 170
MAILDLKSLV LNAINYWGPK NNNGIQGGDF GYPISEKQID TSIITFTHPR LIPYDLTIPQ  60
NLETIFTTTQ VLTNNTDLQQ SQTVSFAKKT TTTTSTSTTN GWTEGGKISD TLEEKVSVSI  120
PFIGXGGGKN STTIEANFAH NSSTTTFQQA STDIEWNISQ PVLVPPSKQV VATLVIMGGN  180
FTIPMDLMTT IDSTEHYSHY SGYPILTWIS SPDNSYSGPF MSWYFANWPN LPSGFGPLNS  240
DNTVTYTGSV VSQVSAGVYA TVRFDQYDIH NLRTIEKTWY ARHATLHNGK KISINNVTEM  300
APTSPIKTN                                                         309

SEQ ID NO: 171            moltype = AA  length = 309
FEATURE                   Location/Qualifiers
REGION                    1..309
                          note = engineered
VARIANT                   133
                          note = is not T
source                    1..309
                          mol_type = protein
                          organism = synthetic construct
SEQUENCE: 171
MAILDLKSLV LNAINYWGPK NNNGIQGGDF GYPISEKQID TSIITFTHPR LIPYDLTIPQ  60
NLETIFTTTQ VLTNNTDLQQ SQTVSFAKKT TTTTSTSTTN GWTEGGKISD TLEEKVSVSI  120
PFIGEGGGKN STXIEANFAH NSSTTTFQQA STDIEWNISQ PVLVPPSKQV VATLVIMGGN  180
FTIPMDLMTT IDSTEHYSHY SGYPILTWIS SPDNSYSGPF MSWYFANWPN LPSGFGPLNS  240
DNTVTYTGSV VSQVSAGVYA TVRFDQYDIH NLRTIEKTWY ARHATLHNGK KISINNVTEM  300
APTSPIKTN                                                         309

SEQ ID NO: 172            moltype = AA  length = 309
FEATURE                   Location/Qualifiers
REGION                    1..309
                          note = engineered
VARIANT                   134
                          note = is not I
source                    1..309
```

```
                              mol_type = protein
                              organism = synthetic construct
SEQUENCE: 172
MAILDLKSLV LNAINYWGPK NNNGIQGGDF GYPISEKQID TSIITFTHPR LIPYDLTIPQ    60
NLETIFTTTQ VLTNNTDLQQ SQTVSFAKKT TTTTSTSTTN GWTEGGKISD TLEEKVSVSI   120
PFIGEGGGKN STTXEANFAH NSSTTTFQQA STDIEWNISQ PVLVPPSKQV VATLVIMGGN   180
FTIPMDLMTT IDSTEHYSHY SGYPILTWIS SPDNSYSGPF MSWYFANWPN LPSGFGPLNS   240
DNTVTYTGSV VSQVSAGVYA TVRFDQYDIH NLRTIEKTWY ARHATLHNGK KISINNVTEM   300
APTSPIKTN                                                           309

SEQ ID NO: 173          moltype = AA  length = 309
FEATURE                 Location/Qualifiers
REGION                  1..309
                        note = engineered
VARIANT                 135
                        note = is not E
source                  1..309
                        mol_type = protein
                        organism = synthetic construct
SEQUENCE: 173
MAILDLKSLV LNAINYWGPK NNNGIQGGDF GYPISEKQID TSIITFTHPR LIPYDLTIPQ    60
NLETIFTTTQ VLTNNTDLQQ SQTVSFAKKT TTTTSTSTTN GWTEGGKISD TLEEKVSVSI   120
PFIGEGGGKN STTIXANFAH NSSTTTFQQA STDIEWNISQ PVLVPPSKQV VATLVIMGGN   180
FTIPMDLMTT IDSTEHYSHY SGYPILTWIS SPDNSYSGPF MSWYFANWPN LPSGFGPLNS   240
DNTVTYTGSV VSQVSAGVYA TVRFDQYDIH NLRTIEKTWY ARHATLHNGK KISINNVTEM   300
APTSPIKTN                                                           309

SEQ ID NO: 174          moltype = AA  length = 309
FEATURE                 Location/Qualifiers
REGION                  1..309
                        note = engineered
VARIANT                 137
                        note = is not N
source                  1..309
                        mol_type = protein
                        organism = synthetic construct
SEQUENCE: 174
MAILDLKSLV LNAINYWGPK NNNGIQGGDF GYPISEKQID TSIITFTHPR LIPYDLTIPQ    60
NLETIFTTTQ VLTNNTDLQQ SQTVSFAKKT TTTTSTSTTN GWTEGGKISD TLEEKVSVSI   120
PFIGEGGGKN STTIEAXFAH NSSTTTFQQA STDIEWNISQ PVLVPPSKQV VATLVIMGGN   180
FTIPMDLMTT IDSTEHYSHY SGYPILTWIS SPDNSYSGPF MSWYFANWPN LPSGFGPLNS   240
DNTVTYTGSV VSQVSAGVYA TVRFDQYDIH NLRTIEKTWY ARHATLHNGK KISINNVTEM   300
APTSPIKTN                                                           309

SEQ ID NO: 175          moltype = AA  length = 309
FEATURE                 Location/Qualifiers
REGION                  1..309
                        note = engineered
VARIANT                 147
                        note = is not F
source                  1..309
                        mol_type = protein
                        organism = synthetic construct
SEQUENCE: 175
MAILDLKSLV LNAINYWGPK NNNGIQGGDF GYPISEKQID TSIITFTHPR LIPYDLTIPQ    60
NLETIFTTTQ VLTNNTDLQQ SQTVSFAKKT TTTTSTSTTN GWTEGGKISD TLEEKVSVSI   120
PFIGEGGGKN STTIEANFAH NSSTTTXQQA STDIEWNISQ PVLVPPSKQV VATLVIMGGN   180
FTIPMDLMTT IDSTEHYSHY SGYPILTWIS SPDNSYSGPF MSWYFANWPN LPSGFGPLNS   240
DNTVTYTGSV VSQVSAGVYA TVRFDQYDIH NLRTIEKTWY ARHATLHNGK KISINNVTEM   300
APTSPIKTN                                                           309

SEQ ID NO: 176          moltype = AA  length = 309
FEATURE                 Location/Qualifiers
REGION                  1..309
                        note = engineered
VARIANT                 149
                        note = is not Q
source                  1..309
                        mol_type = protein
                        organism = synthetic construct
SEQUENCE: 176
MAILDLKSLV LNAINYWGPK NNNGIQGGDF GYPISEKQID TSIITFTHPR LIPYDLTIPQ    60
NLETIFTTTQ VLTNNTDLQQ SQTVSFAKKT TTTTSTSTTN GWTEGGKISD TLEEKVSVSI   120
PFIGEGGGKN STTIEANFAH NSSTTTFQXA STDIEWNISQ PVLVPPSKQV VATLVIMGGN   180
FTIPMDLMTT IDSTEHYSHY SGYPILTWIS SPDNSYSGPF MSWYFANWPN LPSGFGPLNS   240
DNTVTYTGSV VSQVSAGVYA TVRFDQYDIH NLRTIEKTWY ARHATLHNGK KISINNVTEM   300
APTSPIKTN                                                           309

SEQ ID NO: 177          moltype = AA  length = 309
```

```
FEATURE                 Location/Qualifiers
REGION                  1..309
                        note = engineered
VARIANT                 150
                        note = is not A
source                  1..309
                        mol_type = protein
                        organism = synthetic construct
SEQUENCE: 177
MAILDLKSLV LNAINYWGPK NNNGIQGGDF GYPISEKQID TSIITFTHPR LIPYDLTIPQ    60
NLETIFTTTQ VLTNNTDLQQ SQTVSFAKKT TTTTSTSTTN GWTEGGKISD TLEEKVSVSI   120
PFIGEGGGKN STTIEANFAH NSSTTTFQQX STDIEWNISQ PVLVPPSKQV VATLVIMGGN   180
FTIPMDLMTT IDSTEHYSHY SGYPILTWIS SPDNSYSGPF MSWYFANWPN LPSGFGPLNS   240
DNTVTYTGSV VSQVSAGVYA TVRFDQYDIH NLRTIEKTWY ARHATLHNGK KISINNVTEM   300
APTSPIKTN                                                          309

SEQ ID NO: 178          moltype = AA  length = 309
FEATURE                 Location/Qualifiers
REGION                  1..309
                        note = engineered
VARIANT                 155
                        note = is not E
source                  1..309
                        mol_type = protein
                        organism = synthetic construct
SEQUENCE: 178
MAILDLKSLV LNAINYWGPK NNNGIQGGDF GYPISEKQID TSIITFTHPR LIPYDLTIPQ    60
NLETIFTTTQ VLTNNTDLQQ SQTVSFAKKT TTTTSTSTTN GWTEGGKISD TLEEKVSVSI   120
PFIGEGGGKN STTIEANFAH NSSTTTFQQA STDIXWNISQ PVLVPPSKQV VATLVIMGGN   180
FTIPMDLMTT IDSTEHYSHY SGYPILTWIS SPDNSYSGPF MSWYFANWPN LPSGFGPLNS   240
DNTVTYTGSV VSQVSAGVYA TVRFDQYDIH NLRTIEKTWY ARHATLHNGK KISINNVTEM   300
APTSPIKTN                                                          309

SEQ ID NO: 179          moltype = AA  length = 309
FEATURE                 Location/Qualifiers
REGION                  1..309
                        note = engineered
VARIANT                 157
                        note = is not N
source                  1..309
                        mol_type = protein
                        organism = synthetic construct
SEQUENCE: 179
MAILDLKSLV LNAINYWGPK NNNGIQGGDF GYPISEKQID TSIITFTHPR LIPYDLTIPQ    60
NLETIFTTTQ VLTNNTDLQQ SQTVSFAKKT TTTTSTSTTN GWTEGGKISD TLEEKVSVSI   120
PFIGEGGGKN STTIEANFAH NSSTTTFQQA STDIEWXISQ PVLVPPSKQV VATLVIMGGN   180
FTIPMDLMTT IDSTEHYSHY SGYPILTWIS SPDNSYSGPF MSWYFANWPN LPSGFGPLNS   240
DNTVTYTGSV VSQVSAGVYA TVRFDQYDIH NLRTIEKTWY ARHATLHNGK KISINNVTEM   300
APTSPIKTN                                                          309

SEQ ID NO: 180          moltype = AA  length = 309
FEATURE                 Location/Qualifiers
REGION                  1..309
                        note = engineered
REGION                  1..309
                        note = is not TIC807 (SEQ ID NO: 2)
VARIANT                 12
                        note = X can be any naturally occurring amino acid
VARIANT                 46
                        note = X can be any naturally occurring amino acid
VARIANT                 52
                        note = X can be any naturally occurring amino acid
VARIANT                 54
                        note = X can be any naturally occurring amino acid
VARIANT                 68
                        note = X can be any naturally occurring amino acid
VARIANT                 70
                        note = X can be any naturally occurring amino acid
VARIANT                 87
                        note = X can be any naturally occurring amino acid
VARIANT                 93
                        note = X can be any naturally occurring amino acid
VARIANT                 95
                        note = X can be any naturally occurring amino acid
VARIANT                 105
                        note = X can be any naturally occurring amino acid
VARIANT                 117
                        note = X can be any naturally occurring amino acid
VARIANT                 119
```

-continued

```
                        note = X can be any naturally occurring amino acid
VARIANT                 125
                        note = X can be any naturally occurring amino acid
VARIANT                 128
                        note = X can be any naturally occurring amino acid
VARIANT                 133..135
                        note = X can be any naturally occurring amino acid
VARIANT                 137..139
                        note = X can be any naturally occurring amino acid
VARIANT                 145
                        note = X can be any naturally occurring amino acid
VARIANT                 147..151
                        note = X can be any naturally occurring amino acid
VARIANT                 153
                        note = X can be any naturally occurring amino acid
VARIANT                 155
                        note = X can be any naturally occurring amino acid
VARIANT                 157..159
                        note = X can be any naturally occurring amino acid
VARIANT                 167
                        note = X can be any naturally occurring amino acid
VARIANT                 175
                        note = X can be any naturally occurring amino acid
VARIANT                 177
                        note = X can be any naturally occurring amino acid
VARIANT                 180
                        note = X can be any naturally occurring amino acid
VARIANT                 182
                        note = X can be any naturally occurring amino acid
VARIANT                 187
                        note = X can be any naturally occurring amino acid
VARIANT                 196..201
                        note = X can be any naturally occurring amino acid
VARIANT                 208
                        note = X can be any naturally occurring amino acid
VARIANT                 217
                        note = X can be any naturally occurring amino acid
VARIANT                 219
                        note = X can be any naturally occurring amino acid
VARIANT                 223
                        note = X can be any naturally occurring amino acid
VARIANT                 235
                        note = X can be any naturally occurring amino acid
VARIANT                 239
                        note = X can be any naturally occurring amino acid
VARIANT                 241
                        note = X can be any naturally occurring amino acid
VARIANT                 243..247
                        note = X can be any naturally occurring amino acid
VARIANT                 249..252
                        note = X can be any naturally occurring amino acid
VARIANT                 273..275
                        note = X can be any naturally occurring amino acid
VARIANT                 282
                        note = X can be any naturally occurring amino acid
VARIANT                 287
                        note = X can be any naturally occurring amino acid
VARIANT                 293
                        note = X can be any naturally occurring amino acid
VARIANT                 295
                        note = X can be any naturally occurring amino acid
VARIANT                 299..300
                        note = X can be any naturally occurring amino acid
VARIANT                 303
                        note = X can be any naturally occurring amino acid
VARIANT                 305..306
                        note = X can be any naturally occurring amino acid
VARIANT                 308
                        note = X can be any naturally occurring amino acid
source                  1..309
                        mol_type = protein
                        organism = synthetic construct
SEQUENCE: 180
MAILDLKSLV LXAINYWGPK NNNGIQGGDF GYPISEKQID TSIITXTHPR LXPXDLTIPQ  60
NLETIFTXTX VLTNNTDLQQ SQTVSFXKKT TTXTXTSTTN GWTEXGKISD TLEEKVXVXI  120
PFIGXGGXKN STXXXAXXXH NSSTXTXXXX XTXIXWXXXQ PVLVPPXKQV VATLXIXGGX  180
FXIPMDXMTT IDSTEXXXXX XGYPILTXIS SPDNSYXGXF MSXYFANWPN LPSGXGPLXS  240
XNXXXXXGXX XXQVSAGVYA TVRFDQYDIH NLXXXEKTWY AXHATLXNGK KIXIXNVTXX  300
APXSXXKXN                                                         309
```

```
SEQ ID NO: 181         moltype = DNA  length = 927
FEATURE                Location/Qualifiers
misc_feature           1..927
                       note = is a sequence representing a recombinant
                        polynucleotide derived from a native gene from a Bacillus
                        thuringiensis (Bt) species encoding a Cry51Aa1 protein
source                 1..927
                       mol_type = other DNA
                       organism = Bacillus thuringiensis
SEQUENCE: 181
atgattttt tggcaatttt agatttaaaa tctttagtac tcaatgcaat aaattattgg  60
ggtcctaaaa ataataatgg catacagggt ggtgattttg gttaccctat atcagaaaaa  120
caaatagata cgtctattat aacttctact catcctcgtt taattccaca tgatttaaca  180
attcctcaaa atttagaaac tatttttact acaactcaag tattaacaaa taatacagat  240
ttacaacaaa gtcaaactgt ttcttttgct aaaaaaacaa cgacaacaac ttcaacttca  300
actacaaatg gttggacaga aggtgggaaa atttcagata cattagaaga aaaagtaagt  360
gtatctattc cttttattgg agagggagga ggaaaaaaca gtacaactat agaagctaat  420
tttgcacata actctagtac tactactttt caacaggctt caactgatat agagtggaat  480
atttcacaac cagtattggt tcccccacgt aaacaagttg tagcaacatt agttattatg  540
ggaggtaatt ttactattcc tatggatttg atgactacta tagattctac agaacattat  600
agtggttatc caatattaac atggatatcg agccccgata atagttataa tggtccattt  660
atgagttggt attttgcaaa ttggcccaat ttaccatcgg ggtttggtcc tttaaattca  720
gataatacgg tcacttatac aggttctgtt gtaagtcaag tatcagctgg tgtatatgcc  780
actgtacgat ttgatcaata tgatatacac aatttaagga caattgaaaa aacttggtat  840
gcacgacatg caactcttca taatggaaag aaaatatcta taaataatgt tactgaaatg  900
gcaccaacaa gtccaataaa aacaaat                                    927

SEQ ID NO: 182         moltype = AA  length = 309
FEATURE                Location/Qualifiers
REGION                 1..309
                       note = engineered
REGION                 1..309
                       note = is an amino acid sequence translation of nucleotide
                        (NT) positions 1 through 927 of SEQ ID NO: 181
source                 1..309
                       mol_type = protein
                       organism = synthetic construct
SEQUENCE: 182
MIFLAILDLK SLVLNAINYW GPKNNNGIQG GDFGYPISEK QIDTSIITST HPRLIPHDLT  60
IPQNLETIFT TTQVLTNNTD LQQSQTVSFA KKTTTTTSTS TTNGWTEGGK ISDTLEEKVS  120
VSIPFIGEGG GKNSTTIEAN FAHNSSTTTF QQASTDIEWN ISQPVLVPPR KQVVATLVIM  180
GGNFTIPMDL MTTIDSTEHY SGYPILTWIS SPDNSYNGPF MSWYFANWPN LPSGFGPLNS  240
DNTVTYTGSV VSQVSAGVYA TVRFDQYDIH NLRTIEKTWY ARHATLHNGK KISINNVTEM  300
APTSPIKTN                                                        309

SEQ ID NO: 183         moltype = DNA  length = 918
FEATURE                Location/Qualifiers
misc_feature           1..918
                       note = is a sequence representing a recombinant
                        polynucleotide derived from a native gene from a Bacillus
                        thuringiensis (Bt) species encoding a TIC853 protein
source                 1..918
                       mol_type = other DNA
                       organism = Bacillus thuringiensis
SEQUENCE: 183
ttggcaattt tagatttaaa atctttagta ctcgatgcaa taaactattg ggtcctaaa  60
aataataatg gtatacaggg ttataatttt aattacccta tatcagaaag acaaatagat  120
acgtcgatta taacttctac tcattctcgt ttaatgccac atgatttaac aattcctcaa  180
aatttagaaa ctatttttac tacaactcaa gtattaacaa ataatacaga tgtacaacaa  240
agtcaaactg tttcttttc taaaaaaaca acgacaacaa cttcaacttc aactacagat  300
ggttggacag aaggtgggag aatttcagat acattagaag aaaacgtaag tgtatctatt  360
ccttttattg gagcgggagg agcaaaaaac agtacaacta tagaagctaa tgttgcacat  420
aactctagta ctactacttc tcaacaggct tcaactgaga tagagtggaa tatttcacaa  480
ccagtattgg ttcccccacg taaacaagtt gtagcaacat tagttattat gggaggtgat  540
tttactgttc ctatggattt gataactact atagattcta cacaacattt tactggttat  600
ccaatattaa catggataga gaaccccgag cataatgtta gaggtcgatt tctgagttgg  660
ttttttgcaa attggcccaa tttaccatcg gagtttggtt ctttaaattc agataatacg  720
atcacttata aaggttctgt tgtaagtcag atatcagctg gtgtatatgc tactgtacga  780
tttgatcaat atgctataaa taatttaaga acaattgaaa aaacttggta tgcacgacat  840
ggaactcttc ataatggaaa gaaaatatct ataaataatg ttactgaaat ggcaccaaca  900
agtccaatag aaagaaat                                              918

SEQ ID NO: 184         moltype = AA  length = 306
FEATURE                Location/Qualifiers
REGION                 1..306
                       note = engineered
REGION                 1..306
                       note = is an amino acid sequence translation of nucleotide
```

|   |   |   |
|---|---|---|
|   | (NT) positions 1 through 918 of SEQ ID NO: 183 |   |
| source | 1..306 |   |
|   | mol_type = protein |   |
|   | organism = synthetic construct |   |

SEQUENCE: 184
```
MAILDLKSLV LDAINYWGPK NNNGIQGYNF NYPISERQID TSIITSTHSR LMPHDLTIPQ    60
NLETIFTTTQ VLTNNTDVQQ SQTVSFSKKT TTTTSTSTTD GWTEGGRISD TLEENVSVSI   120
PFIGAGGAKN STTIEANVAH NSSTTTSQQA STEIEWNISQ PVLVPPRKQV VATLVIMGGD   180
FTVPMDLITT IDSTQHFTGY PILTWIENPE HNVRGRFLSW FFANWPNLPS EFGSLNSDNT   240
ITYKGSVVSR ISAGVYATVR FDQYAINNLR TIEKTWYARH GTLHNGKKIS INNVTEMAPT   300
SPIERN                                                             306
```

|   |   |   |
|---|---|---|
| SEQ ID NO: 185 | moltype = AA  length = 309 |   |
| FEATURE | Location/Qualifiers |   |
| REGION | 1..309 |   |
|   | note = engineered |   |
| REGION | 1..309 |   |
|   | note = is TIC807 (SEQ ID NO: 2) position 11 Leucine substituted by a Methionine |   |
| source | 1..309 |   |
|   | mol_type = protein |   |
|   | organism = synthetic construct |   |

SEQUENCE: 185
```
MAILDLKSLV MNAINYWGPK NNNGIQGGDF GYPISEKQID TSIITFTHPR LIPYDLTIPQ    60
NLETIFTTTQ VLTNNTDLQQ SQTVSFAKKT TTTTSTSTTN GWTEGGKISD TLEEKVSVSI   120
PFIGEGGGKN STTIEANFAH NSSTTTFQQA STDIEWNISQ PVLVPPSKQV VATLVIMGGN   180
FTIPMDLMTT IDSTEHYSHY SGYPILTWIS SPDNSYSGPF MSWYFANWPN LPSGFGPLNS   240
DNTVTYTGSV VSQVSAGVYA TVRFDQYDIH NLRTIEKTWY ARHATLHNGK KISINNVTEM   300
APTSPIKTN                                                          309
```

|   |   |   |
|---|---|---|
| SEQ ID NO: 186 | moltype = DNA  length = 930 |   |
| FEATURE | Location/Qualifiers |   |
| misc_feature | 1..930 |   |
|   | note = engineered |   |
| misc_feature | 1..930 |   |
|   | note = A nucleotide sequence encoding SEQ ID NO: 4 with an open reading frame from 1 to 927. |   |
| source | 1..930 |   |
|   | mol_type = other DNA |   |
|   | organism = synthetic construct |   |

SEQUENCE: 186
```
atggctatcc tagaccttaa gtccctcgtg ctgaacgcca ttaactactg gggccctaag    60
aacaacaacg gcatccaggg cggtgacttc ggctacccca tctctgagaa gcagatcgac   120
actagcatca ttaccttcac ccaccctcgc ttgatcccct acgatcttac tatccccgag   180
aaccttgaga ccatcttcac cacaacgcag gtgctcacca ataacactga cctccagcaa   240
tcccagaccg tgagctttgc gaagaagacc actaccacga cctcaactag cacgaccaac   300
ggttggacag aaggaggcaa gatcagcgac acgctggagg agaaagtttc ggttagcatt   360
ccgttcatcg gtgcgggtgg cgggaagaac tcgactacca tagaggccaa cttcgcacac   420
aactctagca ccactacctt ccagcaagca agcactgaca ttgagtggaa cattagccaa   480
ccggtgctgg ttcctccctc taaacaagtt gtcgcgaccc ttgtgatcat gggaggcaac   540
tttaccatcc ctatggactt gatgaccacg attgatagta cagagcacta ctcccactac   600
tccggttacc ctatcctcac ctggatcctcg tccccagata actcttactc cggtcccttt   660
atgtcatggt actttgcaaa ctggcctaac cttccgagtg gattcggccc actgaatagt   720
gataacacgt tcatatacac tggctctgtc gtgtcccaag tttcggccgg tgtctacgct   780
accgtccggt tcgatcagta tgacattcac aatctccgta ctatcgagaa gacttggtat   840
gctcgccatg cgacgctgca taatggcaag aagatttcta tcaacaatgt cacggaaatg   900
gctccaacat cccctatcaa gacaaattga                                   930
```

|   |   |   |
|---|---|---|
| SEQ ID NO: 187 | moltype = DNA  length = 930 |   |
| FEATURE | Location/Qualifiers |   |
| misc_feature | 1..930 |   |
|   | note = engineered |   |
| misc_feature | 1..930 |   |
|   | note = A nucleotide sequence encoding SEQ ID NO: 6 with an open reading frame from 1 to 927. |   |
| source | 1..930 |   |
|   | mol_type = other DNA |   |
|   | organism = synthetic construct |   |

SEQUENCE: 187
```
atggctatcc tagaccttaa gtccctcgtg ctgaacgcca ttaactactg gggccctaag    60
aacaacaacg gcatccaggg cggtgacttc ggctacccca tctctgagaa gcagatcgac   120
actagcatca ttaccttcac ccaccctcgc ttgatcccct acgatcttac tatccccgag   180
aaccttgaga ccatcttcac cacaacgcag gtgctcacca ataacactga cctccagcaa   240
tcccagaccg tgagctttgc gaagaagacc actaccacga cctcaactag cacgaccaac   300
ggttggacag aaggaggcaa gatcagcgac acgctggagg agaaagtttc ggttagcatt   360
ccgttcatcg gtgagggtgg cgggaagaac tcgactacca tagaggccaa cttcgcacac   420
aactctagca ccactaccgc ccagcaagca agcactgaca ttgagtggaa cattagccaa   480
ccggtgctgg ttcctccctc taaacaagtt gtcgcgaccc ttgtgatcat gggaggcaac   540
tttaccatcc ctatggactt gatgaccacg attgatagta cagagcacta ctcccactac   600
```

```
tccggttacc ctatcctcac ctggatctcg tccccagata actcttactc cggtcccttt    660
atgtcatggt actttgcaaa ctggcctaac cttccgagtg gattcggccc actgaatagt    720
gataacacgg tcacatacac tggctctgtc gtgtcccaag tttcggccgg tgtctacgct    780
accgtccggt tcgatcagta tgacattcac aatctccgta ctatcgagaa gacttggtat    840
gctcgccatg cgacgctgca taatggcaag aagatttcta tcaacaatgt cacggaaatg    900
gctccaacat cccctatcaa gacaaattga                                     930
```

```
SEQ ID NO: 188            moltype = DNA   length = 921
FEATURE                   Location/Qualifiers
misc_feature              1..921
                          note = engineered
misc_feature              1..921
                          note = A nucleotide sequence encoding SEQ ID NO: 8 with an
                           open reading frame from 1 to 918.
source                    1..921
                          mol_type = other DNA
                          organism = synthetic construct
SEQUENCE: 188
atggctatcc tagaccttaa gtccctcgtg ctgaacgcca ttaactactg gggccctaag    60
aacaacaacg gcatccaggg cggtgacttc ggctacccca tctctgagaa gcagatcgac   120
actagcatca ttacctccac ccaccctcgc ttgatccccc acgatcttac tatcccgcag   180
aaccttgaga ccatcttcac cacaacgcag gtgctcacca ataacactga cctccagcaa   240
tcccagaccg tgagctttgc gaagaagacc actaccgcga cctcaactag cacgaccaac   300
ggttggacag aaggaggcaa gatcagcgac acgctggagg agaaagtttc ggttagcatt   360
ccgttcatcg tgagggtgg cgggaagaac tcgactacca tagaggccaa cttcgcacac   420
aactctagca ccactacctt ccagcaagca agcactgaca ttgagtggaa cattagccaa   480
ccggtccttg tgcctccccg caaacaggtt gttgccactc tcgttatcat gggtggcaac   540
ttcactattc ctatggatct tatgactacc attgactcta ctgagcacta ctctggctac   600
cccattctca cttggatctc ttctcctgac aatagctaca acggtccatt catgtcatgg   660
tacttcgcta actggccgaa tctcccttct ggctttggtc ctcttaactc tgataacact   720
gtgacctaca ctggctctgt cgtcagtcag gtctctgccg gtgtgtacgc aactgttcgc   780
ttcgatcagt atgacatcca taatctcagg actattgaga agacctggta cgctcgtcat   840
gcgacgcttc acaacggcaa gaagatcagc atcaataacg tgacagaaat ggcccctacc   900
agcccgatca agactaactg a                                             921
```

```
SEQ ID NO: 189            moltype = DNA   length = 921
FEATURE                   Location/Qualifiers
misc_feature              1..921
                          note = engineered
misc_feature              1..921
                          note = A nucleotide sequence encoding SEQ ID NO: 10 with an
                           open reading frame from 1 to 918.
source                    1..921
                          mol_type = other DNA
                          organism = synthetic construct
SEQUENCE: 189
atggctatcc tagaccttaa gtccctcgtg ctgaacgcca ttaactactg gggccctaag    60
aacaacaacg gcatccaggg cggtgacttc ggctacccca tctctgagaa gcagatcgac   120
actagcatca ttacctccac ccaccctcgc ttgatccccc acgatcttac tatcccgcag   180
aaccttgaga ccatcttcac cacaacgcag gtgctcacca ataacactga cctccagcaa   240
tcccagaccg tgagctttgc gaagaagacc actaccgcga cctcaactag cacgaccaac   300
ggttggacag aaggaggcaa gatcagcgac acgctggagg agaaagtttc ggttagcatt   360
ccgttcatcg tgagggtgg cgggaagaac tcgactacca tagaggccaa cttcgcacac   420
aactctagca ccactacctt ccagcaagca agcactgaca ttgagtggaa cattagccaa   480
ccggtccttg tgcctccccg caaacaggtt gttgccactc tcgttatcat gggtggcaac   540
ttcactattc ctatggatct tatgactacc attgactcta ctgagcacta ctctggctac   600
cccattctca cttggatctc ttctcctgac aatagctaca acggtccatt catgtcatgg   660
tacttcgcta actggccgaa tctcccttct ggctttggtc ctcttaactc tgataacact   720
gtgacctaca ctggctctgt cgtcagtcag gtctctgccg gtgtgtacgc aactgttcgc   780
ttcgatcagt atgacatcca taatctcagg actattgaga agacctggta cgctcgtcat   840
gcgacgcttc acaacggcaa gaagatcagc atcaataacg tgacagaaat ggcccctacc   900
agcccgatca agactaactg a                                             921
```

```
SEQ ID NO: 190            moltype = DNA   length = 921
FEATURE                   Location/Qualifiers
misc_feature              1..921
                          note = engineered
misc_feature              1..921
                          note = A nucleotide sequence encoding SEQ ID NO: 12 with an
                           open reading frame from 1 to 918.
source                    1..921
                          mol_type = other DNA
                          organism = synthetic construct
SEQUENCE: 190
atggctatcc tagaccttaa gtccctcgtg ctgaacgcca ttaactactg gggccctaag    60
aacaacaacg gcatccaggg cggtgacttc ggctacccca tctctgagaa gcagatcgac   120
actagcatca ttacctccac ccaccctcgc ttgatccccc acgatcttac tatcccgcag   180
aaccttgaga ccatcttcac cacaacgcag gtgctcacca ataacactga cctccagcaa   240
tcccagaccg tgagctttgc gaagaagacc actaccgcga ccgcaactag cacgaccaac   300
```

```
ggttggacag aaggaggcaa gatcagcgac acgctggagg agaaagtttc ggttagcatt   360
ccgttcatcg gtgagggtgg cgggaagaac tcgactacca tagaggccaa cttcgcacac   420
aactctagca ccactacctt ccagcaagca agcactgaca ttgagtggaa cattagccaa   480
ccggtccttg tgcctccccg caaacaggtt gttgccactc tcgttatcat gggtggcaac   540
ttcactattc ctatggatct tatgactacc attgactcta ctgagcacta ctctggctac   600
cccattctca cttggatctc ttctcctgac aatagctaca acggtccatt catgtcatgg   660
tacttcgcta actggccgaa tctcccttct ggctttggtc ctcttaactc tgataacact   720
gtgacctaca ctggctctgt cgtcagtcag gtctctgccg gtgtgtacgc aactgttcgc   780
ttcgatcagt atgacatcca taatctcagg actattgaga agacctggta cgctcgtcat   840
gcgacgcttc acaacggcaa gaagatcagc atcaataacg tgacagaaat ggcccctacc   900
agcccgatca agactaactg a                                            921

SEQ ID NO: 191          moltype = DNA   length = 921
FEATURE                 Location/Qualifiers
misc_feature            1..921
                        note = engineered
misc_feature            1..921
                        note = A nucleotide sequence encoding SEQ ID NO: 14 with an
                         open reading frame from 1 to 918.
source                  1..921
                        mol_type = other DNA
                        organism = synthetic construct
SEQUENCE: 191
atggctatcc tagaccttaa gtccctcgtg ctgaacgcca ttaactactg gggccctaag    60
aacaacaacg gcatccaggg cggtgacttc ggctacccca tctctgagaa gcagatcgac   120
actagcatca ttacctccac ccaccctcgc ttgatccccc acgatcttac tatcccgcag   180
aaccttgaga ccatcttcac cacaacgcag gtgctcacca ataacactga cctccagcaa   240
tcccagaccg tgagctttgc gaagaagacc actaccacga cctcaactag cacgaccaac   300
ggttggacag aaggaggcaa gatcagcgac acgctggagg agaaagtttc ggttagcatt   360
ccgttcatcg gtgagggtgg cgggaagaac tcgactacca tagaggccaa cttcgcacac   420
aactctagca ccactaccgc ccagcaagca agcactgaca ttgagtggaa cattagccaa   480
ccggtccttg tgcctccccg caaacaggtt gttgccactc tcgttatcat gggtggcaac   540
ttcactattc ctatggatct tatgactacc attgactcta ctgagcacta ctctggctac   600
cccattctca cttggatctc ttctcctgac aatagctaca acggtccatt catgtcatgg   660
tacttcgcta actggccgaa tctcccttct ggctttggtc ctcttaactc tgataacact   720
gtgacctaca ctggctctgt cgtcagtcag gtctctgccg gtgtgtacgc aactgttcgc   780
ttcgatcagt atgacatcca taatctcagg actattgaga agacctggta cgctcgtcat   840
gcgacgcttc acaacggcaa gaagatcagc atcaataacg tgacagaaat ggcccctacc   900
agcccgatca agactaactg a                                            921

SEQ ID NO: 192          moltype = DNA   length = 921
FEATURE                 Location/Qualifiers
misc_feature            1..921
                        note = engineered
misc_feature            1..921
                        note = A nucleotide sequence encoding SEQ ID NO: 16 with an
                         open reading frame from 1 to 918.
source                  1..921
                        mol_type = other DNA
                        organism = synthetic construct
SEQUENCE: 192
atggctatcc tagaccttaa gtccctcgtg ctgaacgcca ttaactactg gggccctaag    60
aacaacaacg gcatccaggg cggtgacttc ggctacccca tctctgagaa gcagatcgac   120
actagcatca ttacctccac ccaccctcgc ttgatccccc acgatcttac tatcccgcag   180
aaccttgaga ccatcttcac cacaacgcag gtgctcacca ataacactga cctccagcaa   240
tcccagaccg tgagctttgc gaagaagacc actaccacga ccgcaactag cacgaccaac   300
ggttggacag aaggaggcaa gatcagcgac acgctggagg agaaagtttc ggttagcatt   360
ccgttcatcg gtgagggtgg cgggaagaac tcgactacca tagaggccaa cttcgcacac   420
aactctagca ccactaccgc ccagcaagca agcactgaca ttgagtggaa cattagccaa   480
ccggtccttg tgcctccccg caaacaggtt gttgccactc tcgttatcat gggtggcaac   540
ttcactattc ctatggatct tatgactacc attgactcta ctgagcacta ctctggctac   600
cccattctca cttggatctc ttctcctgac aatagctaca acggtccatt catgtcatgg   660
tacttcgcta actggccgaa tctcccttct ggctttggtc ctcttaactc tgataacact   720
gtgacctaca ctggctctgt cgtcagtcag gtctctgccg gtgtgtacgc aactgttcgc   780
ttcgatcagt atgacatcca taatctcagg actattgaga agacctggta cgctcgtcat   840
gcgacgcttc acaacggcaa gaagatcagc atcaataacg tgacagaaat ggcccctacc   900
agcccgatca agactaactg a                                            921

SEQ ID NO: 193          moltype = DNA   length = 921
FEATURE                 Location/Qualifiers
misc_feature            1..921
                        note = engineered
misc_feature            1..921
                        note = A nucleotide sequence encoding SEQ ID NO: 18 with an
                         open reading frame from 1 to 918.
source                  1..921
                        mol_type = other DNA
                        organism = synthetic construct
SEQUENCE: 193
```

```
atggctatcc tagaccttaa gtccctcgtg ctgaacgcca ttaactactg gggccctaag   60
aacaacaacg gcatccaggg cggtgacttc ggctacccca tctctgagaa gcagatcgac  120
actagcatca ttacctccac ccaccctcgc ttgatccccc acgatcttac tatcccgcag  180
aaccttgaga ccatcttcac cacaacgcag gtgctcacca ataacactga cctccagcaa  240
tcccagaccg tgagctttgc gaagaagacc actaccgcga cctcaactag cacgaccaac  300
ggttggacag aaggaggcaa gatcagcgac acgctggagg agaaagtttc ggttagcatt  360
ccgttcatcg gtgagggtgg cgggaagaac tcgactacca tagaggccaa cttcgcacac  420
aactctagca ccactaccgc ccagcaagca agcactgaca ttgagtggaa cattagccaa  480
ccggtccttg tgcctccccg caaacaggtt gttgccactc tcgttatcat gggtggcaac  540
ttcactattc ctatggatct tatgactacc attgactcta ctgagcacta ctctggctac  600
cccattctca cttggatctc ttctcctgac aatagctaca acggtccatt catgtcatgg  660
tacttcgcta actggccgaa tctcccttct ggctttggtc ctcttaactc tgataacact  720
gtgacctaca ctggctctgt cgtcagtcag gtctctgccg gtgtgtacgc aactgttcgc  780
ttcgatcagt atgacatcca taatctcagg actattgaga agacctggta cgctcgtcat  840
gcgacgcttc acaacggcaa gaagatcagc atcaataacg tgacagaaat ggcccctacc  900
agcccgatca agactaactg a                                             921

SEQ ID NO: 194         moltype = DNA  length = 921
FEATURE                Location/Qualifiers
misc_feature           1..921
                       note = engineered
misc_feature           1..921
                       note = A nucleotide sequence encoding SEQ ID NO: 20 with an
                       open reading frame from 1 to 918.
source                 1..921
                       mol_type = other DNA
                       organism = synthetic construct
SEQUENCE: 194
atggctatcc tagaccttaa gtccctcgtg ctgaacgcca ttaactactg gggccctaag   60
aacaacaacg gcatccaggg cggtgacttc ggctacccca tctctgagaa gcagatcgac  120
actagcatca ttacctccac ccaccctcgc ttgatccccc acgatcttac tatcccgcag  180
aaccttgaga ccatcttcac cacaacgcag gtgctcacca ataacactga cctccagcaa  240
tcccagaccg tgagctttgc gaagaagacc actaccacga cctcaactag cacgaccaac  300
ggttggacag aaggaggcaa gatcagcgac acgctggagg agaaagtttc ggttagcatt  360
ccgttcatcg gtgagggtgg cgggaagaac tcgactacca tagaggccaa cttcgcacac  420
aactctagca ccactaccgc ccaggaggca agcactgaca ttgagtggaa cattagccaa  480
ccggtccttg tgcctccccg caaacaggtt gttgccactc tcgttatcat gggtggcaac  540
ttcactattc ctatggatct tatgactacc attgactcta ctgagcacta ctctggctac  600
cccattctca cttggatctc ttctcctgac aatagctaca acggtccatt catgtcatgg  660
tacttcgcta actggccgaa tctcccttct ggctttggtc ctcttaactc tgataacact  720
gtgacctaca ctggctctgt cgtcagtcag gtctctgccg gtgtgtacgc aactgttcgc  780
ttcgatcagt atgacatcca taatctcagg actattgaga agacctggta cgctcgtcat  840
gcgacgcttc acaacggcaa gaagatcagc atcaataacg tgacagaaat ggcccctacc  900
agcccgatca agactaacta g                                             921

SEQ ID NO: 195         moltype = DNA  length = 921
FEATURE                Location/Qualifiers
misc_feature           1..921
                       note = engineered
misc_feature           1..921
                       note = A nucleotide sequence encoding SEQ ID NO: 22 with an
                       open reading frame from 1 to 918.
source                 1..921
                       mol_type = other DNA
                       organism = synthetic construct
SEQUENCE: 195
atggctatcc tagaccttaa gtccctcgtg ctgaacgcca ttaactactg gggccctaag   60
aacaacaacg gcatccaggg cggtgacttc ggctacccca tctctgagaa gcagatcgac  120
actagcatca ttacctccac ccaccctcgc ttgatccccc acgatcttac tatcccgcag  180
aaccttgaga ccatcttcac cacaacgcag gtgctcacca ataacactga cctccagcaa  240
tcccagaccg tgagctttgc gaagaagacc actaccgcga cctcaactag cacgaccaac  300
ggttggacag aaggaggcaa gatcagcgac acgctggagg agaaagtttc ggttagcatt  360
ccgttcatcg gtgagggtgg cgggaagaac tcgactacca tagaggccaa cttcgcacac  420
aactctagca ccactaccgc ccaggcagca agcactgaca ttgagtggaa cattagccaa  480
ccggtccttg tgcctccccg caaacaggtt gttgccactc tcgttatcat gggtggcaac  540
ttcactattc ctatggatct tatgactacc attgactcta ctgagcacta ctctggctac  600
cccattctca cttggatctc ttctcctgac aatagctaca acggtccatt catgtcatgg  660
tacttcgcta actggccgaa tctcccttct ggctttggtc ctcttaactc tgataacact  720
gtgacctaca ctggctctgt cgtcagtcag gtctctgccg gtgtgtacgc aactgttcgc  780
ttcgatcagt atgacatcca taatctcagg actattgaga agacctggta cgctcgtcat  840
gcgacgcttc acaacggcaa gaagatcagc atcaataacg tgacagaaat ggcccctacc  900
agcccgatca agactaactg a                                             921

SEQ ID NO: 196         moltype = DNA  length = 921
FEATURE                Location/Qualifiers
misc_feature           1..921
                       note = engineered
misc_feature           1..921
                       note = A nucleotide sequence encoding SEQ ID NO: 24 with an
```

```
                              open reading frame from 1 to 918.
source                        1..921
                              mol_type = other DNA
                              organism = synthetic construct
SEQUENCE: 196
atggctatcc tagaccttaa gtccctcgtg ctgaacgcca ttaactactg gggccctaag   60
aacaacaacg gcatccaggg cggtgacttc ggctacccca tctctgagaa gcagatcgac  120
actagcatca ttacctccac ccaccctcgc ttgatccccc acgatcttac tatcccgcag  180
aaccttgaga ccatcttcac cacaacgcag gtgctcacca ataacactga cctccagcaa  240
tcccagaccg tgagctttgc gaagaagacc actaccgcga cctcaactag cacgaccaac  300
ggttggacag aaggaggcaa gatcagcgac acgctggagg agaaagtttc ggttagcatt  360
ccgttcatcg gtgagggtgg cgggaagaac tcgactacca tagaggccaa cttcgcacac  420
aactctagca ccactacctt ccaggaggca agcactgaca ttgagtggaa cattagccaa  480
ccggtccttg tgcctccccg caaacaggtt gttgccactc tcgttatcat gggtggcaac  540
ttcactattc ctatggatct tatgactacc attgactcta ctgagcacta ctctggctac  600
cccattctca cttggatctc ttctcctgac aatagctaca acggtccatt catgtcatgg  660
tacttcgcta actggccgaa tctcccttct ggctttggtc ctcttaactc tgataacact  720
gtgacctaca ctggctctgt cgtcagtcag gtctctgccg gtgtgtacgc aactgttcgc  780
ttcgatcagt atgacatcca taatctcagg actattgaga agacctggta cgctcgtcat  840
gcgacgcttc acaacggcaa gaagatcagc atcaataacg tgacagaaat ggcccctacc  900
agcccgatca agactaactg a                                            921

SEQ ID NO: 197        moltype = DNA   length = 921
FEATURE               Location/Qualifiers
misc_feature          1..921
                      note = engineered
misc_feature          1..921
                      note = A nucleotide sequence encoding SEQ ID NO: 26 with an
                             open reading frame from 1 to 918.
source                1..921
                      mol_type = other DNA
                      organism = synthetic construct
SEQUENCE: 197
atggctatcc tagaccttaa gtccctcgtg ctgaacgcca ttaactactg gggccctaag   60
aacaacaacg gcatccaggg cggtgacttc ggctacccca tctctgagaa gcagatcgac  120
actagcatca ttacctccac ccaccctcgc ttgatccccc acgatcttac tatcccgcag  180
aaccttgaga ccatcttcac cacaacgcag gtgctcacca ataacactga cctccagcaa  240
tcccagaccg tgagctttgc gaagaagacc actaccacga ccgcaactag cacgaccaac  300
ggttggacag aaggaggcaa gatcagcgac acgctggagg agaaagtttc ggttagcatt  360
ccgttcatcg gtgagggtgg cgggaagaac tcgactacca tagaggccaa cttcgcacac  420
aactctagca ccactaccgc ccagcaagca agcactgaca ttgagtggaa cattagccaa  480
ccggtccttg tgcctccccg caaacaggtt gttgccactc tcgttatcat gggtggcaac  540
ttcactattc ctatggatct tatgactacc attgactcta ctgagcacta ctctggctac  600
cccattctca cttggatctc ttctcctgac aatagctaca gcggtccatt catgtcatgg  660
tacttcgcta actggccgaa tctcccttct ggctttggtc ctcttaactc tgataacact  720
gtgacctaca ctggctctgt cgtcagtcag gtctctgccg gtgtgtacgc aactgttcgc  780
ttcgatcagt atgacatcca taatctcagg actattgaga agacctggta cgctcgtcat  840
gcgacgcttc acaacggcaa gaagatcagc atcaataacg tgacagaaat ggcccctacc  900
agcccgatca agactaactg a                                            921

SEQ ID NO: 198        moltype = DNA   length = 921
FEATURE               Location/Qualifiers
misc_feature          1..921
                      note = engineered
misc_feature          1..921
                      note = A nucleotide sequence encoding SEQ ID NO: 28 with an
                             open reading frame from 1 to 918.
source                1..921
                      mol_type = other DNA
                      organism = synthetic construct
SEQUENCE: 198
atggctatcc tagaccttaa gtccctcgtg ctgaacgcca ttaactactg gggccctaag   60
aacaacaacg gcatccaggg cggtgacttc ggctacccca tctctgagaa gcagatcgac  120
actagcatca ttacctccac ccaccctcgc ttgatccccc acgatcttac tatcccgcag  180
aaccttgaga ccatcttcac cacaacgcag gtgctcacca ataacactga cctccagcaa  240
tcccagaccg tgagctttgc gaagaagacc actaccacga ccgcaactag cacgaccaac  300
ggttggacag aaggaggcaa gatcagcgac acgctggagg agaaagtttc ggttagcatt  360
ccgttcatcg gtgagggtgg cgggaagaac tcgactacca tagaggccaa cttcgcacac  420
aactctagca ccactaccgc ccagcaagca agcactgaca ttgagtggaa cattagccaa  480
ccggtccttg tgcctccccg caaacaggtt gttgccactc tcgttatcat gggtggcaac  540
ttcactattc ctatggatct tatgactacc attgactcta ctgagcacta ctctggctac  600
cccattctca cttggatctc ttctcctgac aatagctaca gcggtcgatt catgtcatgg  660
tacttcgcta actggccgaa tctcccttct ggctttggtc ctcttaactc tgataacact  720
gtgacctaca ctggctctgt cgtcagtcag gtctctgccg gtgtgtacgc aactgttcgc  780
ttcgatcagt atgacatcca taatctcagg actattgaga agacctggta cgctcgtcat  840
gcgacgcttc acaacggcaa gaagatcagc atcaataacg tgacagaaat ggcccctacc  900
agcccgatca agactaactg a                                            921

SEQ ID NO: 199        moltype = DNA   length = 921
```

| FEATURE | Location/Qualifiers |
|---|---|
| misc_feature | 1..921 |
| | note = engineered |
| misc_feature | 1..921 |
| | note = A nucleotide sequence encoding SEQ ID NO: 30 with an open reading frame from 1 to 918. |
| source | 1..921 |
| | mol_type = other DNA |
| | organism = synthetic construct |

SEQUENCE: 199

```
atggctatcc tagaccttaa gtccctcgtg ctgaacgcca ttaactactg gggccctaag    60
aacaacaacg gcatccaggg cggtgacttc ggctacccca tctctgagaa gcagatcgac   120
actagcatca ttacctccac ccaccctcgc ttgatccccc acgatcttac tatcccgcag   180
aaccttgaga ccatcttcac cacaacgcag gtgctcacca ataacactga cctccagcaa   240
tcccagaccg tgagctttgc gaagaagacc actaccacga ccgcaactag cacgaccaac   300
ggttggacag aaggaggcaa gatcagcgac acgctggagg agaaagtttc ggttagcatt   360
ccgttcatcg tgagggtgg cgggaagaac tcgactacca tagaggccaa cttcgcacac   420
aactctagca ccactaccgc ccagcaagca agcactgaca ttgagtggaa cattagccaa   480
ccggtccttg tgcctccccg caaacaggtt gttgccactc tcgttatcat gggtggcaac   540
ttcactattc ctatggatct tatgactacc attgactcta ctgagcacta ctctggctac   600
cccattctca cttggatctc ttctcctgac aatagctaca gcggtcgatt catgtcatgg   660
tacttcgcta actggccgaa tctcccttct ggctttggtc ctcttaactc tgataacact   720
gtgacctaca ctggctctgt cgccagtcag gtctctgccg gtgtgtacgc aactgttcgc   780
ttcgatcagt atgacatcca taatctcagg actattgaga agacctggta cgctcgtcat   840
gcgacgcttc acaacggcaa gaagatcagc atcaataacg tgacagaaat ggcccctacc   900
agcccgatca agactaactg a                                              921
```

| SEQ ID NO: 200 | moltype = DNA   length = 921 |
|---|---|
| FEATURE | Location/Qualifiers |
| misc_feature | 1..921 |
| | note = engineered |
| misc_feature | 1..921 |
| | note = A nucleotide sequence encoding SEQ ID NO: 32 with an open reading frame from 1 to 918. |
| source | 1..921 |
| | mol_type = other DNA |
| | organism = synthetic construct |

SEQUENCE: 200

```
atggctatcc tagaccttaa gtccctcgtg ctgaacgcca ttaactactg gggccctaag    60
aacaacaacg gcatccaggg cggtgacttc ggctacccca tctctgagaa gcagatcgac   120
actagcatca ttacctccac ccaccctcgc ttgatccccc acgatcttac tatcccgcag   180
aaccttgaga ccatcttcac cacaacgcag gtgctcacca ataacactga cctccagcaa   240
tcccagaccg tgagctttgc gaagaagacc actaccacga ccgcaactag cacgaccaac   300
ggttggacag aaggaggcaa gatcagcgac acgctggagg agaaagtttc ggttagcatt   360
ccgttcatcg tgagggtgg cgggaagaac tcgactacca tagaggccaa cttcgcacac   420
aactctagca ccactaccgc ccagcaagca agcactgaca ttgagtggaa cattagccaa   480
ccggtccttg tgcctccccg caaacaggtt gttgccactc tcgttatcat gggtggcaac   540
ttcactattc ctatggatct tatgactacc attgactcta ctgagcacta ctctggctac   600
cccattctca cttggatctc ttctcctgac aatagctaca gcggtcgatt catgtcatgg   660
tacttcgcta actggccgaa tctcccttct ggctttggtc ctcttaactc tgataacact   720
gtgacctaca ctggctctgt cgtcagtcag gtctctgccg gtgtgtacgc aactgttcgc   780
ttcgatcagt atgacatcca taatctctgg actattgaga agacctggta cgctcgtcat   840
gcgacgcttc acaacggcaa gaagatcagc atcaataacg tgacagaaat ggcccctacc   900
agcccgatca agactaactg a                                              921
```

| SEQ ID NO: 201 | moltype = DNA   length = 921 |
|---|---|
| FEATURE | Location/Qualifiers |
| misc_feature | 1..921 |
| | note = engineered |
| misc_feature | 1..921 |
| | note = A nucleotide sequence encoding SEQ ID NO: 34 with an open reading frame from 1 to 918. |
| source | 1..921 |
| | mol_type = other DNA |
| | organism = synthetic construct |

SEQUENCE: 201

```
atggctatcc tagaccttaa gtccctcgtg ctgaacgcca ttaactactg gggccctaag    60
aacaacaacg gcatccaggg cggtgacttc ggctacccca tctctgagaa gcagatcgac   120
actagcatca ttacctccac ccaccctcgc ttgatccccc acgatcttac tatcccgcag   180
aaccttgaga ccatcttcac cacaacgcag gtgctcacca ataacactga cctccagcaa   240
tcccagaccg tgagctttgc gaagaagacc actaccacga ccgcaactag cacgaccaac   300
ggttggacag aaggaggcaa gatcagcgac acgctggagg agaaagtttc ggttagcatt   360
ccgttcatcg tgagggtgg cgggaagaac tcgactacca tagaggccaa cttcgcacac   420
aactctagca ccactaccgc ccaggaagca agcactgaca ttgagtggaa cattagccaa   480
ccggtccttg tgcctccccg caaacaggtt gttgccactc tcgttatcat gggtggcaac   540
ttcactattc ctatggatct tatgactacc attgactcta ctgagcacta ctctggctac   600
cccattctca cttggatctc ttctcctgac aatagctaca gcggtcgatt catgtcatgg   660
tacttcgcta actggccgaa tctcccttct ggctttggtc ctcttaactc tgataacact   720
gtgacctaca ctggctctgt cgtcagtcag gtctctgccg gtgtgtacgc aactgttcgc   780
```

```
ttcgatcagt atgacatcca taatctctgg actattgaga agacctggta cgctcgtcat  840
gcgacgcttc acaacggcaa gaagatcagc atcaataacg tgacagaaat ggcccctacc  900
agcccgatca agactaactg a                                            921

SEQ ID NO: 202         moltype = AA  length = 306
FEATURE                Location/Qualifiers
REGION                 1..306
                       note = engineered
REGION                 1..306
                       note = The AA sequence translation of nucleotides 1 through
                        903 of SEQ ID NO: 15.
source                 1..306
                       mol_type = protein
                       organism = synthetic construct
SEQUENCE: 202
MAILDLKSLV LNAINYWGPK NNNGIQGGDF GYPISEKQID TSIITSTHPR LIPHDLTIPQ  60
NLETIFTTTQ VLTNNTDLQQ SQTVSFAKKT TTTTATSTTN GWTEGGKISD TLEEKVSVSI  120
PFIGEGGGKN STTIEANFAH NSSTTTAQQA STDIEWNISQ PVLVPPRKQV VATLVIMGGN  180
FTIPMDLMTT IDSTEHYSGY PILTWISSPD NSYNGPFMSW YFANWPNLPS GFGPLNSDNT  240
VTYTGSVVSQ VSAGVYATVR FDQYDIHNLR TIEKTWYARH ATLHNGKKIS INNVTEMAPT  300
SPIKTN                                                             306

SEQ ID NO: 203         moltype = DNA  length = 921
FEATURE                Location/Qualifiers
misc_feature           1..921
                       note = engineered
misc_feature           1..921
                       note = A nucleotide sequence encoding SEQ ID NO: 204 with
                        an open reading frame from 1 to 918.
source                 1..921
                       mol_type = other DNA
                       organism = synthetic construct
SEQUENCE: 203
atggctatcc tagaccttaa gtccctcgtg ctgaacgcca ttaactactg gggccctaag  60
aacaacaacg gcatccaggg cggtgacttc ggctacccca tctctgagaa gcagatcgac  120
actagcatca ttacctccac ccaccctcgc ttgatccccc acgatcttac tatcccgcag  180
aaccttgaga ccatcttcac cacaacgcag gtgctcacca ataacactga cctccagcaa  240
tcccagaccg tgagctttgc gaagaagacc actaccacga ccgcaactag cacgaccaac  300
ggttggacag aaggaggcaa gatcagcgac acgctggagg agaaagtttc ggttagcatt  360
ccgttcatcg gtgagggtgg cgggaagaac tcgactacca tagaggccaa cttcgcacac  420
aactctagca ccactacctc ccaggaagca agcactgaca ttgagtggaa cattagccaa  480
ccggtccttg tgcctccccg caaacaggtt gttgccactc tcgttatcat gggtggcaac  540
ttcactattc ctatggatct tatgactacc attgactcta ctgagcacta ctctggctac  600
cccattctca cttggatctc ttctcctgac aatagctaca gcggtcgatt catgtcatgg  660
tacttcgcta actggccgaa tctcccttct ggctttggtc ctcttaactc tgataacact  720
gtgacctaca ctggccgggt cgaaagtcgg gtctctgccg gtgtgtacgc aactgttcgc  780
ttcgatcagt atgacatcca taatctctgg actattgaga agacctggta cgctcgtcat  840
gcgacgcttc acaacggcaa gaagatcagc atcaataacg tgacagaaat ggcccctacc  900
agcccgatca agactaactg a                                            921

SEQ ID NO: 204         moltype = AA  length = 306
FEATURE                Location/Qualifiers
REGION                 1..306
                       note = engineered
REGION                 1..306
                       note = The amino acid sequence translation of the open
                        reading frame set forth as SEQ ID NO: 203.
source                 1..306
                       mol_type = protein
                       organism = synthetic construct
SEQUENCE: 204
MAILDLKSLV LNAINYWGPK NNNGIQGGDF GYPISEKQID TSIITSTHPR LIPHDLTIPQ  60
NLETIFTTTQ VLTNNTDLQQ SQTVSFAKKT TTTTATSTTN GWTEGGKISD TLEEKVSVSI  120
PFIGEGGGKN STTIEANFAH NSSTTTSQEA STDIEWNISQ PVLVPPRKQV VATLVIMGGN  180
FTIPMDLMTT IDSTEHYSGY PILTWISSPD NSYSGRFMSW YFANWPNLPS GFGPLNSDNT  240
VTYTGRVESR VSAGVYATVR FDQYDIHNLW TIEKTWYARH ATLHNGKKIS INNVTEMAPT  300
SPIKTN                                                             306

SEQ ID NO: 205         moltype = DNA  length = 2577
FEATURE                Location/Qualifiers
misc_feature           1..2577
                       note = AXMI-171 US2010/0298207 A1 SEQ ID NO:204
source                 1..2577
                       mol_type = unassigned DNA
                       organism = Bacillus thuringiensis
SEQUENCE: 205
atgaaaaata aaaagaaata tatgaagcca ctcgcagtag gcttgctcgc aactaacatt  60
attggatttg gtactcagac agtagcgttt gctgcgacag ataaagcggg ttccaaagaa  120
cagatgcagc aacaaatgaa aacacagaat aagagcttta atccgacagt attagccagt  180
```

```
atgccatcgg atacatcgga gcttcaaaaa atgttggaag acgcgattaa aaataaggat   240
acccagatta ctccggaatt aataaaaaaa cttcaggaca aaggatttga ttaccttagt   300
attgtaaagg gtttaactgg cggattactg aagcaaattc cgtatgcagg ttcaatcctc   360
tccccttttgg tagttggcct ttttccaggt aagggttatg taacgaaggc gaatgtctgg   420
ggagagatac aggatcgcgt ttcaaattta atagatcaaa aattagaaga gtcacaagta   480
aataacttaa ttgggaaact aacgggtatt caggataatt taggaatata ccaaactcgg   540
gttggtttag ttaatgggat aaaaccacca attgctaatt ttatacaaaa ggatgcaaat   600
tctgataaaa ataaggagaa tttaagaagc acaatagact ccttggacaa ggatttaggc   660
cgagtgatac ctgagtttgc tgttaaaggt tacgaggcag cttctcttcc atattatgta   720
caagttgcca atgtgcatct tttcttattg aaagatgcac ttacacatgc agatgagtgg   780
gggcttactg atgatgaaaa gagaggatat tgtcaagac ttcaacaaaa aattcaagag   840
tatagcagcg tcgtatatga ttcctttaat aaaggagtcg aagccgctaa aagtaagggt   900
ggaagtaccg ccgacagttg gaacagaacc aatgcctatg taagaacaat gacattgtat   960
ggtttagatt ttgtggcttt atggccggct tttgatacta acattataa tcagccagta  1020
aaattgcagc aaacacgtga attatattct aacatgatag aagaccaat aaactggcaa  1080
gactatgata caactcttca acaaattcat aatagtgggt atgcgggtta tccaggcgag  1140
ctgaaacaag ttggtgtttc acagtgggat cgtattgatg gaatcaggga atatttgat  1200
tggactggag acggctcacg agattatacg ctacaatggg gccacgcaaa caaaaatggg  1260
tattcggacc gtagccagac cgtcaataac ccagcaatag gaatttcagc atatgaatcc  1320
aataatgcta atttctataa tatgtctact atcacatata acaaaataa cgaagtatct  1380
tggttctatg gtccatttac tactcaaagc gatagtaaag atggaagtag aatagatagc  1440
aaagctccag cgggccataa attatctcgc gtcaaagtac aagaaaaaag atcagatcta  1500
aatacaatat catcttttgt ggctgcatat gttcctgaag aagttcatcc acagaatata  1560
cttgaggcta aagctattac aggggtacca gctgaaaaat atctcgcaca tgcaggattt  1620
gaagataaga ttgaatacat gaatggttcg aatgcgatgg tatcttctaa aaatggtgac  1680
acgatagatt acaatgttca aagtccagga aacaaaaat ataaaatacg cctccgtgtt  1740
gcgacaaata gtgacacatc tgtgggaatc tctataaatg gggattctca gcaagtgaat  1800
ataaaaaata cagaagccgc aacaaagtta aagacggta ttacagttaa aggtgtaaat  1860
gggaagtaca tgttaattga cggaccaact gttgaactta cgaaggtgt aatacaatt  1920
cagcttaaaa atagtggtgg agctaagatt gcattagatc gaatagaatt tgagcctata  1980
ggcggtgagc tacgcaagtg gaaacaggaa ggtgataagt ggtacttta cgatgaaaat  2040
gataaaagt taacaggttg gcaaagatt aatgaaagaa aatactacct tggacattct  2100
ggtgatggtt ctggtatgac cactgaaggg gagatggcaa caggctggaa aacgattgat  2160
ggagtacaat attactttgg acattctggt gatggttctg gtatggtcac tgaagggag  2220
atggcaacag gctgaaaac gataaatgga gtaaaatatt attttggaca gactggtgat  2280
ggctctggta tgcaaacacga aggggaaaag gcaacaggct ggaaaacgat tgatggagta  2340
aaatattact tcaataaaac tggtgatggc tctggtatgc aacacgaagg ggaaaaggca  2400
ataggctgga aaacgattga tggagtaaaa tattacttca ataaaactgg tgatggctct  2460
ggtatgcaac acgaaggaga aatggcatta gagatatga cgattgatgg agtaaaacat  2520
cactttaata aaactggtga tggaacgggt cgcgaccatg aaggagagct cgtatgg    2577

SEQ ID NO: 206      moltype = AA  length = 859
FEATURE             Location/Qualifiers
REGION              1..859
                    note = AXMI-171 US2010/0298207 A1 SEQ ID NO:205
source              1..859
                    mol_type = protein
                    organism = Bacillus thuringiensis
SEQUENCE: 206
MKNKKKYMKP LAVGLLATNI IGFGTQTVAF AATDKAGSKE QMQQQMKTQN KSFNPTVLAS   60
MPSDTSELQK MLEDAIKNKD TQITPELIKK LQDKGFDYLS IVKGLTGGLL KQIPYAGSIL  120
SPLVVGLFPG KGYVTKANVW GEIQDRVSNL IDQKLEESQV NNLIGKLTGI QDNLGIYQTR  180
VGLVNGIKPP IANFIQKDAN SDKNKENLRS TIDSLDKDLG RVIPEFAVKG YEAASLPYYV  240
QVANVHLFLL KDALTHADEW GLTDDEKRGY LSRLQQKIQE YSSVVYDSFN KGVEAAKSKG  300
GSTADSWNRT NAYVRTMTLY GLDFVALWPA FDTKHYNQPV KLQQTRELYS NMIGRPINWQ  360
DYDTTLQQIH NSGYAGYPGE LKQVGVSQWD RIDGIREIFD WTGDSRDYT LQWGHANKNG  420
YSDRSQTVNN PAIGISAYES NNANFYNMST ITYKQNNEVS WFYGPFTTQS DSKDGSRIDS  480
KAPAGHKLSR VKVQEKRSDL NTISSFVAAY VPEEVHPQNI LEAKAITGVP AEKYLAHAGF  540
EDKIEYMNGS NAMVSSKNGD TIDYNVQSPG KQKYKIRLRV ATNSDTSVGI SINGDSQQVN  600
IKNTEAATKL EDGITVKGVN GKYMLIDGPT VELSEGVNTI QLKNSGGAKI ALDRIEFEPI  660
GGELRKWKQE GDKWYFYDEN DKKLTGWQKI NERKYYLGHS GDGSGMTTEG EMATGWKTID  720
GVQYYFGHSG DGSGMVTEGE MATGWKTING VKYYFGQTGD GSGMQHEGEK ATGWKTIDGV  780
KYYFNKTGDG SGMQHEGEKA IGWKTIDGVK YYFNKTGDGS GMQHEGEMAL GDMTIDGVKH  840
HFNKTGDGTG RDHEGELVW                                              859
```